(12) United States Patent
Epstein et al.

(10) Patent No.: US 10,961,317 B2
(45) Date of Patent: Mar. 30, 2021

(54) CD20 SCFV-ELPS METHODS AND THERAPEUTICS

(71) Applicant: University of Southern California, Los Angeles, CA (US)

(72) Inventors: Alan L. Epstein, La Canada, CA (US); John Andrew MacKay, Pasadena, CA (US); Peisheng Hu, Covina, CA (US); Suhaas Aluri, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/254,531

(22) Filed: Jan. 22, 2019

(65) Prior Publication Data

US 2020/0079868 A1 Mar. 12, 2020

Related U.S. Application Data

(63) Continuation of application No. 14/420,308, filed as application No. PCT/US2013/054218 on Aug. 8, 2013, now abandoned.

(60) Provisional application No. 61/682,029, filed on Aug. 10, 2012.

(51) Int. Cl.
| | |
|---|---|
| *C07K 16/28* | (2006.01) |
| *C07K 14/78* | (2006.01) |
| *A61K 47/69* | (2017.01) |
| *A61K 47/68* | (2017.01) |
| *A61K 47/64* | (2017.01) |
| *A61K 38/00* | (2006.01) |
| *A61K 9/107* | (2006.01) |
| *A61K 9/51* | (2006.01) |
| *A61K 39/00* | (2006.01) |
| *A61K 48/00* | (2006.01) |

(52) U.S. Cl.
CPC ...... *C07K 16/2887* (2013.01); *A61K 47/6435* (2017.08); *A61K 47/6849* (2017.08); *A61K 47/6929* (2017.08); *C07K 14/78* (2013.01); *A61K 9/1075* (2013.01); *A61K 9/51* (2013.01); *A61K 38/00* (2013.01); *A61K 48/005* (2013.01); *A61K 2039/505* (2013.01); *C07K 2317/622* (2013.01); *C07K 2317/73* (2013.01); *C07K 2319/33* (2013.01); *C07K 2319/735* (2013.01); *C07K 2319/74* (2013.01)

(58) Field of Classification Search
CPC .............. C07K 16/2887; C07K 16/622; C07K 2319/73; C07K 2319/74; C07K 14/78; C07K 2319/33; A61K 47/6929; A61K 47/6849; A61K 47/6435; A61K 2039/505
See application file for complete search history.

(56) References Cited

U.S. PATENT DOCUMENTS

| | | | |
|---|---|---|---|
| 4,898,926 A | 2/1990 | Urry | |
| 6,015,662 A * | 1/2000 | Hackett, Jr. | ........ G01N 33/6854 435/5 |
| 6,852,834 B2 | 2/2005 | Chilkoti | |
| 7,700,727 B2 | 4/2010 | Berthet et al. | |
| 8,252,740 B2 | 8/2012 | Raucher et al. | |
| 8,367,626 B2 | 2/2013 | Furgeson et al. | |
| 8,563,521 B2 | 10/2013 | Skerra et al. | |
| 8,680,045 B2 | 3/2014 | Primiano et al. | |
| 8,841,414 B1 | 9/2014 | Raucher et al. | |
| 8,933,197 B2 | 1/2015 | Stemmer et al. | |
| 9,102,763 B2 | 8/2015 | Mackay et al. | |
| 2002/0013344 A1 | 1/2002 | Steiner et al. | |
| 2004/0254108 A1 * | 12/2004 | Ma | ..................... A61K 38/1709 424/85.1 |
| 2007/0265197 A1 | 11/2007 | Furgeson et al. | |
| 2008/0312156 A1 | 12/2008 | Setton et al. | |
| 2010/0048473 A1 | 2/2010 | Chaikof et al. | |
| 2010/0104554 A1 | 4/2010 | Scott et al. | |
| 2010/0119529 A1 | 5/2010 | Furgeson et al. | |
| 2010/0189643 A1 | 7/2010 | Chilkoti et al. | |
| 2011/0039776 A1 | 2/2011 | Chilkoti | |
| 2011/0110866 A1 | 5/2011 | Chilkoti et al. | |
| 2012/0213781 A1 * | 8/2012 | Hilbert | ................... C07K 14/78 424/134.1 |
| 2013/0196926 A1 | 8/2013 | Mackay et al. | |
| 2013/0210747 A1 | 8/2013 | Hamm-Alvarez et al. | |
| 2014/0294932 A1 | 10/2014 | Kim et al. | |
| 2015/0209335 A1 | 7/2015 | Mackay et al. | |
| 2015/0218280 A1 | 8/2015 | Epstein et al. | |
| 2015/0238431 A1 | 8/2015 | Hamm-Alvarez et al. | |
| 2016/0017004 A1 | 1/2016 | Hamm-Alvarez et al. | |
| 2016/0168228 A1 | 6/2016 | Despanie | |
| 2019/0282656 A1 | 9/2019 | Mackay et al. | |
| 2020/0062825 A1 | 2/2020 | Despanie et al. | |

FOREIGN PATENT DOCUMENTS

| | | |
|---|---|---|
| CN | 101544694 | 9/2009 |
| JP | 2006-182721 A | 7/2006 |
| WO | WO-2008/033847 | 3/2008 |

(Continued)

OTHER PUBLICATIONS

Jubala et al., Vet Pathol 42: 468-476 (Year: 2005).*

(Continued)

*Primary Examiner* — Phuong Huynh

(74) *Attorney, Agent, or Firm* — Foley & Lardner LLP

(57) ABSTRACT

Disclosed herein are recombinant polypeptides comprising an elastin-like peptide (ELP) and a scFv, or a biological equivalent of the scFv. Also disclosed are compositions containing scFv-ELP polypeptides and methods of use.

22 Claims, 17 Drawing Sheets

Specification includes a Sequence Listing.

(56) References Cited

FOREIGN PATENT DOCUMENTS

| WO | WO-2011/006069 A1 | 1/2011 |
| WO | WO-2011/133635 A2 | 10/2011 |
| WO | WO-2013/016578 A2 | 1/2013 |
| WO | WO-2014/059384 | 4/2014 |
| WO | WO-2014/059385 A1 | 4/2014 |
| WO | WO-2017/020686 A1 | 2/2017 |

OTHER PUBLICATIONS

Kussie et al., J. Immunol. 152: 146-152 (Year: 1994).*
Chen et al., EMBO J 14: 2784-2794 (Year: 1995).*
MacCalium et al., J. Mol. Biol, 262: 732-745 (Year: 1996).*
De Pascalis et al., Journal of Immunology 169: 3076-3084 (Year: 2002).*
Vajdos et al., J. Mol. Biol. 320, 415-428 (Year: 2002).*
Rudikoff et al., Proc Natl Acad Sci USA 1982 vol. 79: 1979-1983 (Year: 1982).*
Wu et al., J. Mol. Biol. 294, 151-162 (Year: 1999).*
Dufner et al., Trends Biotechnol. 24(11):523-529 (Year: 2006).*
Joensuu et al., Transgenic Res 18: 685-696 (Year: 2009).*
Bork, Peer, "Powers and Pitfalls in Sequence Analysis: The 70% Hurdle", Genome Research, 2000, 10: pp. 398-400.
Bowie, et al., "Deciphering the Message in Protein Sequences: Tolerance to Amino Acid Substitutions", Science, vol. 247, No. 4948 (Mar. 16, 1990). pp. 1306-1310.
Burgess, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, vol. 111, Nov. 1990, pp. 2129-2138.
Chen, et al., "Enhancement and destruction of antibody function by somatic mutation: unequal occurrence is controlled by V gene combinatorial associations", The EMBO Journal, vol. 14, No. 12, pp. 2784-2794, 1995.
Chilkoti et al., "Design of thermally responsive, recombinant polypeptide carriers for targeted drug delivery." Advanced Drug Delivery Reviews 54(8):1093-1111 (2002).
Dhandhukia et al., "Switchable elaslin-like polypeptides that respond to chemical inducers of dimerization." Biomacromolecules Apr. 8, 2013, 14(4):976-85.
Dijoseph, et al., "CD20-Specific Antibody-Targeted Chemotherapy of Non-Hodgkins B-Cell Lymphoma Using Calicheamicin-Conjugated Rituximab." Cancer Immunol. Immunother, 56(7), pp. 1107-1117 (2007).
Dreher et. al., "Temperature Triggered Self-Assembly of Polypeptides into Multivalent Spherical Micelles." J Am Chem Soc 130(2):687-694 (2008).
Final Office Action dated Jul. 23, 2018, from U.S. Appl. No. 14/420,308.
Final Office Action dated Jun. 28, 2018, from U.S. Appl. No. 14/811,720.
Floss, et al., "Elastin-Like Polypeptides Revolutionize Recombinant Protein Expression and their Biomedical Application." Trends in Biotechnology, vol. 28, No. 1, 37-45 (2009).
Floss, et al., "Influence of Elastin-Like Peptide Fusions on the Quantity and Quality of a Tobacco-Derived Human Immunodeficiency Virus-Neutralizing Antibody", Plant Biotechnology Journal 7, pp. 899-913 (2009).
Guo et al., "Anti-CD20 Tetravalent Antibody and Preparation Method and Application Thereof"., Google.com/patents pp. 1-19 (2009).
Hamm-Alvarez, "Design And Cellular Internalization Of Genetically Engineered Polypeptide Nanoparticles Displaying Adenovirus Knob Domain." Utah Drug Delivery Conference, 15th International Symposium on Recent Advances in Drug Delivery Systems "Drug Delivery: New Directions In A New Decade". Salt Lake City, Utah (Feb. 13-16, 2011).
Hassouneh, et al., "Fusions of Elastin-Like Polypeptides to Pharmaceutical Proteins", Methods of Enzymology, vol. 502, pp. 215-237 (2012).
Holliger P et al. (2005), "Engineered antibody fragments and the rise of single domains", Nature Biotechnology, vol. 23, No. 9, pp. 1126-1136.
Hsueh et al., "Development Of Novel Peptide Nanoparticles Targeted To Coxsackievirus-Adenovirus Receptor Expressing Cells." AAPS 2011, Washington, DC (Oct. 23-27, 2011).
International Search Report for Application No. PCT/US2013/054218 dated Apr. 10, 2014.
Jubala, et al., "CD20 Expression in Normal Canine B Cells and in Canine non-Hodgkin Lymphoma", Vet Pathol 24, pp. 468-476, 2005.
Lazar, et al., "Transforming Growth Factor α: Mutation of Aspartic Acid 47 and Leucine 48 Results in Different Biological Activities", Molecular and Cellular Biology, Mar. 1988, vol. 8, No. 3, pp. 1247-1252.
Macewan et al., "Elastin-like polypeptides: biomedical applications of tunable biopolymers." Biopolymers 94(1):60-77 (2010).
Mackay et al., "Ocular Drug Delivery Using A Thermo-responsive Lacritin Fusion Protein," Abstract of presentation at ARVO 2012, Fort Lauderdale, FL (May 4-6, 2012).
Mackay, "Genetically Engineered Polypeptide Nanoparticles." ACS Western Regional Meeting 2011, Pasadena, CA (Nov. 11, 2011).
Mackay, "Protein polymers—a platform for biopharmaceutical delivery and self-assembly." Keck Seminar (posted online Jun. 27, 2011).
McDaniel et al., "Drug delivery to solid tumors by elastin-like polypeptides." Adv Drug Deliv Rev. 2010, 62(15):1456-67.
McDaniel et al., "Recursive Directional Ligation by Plasmid Reconstruction Allows Rapid and Seamless Cloning of Oligomeric Genes." Biomacromolecules 11(4):944-952 (2010).
Meyer et al., "Purification of recombinant proteins by fusion with thermally-responsive polypeptides." Nature Biotechnology 17(11):1112-1115 (1999).
Non-Final Office Action dated Apr. 26, 2019, from U.S. Appl. No. 14/683,033.
Rudikoff, et al., "Single amino acid substitution altering antigen-binding specificity", Proc. Natl. Acad. Sci. USA, vol. 27 pp. 1979-1983, 1982.
Scheller, et al., "Forcing Single-Chain Variable Fragment Production in Tobacco Seeds by Fusion to Elastin-like Polypeptides". Plant Biotech. Journ, pp. 243-249, (2006).
Shah et al., "Biodegradation of elastin-like polypeptide nanoparticles." Protein Sci. Epub May 14, 2012, 21(6):743-50.
Shi et al., "Elastin-based protein polymer nanoparticles carrying drug at both corona and core suppress tumor growth in vivo." J Control Release Epub May 25, 2013, 171(3):330-8.
Sun et al. "Design and cellular internalization of genetically engineered polypeptide nanoparticles displaying adenovirus knob domain" J Control Release. Oct. 30, 2011; 155(2):218-26. (Epub Jun. 14, 2011).
Sun et al., "Genetically engineered polypeptide nanoparticles targeted to lacrimal gland acinar cells." Presented at ARVO 2011, Fort Lauderdale, FL (May 1-5, 2011).
Supplement for Sun et al. "Design and cellular internalization of genetically engineered polypeptide nanoparticles displaying adenovirus knob domain" J Control Release. Oct. 30, 2011; 155(2):218-26. (Epub Jun. 14, 2011).
Trabbic-Carlson et al., "Expression and purification of recombinant proteins from *Escherichia coli*: Comparison of an elastin-like polypeptide fusion with an oligohistidine fusion." Protein Sci 13(12):3274-3284 (2004).
U.S. Final Office Action dated Mar. 9, 2017, for U.S. Appl. No. 14/684,162.
U.S. Office Action dated Jan. 4, 2018, from U.S. Appl. No. 14/683,033.
U.S. Office Action dated Mar. 31, 2017, from U.S. Appl. No. 14/420,308.
U.S. Office Action dated Mar. 9, 2018, from U.S. Appl. No. 14/684,162.
U.S. Office Action dated May 22, 2018, from U.S. Appl. No. 14/683,033.

(56) References Cited

OTHER PUBLICATIONS

UniProtKB/Swiss-Prot Direct Submission P62937.2. Locus PPIA_Human. Oct. 3, 2012.[Retrieved from the Internet Jan. 17, 2014: <http://www.ncbi.nlm.nih.gov/protein/51702775?sat=16&satkey=10893480>].
U.S. Final Office Action for U.S. Appl. No. 13/764,476 dated Jun. 30, 2014, 15 pages.
U.S. Non-Final Office Action for U.S. Appl. No. 13/764,476 dated Nov. 1, 2013, 17 pages.
U.S. Non-Final Office Action for U.S. Appl. No. 14/684,162 dated Aug. 5, 2016, 16 pages.
U.S. Office Action dated Oct. 4, 2017, from U.S. Appl. No. 14/811,720.
U.S. Restriction Requirement for U.S. Appl. No. 14/420,308 dated Aug. 30, 2016, 8 pages.
Wang et al., "Control Of Ocular Drug Bioavailability Using Thermal-Responsive Polypeptides." Controlled Release Meeting (Aug. 3, 2011).
Welply et al. (1996), "A peptide isolated by phage display binds to ICAM-1 and inhibits binding to LFA-1", Proteins: Structure, Function and Genetics, 26:262-270.
Wu et al., "Fabrication of elastin-like polypeptide nanoparticles for drug delivery by electrospraying," Biomacromolecules 2009, 10(1):19-24.
Wu, et al., "Humanization of a Murine Monoclonal Antibody by Simultaneous Optimization of Framework and CDR Residues", J. Mol. Biol., vol. 194, pp. 151-162, 1999.
Amiram M et al: "A depot-forming glucagon-like peptide-1 fusion protein reduces blood glucose for five days with a single injection", Journal of Controlled Release, vol. 172, No. 1, pp. 144-151, XP028772905, ISSN: 0168-3659, DOI: 10.1016/J.JCONREL.2013. 07.021.
Andre F. Palmer et al: "Blood Substitutes", Annual Review of Biomedical Engineering, vol. 16, No. 1, Jul. 11, 2014 (Jul. 11, 2014), pp. 77-101, XP055202930, ISSN: 1523-9829, DOI: 10.1146/annurev-bioeng-071813-104950.
Chang, T. M. S., "Modified hemoglobin-based blood substitutes: crosslinked, recombinant and encapsulated hemoglobin", Vox Sanguinis, 1998, vol. 74 (Suppl. 2), pp. 233-241.
Chilkoti A et al: "Stimulus responsive elastin biopolymers: applications in medicine and biotechnology", Current Opinion in Chemical Biology, Current Biology Ltd, London, GB, vol. 10, No. 6, Dec. 1, 2006 (Dec. 1, 2006), pp. 652-657, XP028014524, ISSN: 1367-5931, DOI: 10.1016/J.CBPA.2006.10.010 [retrieved on Dec. 1, 2006].
Database Geneseq [Online] Jun. 19, 2014 (Jun. 19, 2014), "ELP component reference polypeptide construct S48I48, SEQ ID 4 #1.", retrieved from EBI accession No. GSP:BBF47655 Database accession No. BBF47655.
Despanie et al. "Elastin-like polypeptides: Therapeutic applications for an emerging class of nanomedicines," J Control Release, Nov. 11, 2015 (Nov. 11, 2015), vol. 240, pp. 93-108.
Doreen Manuela Floss et al: "Expression and Immunogenicity of the Mycobacterial Ag85B/ESAT-6 Antigens Produced in Transgenic Plants by Elastin-Like Peptide Fusion Strategy", Journal of Biomedicine and Biotechnology, vol. 2010, Jan. 1, 2010 (Jan. 1, 2010), pp. 1-14, XP055476450, US, ISSN: 1110-7243, DOI: 10.1155/2010/274346.
Final Office Action on U.S. Appl. No. 14/683,033 dated Dec. 6, 2019, 7 pages.
Giselle C. Yeo et al: "Fabricated Elastin", Advanced Healthcare Materials, vol. 4, No. 16, Nov. 1, 2015 (Nov. 1, 2015), pp. 2530-2556, XP055330918, DE, ISSN: 2192-2640, DOI: 10.1002/adhm.201400781.

Hassouneh, Wafa et al., "Fusions of elastin-like polypeptides to pharmaceutical proteins", Methods in Enzymology, 2012, vol. 502, pp. 215-237, NIH Public Access Author Manuscript Version internal p. 1-24.
International Search Report and Written Opinion dated Aug. 16, 2017, from application No. PCT/US2017/035993, 11 pages.
International Search Report and Written Opinion for application No. PCT/US2015/064938 dated Apr. 12, 2016.
Janib et al., "Kinetic quantification of protein polymer nanoparticles using non-invasive imaging," Integr. Biol., pp. 1-12 (2013).
NCBI, GenBank accession No. AAB59408.1 (Aug. 10, 2004).
NCBI, GenBank accession No. NM_000558.3 (May 24, 2014).
Non-final Office Action on U.S. Appl. No. 14/965,053 dated Jun. 1, 2018, 23 pages.
Non-Final Office Action on U.S. Appl. No. 16/038,051 dated Dec. 31, 2019, 22 pages.
Non-Final Office Action on U.S. Appl. No. 16/125,538 dated Dec. 2, 2019, 22 pages.
Restriction Requirement dated Oct. 18, 2019, from U.S. Appl. No. 16/306,825.
Shi Pu et al: "Elastin-based protein polymer nanoparticles carrying drug at both corona and core suppress tumor growthin vivo", Journal of Controlled Release, vol. 171, No. 3, pp. 330-338, XP028740202, ISSN: 0168-3659, DOI: 10.1016/J.JCONREL.2013. 05.013.
UnitProt Accession No. P68871, accessed May 28, 2018 at URL .unitprot.org/unitprot/ P68871.
UnitProt Accession No. P69891, accessed May 28, 2018 at URL .unitprot.org/unitprot/ P69891.
UnitProt Accession No. P69905, accessed May 28, 2018 at URL .unitprot.org/unitprot/ P69905.
Yampolsky et al., "The Exchangeability of Amino Acids in Proteins," Genetics, vol. 170, pp. 1459-1472 (2005).
Conference Program for the Division of Biochemical Technology (BIOT) of the American Chemical Society (ACS)National Meeting. pp. 18-193. San Diego, Mar. 25-29, 2012, Retrieved from the Internet on Feb. 23, 2014: http://www.che.udel.edu/mranton/pdf/acsbiot2012_conf.pdf, Mar. 4, 2012 (according to document properties for posted document).
Dreher et al. Temperature triggered self-assembly of polypeptides into multivalent spherical micelles. J Am Chem Soc. Jan. 16, 2008;130(2):687-94. doi: 10.1021/ja0764862. Epub Dec. 18, 2007.
Non-Final Office Action dated Sep. 4, 2020, from U.S. Appl. No. 16/230,698.
Non-Final Office Action on U.S. Appl. No. 16/206,896 dated May 22, 2020, 23 pages.
Non-Final Office Action on U.S. Appl. No. 16/306,825 dated Apr. 16, 2020, 25 pages.
Sheth et al., "Purification of monoclonal antibodies by affinity precipitation using thermally responsive elastin-like polypeptides(ELPs) fused to IgG binding domains: High-throughput analysis and scale up considerations.," Mar. 27, 2012, 1 page.
Urry. Physical Chemistry of Biological Free Energy Transduction As Demonstrated by Elastic Protein-Based Polymers. J. Phys. Chem. B 1997, 101, 51, 11007-11028. Publication Date: Dec. 18, 1997.
White KD and Capra JD. Targeting mucosal sites by polymeric immunoglobulin receptor-directed peptides. J Exp Med. 2002;196(4):551-555. doi:10.1084/jem.20020581. Aug. 19, 2002.
Xie et al. Novel fiber-dependent entry mechanism for adenovirus serotype 5 in lacrimal acini.J Virol. Dec. 2006;80(23):11833-51. doi: 10.1128/JVI.00857-06. Epub Sep. 20, 2006.
Non-Final Office Action for U.S. Appl. No. 16/274,192 dated Oct. 16, 2020 (24 pages).

* cited by examiner

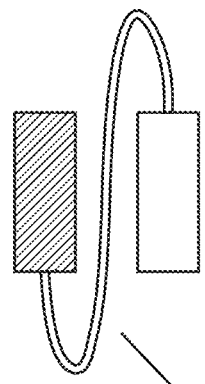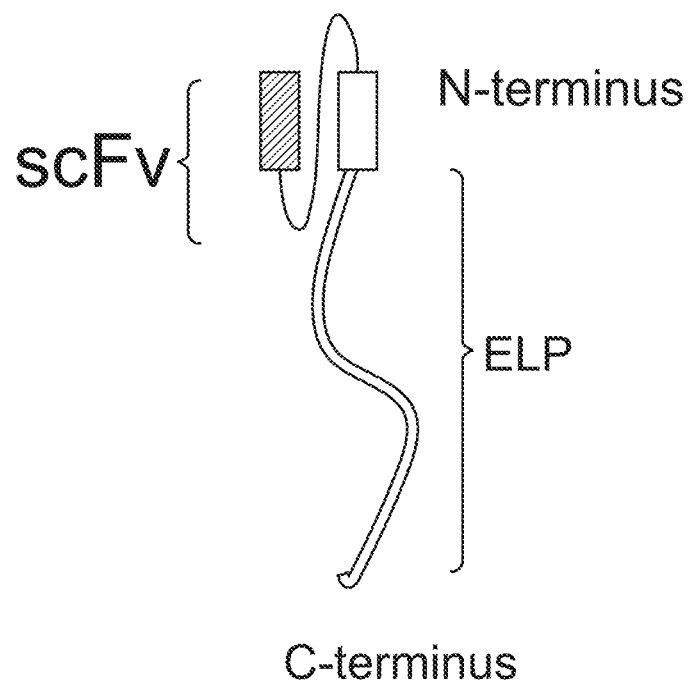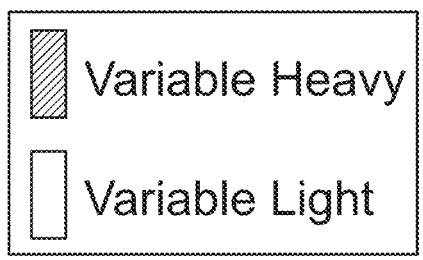
FIG. 3

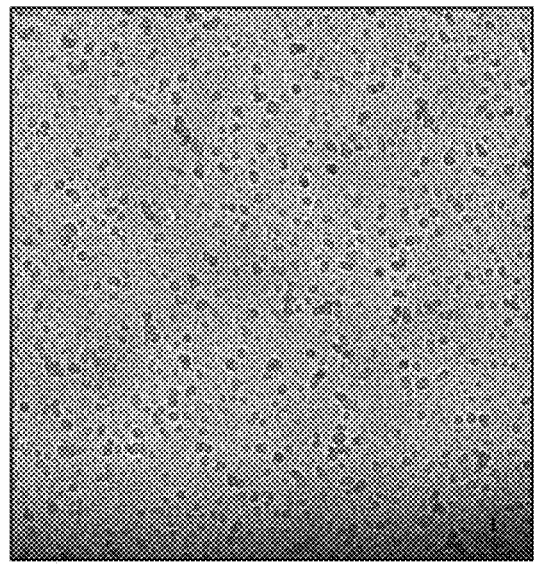
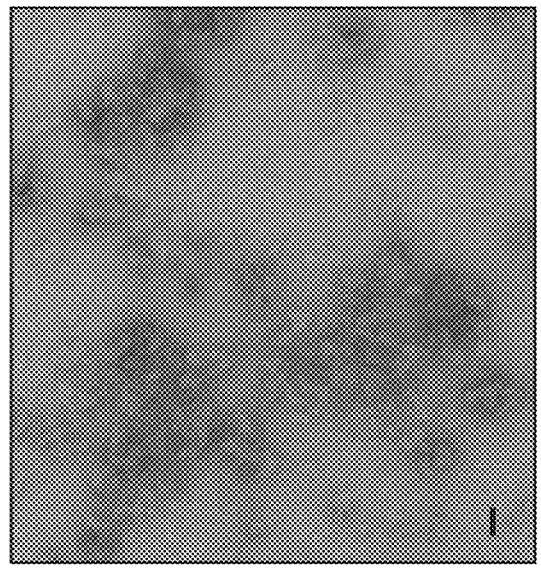

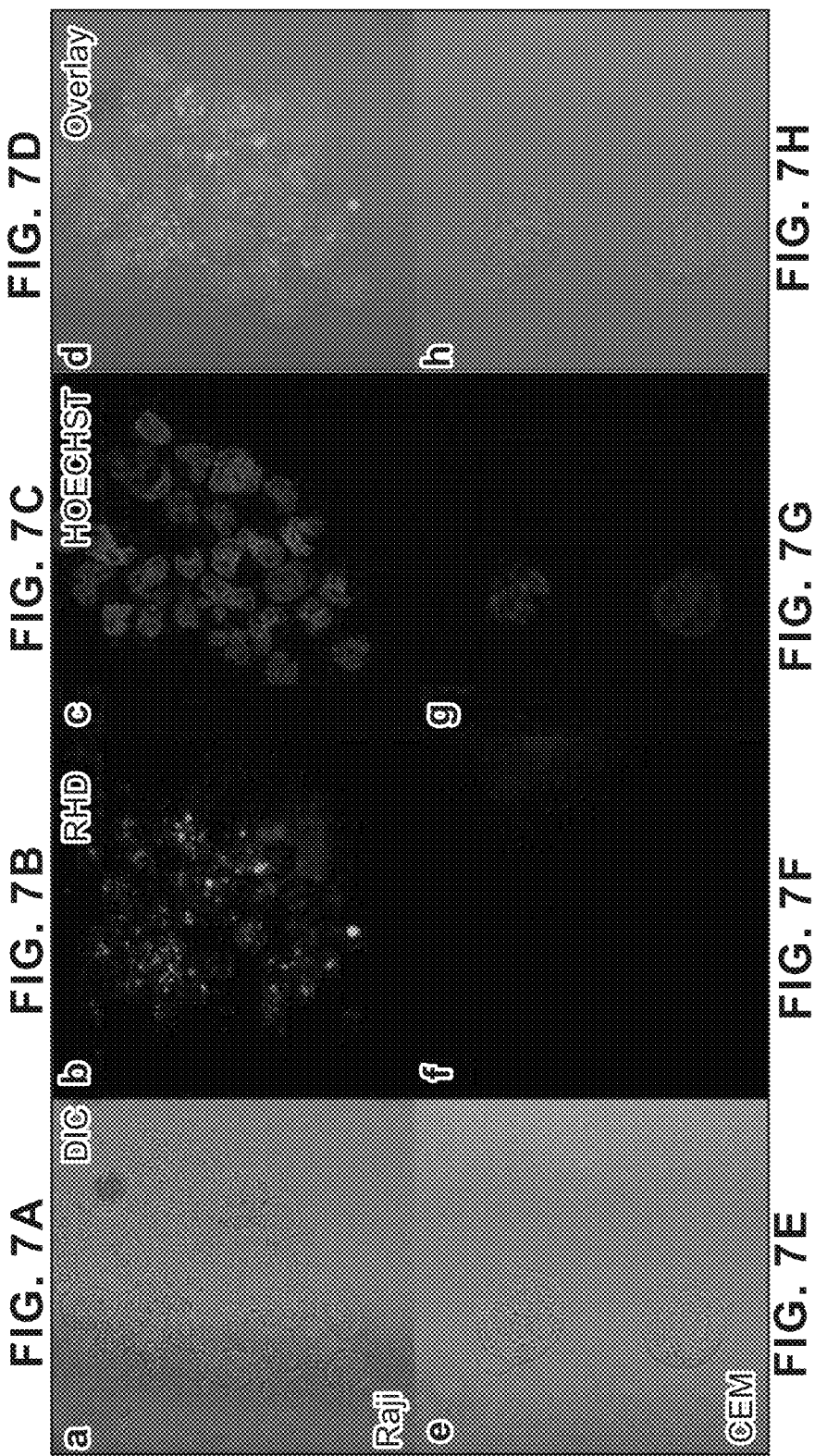

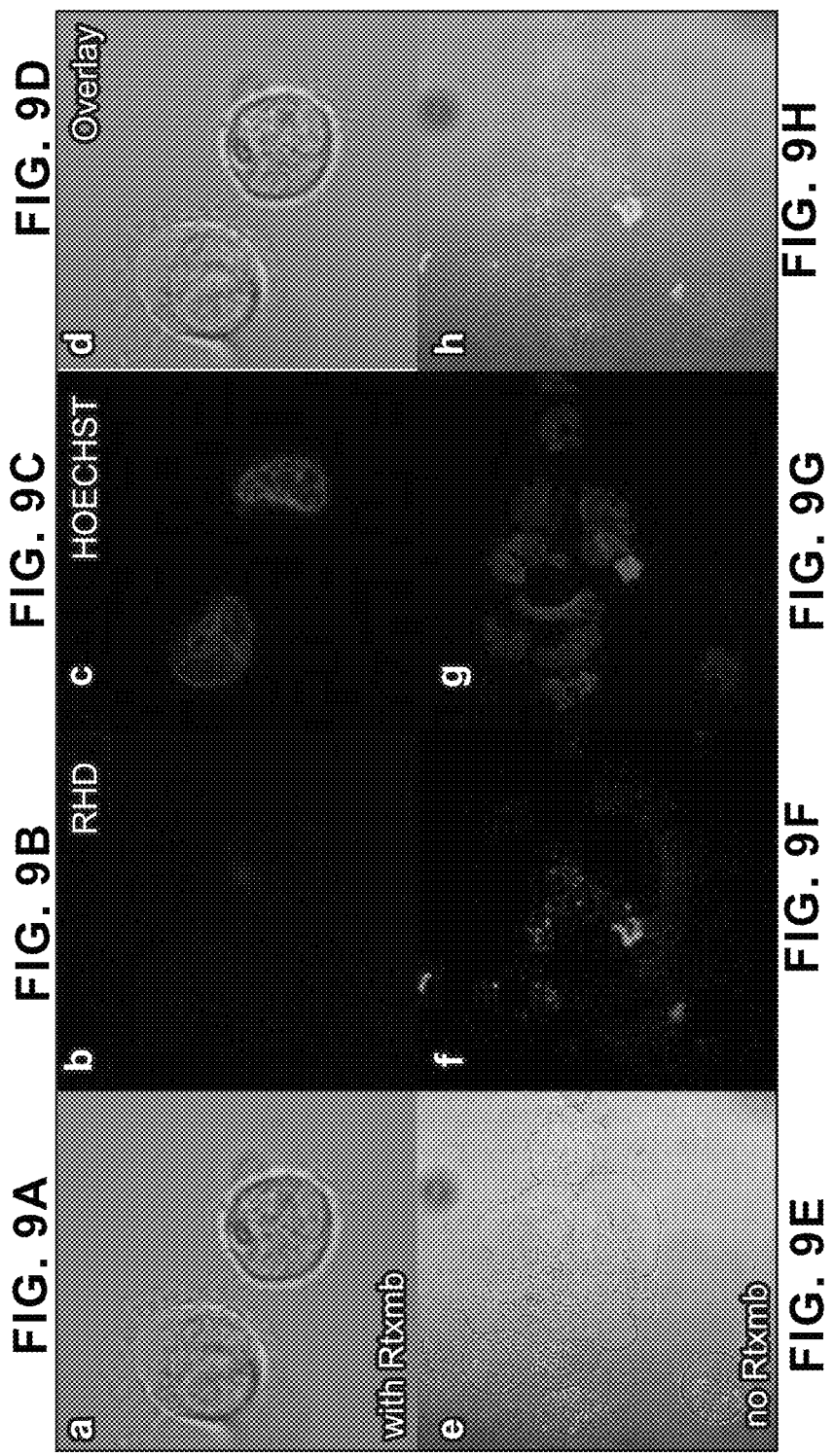

Step 1:
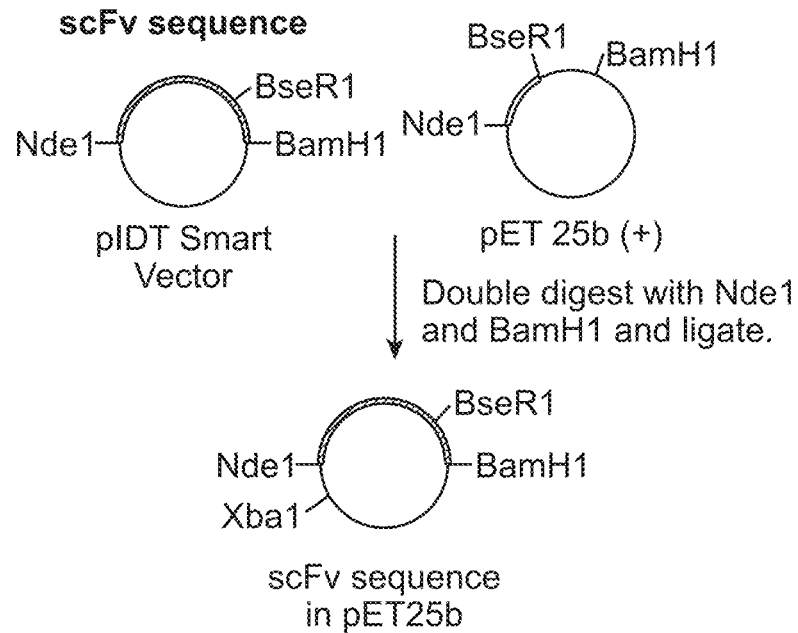
Step 2:
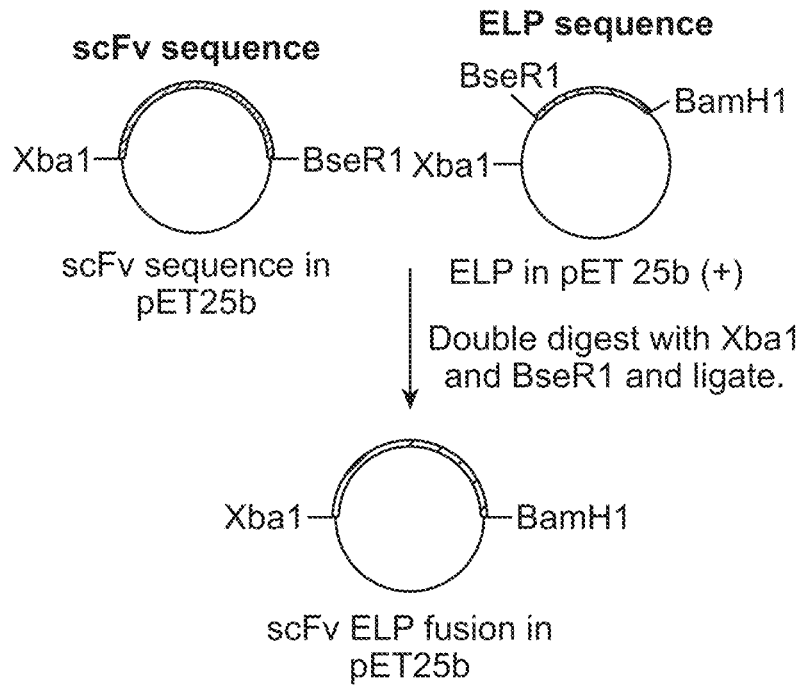
FIG. 13

FIG. 14A
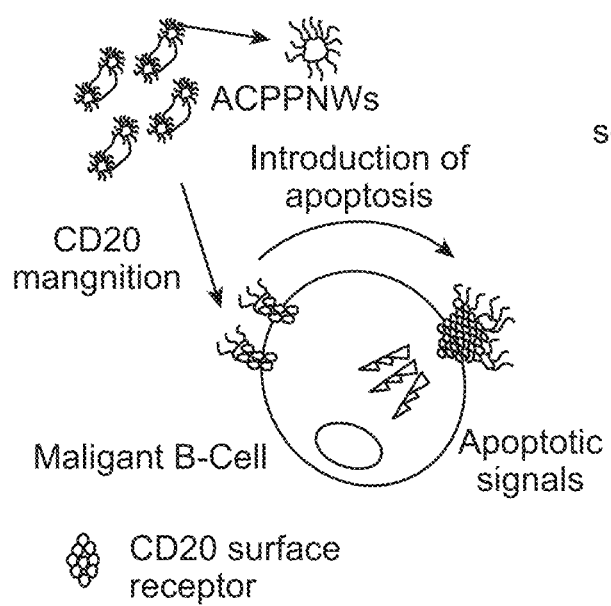
FIG. 14B
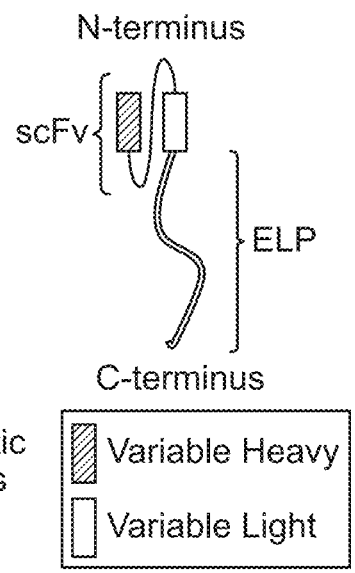
FIG. 15A     FIG. 15B
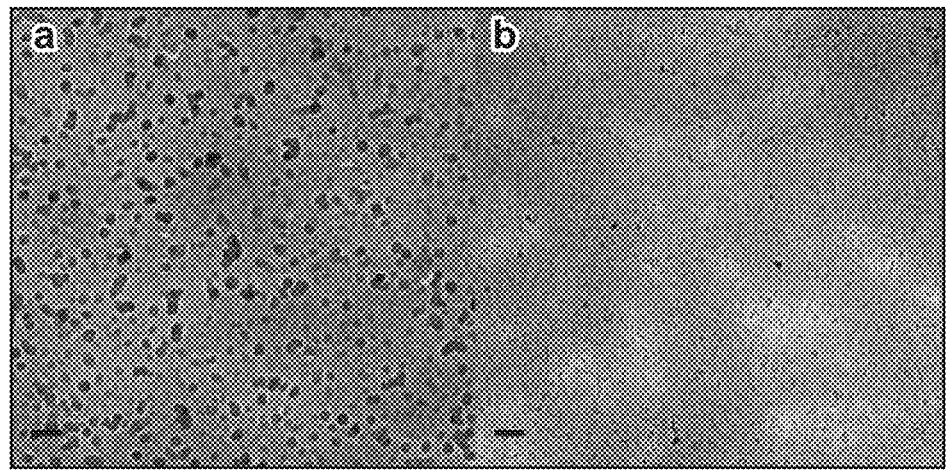

FIG. 16A
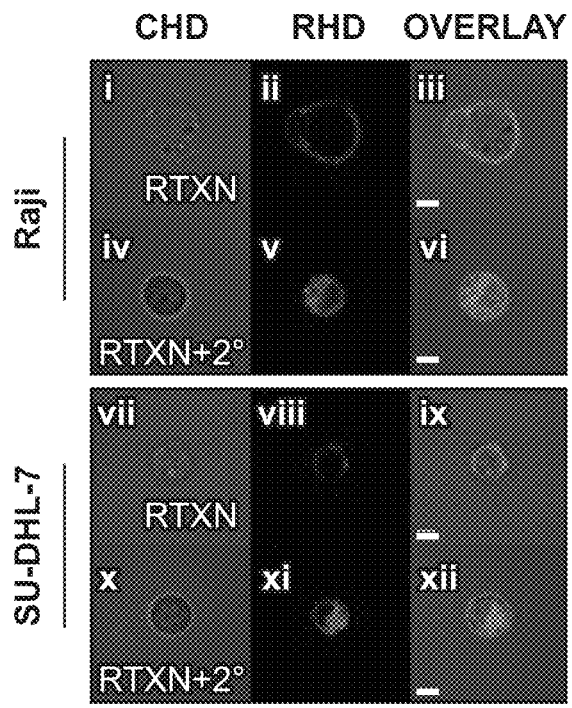
FIG. 16B
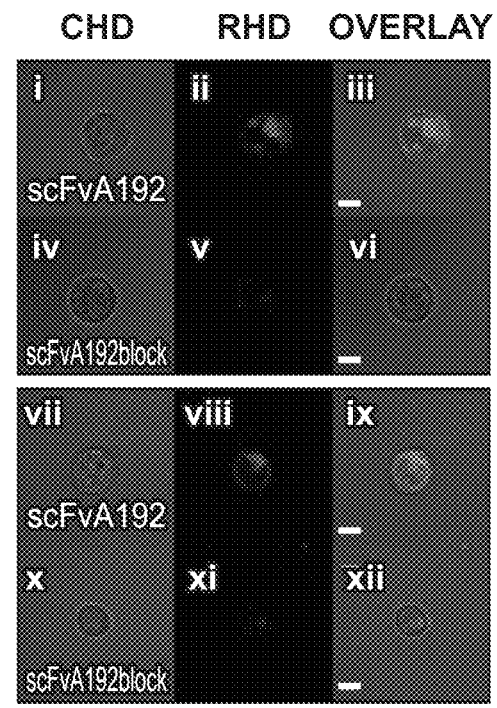
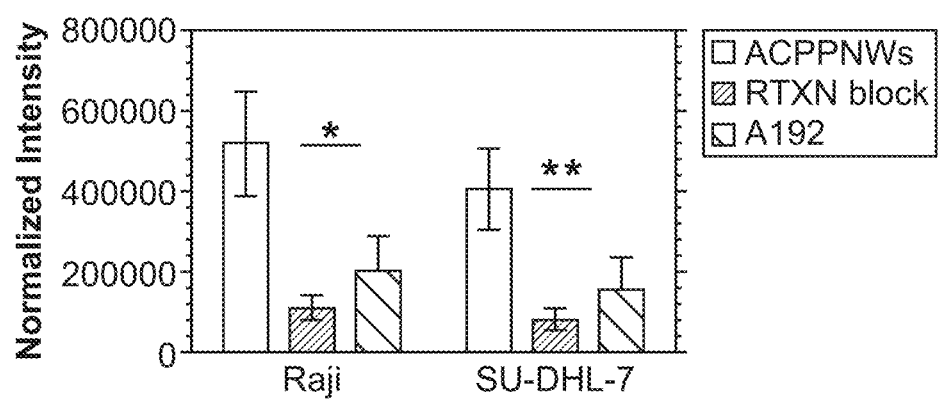
FIG. 16C

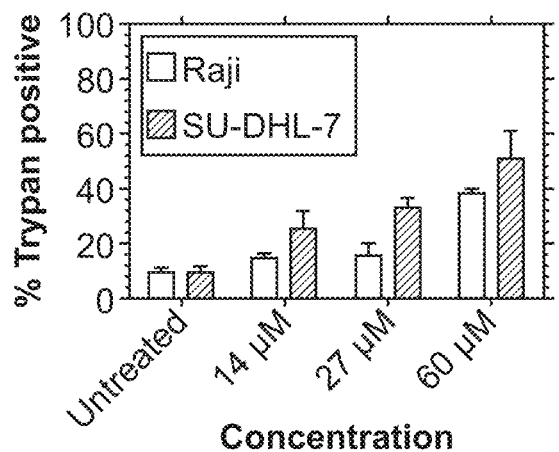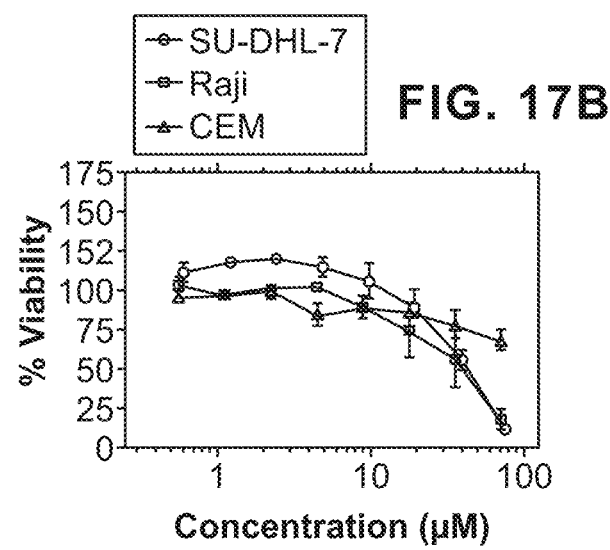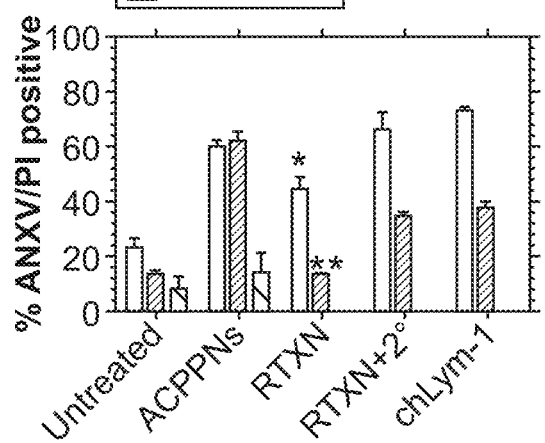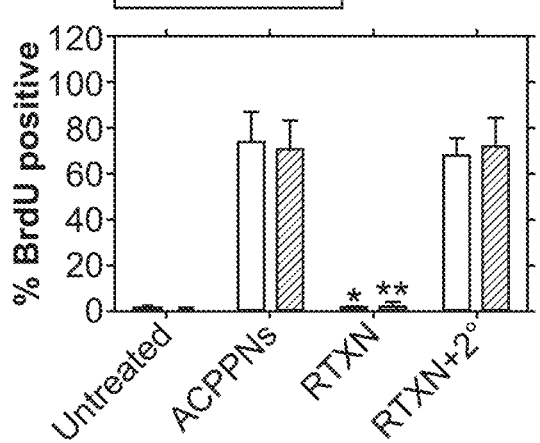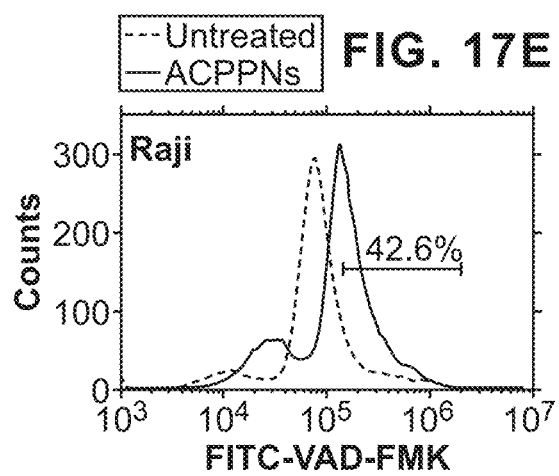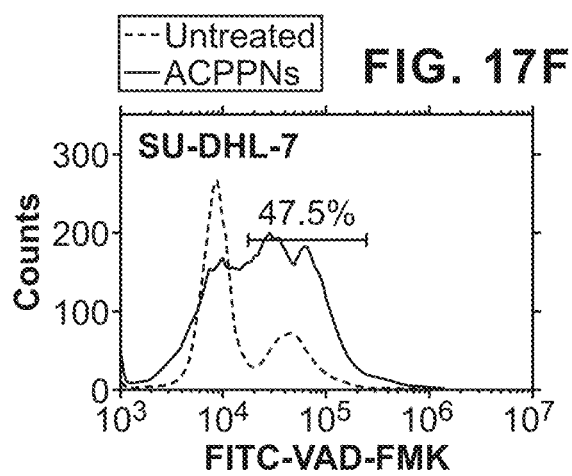

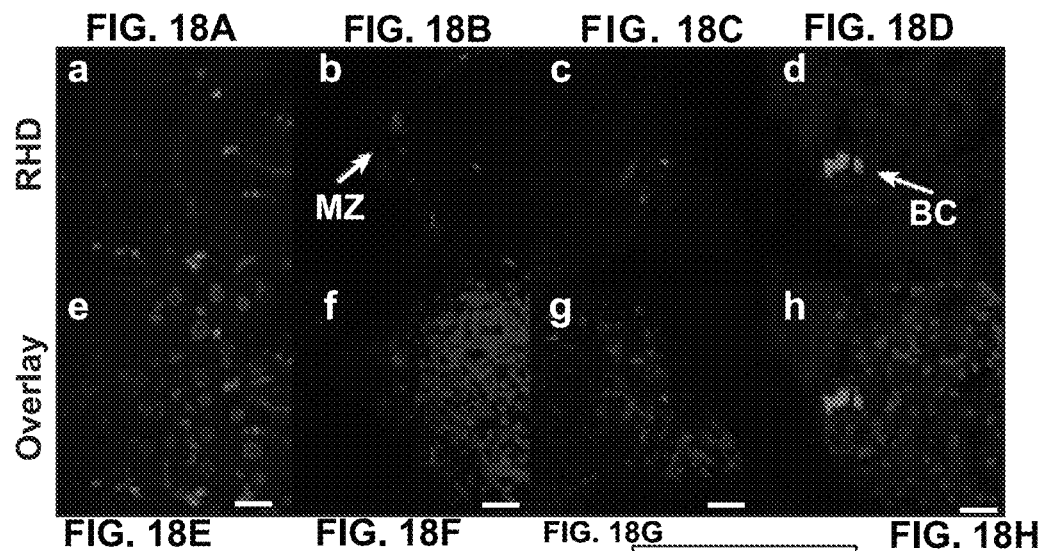
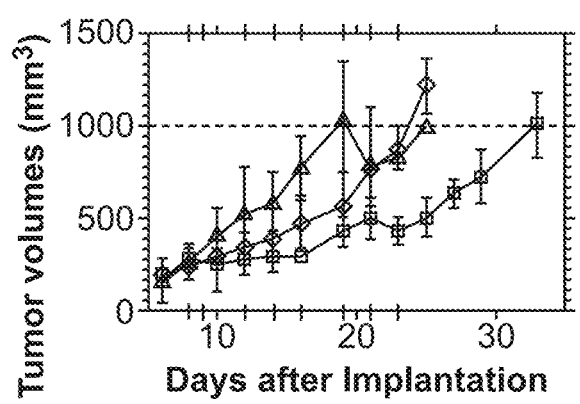
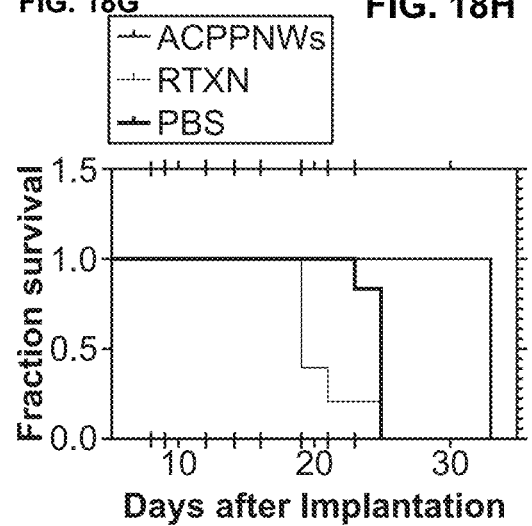
FIG. 18A  FIG. 18B  FIG. 18C  FIG. 18D
FIG. 18E  FIG. 18F  FIG. 18G  FIG. 18H
FIG. 18I  FIG. 18J

SEQUENCE LISTING

<160> NUMBER OF SEQ ID NOS: 15

<210> SEQ ID NO 1
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Gly Gly Gly Gly Ser Gly Gly
        115                 120                 125

Gly Gly Ser Gly Gly Gly Gly Ser Gln Ile Val Leu Ser Gln Ser Pro
    130                 135                 140

Ala Ile Leu Ser Ala Ser Pro Gly Glu Lys Val Thr Met Thr Cys Arg
145                 150                 155                 160

Ala Ser Ser Ser Val Ser Tyr Ile His Trp Phe Gln Gln Lys Pro Gly
                165                 170                 175

Ser Ser Pro Lys Pro Trp Ile Tyr Ala Thr Ser Asn Leu Ala Ser Gly
            180                 185                 190

Val Pro Val Arg Phe Ser Gly Ser Gly Ser Gly Thr Ser Tyr Ser Leu
        195                 200                 205

Thr Ile Ser Arg Val Glu Ala Glu Asp Ala Ala Thr Tyr Tyr Cys Gln
    210                 215                 220

Gln Trp Thr Ser Asn Pro Pro Thr Phe Gly Gly Gly Thr Lys Leu Glu
225                 230                 235                 240

Ile Lys Arg Thr Gly
                245

<210> SEQ ID NO 2
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile

```
                35                  40                  45
Gly Ala Ile Tyr Pro Gly Asn Gly Asp Thr Ser Tyr Asn Gln Lys Phe
 50                  55                  60
Lys Gly Lys Ala Thr Leu Thr Ala Asp Lys Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Ser Thr Tyr Tyr Gly Gly Asp Trp Tyr Phe Asn Val Trp Gly
                100                 105                 110
Ala Gly Thr Thr Val Thr Val Ser Ala Gly Gly Gly Ser Gly Gly
                115                 120                 125
Gly Gly Ser Gly Gly Gly Ser Gly Gly Gly Ser Gln Ile Val
            130                 135                 140
Leu Ser Gln Ser Pro Ala Ile Leu Ser Ala Ser Pro Gly Glu Lys Val
145                 150                 155                 160
Thr Met Thr Cys Arg Ala Ser Ser Ser Val Ser Tyr Ile His Trp Phe
                165                 170                 175
Gln Gln Lys Pro Gly Ser Ser Pro Lys Pro Trp Ile Tyr Ala Thr Ser
                180                 185                 190
Asn Leu Ala Ser Gly Val Pro Val Arg Phe Ser Gly Ser Gly Ser Gly
            195                 200                 205
Thr Ser Tyr Ser Leu Thr Ile Ser Arg Val Glu Ala Glu Asp Ala Ala
        210                 215                 220
Thr Tyr Tyr Cys Gln Gln Trp Thr Ser Asn Pro Pro Thr Phe Gly Gly
225                 230                 235                 240
Gly Thr Gly Leu Glu Ile Gly Arg Thr Gly
                245                 250

<210> SEQ ID NO 3
<211> LENGTH: 1208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Gln Val Gln Leu Gln Gln Pro Gly Ala Glu Leu Val Lys Pro
 1               5                  10                  15
Gly Ala Ser Val Lys Met Ser Cys Lys Ala Ser Gly Tyr Thr Phe Thr
                20                  25                  30
Ser Tyr Asn Met His Trp Val Lys Gln Thr Pro Gly Arg Gly Leu Glu
                35                  40                  45
Trp Ile Gly Ala Ile Tyr Pro Gly Asn Gly Asp Thr Ser Tyr Asn Gln
 50                  55                  60
Lys Phe Lys Gly Lys Ala Thr Leu Thr Ala Asp Lys Ser Ser Thr
 65                  70                  75                  80
Ala Tyr Met Gln Leu Ser Ser Leu Thr Ser Glu Asp Ser Ala Val Tyr
                 85                  90                  95
Tyr Cys Ala Arg Ser Thr Tyr Tyr Gly Gly Asp Trp Tyr Phe Asn Val
                100                 105                 110
Trp Gly Ala Gly Thr Thr Val Thr Val Ser Ala Gly Gly Gly Gly Ser
            115                 120                 125
Gly Gly Gly Gly Ser Gly Gly Gly Ser Gln Ile Val Leu Ser Gln
            130                 135                 140
```

```
Ser Pro Ala Ile Leu Ser Ala Ser Pro Gly Glu Lys Val Thr Met Thr
145                 150                 155                 160

Cys Arg Ala Ser Ser Val Ser Tyr Ile His Trp Phe Gln Gln Lys
            165                 170                 175

Pro Gly Ser Ser Pro Lys Pro Trp Ile Tyr Ala Thr Ser Asn Leu Ala
            180                 185                 190

Ser Gly Val Pro Val Arg Phe Ser Gly Ser Gly Ser Gly Thr Ser Tyr
            195                 200                 205

Ser Leu Thr Ile Ser Arg Val Glu Ala Glu Asp Ala Ala Thr Tyr Tyr
            210                 215                 220

Cys Gln Gln Trp Thr Ser Asn Pro Pro Thr Phe Gly Gly Gly Thr Lys
225                 230                 235                 240

Leu Glu Ile Lys Arg Thr Gly Val Pro Gly Ala Gly Val Pro Gly Ala
                245                 250                 255

Gly Val Pro Gly Ala Gly Val Pro Gly Ala Gly Val Pro Gly Ala Gly
            260                 265                 270

Val Pro Gly Ala Gly Val Pro Gly Ala Gly Val Pro Gly Ala Gly Val
            275                 280                 285

Pro Gly Ala Gly Val Pro Gly Ala Gly Val Pro Gly Ala Gly Val Pro
290                 295                 300

Gly Ala Gly Val Pro Gly Ala Gly Val Pro Gly Ala Gly Val Pro Gly
305                 310                 315                 320

Ala Gly Val Pro Gly Ala Gly Val Pro Gly Ala Gly Val Pro Gly Ala
            325                 330                 335

Gly Val Pro Gly Ala Gly Val Pro Gly Ala Gly Val Pro Gly Ala Gly
            340                 345                 350

Val Pro Gly Ala Gly Val Pro Gly Ala Gly Val Pro Gly Ala Gly Val
            355                 360                 365

Pro Gly Ala Gly Val Pro Gly Ala Gly Val Pro Gly Ala Gly Val Pro
            370                 375                 380

Gly Ala Gly Val Pro Gly Ala Gly Val Pro Gly Ala Gly Val Pro Gly
385                 390                 395                 400

Ala Gly Val Pro Gly Ala Gly Val Pro Gly Ala Gly Val Pro Gly Ala
            405                 410                 415

Gly Val Pro Gly Ala Gly Val Pro Gly Ala Gly Val Pro Gly Ala Gly
            420                 425                 430

Val Pro Gly Ala Gly Val Pro Gly Ala Gly Val Pro Gly Ala Gly Val
            435                 440                 445

Pro Gly Ala Gly Val Pro Gly Ala Gly Val Pro Gly Ala Gly Val Pro
            450                 455                 460

Gly Ala Gly Val Pro Gly Ala Gly Val Pro Gly Ala Gly Val Pro Gly
465                 470                 475                 480

Ala Gly Val Pro Gly Ala Gly Val Pro Gly Ala Gly Val Pro Gly Ala
            485                 490                 495

Gly Val Pro Gly Ala Gly Val Pro Gly Ala Gly Val Pro Gly Ala Gly
            500                 505                 510

Val Pro Gly Ala Gly Val Pro Gly Ala Gly Val Pro Gly Ala Gly Val
            515                 520                 525

Pro Gly Ala Gly Val Pro Gly Ala Gly Val Pro Gly Ala Gly Val Pro
            530                 535                 540

Gly Ala Gly Val Pro Gly Ala Gly Val Pro Gly Ala Gly Val Pro Gly
545                 550                 555                 560

Ala Gly Val Pro Gly Ala Gly Val Pro Gly Ala Gly Val Pro Gly Ala
```

```
                    565                 570                 575

Gly Val Pro Gly Ala Gly Val Pro Gly Ala Gly Val Pro Gly Ala Gly
                580                 585                 590

Val Pro Gly Ala Gly Val Pro Gly Ala Gly Val Pro Gly Ala Gly Val
                595                 600                 605

Pro Gly Ala Gly Val Pro Gly Ala Gly Val Pro Gly Ala Gly Val Pro
            610                 615                 620

Gly Ala Gly Val Pro Gly Ala Gly Val Pro Gly Ala Gly Val Pro Gly
625                 630                 635                 640

Ala Gly Val Pro Gly Ala Gly Val Pro Gly Ala Gly Val Pro Gly Ala
                645                 650                 655

Gly Val Pro Gly Ala Gly Val Pro Gly Ala Gly Val Pro Gly Ala Gly
                660                 665                 670

Val Pro Gly Ala Gly Val Pro Gly Ala Gly Val Pro Gly Ala Gly Val
                675                 680                 685

Pro Gly Ala Gly Val Pro Gly Ala Gly Val Pro Gly Ala Gly Val Pro
            690                 695                 700

Gly Ala Gly Val Pro Gly Ala Gly Val Pro Gly Ala Gly Val Pro Gly
705                 710                 715                 720

Ala Gly Val Pro Gly Ala Gly Val Pro Gly Ile Gly Val Pro Gly Ile
                725                 730                 735

Gly Val Pro Gly Ile Gly Val Pro Gly Ile Gly Val Pro Gly Ile Gly
                740                 745                 750

Val Pro Gly Ile Gly Val Pro Gly Ile Gly Val Pro Gly Ile Gly Val
                755                 760                 765

Pro Gly Ile Gly Val Pro Gly Ile Gly Val Pro Gly Ile Gly Val Pro
            770                 775                 780

Gly Ile Gly Val Pro Gly Ile Gly Val Pro Gly Ile Gly Val Pro Gly
785                 790                 795                 800

Ile Gly Val Pro Gly Ile Gly Val Pro Gly Ile Gly Val Pro Gly Ile
                805                 810                 815

Gly Val Pro Gly Ile Gly Val Pro Gly Ile Gly Val Pro Gly Ile Gly
                820                 825                 830

Val Pro Gly Ile Gly Val Pro Gly Ile Gly Val Pro Gly Ile Gly Val
                835                 840                 845

Pro Gly Ile Gly Val Pro Gly Ile Gly Val Pro Gly Ile Gly Val Pro
            850                 855                 860

Gly Ile Gly Val Pro Gly Ile Gly Val Pro Gly Ile Gly Val Pro Gly
865                 870                 875                 880

Ile Gly Val Pro Gly Ile Gly Val Pro Gly Ile Gly Val Pro Gly Ile
                885                 890                 895

Gly Val Pro Gly Ile Gly Val Pro Gly Ile Gly Val Pro Gly Ile Gly
                900                 905                 910

Val Pro Gly Ile Gly Val Pro Gly Ile Gly Val Pro Gly Ile Gly Val
                915                 920                 925

Pro Gly Ile Gly Val Pro Gly Ile Gly Val Pro Gly Ile Gly Val Pro
            930                 935                 940

Gly Ile Gly Val Pro Gly Ile Gly Val Pro Gly Ile Gly Val Pro Gly
945                 950                 955                 960

Ile Gly Val Pro Gly Ile Gly Val Pro Gly Ile Gly Val Pro Gly Ile
                965                 970                 975

Gly Val Pro Gly Ile Gly Val Pro Gly Ile Gly Val Pro Gly Ile Gly
                980                 985                 990
```

Val Pro Gly Ile Gly Val Pro Gly Ile Gly Val Pro Gly Ile Gly Val
        995                 1000                1005

Pro Gly Ile Gly Val Pro Gly Ile Gly Val Pro Gly Ile Gly Val
    1010                1015                1020

Pro Gly Ile Gly Val Pro Gly Ile Gly Val Pro Gly Ile Gly Val
    1025                1030                1035

Pro Gly Ile Gly Val Pro Gly Ile Gly Val Pro Gly Ile Gly Val
    1040                1045                1050

Pro Gly Ile Gly Val Pro Gly Ile Gly Val Pro Gly Ile Gly Val
    1055                1060                1065

Pro Gly Ile Gly Val Pro Gly Ile Gly Val Pro Gly Ile Gly Val
    1070                1075                1080

Pro Gly Ile Gly Val Pro Gly Ile Gly Val Pro Gly Ile Gly Val
    1085                1090                1095

Pro Gly Ile Gly Val Pro Gly Ile Gly Val Pro Gly Ile Gly Val
    1100                1105                1110

Pro Gly Ile Gly Val Pro Gly Ile Gly Val Pro Gly Ile Gly Val
    1115                1120                1125

Pro Gly Ile Gly Val Pro Gly Ile Gly Val Pro Gly Ile Gly Val
    1130                1135                1140

Pro Gly Ile Gly Val Pro Gly Ile Gly Val Pro Gly Ile Gly Val
    1145                1150                1155

Pro Gly Ile Gly Val Pro Gly Ile Gly Val Pro Gly Ile Gly Val
    1160                1165                1170

Pro Gly Ile Gly Val Pro Gly Ile Gly Val Pro Gly Ile Gly Val
    1175                1180                1185

Pro Gly Ile Gly Val Pro Gly Ile Gly Val Pro Gly Ile Gly Val
    1190                1195                1200

Pro Gly Ile Gly Tyr
    1205

<210> SEQ ID NO 4
<211> LENGTH: 1208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Gln Val Gln Leu Gln Gln Pro Gly Ala Glu Leu Val Lys Pro
1               5                   10                  15

Gly Ala Ser Val Lys Met Ser Cys Lys Ala Ser Gly Tyr Thr Phe Thr
            20                  25                  30

Ser Tyr Asn Met His Trp Val Lys Gln Thr Pro Gly Arg Gly Leu Glu
        35                  40                  45

Trp Ile Gly Ala Ile Tyr Pro Gly Asn Gly Asp Thr Ser Tyr Asn Gln
    50                  55                  60

Lys Phe Lys Gly Lys Ala Thr Leu Thr Ala Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Ser Thr Tyr Tyr Gly Gly Asp Trp Tyr Phe Asn Val
            100                 105                 110

Trp Gly Ala Gly Thr Thr Val Thr Val Ser Ala Gly Gly Gly Gly Ser

```
                115                 120                 125
Gly Gly Gly Gly Ser Gly Gly Gly Ser Gln Ile Val Leu Ser Gln
            130                 135                 140

Ser Pro Ala Ile Leu Ser Ala Ser Pro Gly Glu Lys Val Thr Met Thr
145                 150                 155                 160

Cys Arg Ala Ser Ser Val Ser Tyr Ile His Trp Phe Gln Gln Lys
                165                 170                 175

Pro Gly Ser Ser Pro Lys Pro Trp Ile Tyr Ala Thr Ser Asn Leu Ala
            180                 185                 190

Ser Gly Val Pro Val Arg Phe Ser Gly Ser Gly Ser Gly Thr Ser Tyr
            195                 200                 205

Ser Leu Thr Ile Ser Arg Val Glu Ala Glu Asp Ala Ala Thr Tyr Tyr
            210                 215                 220

Cys Gln Gln Trp Thr Ser Asn Pro Pro Thr Phe Gly Gly Gly Thr Lys
225                 230                 235                 240

Leu Glu Ile Lys Arg Thr Gly Val Pro Gly Ala Gly Val Pro Gly Ala
                245                 250                 255

Gly Val Pro Gly Ala Gly Val Pro Gly Ala Gly Val Pro Gly Ala Gly
            260                 265                 270

Val Pro Gly Ala Gly Val Pro Gly Ala Gly Val Pro Gly Ala Gly Val
            275                 280                 285

Pro Gly Ala Gly Val Pro Gly Ala Gly Val Pro Gly Ala Gly Val Pro
            290                 295                 300

Gly Ala Gly Val Pro Gly Ala Gly Val Pro Gly Ala Gly Val Pro Gly
305                 310                 315                 320

Ala Gly Val Pro Gly Ala Gly Val Pro Gly Ala Gly Val Pro Gly Ala
                325                 330                 335

Gly Val Pro Gly Ala Gly Val Pro Gly Ala Gly Val Pro Gly Ala Gly
            340                 345                 350

Val Pro Gly Ala Gly Val Pro Gly Ala Gly Val Pro Gly Ala Gly Val
            355                 360                 365

Pro Gly Ala Gly Val Pro Gly Ala Gly Val Pro Gly Ala Gly Val Pro
            370                 375                 380

Gly Ala Gly Val Pro Gly Ala Gly Val Pro Gly Ala Gly Val Pro Gly
385                 390                 395                 400

Ala Gly Val Pro Gly Ala Gly Val Pro Gly Ala Gly Val Pro Gly Ala
                405                 410                 415

Gly Val Pro Gly Ala Gly Val Pro Gly Ala Gly Val Pro Gly Ala Gly
            420                 425                 430

Val Pro Gly Ala Gly Val Pro Gly Ala Gly Val Pro Gly Ala Gly Val
            435                 440                 445

Pro Gly Ala Gly Val Pro Gly Ala Gly Val Pro Gly Ala Gly Val Pro
            450                 455                 460

Gly Ala Gly Val Pro Gly Ala Gly Val Pro Gly Ala Gly Val Pro Gly
465                 470                 475                 480

Ala Gly Val Pro Gly Ala Gly Val Pro Gly Ala Gly Val Pro Gly Ala
                485                 490                 495

Gly Val Pro Gly Ala Gly Val Pro Gly Ala Gly Val Pro Gly Ala Gly
            500                 505                 510

Val Pro Gly Ala Gly Val Pro Gly Ala Gly Val Pro Gly Ala Gly Val
            515                 520                 525

Pro Gly Ala Gly Val Pro Gly Ala Gly Val Pro Gly Ala Gly Val Pro
            530                 535                 540
```

Gly Ala Gly Val Pro Gly Ala Gly Val Pro Gly Ala Gly Val Pro Gly
545                 550                 555                 560

Ala Gly Val Pro Gly Ala Gly Val Pro Gly Ala Gly Val Pro Gly Ala
                565                 570                 575

Gly Val Pro Gly Ala Gly Val Pro Gly Ala Gly Val Pro Gly Ala Gly
            580                 585                 590

Val Pro Gly Ala Gly Val Pro Gly Ala Gly Val Pro Gly Ala Gly Val
        595                 600                 605

Pro Gly Ala Gly Val Pro Gly Ala Gly Val Pro Gly Ala Gly Val Pro
    610                 615                 620

Gly Ala Gly Val Pro Gly Ala Gly Val Pro Gly Ala Gly Val Pro Gly
625                 630                 635                 640

Ala Gly Val Pro Gly Ala Gly Val Pro Gly Ala Gly Val Pro Gly Ala
                645                 650                 655

Gly Val Pro Gly Ala Gly Val Pro Gly Ala Gly Val Pro Gly Ala Gly
            660                 665                 670

Val Pro Gly Ala Gly Val Pro Gly Ala Gly Val Pro Gly Ala Gly Val
        675                 680                 685

Pro Gly Ala Gly Val Pro Gly Ala Gly Val Pro Gly Ala Gly Val Pro
    690                 695                 700

Gly Ala Gly Val Pro Gly Ala Gly Val Pro Gly Ala Gly Val Pro Gly
705                 710                 715                 720

Ala Gly Val Pro Gly Ala Gly Val Pro Gly Ala Gly Val Pro Gly Ala
                725                 730                 735

Gly Val Pro Gly Ala Gly Val Pro Gly Ala Gly Val Pro Gly Ala Gly
            740                 745                 750

Val Pro Gly Ala Gly Val Pro Gly Ala Gly Val Pro Gly Ala Gly Val
        755                 760                 765

Pro Gly Ala Gly Val Pro Gly Ala Gly Val Pro Gly Ala Gly Val Pro
    770                 775                 780

Gly Ala Gly Val Pro Gly Ala Gly Val Pro Gly Ala Gly Val Pro Gly
785                 790                 795                 800

Ala Gly Val Pro Gly Ala Gly Val Pro Gly Ala Gly Val Pro Gly Ala
                805                 810                 815

Gly Val Pro Gly Ala Gly Val Pro Gly Ala Gly Val Pro Gly Ala Gly
            820                 825                 830

Val Pro Gly Ala Gly Val Pro Gly Ala Gly Val Pro Gly Ala Gly Val
        835                 840                 845

Pro Gly Ala Gly Val Pro Gly Ala Gly Val Pro Gly Ala Gly Val Pro
    850                 855                 860

Gly Ala Gly Val Pro Gly Ala Gly Val Pro Gly Ala Gly Val Pro Gly
865                 870                 875                 880

Ala Gly Val Pro Gly Ala Gly Val Pro Gly Ala Gly Val Pro Gly Ala
                885                 890                 895

Gly Val Pro Gly Ala Gly Val Pro Gly Ala Gly Val Pro Gly Ala Gly
            900                 905                 910

Val Pro Gly Ala Gly Val Pro Gly Ala Gly Val Pro Gly Ala Gly Val
        915                 920                 925

Pro Gly Ala Gly Val Pro Gly Ala Gly Val Pro Gly Ala Gly Val Pro
    930                 935                 940

Gly Ala Gly Val Pro Gly Ala Gly Val Pro Gly Ala Gly Val Pro Gly
945                 950                 955                 960

-continued

```
Ala Gly Val Pro Gly Ala Gly Val Pro Gly Ala Gly Val Pro Gly Ala
            965                 970                 975
Gly Val Pro Gly Ala Gly Val Pro Gly Ala Gly Val Pro Gly Ala Gly
        980                 985                 990
Val Pro Gly Ala Gly Val Pro  Gly Ala Gly Val Pro  Gly Ala Gly Val
    995                 1000                1005
Pro Gly  Ala Gly Val Pro  Gly Ala Gly Val Pro  Gly Ala Gly Val
    1010                1015                1020
Pro Gly  Ala Gly Val Pro  Gly Ala Gly Val Pro  Gly Ala Gly Val
    1025                1030                1035
Pro Gly  Ala Gly Val Pro  Gly Ala Gly Val Pro  Gly Ala Gly Val
    1040                1045                1050
Pro Gly  Ala Gly Val Pro  Gly Ala Gly Val Pro  Gly Ala Gly Val
    1055                1060                1065
Pro Gly  Ala Gly Val Pro  Gly Ala Gly Val Pro  Gly Ala Gly Val
    1070                1075                1080
Pro Gly  Ala Gly Val Pro  Gly Ala Gly Val Pro  Gly Ala Gly Val
    1085                1090                1095
Pro Gly  Ala Gly Val Pro  Gly Ala Gly Val Pro  Gly Ala Gly Val
    1100                1105                1110
Pro Gly  Ala Gly Val Pro  Gly Ala Gly Val Pro  Gly Ala Gly Val
    1115                1120                1125
Pro Gly  Ala Gly Val Pro  Gly Ala Gly Val Pro  Gly Ala Gly Val
    1130                1135                1140
Pro Gly  Ala Gly Val Pro  Gly Ala Gly Val Pro  Gly Ala Gly Val
    1145                1150                1155
Pro Gly  Ala Gly Val Pro  Gly Ala Gly Val Pro  Gly Ala Gly Val
    1160                1165                1170
Pro Gly  Ala Gly Val Pro  Gly Ala Gly Val Pro  Gly Ala Gly Val
    1175                1180                1185
Pro Gly  Ala Gly Val Pro  Gly Ala Gly Val Pro  Gly Ala Gly Val
    1190                1195                1200
Pro Gly  Ala Gly Tyr
    1205

<210> SEQ ID NO 5
<211> LENGTH: 728
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Gln Val Gln Leu Gln Gln Pro Gly Ala Glu Leu Val Lys Pro
1               5                   10                  15
Gly Ala Ser Val Lys Met Ser Cys Lys Ala Ser Gly Tyr Thr Phe Thr
            20                  25                  30
Ser Tyr Asn Met His Trp Val Lys Gln Thr Pro Gly Arg Gly Leu Glu
        35                  40                  45
Trp Ile Gly Ala Ile Tyr Pro Gly Asn Gly Asp Thr Ser Tyr Asn Gln
    50                  55                  60
Lys Phe Lys Gly Lys Ala Thr Leu Thr Ala Asp Lys Ser Ser Ser Thr
65                  70                  75                  80
Ala Tyr Met Gln Leu Ser Ser Leu Thr Ser Glu Asp Ser Ala Val Tyr
                85                  90                  95
```

```
Tyr Cys Ala Arg Ser Thr Tyr Gly Gly Asp Trp Tyr Phe Asn Val
            100                 105                 110
Trp Gly Ala Gly Thr Thr Val Thr Val Ser Ala Gly Gly Gly Ser
            115                 120                 125
Gly Gly Gly Gly Ser Gly Gly Gly Ser Gln Ile Val Leu Ser Gln
130                 135                 140
Ser Pro Ala Ile Leu Ser Ala Ser Pro Gly Glu Lys Val Thr Met Thr
145                 150                 155                 160
Cys Arg Ala Ser Ser Ser Val Ser Tyr Ile His Trp Phe Gln Gln Lys
                165                 170                 175
Pro Gly Ser Ser Pro Lys Pro Trp Ile Tyr Ala Thr Ser Asn Leu Ala
            180                 185                 190
Ser Gly Val Pro Val Arg Phe Ser Gly Ser Gly Ser Gly Thr Ser Tyr
            195                 200                 205
Ser Leu Thr Ile Ser Arg Val Glu Ala Glu Asp Ala Ala Thr Tyr Tyr
            210                 215                 220
Cys Gln Gln Trp Thr Ser Asn Pro Pro Thr Phe Gly Gly Gly Thr Lys
225                 230                 235                 240
Leu Glu Ile Lys Arg Thr Gly Val Pro Gly Ser Gly Val Pro Gly Ser
                245                 250                 255
Gly Val Pro Gly Ser Gly Val Pro Gly Ser Gly Val Pro Gly Ser Gly
            260                 265                 270
Val Pro Gly Ser Gly Val Pro Gly Ser Gly Val Pro Gly Ser Gly Val
            275                 280                 285
Pro Gly Ser Gly Val Pro Gly Ser Gly Val Pro Gly Ser Gly Val Pro
290                 295                 300
Gly Ser Gly Val Pro Gly Ser Gly Val Pro Gly Ser Gly Val Pro Gly
305                 310                 315                 320
Ser Gly Val Pro Gly Ser Gly Val Pro Gly Ser Gly Val Pro Gly Ser
            325                 330                 335
Gly Val Pro Gly Ser Gly Val Pro Gly Ser Gly Val Pro Gly Ser Gly
            340                 345                 350
Val Pro Gly Ser Gly Val Pro Gly Ser Gly Val Pro Gly Ser Gly Val
            355                 360                 365
Pro Gly Ser Gly Val Pro Gly Ser Gly Val Pro Gly Ser Gly Val Pro
            370                 375                 380
Gly Ser Gly Val Pro Gly Ser Gly Val Pro Gly Ser Gly Val Pro Gly
385                 390                 395                 400
Ser Gly Val Pro Gly Ser Gly Val Pro Gly Ser Gly Val Pro Gly Ser
                405                 410                 415
Gly Val Pro Gly Ser Gly Val Pro Gly Ser Gly Val Pro Gly Ser Gly
            420                 425                 430
Val Pro Gly Ser Gly Val Pro Gly Ser Gly Val Pro Gly Ser Gly Val
            435                 440                 445
Pro Gly Ser Gly Val Pro Gly Ser Gly Val Pro Gly Ser Gly Val Pro
            450                 455                 460
Gly Ser Gly Val Pro Gly Ser Gly Val Pro Gly Ser Gly Val Pro Gly
465                 470                 475                 480
Phe Gly Val Pro Gly Ser Gly Val Pro Gly Ile Gly Val Pro Gly Ile
                485                 490                 495
Gly Val Pro Gly Ile Gly Val Pro Gly Ile Gly Val Pro Gly Ile Gly
            500                 505                 510
```

```
Val Pro Gly Ile Gly Val Pro Gly Ile Gly Val Pro Gly Ile Gly Val
    515                 520                 525

Pro Gly Ile Gly Val Pro Gly Ile Gly Val Pro Gly Ile Gly Val Pro
    530                 535                 540

Gly Ile Gly Val Pro Gly Ile Gly Val Pro Gly Ile Gly Val Pro Gly
545                 550                 555                 560

Ile Gly Val Pro Gly Ile Gly Val Pro Gly Ile Gly Val Pro Gly Ile
                565                 570                 575

Gly Val Pro Gly Ile Gly Val Pro Gly Ile Gly Val Pro Gly Ile Gly
            580                 585                 590

Val Pro Gly Ile Gly Val Pro Gly Ile Gly Val Pro Gly Ile Gly Val
    595                 600                 605

Pro Gly Ile Gly Val Pro Gly Ile Gly Val Pro Gly Ile Gly Val Pro
    610                 615                 620

Gly Ile Gly Val Pro Gly Ile Gly Val Pro Gly Ile Gly Val Pro Gly
625                 630                 635                 640

Ile Gly Val Pro Gly Ile Gly Val Pro Gly Ile Gly Val Pro Gly Ile
                645                 650                 655

Gly Val Pro Gly Ile Gly Val Pro Gly Ile Gly Val Pro Gly Ile Gly
            660                 665                 670

Val Pro Gly Ile Gly Val Pro Gly Ile Gly Val Pro Gly Ile Gly Val
    675                 680                 685

Pro Gly Ile Gly Val Pro Gly Ile Gly Val Pro Gly Ile Gly Val Pro
    690                 695                 700

Gly Ile Gly Val Pro Gly Ile Gly Val Pro Gly Ile Gly Val Pro Gly
705                 710                 715                 720

Ile Gly Val Pro Gly Ile Gly Tyr
                725

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 6

Val Pro Gly Xaa Gly
1               5

<210> SEQ ID NO 7
<211> LENGTH: 2500
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(2500)
<223> OTHER INFORMATION: This sequence may encompass 1 to 500 "VPGAG"
      repeats
<220> FEATURE:
<223> OTHER INFORMATION: See specification as filed for detailed
      description of substitutions and preferred embodiments

<400> SEQUENCE: 7
```

```
Val Pro Gly Ala Gly Val Pro Gly Ala Gly Val Pro Gly Ala Gly Val
  1               5                  10                  15
Pro Gly Ala Gly Val Pro Gly Ala Gly Val Pro Gly Ala Gly Val Pro
                 20                  25                  30
Gly Ala Gly Val Pro Gly Ala Gly Val Pro Gly Ala Gly Val Pro Gly
             35                  40                  45
Ala Gly Val Pro Gly Ala Gly Val Pro Gly Ala Gly Val Pro Gly Ala
         50                  55                  60
Gly Val Pro Gly Ala Gly Val Pro Gly Ala Gly Val Pro Gly Ala Gly
 65                  70                  75                  80
Val Pro Gly Ala Gly Val Pro Gly Ala Gly Val Pro Gly Ala Gly Val
                 85                  90                  95
Pro Gly Ala Gly Val Pro Gly Ala Gly Val Pro Gly Ala Gly Val Pro
                100                 105                 110
Gly Ala Gly Val Pro Gly Ala Gly Val Pro Gly Ala Gly Val Pro Gly
            115                 120                 125
Ala Gly Val Pro Gly Ala Gly Val Pro Gly Ala Gly Val Pro Gly Ala
        130                 135                 140
Gly Val Pro Gly Ala Gly Val Pro Gly Ala Gly Val Pro Gly Ala Gly
145                 150                 155                 160
Val Pro Gly Ala Gly Val Pro Gly Ala Gly Val Pro Gly Ala Gly Val
                165                 170                 175
Pro Gly Ala Gly Val Pro Gly Ala Gly Val Pro Gly Ala Gly Val Pro
                180                 185                 190
Gly Ala Gly Val Pro Gly Ala Gly Val Pro Gly Ala Gly Val Pro Gly
            195                 200                 205
Ala Gly Val Pro Gly Ala Gly Val Pro Gly Ala Gly Val Pro Gly Ala
        210                 215                 220
Gly Val Pro Gly Ala Gly Val Pro Gly Ala Gly Val Pro Gly Ala Gly
225                 230                 235                 240
Val Pro Gly Ala Gly Val Pro Gly Ala Gly Val Pro Gly Ala Gly Val
                245                 250                 255
Pro Gly Ala Gly Val Pro Gly Ala Gly Val Pro Gly Ala Gly Val Pro
                260                 265                 270
Gly Ala Gly Val Pro Gly Ala Gly Val Pro Gly Ala Gly Val Pro Gly
            275                 280                 285
Ala Gly Val Pro Gly Ala Gly Val Pro Gly Ala Gly Val Pro Gly Ala
        290                 295                 300
Gly Val Pro Gly Ala Gly Val Pro Gly Ala Gly Val Pro Gly Ala Gly
305                 310                 315                 320
Val Pro Gly Ala Gly Val Pro Gly Ala Gly Val Pro Gly Ala Gly Val
                325                 330                 335
Pro Gly Ala Gly Val Pro Gly Ala Gly Val Pro Gly Ala Gly Val Pro
                340                 345                 350
Gly Ala Gly Val Pro Gly Ala Gly Val Pro Gly Ala Gly Val Pro Gly
            355                 360                 365
Ala Gly Val Pro Gly Ala Gly Val Pro Gly Ala Gly Val Pro Gly Ala
        370                 375                 380
Gly Val Pro Gly Ala Gly Val Pro Gly Ala Gly Val Pro Gly Ala Gly
385                 390                 395                 400
Val Pro Gly Ala Gly Val Pro Gly Ala Gly Val Pro Gly Ala Gly Val
                405                 410                 415
Pro Gly Ala Gly Val Pro Gly Ala Gly Val Pro Gly Ala Gly Val Pro
```

```
                420             425             430
Gly Ala Gly Val Pro Gly Ala Gly Val Pro Gly Ala Gly Val Pro Gly
            435             440             445
Ala Gly Val Pro Gly Ala Gly Val Pro Gly Ala Gly Val Pro Gly Ala
        450             455             460
Gly Val Pro Gly Ala Gly Val Pro Gly Ala Gly Val Pro Gly Ala Gly
465             470             475             480
Val Pro Gly Ala Gly Val Pro Gly Ala Gly Val Pro Gly Ala Gly Val
                485             490             495
Pro Gly Ala Gly Val Pro Gly Ala Gly Val Pro Gly Ala Gly Val Pro
            500             505             510
Gly Ala Gly Val Pro Gly Ala Gly Val Pro Gly Ala Gly Val Pro Gly
        515             520             525
Ala Gly Val Pro Gly Ala Gly Val Pro Gly Ala Gly Val Pro Gly Ala
    530             535             540
Gly Val Pro Gly Ala Gly Val Pro Gly Ala Gly Val Pro Gly Ala Gly
545             550             555             560
Val Pro Gly Ala Gly Val Pro Gly Ala Gly Val Pro Gly Ala Gly Val
                565             570             575
Pro Gly Ala Gly Val Pro Gly Ala Gly Val Pro Gly Ala Gly Val Pro
            580             585             590
Gly Ala Gly Val Pro Gly Ala Gly Val Pro Gly Ala Gly Val Pro Gly
        595             600             605
Ala Gly Val Pro Gly Ala Gly Val Pro Gly Ala Gly Val Pro Gly Ala
    610             615             620
Gly Val Pro Gly Ala Gly Val Pro Gly Ala Gly Val Pro Gly Ala Gly
625             630             635             640
Val Pro Gly Ala Gly Val Pro Gly Ala Gly Val Pro Gly Ala Gly Val
                645             650             655
Pro Gly Ala Gly Val Pro Gly Ala Gly Val Pro Gly Ala Gly Val Pro
            660             665             670
Gly Ala Gly Val Pro Gly Ala Gly Val Pro Gly Ala Gly Val Pro Gly
        675             680             685
Ala Gly Val Pro Gly Ala Gly Val Pro Gly Ala Gly Val Pro Gly Ala
    690             695             700
Gly Val Pro Gly Ala Gly Val Pro Gly Ala Gly Val Pro Gly Ala Gly
705             710             715             720
Val Pro Gly Ala Gly Val Pro Gly Ala Gly Val Pro Gly Ala Gly Val
                725             730             735
Pro Gly Ala Gly Val Pro Gly Ala Gly Val Pro Gly Ala Gly Val Pro
            740             745             750
Gly Ala Gly Val Pro Gly Ala Gly Val Pro Gly Ala Gly Val Pro Gly
        755             760             765
Ala Gly Val Pro Gly Ala Gly Val Pro Gly Ala Gly Val Pro Gly Ala
    770             775             780
Gly Val Pro Gly Ala Gly Val Pro Gly Ala Gly Val Pro Gly Ala Gly
785             790             795             800
Val Pro Gly Ala Gly Val Pro Gly Ala Gly Val Pro Gly Ala Gly Val
                805             810             815
Pro Gly Ala Gly Val Pro Gly Ala Gly Val Pro Gly Ala Gly Val Pro
            820             825             830
Gly Ala Gly Val Pro Gly Ala Gly Val Pro Gly Ala Gly Val Pro Gly
        835             840             845
```

```
Ala Gly Val Pro Gly Ala Gly Val Pro Gly Ala Gly Val Pro Gly Ala
        850                 855                 860
Gly Val Pro Gly Ala Gly Val Pro Gly Ala Gly Val Pro Gly Ala Gly
865                 870                 875                 880
Val Pro Gly Ala Gly Val Pro Gly Ala Gly Val Pro Gly Ala Gly Val
                885                 890                 895
Pro Gly Ala Gly Val Pro Gly Ala Gly Val Pro Gly Ala Gly Val Pro
            900                 905                 910
Gly Ala Gly Val Pro Gly Ala Gly Val Pro Gly Ala Gly Val Pro Gly
        915                 920                 925
Ala Gly Val Pro Gly Ala Gly Val Pro Gly Ala Gly Val Pro Gly Ala
    930                 935                 940
Gly Val Pro Gly Ala Gly Val Pro Gly Ala Gly Val Pro Gly Ala Gly
945                 950                 955                 960
Val Pro Gly Ala Gly Val Pro Gly Ala Gly Val Pro Gly Ala Gly Val
                965                 970                 975
Pro Gly Ala Gly Val Pro Gly Ala Gly Val Pro Gly Ala Gly Val Pro
            980                 985                 990
Gly Ala Gly Val Pro Gly Ala Gly  Val Pro Gly Ala Gly  Val Pro Gly
        995                 1000                1005
Ala Gly  Val Pro Gly Ala Gly  Val Pro Gly Ala Gly  Val Pro Gly
    1010                1015                1020
Ala Gly  Val Pro Gly Ala Gly  Val Pro Gly Ala Gly  Val Pro Gly
    1025                1030                1035
Ala Gly  Val Pro Gly Ala Gly  Val Pro Gly Ala Gly  Val Pro Gly
    1040                1045                1050
Ala Gly  Val Pro Gly Ala Gly  Val Pro Gly Ala Gly  Val Pro Gly
    1055                1060                1065
Ala Gly  Val Pro Gly Ala Gly  Val Pro Gly Ala Gly  Val Pro Gly
    1070                1075                1080
Ala Gly  Val Pro Gly Ala Gly  Val Pro Gly Ala Gly  Val Pro Gly
    1085                1090                1095
Ala Gly  Val Pro Gly Ala Gly  Val Pro Gly Ala Gly  Val Pro Gly
    1100                1105                1110
Ala Gly  Val Pro Gly Ala Gly  Val Pro Gly Ala Gly  Val Pro Gly
    1115                1120                1125
Ala Gly  Val Pro Gly Ala Gly  Val Pro Gly Ala Gly  Val Pro Gly
    1130                1135                1140
Ala Gly  Val Pro Gly Ala Gly  Val Pro Gly Ala Gly  Val Pro Gly
    1145                1150                1155
Ala Gly  Val Pro Gly Ala Gly  Val Pro Gly Ala Gly  Val Pro Gly
    1160                1165                1170
Ala Gly  Val Pro Gly Ala Gly  Val Pro Gly Ala Gly  Val Pro Gly
    1175                1180                1185
Ala Gly  Val Pro Gly Ala Gly  Val Pro Gly Ala Gly  Val Pro Gly
    1190                1195                1200
Ala Gly  Val Pro Gly Ala Gly  Val Pro Gly Ala Gly  Val Pro Gly
    1205                1210                1215
Ala Gly  Val Pro Gly Ala Gly  Val Pro Gly Ala Gly  Val Pro Gly
    1220                1225                1230
Ala Gly  Val Pro Gly Ala Gly  Val Pro Gly Ala Gly  Val Pro Gly
    1235                1240                1245
```

Ala Gly Val Pro Gly Ala Gly Val Pro Gly Ala Gly Val Pro Gly
1250                1255                1260

Ala Gly Val Pro Gly Ala Gly Val Pro Gly Ala Gly Val Pro Gly
1265                1270                1275

Ala Gly Val Pro Gly Ala Gly Val Pro Gly Ala Gly Val Pro Gly
1280                1285                1290

Ala Gly Val Pro Gly Ala Gly Val Pro Gly Ala Gly Val Pro Gly
1295                1300                1305

Ala Gly Val Pro Gly Ala Gly Val Pro Gly Ala Gly Val Pro Gly
1310                1315                1320

Ala Gly Val Pro Gly Ala Gly Val Pro Gly Ala Gly Val Pro Gly
1325                1330                1335

Ala Gly Val Pro Gly Ala Gly Val Pro Gly Ala Gly Val Pro Gly
1340                1345                1350

Ala Gly Val Pro Gly Ala Gly Val Pro Gly Ala Gly Val Pro Gly
1355                1360                1365

Ala Gly Val Pro Gly Ala Gly Val Pro Gly Ala Gly Val Pro Gly
1370                1375                1380

Ala Gly Val Pro Gly Ala Gly Val Pro Gly Ala Gly Val Pro Gly
1385                1390                1395

Ala Gly Val Pro Gly Ala Gly Val Pro Gly Ala Gly Val Pro Gly
1400                1405                1410

Ala Gly Val Pro Gly Ala Gly Val Pro Gly Ala Gly Val Pro Gly
1415                1420                1425

Ala Gly Val Pro Gly Ala Gly Val Pro Gly Ala Gly Val Pro Gly
1430                1435                1440

Ala Gly Val Pro Gly Ala Gly Val Pro Gly Ala Gly Val Pro Gly
1445                1450                1455

Ala Gly Val Pro Gly Ala Gly Val Pro Gly Ala Gly Val Pro Gly
1460                1465                1470

Ala Gly Val Pro Gly Ala Gly Val Pro Gly Ala Gly Val Pro Gly
1475                1480                1485

Ala Gly Val Pro Gly Ala Gly Val Pro Gly Ala Gly Val Pro Gly
1490                1495                1500

Ala Gly Val Pro Gly Ala Gly Val Pro Gly Ala Gly Val Pro Gly
1505                1510                1515

Ala Gly Val Pro Gly Ala Gly Val Pro Gly Ala Gly Val Pro Gly
1520                1525                1530

Ala Gly Val Pro Gly Ala Gly Val Pro Gly Ala Gly Val Pro Gly
1535                1540                1545

Ala Gly Val Pro Gly Ala Gly Val Pro Gly Ala Gly Val Pro Gly
1550                1555                1560

Ala Gly Val Pro Gly Ala Gly Val Pro Gly Ala Gly Val Pro Gly
1565                1570                1575

Ala Gly Val Pro Gly Ala Gly Val Pro Gly Ala Gly Val Pro Gly
1580                1585                1590

Ala Gly Val Pro Gly Ala Gly Val Pro Gly Ala Gly Val Pro Gly
1595                1600                1605

Ala Gly Val Pro Gly Ala Gly Val Pro Gly Ala Gly Val Pro Gly
1610                1615                1620

Ala Gly Val Pro Gly Ala Gly Val Pro Gly Ala Gly Val Pro Gly
1625                1630                1635

Ala Gly Val Pro Gly Ala Gly Val Pro Gly Ala Gly Val Pro Gly

-continued

```
            1640               1645               1650
Ala Gly Val Pro Gly Ala Gly Val Pro Gly Ala Gly Val Pro Gly
    1655               1660               1665
Ala Gly Val Pro Gly Ala Gly Val Pro Gly Ala Gly Val Pro Gly
    1670               1675               1680
Ala Gly Val Pro Gly Ala Gly Val Pro Gly Ala Gly Val Pro Gly
    1685               1690               1695
Ala Gly Val Pro Gly Ala Gly Val Pro Gly Ala Gly Val Pro Gly
    1700               1705               1710
Ala Gly Val Pro Gly Ala Gly Val Pro Gly Ala Gly Val Pro Gly
    1715               1720               1725
Ala Gly Val Pro Gly Ala Gly Val Pro Gly Ala Gly Val Pro Gly
    1730               1735               1740
Ala Gly Val Pro Gly Ala Gly Val Pro Gly Ala Gly Val Pro Gly
    1745               1750               1755
Ala Gly Val Pro Gly Ala Gly Val Pro Gly Ala Gly Val Pro Gly
    1760               1765               1770
Ala Gly Val Pro Gly Ala Gly Val Pro Gly Ala Gly Val Pro Gly
    1775               1780               1785
Ala Gly Val Pro Gly Ala Gly Val Pro Gly Ala Gly Val Pro Gly
    1790               1795               1800
Ala Gly Val Pro Gly Ala Gly Val Pro Gly Ala Gly Val Pro Gly
    1805               1810               1815
Ala Gly Val Pro Gly Ala Gly Val Pro Gly Ala Gly Val Pro Gly
    1820               1825               1830
Ala Gly Val Pro Gly Ala Gly Val Pro Gly Ala Gly Val Pro Gly
    1835               1840               1845
Ala Gly Val Pro Gly Ala Gly Val Pro Gly Ala Gly Val Pro Gly
    1850               1855               1860
Ala Gly Val Pro Gly Ala Gly Val Pro Gly Ala Gly Val Pro Gly
    1865               1870               1875
Ala Gly Val Pro Gly Ala Gly Val Pro Gly Ala Gly Val Pro Gly
    1880               1885               1890
Ala Gly Val Pro Gly Ala Gly Val Pro Gly Ala Gly Val Pro Gly
    1895               1900               1905
Ala Gly Val Pro Gly Ala Gly Val Pro Gly Ala Gly Val Pro Gly
    1910               1915               1920
Ala Gly Val Pro Gly Ala Gly Val Pro Gly Ala Gly Val Pro Gly
    1925               1930               1935
Ala Gly Val Pro Gly Ala Gly Val Pro Gly Ala Gly Val Pro Gly
    1940               1945               1950
Ala Gly Val Pro Gly Ala Gly Val Pro Gly Ala Gly Val Pro Gly
    1955               1960               1965
Ala Gly Val Pro Gly Ala Gly Val Pro Gly Ala Gly Val Pro Gly
    1970               1975               1980
Ala Gly Val Pro Gly Ala Gly Val Pro Gly Ala Gly Val Pro Gly
    1985               1990               1995
Ala Gly Val Pro Gly Ala Gly Val Pro Gly Ala Gly Val Pro Gly
    2000               2005               2010
Ala Gly Val Pro Gly Ala Gly Val Pro Gly Ala Gly Val Pro Gly
    2015               2020               2025
Ala Gly Val Pro Gly Ala Gly Val Pro Gly Ala Gly Val Pro Gly
    2030               2035               2040
```

```
Ala Gly Val Pro Gly Ala Gly Val Pro Gly Ala Gly Val Pro Gly
    2045                2050                2055

Ala Gly Val Pro Gly Ala Gly Val Pro Gly Ala Gly Val Pro Gly
    2060                2065                2070

Ala Gly Val Pro Gly Ala Gly Val Pro Gly Ala Gly Val Pro Gly
    2075                2080                2085

Ala Gly Val Pro Gly Ala Gly Val Pro Gly Ala Gly Val Pro Gly
    2090                2095                2100

Ala Gly Val Pro Gly Ala Gly Val Pro Gly Ala Gly Val Pro Gly
    2105                2110                2115

Ala Gly Val Pro Gly Ala Gly Val Pro Gly Ala Gly Val Pro Gly
    2120                2125                2130

Ala Gly Val Pro Gly Ala Gly Val Pro Gly Ala Gly Val Pro Gly
    2135                2140                2145

Ala Gly Val Pro Gly Ala Gly Val Pro Gly Ala Gly Val Pro Gly
    2150                2155                2160

Ala Gly Val Pro Gly Ala Gly Val Pro Gly Ala Gly Val Pro Gly
    2165                2170                2175

Ala Gly Val Pro Gly Ala Gly Val Pro Gly Ala Gly Val Pro Gly
    2180                2185                2190

Ala Gly Val Pro Gly Ala Gly Val Pro Gly Ala Gly Val Pro Gly
    2195                2200                2205

Ala Gly Val Pro Gly Ala Gly Val Pro Gly Ala Gly Val Pro Gly
    2210                2215                2220

Ala Gly Val Pro Gly Ala Gly Val Pro Gly Ala Gly Val Pro Gly
    2225                2230                2235

Ala Gly Val Pro Gly Ala Gly Val Pro Gly Ala Gly Val Pro Gly
    2240                2245                2250

Ala Gly Val Pro Gly Ala Gly Val Pro Gly Ala Gly Val Pro Gly
    2255                2260                2265

Ala Gly Val Pro Gly Ala Gly Val Pro Gly Ala Gly Val Pro Gly
    2270                2275                2280

Ala Gly Val Pro Gly Ala Gly Val Pro Gly Ala Gly Val Pro Gly
    2285                2290                2295

Ala Gly Val Pro Gly Ala Gly Val Pro Gly Ala Gly Val Pro Gly
    2300                2305                2310

Ala Gly Val Pro Gly Ala Gly Val Pro Gly Ala Gly Val Pro Gly
    2315                2320                2325

Ala Gly Val Pro Gly Ala Gly Val Pro Gly Ala Gly Val Pro Gly
    2330                2335                2340

Ala Gly Val Pro Gly Ala Gly Val Pro Gly Ala Gly Val Pro Gly
    2345                2350                2355

Ala Gly Val Pro Gly Ala Gly Val Pro Gly Ala Gly Val Pro Gly
    2360                2365                2370

Ala Gly Val Pro Gly Ala Gly Val Pro Gly Ala Gly Val Pro Gly
    2375                2380                2385

Ala Gly Val Pro Gly Ala Gly Val Pro Gly Ala Gly Val Pro Gly
    2390                2395                2400

Ala Gly Val Pro Gly Ala Gly Val Pro Gly Ala Gly Val Pro Gly
    2405                2410                2415

Ala Gly Val Pro Gly Ala Gly Val Pro Gly Ala Gly Val Pro Gly
    2420                2425                2430
```

```
Ala Gly Val Pro Gly Ala Gly Val Pro Gly Ala Gly Val Pro Gly
        2435                2440                2445

Ala Gly Val Pro Gly Ala Gly Val Pro Gly Ala Gly Val Pro Gly
        2450                2455                2460

Ala Gly Val Pro Gly Ala Gly Val Pro Gly Ala Gly Val Pro Gly
        2465                2470                2475

Ala Gly Val Pro Gly Ala Gly Val Pro Gly Ala Gly Val Pro Gly
        2480                2485                2490

Ala Gly Val Pro Gly Ala Gly
        2495            2500

<210> SEQ ID NO 8
<211> LENGTH: 5000
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(2500)
<223> OTHER INFORMATION: This region may encompass 1 to 500 "VPGAG"
      repeats
<220> FEATURE:
<221> NAME/KEY: misc_feature
<222> LOCATION: (2501)..(5000)
<223> OTHER INFORMATION: This region may encompass 1 to 500 "VPGIG"
      repeats
<220> FEATURE:
<223> OTHER INFORMATION: See specification as filed for detailed
      description of substitutions and preferred embodiments

<400> SEQUENCE: 8

Val Pro Gly Ala Gly Val Pro Gly Ala Gly Val Pro Gly Ala Gly Val
1               5                   10                  15

Pro Gly Ala Gly Val Pro Gly Ala Gly Val Pro Gly Ala Gly Val Pro
            20                  25                  30

Gly Ala Gly Val Pro Gly Ala Gly Val Pro Gly Ala Gly Val Pro Gly
        35                  40                  45

Ala Gly Val Pro Gly Ala Gly Val Pro Gly Ala Gly Val Pro Gly Ala
    50                  55                  60

Gly Val Pro Gly Ala Gly Val Pro Gly Ala Gly Val Pro Gly Ala Gly
65                  70                  75                  80

Val Pro Gly Ala Gly Val Pro Gly Ala Gly Val Pro Gly Ala Gly Val
                85                  90                  95

Pro Gly Ala Gly Val Pro Gly Ala Gly Val Pro Gly Ala Gly Val Pro
            100                 105                 110

Gly Ala Gly Val Pro Gly Ala Gly Val Pro Gly Ala Gly Val Pro Gly
        115                 120                 125

Ala Gly Val Pro Gly Ala Gly Val Pro Gly Ala Gly Val Pro Gly Ala
    130                 135                 140

Gly Val Pro Gly Ala Gly Val Pro Gly Ala Gly Val Pro Gly Ala Gly
145                 150                 155                 160

Val Pro Gly Ala Gly Val Pro Gly Ala Gly Val Pro Gly Ala Gly Val
                165                 170                 175

Pro Gly Ala Gly Val Pro Gly Ala Gly Val Pro Gly Ala Gly Val Pro
            180                 185                 190

Gly Ala Gly Val Pro Gly Ala Gly Val Pro Gly Ala Gly Val Pro Gly
        195                 200                 205

Ala Gly Val Pro Gly Ala Gly Val Pro Gly Ala Gly Val Pro Gly Ala
```

```
            210                 215                 220
Gly Val Pro Gly Ala Gly Val Pro Gly Ala Gly Val Pro Gly Ala Gly
225                 230                 235                 240

Val Pro Gly Ala Gly Val Pro Gly Ala Gly Val Pro Gly Ala Gly Val
                245                 250                 255

Pro Gly Ala Gly Val Pro Gly Ala Gly Val Pro Gly Ala Gly Val Pro
            260                 265                 270

Gly Ala Gly Val Pro Gly Ala Gly Val Pro Gly Ala Gly Val Pro Gly
        275                 280                 285

Ala Gly Val Pro Gly Ala Gly Val Pro Gly Ala Gly Val Pro Gly Ala
    290                 295                 300

Gly Val Pro Gly Ala Gly Val Pro Gly Ala Gly Val Pro Gly Ala Gly
305                 310                 315                 320

Val Pro Gly Ala Gly Val Pro Gly Ala Gly Val Pro Gly Ala Gly Val
                325                 330                 335

Pro Gly Ala Gly Val Pro Gly Ala Gly Val Pro Gly Ala Gly Val Pro
            340                 345                 350

Gly Ala Gly Val Pro Gly Ala Gly Val Pro Gly Ala Gly Val Pro Gly
        355                 360                 365

Ala Gly Val Pro Gly Ala Gly Val Pro Gly Ala Gly Val Pro Gly Ala
    370                 375                 380

Gly Val Pro Gly Ala Gly Val Pro Gly Ala Gly Val Pro Gly Ala Gly
385                 390                 395                 400

Val Pro Gly Ala Gly Val Pro Gly Ala Gly Val Pro Gly Ala Gly Val
                405                 410                 415

Pro Gly Ala Gly Val Pro Gly Ala Gly Val Pro Gly Ala Gly Val Pro
            420                 425                 430

Gly Ala Gly Val Pro Gly Ala Gly Val Pro Gly Ala Gly Val Pro Gly
        435                 440                 445

Ala Gly Val Pro Gly Ala Gly Val Pro Gly Ala Gly Val Pro Gly Ala
    450                 455                 460

Gly Val Pro Gly Ala Gly Val Pro Gly Ala Gly Val Pro Gly Ala Gly
465                 470                 475                 480

Val Pro Gly Ala Gly Val Pro Gly Ala Gly Val Pro Gly Ala Gly Val
                485                 490                 495

Pro Gly Ala Gly Val Pro Gly Ala Gly Val Pro Gly Ala Gly Val Pro
            500                 505                 510

Gly Ala Gly Val Pro Gly Ala Gly Val Pro Gly Ala Gly Val Pro Gly
        515                 520                 525

Ala Gly Val Pro Gly Ala Gly Val Pro Gly Ala Gly Val Pro Gly Ala
    530                 535                 540

Gly Val Pro Gly Ala Gly Val Pro Gly Ala Gly Val Pro Gly Ala Gly
545                 550                 555                 560

Val Pro Gly Ala Gly Val Pro Gly Ala Gly Val Pro Gly Ala Gly Val
                565                 570                 575

Pro Gly Ala Gly Val Pro Gly Ala Gly Val Pro Gly Ala Gly Val Pro
            580                 585                 590

Gly Ala Gly Val Pro Gly Ala Gly Val Pro Gly Ala Gly Val Pro Gly
        595                 600                 605

Ala Gly Val Pro Gly Ala Gly Val Pro Gly Ala Gly Val Pro Gly Ala
    610                 615                 620

Gly Val Pro Gly Ala Gly Val Pro Gly Ala Gly Val Pro Gly Ala Gly
625                 630                 635                 640
```

-continued

Val Pro Gly Ala Gly Val Pro Gly Ala Gly Val
        645             650             655

Pro Gly Ala Gly Val Pro Gly Ala Gly Val Pro
        660             665             670

Gly Ala Gly Val Pro Gly Ala Gly Val Pro Gly
        675             680             685

Ala Gly Val Pro Gly Ala Gly Val Pro Gly Ala
        690             695             700

Gly Val Pro Gly Ala Gly Val Pro Gly Ala Gly
705             710             715             720

Val Pro Gly Ala Gly Val Pro Gly Ala Gly Val
        725             730             735

Pro Gly Ala Gly Val Pro Gly Ala Gly Val Pro
        740             745             750

Gly Ala Gly Val Pro Gly Ala Gly Val Pro Gly
        755             760             765

Ala Gly Val Pro Gly Ala Gly Val Pro Gly Ala
        770             775             780

Gly Val Pro Gly Ala Gly Val Pro Gly Ala Gly
785             790             795             800

Val Pro Gly Ala Gly Val Pro Gly Ala Gly Val
        805             810             815

Pro Gly Ala Gly Val Pro Gly Ala Gly Val Pro
        820             825             830

Gly Ala Gly Val Pro Gly Ala Gly Val Pro Gly
        835             840             845

Ala Gly Val Pro Gly Ala Gly Val Pro Gly Ala
        850             855             860

Gly Val Pro Gly Ala Gly Val Pro Gly Ala Gly
865             870             875             880

Val Pro Gly Ala Gly Val Pro Gly Ala Gly Val
        885             890             895

Pro Gly Ala Gly Val Pro Gly Ala Gly Val Pro
        900             905             910

Gly Ala Gly Val Pro Gly Ala Gly Val Pro Gly
        915             920             925

Ala Gly Val Pro Gly Ala Gly Val Pro Gly Ala
        930             935             940

Gly Val Pro Gly Ala Gly Val Pro Gly Ala Gly
945             950             955             960

Val Pro Gly Ala Gly Val Pro Gly Ala Gly Val
        965             970             975

Pro Gly Ala Gly Val Pro Gly Ala Gly Val Pro
        980             985             990

Gly Ala Gly Val Pro Gly Ala Gly  Val Pro Gly Ala Gly  Val Pro Gly
        995                 1000                1005

Ala Gly  Val Pro Gly Ala Gly  Val Pro Gly Ala Gly  Val Pro Gly
        1010                1015                1020

Ala Gly  Val Pro Gly Ala Gly  Val Pro Gly Ala Gly  Val Pro Gly
        1025                1030                1035

Ala Gly  Val Pro Gly Ala Gly  Val Pro Gly Ala Gly  Val Pro Gly
        1040                1045                1050

```
Ala Gly  Val Pro Gly Ala Gly  Val Pro Gly Ala Gly  Val Pro Gly
    1055                 1060                 1065

Ala Gly  Val Pro Gly Ala Gly  Val Pro Gly Ala Gly  Val Pro Gly
    1070                 1075                 1080

Ala Gly  Val Pro Gly Ala Gly  Val Pro Gly Ala Gly  Val Pro Gly
    1085                 1090                 1095

Ala Gly  Val Pro Gly Ala Gly  Val Pro Gly Ala Gly  Val Pro Gly
    1100                 1105                 1110

Ala Gly  Val Pro Gly Ala Gly  Val Pro Gly Ala Gly  Val Pro Gly
    1115                 1120                 1125

Ala Gly  Val Pro Gly Ala Gly  Val Pro Gly Ala Gly  Val Pro Gly
    1130                 1135                 1140

Ala Gly  Val Pro Gly Ala Gly  Val Pro Gly Ala Gly  Val Pro Gly
    1145                 1150                 1155

Ala Gly  Val Pro Gly Ala Gly  Val Pro Gly Ala Gly  Val Pro Gly
    1160                 1165                 1170

Ala Gly  Val Pro Gly Ala Gly  Val Pro Gly Ala Gly  Val Pro Gly
    1175                 1180                 1185

Ala Gly  Val Pro Gly Ala Gly  Val Pro Gly Ala Gly  Val Pro Gly
    1190                 1195                 1200

Ala Gly  Val Pro Gly Ala Gly  Val Pro Gly Ala Gly  Val Pro Gly
    1205                 1210                 1215

Ala Gly  Val Pro Gly Ala Gly  Val Pro Gly Ala Gly  Val Pro Gly
    1220                 1225                 1230

Ala Gly  Val Pro Gly Ala Gly  Val Pro Gly Ala Gly  Val Pro Gly
    1235                 1240                 1245

Ala Gly  Val Pro Gly Ala Gly  Val Pro Gly Ala Gly  Val Pro Gly
    1250                 1255                 1260

Ala Gly  Val Pro Gly Ala Gly  Val Pro Gly Ala Gly  Val Pro Gly
    1265                 1270                 1275

Ala Gly  Val Pro Gly Ala Gly  Val Pro Gly Ala Gly  Val Pro Gly
    1280                 1285                 1290

Ala Gly  Val Pro Gly Ala Gly  Val Pro Gly Ala Gly  Val Pro Gly
    1295                 1300                 1305

Ala Gly  Val Pro Gly Ala Gly  Val Pro Gly Ala Gly  Val Pro Gly
    1310                 1315                 1320

Ala Gly  Val Pro Gly Ala Gly  Val Pro Gly Ala Gly  Val Pro Gly
    1325                 1330                 1335

Ala Gly  Val Pro Gly Ala Gly  Val Pro Gly Ala Gly  Val Pro Gly
    1340                 1345                 1350

Ala Gly  Val Pro Gly Ala Gly  Val Pro Gly Ala Gly  Val Pro Gly
    1355                 1360                 1365

Ala Gly  Val Pro Gly Ala Gly  Val Pro Gly Ala Gly  Val Pro Gly
    1370                 1375                 1380

Ala Gly  Val Pro Gly Ala Gly  Val Pro Gly Ala Gly  Val Pro Gly
    1385                 1390                 1395

Ala Gly  Val Pro Gly Ala Gly  Val Pro Gly Ala Gly  Val Pro Gly
    1400                 1405                 1410

Ala Gly  Val Pro Gly Ala Gly  Val Pro Gly Ala Gly  Val Pro Gly
    1415                 1420                 1425

Ala Gly  Val Pro Gly Ala Gly  Val Pro Gly Ala Gly  Val Pro Gly
    1430                 1435                 1440

Ala Gly  Val Pro Gly Ala Gly  Val Pro Gly Ala Gly  Val Pro Gly
```

-continued

```
            1445                1450                1455

Ala Gly Val Pro Gly Ala Gly Val Pro Gly Ala Gly Val Pro Gly
        1460                1465                1470

Ala Gly Val Pro Gly Ala Gly Val Pro Gly Ala Gly Val Pro Gly
    1475                1480                1485

Ala Gly Val Pro Gly Ala Gly Val Pro Gly Ala Gly Val Pro Gly
    1490                1495                1500

Ala Gly Val Pro Gly Ala Gly Val Pro Gly Ala Gly Val Pro Gly
    1505                1510                1515

Ala Gly Val Pro Gly Ala Gly Val Pro Gly Ala Gly Val Pro Gly
    1520                1525                1530

Ala Gly Val Pro Gly Ala Gly Val Pro Gly Ala Gly Val Pro Gly
    1535                1540                1545

Ala Gly Val Pro Gly Ala Gly Val Pro Gly Ala Gly Val Pro Gly
    1550                1555                1560

Ala Gly Val Pro Gly Ala Gly Val Pro Gly Ala Gly Val Pro Gly
    1565                1570                1575

Ala Gly Val Pro Gly Ala Gly Val Pro Gly Ala Gly Val Pro Gly
    1580                1585                1590

Ala Gly Val Pro Gly Ala Gly Val Pro Gly Ala Gly Val Pro Gly
    1595                1600                1605

Ala Gly Val Pro Gly Ala Gly Val Pro Gly Ala Gly Val Pro Gly
    1610                1615                1620

Ala Gly Val Pro Gly Ala Gly Val Pro Gly Ala Gly Val Pro Gly
    1625                1630                1635

Ala Gly Val Pro Gly Ala Gly Val Pro Gly Ala Gly Val Pro Gly
    1640                1645                1650

Ala Gly Val Pro Gly Ala Gly Val Pro Gly Ala Gly Val Pro Gly
    1655                1660                1665

Ala Gly Val Pro Gly Ala Gly Val Pro Gly Ala Gly Val Pro Gly
    1670                1675                1680

Ala Gly Val Pro Gly Ala Gly Val Pro Gly Ala Gly Val Pro Gly
    1685                1690                1695

Ala Gly Val Pro Gly Ala Gly Val Pro Gly Ala Gly Val Pro Gly
    1700                1705                1710

Ala Gly Val Pro Gly Ala Gly Val Pro Gly Ala Gly Val Pro Gly
    1715                1720                1725

Ala Gly Val Pro Gly Ala Gly Val Pro Gly Ala Gly Val Pro Gly
    1730                1735                1740

Ala Gly Val Pro Gly Ala Gly Val Pro Gly Ala Gly Val Pro Gly
    1745                1750                1755

Ala Gly Val Pro Gly Ala Gly Val Pro Gly Ala Gly Val Pro Gly
    1760                1765                1770

Ala Gly Val Pro Gly Ala Gly Val Pro Gly Ala Gly Val Pro Gly
    1775                1780                1785

Ala Gly Val Pro Gly Ala Gly Val Pro Gly Ala Gly Val Pro Gly
    1790                1795                1800

Ala Gly Val Pro Gly Ala Gly Val Pro Gly Ala Gly Val Pro Gly
    1805                1810                1815

Ala Gly Val Pro Gly Ala Gly Val Pro Gly Ala Gly Val Pro Gly
    1820                1825                1830

Ala Gly Val Pro Gly Ala Gly Val Pro Gly Ala Gly Val Pro Gly
    1835                1840                1845
```

```
Ala Gly Val Pro Gly Ala Gly Val Pro Gly Ala Gly Val Pro Gly
    1850                1855                1860

Ala Gly Val Pro Gly Ala Gly Val Pro Gly Ala Gly Val Pro Gly
    1865                1870                1875

Ala Gly Val Pro Gly Ala Gly Val Pro Gly Ala Gly Val Pro Gly
    1880                1885                1890

Ala Gly Val Pro Gly Ala Gly Val Pro Gly Ala Gly Val Pro Gly
    1895                1900                1905

Ala Gly Val Pro Gly Ala Gly Val Pro Gly Ala Gly Val Pro Gly
    1910                1915                1920

Ala Gly Val Pro Gly Ala Gly Val Pro Gly Ala Gly Val Pro Gly
    1925                1930                1935

Ala Gly Val Pro Gly Ala Gly Val Pro Gly Ala Gly Val Pro Gly
    1940                1945                1950

Ala Gly Val Pro Gly Ala Gly Val Pro Gly Ala Gly Val Pro Gly
    1955                1960                1965

Ala Gly Val Pro Gly Ala Gly Val Pro Gly Ala Gly Val Pro Gly
    1970                1975                1980

Ala Gly Val Pro Gly Ala Gly Val Pro Gly Ala Gly Val Pro Gly
    1985                1990                1995

Ala Gly Val Pro Gly Ala Gly Val Pro Gly Ala Gly Val Pro Gly
    2000                2005                2010

Ala Gly Val Pro Gly Ala Gly Val Pro Gly Ala Gly Val Pro Gly
    2015                2020                2025

Ala Gly Val Pro Gly Ala Gly Val Pro Gly Ala Gly Val Pro Gly
    2030                2035                2040

Ala Gly Val Pro Gly Ala Gly Val Pro Gly Ala Gly Val Pro Gly
    2045                2050                2055

Ala Gly Val Pro Gly Ala Gly Val Pro Gly Ala Gly Val Pro Gly
    2060                2065                2070

Ala Gly Val Pro Gly Ala Gly Val Pro Gly Ala Gly Val Pro Gly
    2075                2080                2085

Ala Gly Val Pro Gly Ala Gly Val Pro Gly Ala Gly Val Pro Gly
    2090                2095                2100

Ala Gly Val Pro Gly Ala Gly Val Pro Gly Ala Gly Val Pro Gly
    2105                2110                2115

Ala Gly Val Pro Gly Ala Gly Val Pro Gly Ala Gly Val Pro Gly
    2120                2125                2130

Ala Gly Val Pro Gly Ala Gly Val Pro Gly Ala Gly Val Pro Gly
    2135                2140                2145

Ala Gly Val Pro Gly Ala Gly Val Pro Gly Ala Gly Val Pro Gly
    2150                2155                2160

Ala Gly Val Pro Gly Ala Gly Val Pro Gly Ala Gly Val Pro Gly
    2165                2170                2175

Ala Gly Val Pro Gly Ala Gly Val Pro Gly Ala Gly Val Pro Gly
    2180                2185                2190

Ala Gly Val Pro Gly Ala Gly Val Pro Gly Ala Gly Val Pro Gly
    2195                2200                2205

Ala Gly Val Pro Gly Ala Gly Val Pro Gly Ala Gly Val Pro Gly
    2210                2215                2220

Ala Gly Val Pro Gly Ala Gly Val Pro Gly Ala Gly Val Pro Gly
    2225                2230                2235
```

```
Ala Gly  Val Pro Gly Ala Gly  Val Pro Gly Ala Gly  Val Pro Gly
    2240                 2245                 2250

Ala Gly  Val Pro Gly Ala Gly  Val Pro Gly Ala Gly  Val Pro Gly
    2255                 2260                 2265

Ala Gly  Val Pro Gly Ala Gly  Val Pro Gly Ala Gly  Val Pro Gly
    2270                 2275                 2280

Ala Gly  Val Pro Gly Ala Gly  Val Pro Gly Ala Gly  Val Pro Gly
    2285                 2290                 2295

Ala Gly  Val Pro Gly Ala Gly  Val Pro Gly Ala Gly  Val Pro Gly
    2300                 2305                 2310

Ala Gly  Val Pro Gly Ala Gly  Val Pro Gly Ala Gly  Val Pro Gly
    2315                 2320                 2325

Ala Gly  Val Pro Gly Ala Gly  Val Pro Gly Ala Gly  Val Pro Gly
    2330                 2335                 2340

Ala Gly  Val Pro Gly Ala Gly  Val Pro Gly Ala Gly  Val Pro Gly
    2345                 2350                 2355

Ala Gly  Val Pro Gly Ala Gly  Val Pro Gly Ala Gly  Val Pro Gly
    2360                 2365                 2370

Ala Gly  Val Pro Gly Ala Gly  Val Pro Gly Ala Gly  Val Pro Gly
    2375                 2380                 2385

Ala Gly  Val Pro Gly Ala Gly  Val Pro Gly Ala Gly  Val Pro Gly
    2390                 2395                 2400

Ala Gly  Val Pro Gly Ala Gly  Val Pro Gly Ala Gly  Val Pro Gly
    2405                 2410                 2415

Ala Gly  Val Pro Gly Ala Gly  Val Pro Gly Ala Gly  Val Pro Gly
    2420                 2425                 2430

Ala Gly  Val Pro Gly Ala Gly  Val Pro Gly Ala Gly  Val Pro Gly
    2435                 2440                 2445

Ala Gly  Val Pro Gly Ala Gly  Val Pro Gly Ala Gly  Val Pro Gly
    2450                 2455                 2460

Ala Gly  Val Pro Gly Ala Gly  Val Pro Gly Ala Gly  Val Pro Gly
    2465                 2470                 2475

Ala Gly  Val Pro Gly Ala Gly  Val Pro Gly Ala Gly  Val Pro Gly
    2480                 2485                 2490

Ala Gly  Val Pro Gly Ala Gly  Val Pro Gly Ile Gly  Val Pro Gly
    2495                 2500                 2505

Ile Gly  Val Pro Gly Ile Gly  Val Pro Gly Ile Gly  Val Pro Gly
    2510                 2515                 2520

Ile Gly  Val Pro Gly Ile Gly  Val Pro Gly Ile Gly  Val Pro Gly
    2525                 2530                 2535

Ile Gly  Val Pro Gly Ile Gly  Val Pro Gly Ile Gly  Val Pro Gly
    2540                 2545                 2550

Ile Gly  Val Pro Gly Ile Gly  Val Pro Gly Ile Gly  Val Pro Gly
    2555                 2560                 2565

Ile Gly  Val Pro Gly Ile Gly  Val Pro Gly Ile Gly  Val Pro Gly
    2570                 2575                 2580

Ile Gly  Val Pro Gly Ile Gly  Val Pro Gly Ile Gly  Val Pro Gly
    2585                 2590                 2595

Ile Gly  Val Pro Gly Ile Gly  Val Pro Gly Ile Gly  Val Pro Gly
    2600                 2605                 2610

Ile Gly  Val Pro Gly Ile Gly  Val Pro Gly Ile Gly  Val Pro Gly
    2615                 2620                 2625

Ile Gly  Val Pro Gly Ile Gly  Val Pro Gly Ile Gly  Val Pro Gly
```

-continued

```
            2630                2635                2640

Ile Gly Val Pro Gly Ile Gly Val Pro Gly Ile Gly Val Pro Gly
            2645                2650                2655

Ile Gly Val Pro Gly Ile Gly Val Pro Gly Ile Gly Val Pro Gly
            2660                2665                2670

Ile Gly Val Pro Gly Ile Gly Val Pro Gly Ile Gly Val Pro Gly
            2675                2680                2685

Ile Gly Val Pro Gly Ile Gly Val Pro Gly Ile Gly Val Pro Gly
            2690                2695                2700

Ile Gly Val Pro Gly Ile Gly Val Pro Gly Ile Gly Val Pro Gly
            2705                2710                2715

Ile Gly Val Pro Gly Ile Gly Val Pro Gly Ile Gly Val Pro Gly
            2720                2725                2730

Ile Gly Val Pro Gly Ile Gly Val Pro Gly Ile Gly Val Pro Gly
            2735                2740                2745

Ile Gly Val Pro Gly Ile Gly Val Pro Gly Ile Gly Val Pro Gly
            2750                2755                2760

Ile Gly Val Pro Gly Ile Gly Val Pro Gly Ile Gly Val Pro Gly
            2765                2770                2775

Ile Gly Val Pro Gly Ile Gly Val Pro Gly Ile Gly Val Pro Gly
            2780                2785                2790

Ile Gly Val Pro Gly Ile Gly Val Pro Gly Ile Gly Val Pro Gly
            2795                2800                2805

Ile Gly Val Pro Gly Ile Gly Val Pro Gly Ile Gly Val Pro Gly
            2810                2815                2820

Ile Gly Val Pro Gly Ile Gly Val Pro Gly Ile Gly Val Pro Gly
            2825                2830                2835

Ile Gly Val Pro Gly Ile Gly Val Pro Gly Ile Gly Val Pro Gly
            2840                2845                2850

Ile Gly Val Pro Gly Ile Gly Val Pro Gly Ile Gly Val Pro Gly
            2855                2860                2865

Ile Gly Val Pro Gly Ile Gly Val Pro Gly Ile Gly Val Pro Gly
            2870                2875                2880

Ile Gly Val Pro Gly Ile Gly Val Pro Gly Ile Gly Val Pro Gly
            2885                2890                2895

Ile Gly Val Pro Gly Ile Gly Val Pro Gly Ile Gly Val Pro Gly
            2900                2905                2910

Ile Gly Val Pro Gly Ile Gly Val Pro Gly Ile Gly Val Pro Gly
            2915                2920                2925

Ile Gly Val Pro Gly Ile Gly Val Pro Gly Ile Gly Val Pro Gly
            2930                2935                2940

Ile Gly Val Pro Gly Ile Gly Val Pro Gly Ile Gly Val Pro Gly
            2945                2950                2955

Ile Gly Val Pro Gly Ile Gly Val Pro Gly Ile Gly Val Pro Gly
            2960                2965                2970

Ile Gly Val Pro Gly Ile Gly Val Pro Gly Ile Gly Val Pro Gly
            2975                2980                2985

Ile Gly Val Pro Gly Ile Gly Val Pro Gly Ile Gly Val Pro Gly
            2990                2995                3000

Ile Gly Val Pro Gly Ile Gly Val Pro Gly Ile Gly Val Pro Gly
            3005                3010                3015

Ile Gly Val Pro Gly Ile Gly Val Pro Gly Ile Gly Val Pro Gly
            3020                3025                3030
```

-continued

```
Ile Gly Val Pro Gly Ile Gly Val Pro Gly Ile Gly Val Pro Gly
    3035                3040                3045
Ile Gly Val Pro Gly Ile Gly Val Pro Gly Ile Gly Val Pro Gly
    3050                3055                3060
Ile Gly Val Pro Gly Ile Gly Val Pro Gly Ile Gly Val Pro Gly
    3065                3070                3075
Ile Gly Val Pro Gly Ile Gly Val Pro Gly Ile Gly Val Pro Gly
    3080                3085                3090
Ile Gly Val Pro Gly Ile Gly Val Pro Gly Ile Gly Val Pro Gly
    3095                3100                3105
Ile Gly Val Pro Gly Ile Gly Val Pro Gly Ile Gly Val Pro Gly
    3110                3115                3120
Ile Gly Val Pro Gly Ile Gly Val Pro Gly Ile Gly Val Pro Gly
    3125                3130                3135
Ile Gly Val Pro Gly Ile Gly Val Pro Gly Ile Gly Val Pro Gly
    3140                3145                3150
Ile Gly Val Pro Gly Ile Gly Val Pro Gly Ile Gly Val Pro Gly
    3155                3160                3165
Ile Gly Val Pro Gly Ile Gly Val Pro Gly Ile Gly Val Pro Gly
    3170                3175                3180
Ile Gly Val Pro Gly Ile Gly Val Pro Gly Ile Gly Val Pro Gly
    3185                3190                3195
Ile Gly Val Pro Gly Ile Gly Val Pro Gly Ile Gly Val Pro Gly
    3200                3205                3210
Ile Gly Val Pro Gly Ile Gly Val Pro Gly Ile Gly Val Pro Gly
    3215                3220                3225
Ile Gly Val Pro Gly Ile Gly Val Pro Gly Ile Gly Val Pro Gly
    3230                3235                3240
Ile Gly Val Pro Gly Ile Gly Val Pro Gly Ile Gly Val Pro Gly
    3245                3250                3255
Ile Gly Val Pro Gly Ile Gly Val Pro Gly Ile Gly Val Pro Gly
    3260                3265                3270
Ile Gly Val Pro Gly Ile Gly Val Pro Gly Ile Gly Val Pro Gly
    3275                3280                3285
Ile Gly Val Pro Gly Ile Gly Val Pro Gly Ile Gly Val Pro Gly
    3290                3295                3300
Ile Gly Val Pro Gly Ile Gly Val Pro Gly Ile Gly Val Pro Gly
    3305                3310                3315
Ile Gly Val Pro Gly Ile Gly Val Pro Gly Ile Gly Val Pro Gly
    3320                3325                3330
Ile Gly Val Pro Gly Ile Gly Val Pro Gly Ile Gly Val Pro Gly
    3335                3340                3345
Ile Gly Val Pro Gly Ile Gly Val Pro Gly Ile Gly Val Pro Gly
    3350                3355                3360
Ile Gly Val Pro Gly Ile Gly Val Pro Gly Ile Gly Val Pro Gly
    3365                3370                3375
Ile Gly Val Pro Gly Ile Gly Val Pro Gly Ile Gly Val Pro Gly
    3380                3385                3390
Ile Gly Val Pro Gly Ile Gly Val Pro Gly Ile Gly Val Pro Gly
    3395                3400                3405
Ile Gly Val Pro Gly Ile Gly Val Pro Gly Ile Gly Val Pro Gly
    3410                3415                3420
```

```
Ile Gly  Val Pro Gly Ile Gly  Val Pro Gly Ile Gly  Val Pro Gly
    3425                 3430                 3435

Ile Gly  Val Pro Gly Ile Gly  Val Pro Gly Ile Gly  Val Pro Gly
    3440                 3445                 3450

Ile Gly  Val Pro Gly Ile Gly  Val Pro Gly Ile Gly  Val Pro Gly
    3455                 3460                 3465

Ile Gly  Val Pro Gly Ile Gly  Val Pro Gly Ile Gly  Val Pro Gly
    3470                 3475                 3480

Ile Gly  Val Pro Gly Ile Gly  Val Pro Gly Ile Gly  Val Pro Gly
    3485                 3490                 3495

Ile Gly  Val Pro Gly Ile Gly  Val Pro Gly Ile Gly  Val Pro Gly
    3500                 3505                 3510

Ile Gly  Val Pro Gly Ile Gly  Val Pro Gly Ile Gly  Val Pro Gly
    3515                 3520                 3525

Ile Gly  Val Pro Gly Ile Gly  Val Pro Gly Ile Gly  Val Pro Gly
    3530                 3535                 3540

Ile Gly  Val Pro Gly Ile Gly  Val Pro Gly Ile Gly  Val Pro Gly
    3545                 3550                 3555

Ile Gly  Val Pro Gly Ile Gly  Val Pro Gly Ile Gly  Val Pro Gly
    3560                 3565                 3570

Ile Gly  Val Pro Gly Ile Gly  Val Pro Gly Ile Gly  Val Pro Gly
    3575                 3580                 3585

Ile Gly  Val Pro Gly Ile Gly  Val Pro Gly Ile Gly  Val Pro Gly
    3590                 3595                 3600

Ile Gly  Val Pro Gly Ile Gly  Val Pro Gly Ile Gly  Val Pro Gly
    3605                 3610                 3615

Ile Gly  Val Pro Gly Ile Gly  Val Pro Gly Ile Gly  Val Pro Gly
    3620                 3625                 3630

Ile Gly  Val Pro Gly Ile Gly  Val Pro Gly Ile Gly  Val Pro Gly
    3635                 3640                 3645

Ile Gly  Val Pro Gly Ile Gly  Val Pro Gly Ile Gly  Val Pro Gly
    3650                 3655                 3660

Ile Gly  Val Pro Gly Ile Gly  Val Pro Gly Ile Gly  Val Pro Gly
    3665                 3670                 3675

Ile Gly  Val Pro Gly Ile Gly  Val Pro Gly Ile Gly  Val Pro Gly
    3680                 3685                 3690

Ile Gly  Val Pro Gly Ile Gly  Val Pro Gly Ile Gly  Val Pro Gly
    3695                 3700                 3705

Ile Gly  Val Pro Gly Ile Gly  Val Pro Gly Ile Gly  Val Pro Gly
    3710                 3715                 3720

Ile Gly  Val Pro Gly Ile Gly  Val Pro Gly Ile Gly  Val Pro Gly
    3725                 3730                 3735

Ile Gly  Val Pro Gly Ile Gly  Val Pro Gly Ile Gly  Val Pro Gly
    3740                 3745                 3750

Ile Gly  Val Pro Gly Ile Gly  Val Pro Gly Ile Gly  Val Pro Gly
    3755                 3760                 3765

Ile Gly  Val Pro Gly Ile Gly  Val Pro Gly Ile Gly  Val Pro Gly
    3770                 3775                 3780

Ile Gly  Val Pro Gly Ile Gly  Val Pro Gly Ile Gly  Val Pro Gly
    3785                 3790                 3795

Ile Gly  Val Pro Gly Ile Gly  Val Pro Gly Ile Gly  Val Pro Gly
    3800                 3805                 3810

Ile Gly  Val Pro Gly Ile Gly  Val Pro Gly Ile Gly  Val Pro Gly
```

-continued

```
            3815                3820                3825

Ile Gly Val Pro Gly Ile Gly Val Pro Gly Ile Gly Val Pro Gly
            3830                3835                3840

Ile Gly Val Pro Gly Ile Gly Val Pro Gly Ile Gly Val Pro Gly
            3845                3850                3855

Ile Gly Val Pro Gly Ile Gly Val Pro Gly Ile Gly Val Pro Gly
            3860                3865                3870

Ile Gly Val Pro Gly Ile Gly Val Pro Gly Ile Gly Val Pro Gly
            3875                3880                3885

Ile Gly Val Pro Gly Ile Gly Val Pro Gly Ile Gly Val Pro Gly
            3890                3895                3900

Ile Gly Val Pro Gly Ile Gly Val Pro Gly Ile Gly Val Pro Gly
            3905                3910                3915

Ile Gly Val Pro Gly Ile Gly Val Pro Gly Ile Gly Val Pro Gly
            3920                3925                3930

Ile Gly Val Pro Gly Ile Gly Val Pro Gly Ile Gly Val Pro Gly
            3935                3940                3945

Ile Gly Val Pro Gly Ile Gly Val Pro Gly Ile Gly Val Pro Gly
            3950                3955                3960

Ile Gly Val Pro Gly Ile Gly Val Pro Gly Ile Gly Val Pro Gly
            3965                3970                3975

Ile Gly Val Pro Gly Ile Gly Val Pro Gly Ile Gly Val Pro Gly
            3980                3985                3990

Ile Gly Val Pro Gly Ile Gly Val Pro Gly Ile Gly Val Pro Gly
            3995                4000                4005

Ile Gly Val Pro Gly Ile Gly Val Pro Gly Ile Gly Val Pro Gly
            4010                4015                4020

Ile Gly Val Pro Gly Ile Gly Val Pro Gly Ile Gly Val Pro Gly
            4025                4030                4035

Ile Gly Val Pro Gly Ile Gly Val Pro Gly Ile Gly Val Pro Gly
            4040                4045                4050

Ile Gly Val Pro Gly Ile Gly Val Pro Gly Ile Gly Val Pro Gly
            4055                4060                4065

Ile Gly Val Pro Gly Ile Gly Val Pro Gly Ile Gly Val Pro Gly
            4070                4075                4080

Ile Gly Val Pro Gly Ile Gly Val Pro Gly Ile Gly Val Pro Gly
            4085                4090                4095

Ile Gly Val Pro Gly Ile Gly Val Pro Gly Ile Gly Val Pro Gly
            4100                4105                4110

Ile Gly Val Pro Gly Ile Gly Val Pro Gly Ile Gly Val Pro Gly
            4115                4120                4125

Ile Gly Val Pro Gly Ile Gly Val Pro Gly Ile Gly Val Pro Gly
            4130                4135                4140

Ile Gly Val Pro Gly Ile Gly Val Pro Gly Ile Gly Val Pro Gly
            4145                4150                4155

Ile Gly Val Pro Gly Ile Gly Val Pro Gly Ile Gly Val Pro Gly
            4160                4165                4170

Ile Gly Val Pro Gly Ile Gly Val Pro Gly Ile Gly Val Pro Gly
            4175                4180                4185

Ile Gly Val Pro Gly Ile Gly Val Pro Gly Ile Gly Val Pro Gly
            4190                4195                4200

Ile Gly Val Pro Gly Ile Gly Val Pro Gly Ile Gly Val Pro Gly
            4205                4210                4215
```

```
Ile Gly Val Pro Gly Ile Gly Val Pro Gly Ile Gly Val Pro Gly
    4220              4225              4230

Ile Gly Val Pro Gly Ile Gly Val Pro Gly Ile Gly Val Pro Gly
    4235              4240              4245

Ile Gly Val Pro Gly Ile Gly Val Pro Gly Ile Gly Val Pro Gly
    4250              4255              4260

Ile Gly Val Pro Gly Ile Gly Val Pro Gly Ile Gly Val Pro Gly
    4265              4270              4275

Ile Gly Val Pro Gly Ile Gly Val Pro Gly Ile Gly Val Pro Gly
    4280              4285              4290

Ile Gly Val Pro Gly Ile Gly Val Pro Gly Ile Gly Val Pro Gly
    4295              4300              4305

Ile Gly Val Pro Gly Ile Gly Val Pro Gly Ile Gly Val Pro Gly
    4310              4315              4320

Ile Gly Val Pro Gly Ile Gly Val Pro Gly Ile Gly Val Pro Gly
    4325              4330              4335

Ile Gly Val Pro Gly Ile Gly Val Pro Gly Ile Gly Val Pro Gly
    4340              4345              4350

Ile Gly Val Pro Gly Ile Gly Val Pro Gly Ile Gly Val Pro Gly
    4355              4360              4365

Ile Gly Val Pro Gly Ile Gly Val Pro Gly Ile Gly Val Pro Gly
    4370              4375              4380

Ile Gly Val Pro Gly Ile Gly Val Pro Gly Ile Gly Val Pro Gly
    4385              4390              4395

Ile Gly Val Pro Gly Ile Gly Val Pro Gly Ile Gly Val Pro Gly
    4400              4405              4410

Ile Gly Val Pro Gly Ile Gly Val Pro Gly Ile Gly Val Pro Gly
    4415              4420              4425

Ile Gly Val Pro Gly Ile Gly Val Pro Gly Ile Gly Val Pro Gly
    4430              4435              4440

Ile Gly Val Pro Gly Ile Gly Val Pro Gly Ile Gly Val Pro Gly
    4445              4450              4455

Ile Gly Val Pro Gly Ile Gly Val Pro Gly Ile Gly Val Pro Gly
    4460              4465              4470

Ile Gly Val Pro Gly Ile Gly Val Pro Gly Ile Gly Val Pro Gly
    4475              4480              4485

Ile Gly Val Pro Gly Ile Gly Val Pro Gly Ile Gly Val Pro Gly
    4490              4495              4500

Ile Gly Val Pro Gly Ile Gly Val Pro Gly Ile Gly Val Pro Gly
    4505              4510              4515

Ile Gly Val Pro Gly Ile Gly Val Pro Gly Ile Gly Val Pro Gly
    4520              4525              4530

Ile Gly Val Pro Gly Ile Gly Val Pro Gly Ile Gly Val Pro Gly
    4535              4540              4545

Ile Gly Val Pro Gly Ile Gly Val Pro Gly Ile Gly Val Pro Gly
    4550              4555              4560

Ile Gly Val Pro Gly Ile Gly Val Pro Gly Ile Gly Val Pro Gly
    4565              4570              4575

Ile Gly Val Pro Gly Ile Gly Val Pro Gly Ile Gly Val Pro Gly
    4580              4585              4590

Ile Gly Val Pro Gly Ile Gly Val Pro Gly Ile Gly Val Pro Gly
    4595              4600              4605
```

-continued

```
Ile Gly Val Pro Gly Ile Gly Val Pro Gly Ile Gly Val Pro Gly
    4610                4615                4620
Ile Gly Val Pro Gly Ile Gly Val Pro Gly Ile Gly Val Pro Gly
    4625                4630                4635
Ile Gly Val Pro Gly Ile Gly Val Pro Gly Ile Gly Val Pro Gly
    4640                4645                4650
Ile Gly Val Pro Gly Ile Gly Val Pro Gly Ile Gly Val Pro Gly
    4655                4660                4665
Ile Gly Val Pro Gly Ile Gly Val Pro Gly Ile Gly Val Pro Gly
    4670                4675                4680
Ile Gly Val Pro Gly Ile Gly Val Pro Gly Ile Gly Val Pro Gly
    4685                4690                4695
Ile Gly Val Pro Gly Ile Gly Val Pro Gly Ile Gly Val Pro Gly
    4700                4705                4710
Ile Gly Val Pro Gly Ile Gly Val Pro Gly Ile Gly Val Pro Gly
    4715                4720                4725
Ile Gly Val Pro Gly Ile Gly Val Pro Gly Ile Gly Val Pro Gly
    4730                4735                4740
Ile Gly Val Pro Gly Ile Gly Val Pro Gly Ile Gly Val Pro Gly
    4745                4750                4755
Ile Gly Val Pro Gly Ile Gly Val Pro Gly Ile Gly Val Pro Gly
    4760                4765                4770
Ile Gly Val Pro Gly Ile Gly Val Pro Gly Ile Gly Val Pro Gly
    4775                4780                4785
Ile Gly Val Pro Gly Ile Gly Val Pro Gly Ile Gly Val Pro Gly
    4790                4795                4800
Ile Gly Val Pro Gly Ile Gly Val Pro Gly Ile Gly Val Pro Gly
    4805                4810                4815
Ile Gly Val Pro Gly Ile Gly Val Pro Gly Ile Gly Val Pro Gly
    4820                4825                4830
Ile Gly Val Pro Gly Ile Gly Val Pro Gly Ile Gly Val Pro Gly
    4835                4840                4845
Ile Gly Val Pro Gly Ile Gly Val Pro Gly Ile Gly Val Pro Gly
    4850                4855                4860
Ile Gly Val Pro Gly Ile Gly Val Pro Gly Ile Gly Val Pro Gly
    4865                4870                4875
Ile Gly Val Pro Gly Ile Gly Val Pro Gly Ile Gly Val Pro Gly
    4880                4885                4890
Ile Gly Val Pro Gly Ile Gly Val Pro Gly Ile Gly Val Pro Gly
    4895                4900                4905
Ile Gly Val Pro Gly Ile Gly Val Pro Gly Ile Gly Val Pro Gly
    4910                4915                4920
Ile Gly Val Pro Gly Ile Gly Val Pro Gly Ile Gly Val Pro Gly
    4925                4930                4935
Ile Gly Val Pro Gly Ile Gly Val Pro Gly Ile Gly Val Pro Gly
    4940                4945                4950
Ile Gly Val Pro Gly Ile Gly Val Pro Gly Ile Gly Val Pro Gly
    4955                4960                4965
Ile Gly Val Pro Gly Ile Gly Val Pro Gly Ile Gly Val Pro Gly
    4970                4975                4980
Ile Gly Val Pro Gly Ile Gly Val Pro Gly Ile Gly Val Pro Gly
    4985                4990                4995

Ile Gly
```

```
                                5000

<210> SEQ ID NO 9
<211> LENGTH: 5000
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(2500)
<223> OTHER INFORMATION: This region may encompass 1 to 500 "VPGSG"
      repeats
<220> FEATURE:
<221> NAME/KEY: misc_feature
<222> LOCATION: (2501)..(5000)
<223> OTHER INFORMATION: This region may encompass 1 to 500 "VPGIG"
      repeats
<220> FEATURE:
<223> OTHER INFORMATION: See specification as filed for detailed
      description of substitutions and preferred embodiments

<400> SEQUENCE: 9

Val Pro Gly Ser Gly Val Pro Gly Ser Gly Val Pro Gly Ser Gly Val
1               5                   10                  15

Pro Gly Ser Gly Val Pro Gly Ser Gly Val Pro Gly Ser Gly Val Pro
            20                  25                  30

Gly Ser Gly Val Pro Gly Ser Gly Val Pro Gly Ser Gly Val Pro Gly
        35                  40                  45

Ser Gly Val Pro Gly Ser Gly Val Pro Gly Ser Gly Val Pro Gly Ser
    50                  55                  60

Gly Val Pro Gly Ser Gly Val Pro Gly Ser Gly Val Pro Gly Ser Gly
65                  70                  75                  80

Val Pro Gly Ser Gly Val Pro Gly Ser Gly Val Pro Gly Ser Gly Val
                85                  90                  95

Pro Gly Ser Gly Val Pro Gly Ser Gly Val Pro Gly Ser Gly Val Pro
            100                 105                 110

Gly Ser Gly Val Pro Gly Ser Gly Val Pro Gly Ser Gly Val Pro Gly
        115                 120                 125

Ser Gly Val Pro Gly Ser Gly Val Pro Gly Ser Gly Val Pro Gly Ser
    130                 135                 140

Gly Val Pro Gly Ser Gly Val Pro Gly Ser Gly Val Pro Gly Ser Gly
145                 150                 155                 160

Val Pro Gly Ser Gly Val Pro Gly Ser Gly Val Pro Gly Ser Gly Val
                165                 170                 175

Pro Gly Ser Gly Val Pro Gly Ser Gly Val Pro Gly Ser Gly Val Pro
            180                 185                 190

Gly Ser Gly Val Pro Gly Ser Gly Val Pro Gly Ser Gly Val Pro Gly
        195                 200                 205

Ser Gly Val Pro Gly Ser Gly Val Pro Gly Ser Gly Val Pro Gly Ser
    210                 215                 220

Gly Val Pro Gly Ser Gly Val Pro Gly Ser Gly Val Pro Gly Ser Gly
225                 230                 235                 240

Val Pro Gly Ser Gly Val Pro Gly Ser Gly Val Pro Gly Ser Gly Val
                245                 250                 255

Pro Gly Ser Gly Val Pro Gly Ser Gly Val Pro Gly Ser Gly Val Pro
            260                 265                 270

Gly Ser Gly Val Pro Gly Ser Gly Val Pro Gly Ser Gly Val Pro Gly
        275                 280                 285
```

```
Ser Gly Val Pro Gly Ser Gly Val Pro Gly Ser
    290                 295                 300

Gly Val Pro Gly Ser Gly Val Pro Gly Ser Gly
305                 310                 315                 320

Val Pro Gly Ser Gly Val Pro Gly Ser Gly Val
                325                 330                 335

Pro Gly Ser Gly Val Pro Gly Ser Gly Val Pro
            340                 345                 350

Gly Ser Gly Val Pro Gly Ser Gly Val Pro Gly
        355                 360                 365

Ser Gly Val Pro Gly Ser Gly Val Pro Gly Ser
    370                 375                 380

Gly Val Pro Gly Ser Gly Val Pro Gly Ser Gly
385                 390                 395                 400

Val Pro Gly Ser Gly Val Pro Gly Ser Gly Val
                405                 410                 415

Pro Gly Ser Gly Val Pro Gly Ser Gly Val Pro
            420                 425                 430

Gly Ser Gly Val Pro Gly Ser Gly Val Pro Gly
        435                 440                 445

Ser Gly Val Pro Gly Ser Gly Val Pro Gly Ser
    450                 455                 460

Gly Val Pro Gly Ser Gly Val Pro Gly Ser Gly
465                 470                 475                 480

Val Pro Gly Ser Gly Val Pro Gly Ser Gly Val
                485                 490                 495

Pro Gly Ser Gly Val Pro Gly Ser Gly Val Pro
            500                 505                 510

Gly Ser Gly Val Pro Gly Ser Gly Val Pro Gly
        515                 520                 525

Ser Gly Val Pro Gly Ser Gly Val Pro Gly Ser
    530                 535                 540

Gly Val Pro Gly Ser Gly Val Pro Gly Ser Gly
545                 550                 555                 560

Val Pro Gly Ser Gly Val Pro Gly Ser Gly Val
                565                 570                 575

Pro Gly Ser Gly Val Pro Gly Ser Gly Val Pro
            580                 585                 590

Gly Ser Gly Val Pro Gly Ser Gly Val Pro Gly
        595                 600                 605

Ser Gly Val Pro Gly Ser Gly Val Pro Gly Ser
    610                 615                 620

Gly Val Pro Gly Ser Gly Val Pro Gly Ser Gly
625                 630                 635                 640

Val Pro Gly Ser Gly Val Pro Gly Ser Gly Val
                645                 650                 655

Pro Gly Ser Gly Val Pro Gly Ser Gly Val Pro
            660                 665                 670

Gly Ser Gly Val Pro Gly Ser Gly Val Pro Gly
        675                 680                 685

Ser Gly Val Pro Gly Ser Gly Val Pro Gly Ser
    690                 695                 700
```

-continued

Gly Val Pro Gly Ser Gly Val Pro Gly Ser Gly Val Pro Gly Ser Gly
705                 710                 715                 720

Val Pro Gly Ser Gly Val Pro Gly Ser Gly Val Pro Gly Ser Gly Val
            725                 730                 735

Pro Gly Ser Gly Val Pro Gly Ser Gly Val Pro Gly Ser Gly Val Pro
        740                 745                 750

Gly Ser Gly Val Pro Gly Ser Gly Val Pro Gly Ser Gly Val Pro Gly
    755                 760                 765

Ser Gly Val Pro Gly Ser Gly Val Pro Gly Ser Gly Val Pro Gly Ser
770                 775                 780

Gly Val Pro Gly Ser Gly Val Pro Gly Ser Gly Val Pro Gly Ser Gly
785                 790                 795                 800

Val Pro Gly Ser Gly Val Pro Gly Ser Gly Val Pro Gly Ser Gly Val
            805                 810                 815

Pro Gly Ser Gly Val Pro Gly Ser Gly Val Pro Gly Ser Gly Val Pro
        820                 825                 830

Gly Ser Gly Val Pro Gly Ser Gly Val Pro Gly Ser Gly Val Pro Gly
    835                 840                 845

Ser Gly Val Pro Gly Ser Gly Val Pro Gly Ser Gly Val Pro Gly Ser
850                 855                 860

Gly Val Pro Gly Ser Gly Val Pro Gly Ser Gly Val Pro Gly Ser Gly
865                 870                 875                 880

Val Pro Gly Ser Gly Val Pro Gly Ser Gly Val Pro Gly Ser Gly Val
            885                 890                 895

Pro Gly Ser Gly Val Pro Gly Ser Gly Val Pro Gly Ser Gly Val Pro
        900                 905                 910

Gly Ser Gly Val Pro Gly Ser Gly Val Pro Gly Ser Gly Val Pro Gly
    915                 920                 925

Ser Gly Val Pro Gly Ser Gly Val Pro Gly Ser Gly Val Pro Gly Ser
930                 935                 940

Gly Val Pro Gly Ser Gly Val Pro Gly Ser Gly Val Pro Gly Ser Gly
945                 950                 955                 960

Val Pro Gly Ser Gly Val Pro Gly Ser Gly Val Pro Gly Ser Gly Val
            965                 970                 975

Pro Gly Ser Gly Val Pro Gly Ser Gly Val Pro Gly Ser Gly Val Pro
        980                 985                 990

Gly Ser Gly Val Pro Gly Ser Gly Val Pro Gly Ser Gly Val Pro Gly
    995                 1000                1005

Ser Gly Val Pro Gly Ser Gly Val Pro Gly Ser Gly Val Pro Gly
    1010                1015                1020

Ser Gly Val Pro Gly Ser Gly Val Pro Gly Ser Gly Val Pro Gly
    1025                1030                1035

Ser Gly Val Pro Gly Ser Gly Val Pro Gly Ser Gly Val Pro Gly
    1040                1045                1050

Ser Gly Val Pro Gly Ser Gly Val Pro Gly Ser Gly Val Pro Gly
    1055                1060                1065

Ser Gly Val Pro Gly Ser Gly Val Pro Gly Ser Gly Val Pro Gly
    1070                1075                1080

Ser Gly Val Pro Gly Ser Gly Val Pro Gly Ser Gly Val Pro Gly
    1085                1090                1095

Ser Gly Val Pro Gly Ser Gly Val Pro Gly Ser Gly Val Pro Gly
    1100                1105                1110

Ser Gly Val Pro Gly Ser Gly Val Pro Gly Ser Gly Val Pro Gly

-continued

```
            1115                1120                1125

Ser Gly Val Pro Gly Ser Gly Val Pro Gly Ser Gly Val Pro Gly
    1130                1135                1140

Ser Gly Val Pro Gly Ser Gly Val Pro Gly Ser Gly Val Pro Gly
    1145                1150                1155

Ser Gly Val Pro Gly Ser Gly Val Pro Gly Ser Gly Val Pro Gly
    1160                1165                1170

Ser Gly Val Pro Gly Ser Gly Val Pro Gly Ser Gly Val Pro Gly
    1175                1180                1185

Ser Gly Val Pro Gly Ser Gly Val Pro Gly Ser Gly Val Pro Gly
    1190                1195                1200

Ser Gly Val Pro Gly Ser Gly Val Pro Gly Ser Gly Val Pro Gly
    1205                1210                1215

Ser Gly Val Pro Gly Ser Gly Val Pro Gly Ser Gly Val Pro Gly
    1220                1225                1230

Ser Gly Val Pro Gly Ser Gly Val Pro Gly Ser Gly Val Pro Gly
    1235                1240                1245

Ser Gly Val Pro Gly Ser Gly Val Pro Gly Ser Gly Val Pro Gly
    1250                1255                1260

Ser Gly Val Pro Gly Ser Gly Val Pro Gly Ser Gly Val Pro Gly
    1265                1270                1275

Ser Gly Val Pro Gly Ser Gly Val Pro Gly Ser Gly Val Pro Gly
    1280                1285                1290

Ser Gly Val Pro Gly Ser Gly Val Pro Gly Ser Gly Val Pro Gly
    1295                1300                1305

Ser Gly Val Pro Gly Ser Gly Val Pro Gly Ser Gly Val Pro Gly
    1310                1315                1320

Ser Gly Val Pro Gly Ser Gly Val Pro Gly Ser Gly Val Pro Gly
    1325                1330                1335

Ser Gly Val Pro Gly Ser Gly Val Pro Gly Ser Gly Val Pro Gly
    1340                1345                1350

Ser Gly Val Pro Gly Ser Gly Val Pro Gly Ser Gly Val Pro Gly
    1355                1360                1365

Ser Gly Val Pro Gly Ser Gly Val Pro Gly Ser Gly Val Pro Gly
    1370                1375                1380

Ser Gly Val Pro Gly Ser Gly Val Pro Gly Ser Gly Val Pro Gly
    1385                1390                1395

Ser Gly Val Pro Gly Ser Gly Val Pro Gly Ser Gly Val Pro Gly
    1400                1405                1410

Ser Gly Val Pro Gly Ser Gly Val Pro Gly Ser Gly Val Pro Gly
    1415                1420                1425

Ser Gly Val Pro Gly Ser Gly Val Pro Gly Ser Gly Val Pro Gly
    1430                1435                1440

Ser Gly Val Pro Gly Ser Gly Val Pro Gly Ser Gly Val Pro Gly
    1445                1450                1455

Ser Gly Val Pro Gly Ser Gly Val Pro Gly Ser Gly Val Pro Gly
    1460                1465                1470

Ser Gly Val Pro Gly Ser Gly Val Pro Gly Ser Gly Val Pro Gly
    1475                1480                1485

Ser Gly Val Pro Gly Ser Gly Val Pro Gly Ser Gly Val Pro Gly
    1490                1495                1500

Ser Gly Val Pro Gly Ser Gly Val Pro Gly Ser Gly Val Pro Gly
    1505                1510                1515
```

```
Ser Gly Val Pro Gly Ser Gly Val Pro Gly Ser Gly  Val Pro Gly
    1520                1525            1530

Ser Gly Val Pro Gly Ser Gly Val Pro Gly Ser Gly  Val Pro Gly
    1535                1540            1545

Ser Gly Val Pro Gly Ser Gly Val Pro Gly Ser Gly  Val Pro Gly
    1550                1555            1560

Ser Gly Val Pro Gly Ser Gly Val Pro Gly Ser Gly  Val Pro Gly
    1565                1570            1575

Ser Gly Val Pro Gly Ser Gly Val Pro Gly Ser Gly  Val Pro Gly
    1580                1585            1590

Ser Gly Val Pro Gly Ser Gly Val Pro Gly Ser Gly  Val Pro Gly
    1595                1600            1605

Ser Gly Val Pro Gly Ser Gly Val Pro Gly Ser Gly  Val Pro Gly
    1610                1615            1620

Ser Gly Val Pro Gly Ser Gly Val Pro Gly Ser Gly  Val Pro Gly
    1625                1630            1635

Ser Gly Val Pro Gly Ser Gly Val Pro Gly Ser Gly  Val Pro Gly
    1640                1645            1650

Ser Gly Val Pro Gly Ser Gly Val Pro Gly Ser Gly  Val Pro Gly
    1655                1660            1665

Ser Gly Val Pro Gly Ser Gly Val Pro Gly Ser Gly  Val Pro Gly
    1670                1675            1680

Ser Gly Val Pro Gly Ser Gly Val Pro Gly Ser Gly  Val Pro Gly
    1685                1690            1695

Ser Gly Val Pro Gly Ser Gly Val Pro Gly Ser Gly  Val Pro Gly
    1700                1705            1710

Ser Gly Val Pro Gly Ser Gly Val Pro Gly Ser Gly  Val Pro Gly
    1715                1720            1725

Ser Gly Val Pro Gly Ser Gly Val Pro Gly Ser Gly  Val Pro Gly
    1730                1735            1740

Ser Gly Val Pro Gly Ser Gly Val Pro Gly Ser Gly  Val Pro Gly
    1745                1750            1755

Ser Gly Val Pro Gly Ser Gly Val Pro Gly Ser Gly  Val Pro Gly
    1760                1765            1770

Ser Gly Val Pro Gly Ser Gly Val Pro Gly Ser Gly  Val Pro Gly
    1775                1780            1785

Ser Gly Val Pro Gly Ser Gly Val Pro Gly Ser Gly  Val Pro Gly
    1790                1795            1800

Ser Gly Val Pro Gly Ser Gly Val Pro Gly Ser Gly  Val Pro Gly
    1805                1810            1815

Ser Gly Val Pro Gly Ser Gly Val Pro Gly Ser Gly  Val Pro Gly
    1820                1825            1830

Ser Gly Val Pro Gly Ser Gly Val Pro Gly Ser Gly  Val Pro Gly
    1835                1840            1845

Ser Gly Val Pro Gly Ser Gly Val Pro Gly Ser Gly  Val Pro Gly
    1850                1855            1860

Ser Gly Val Pro Gly Ser Gly Val Pro Gly Ser Gly  Val Pro Gly
    1865                1870            1875

Ser Gly Val Pro Gly Ser Gly Val Pro Gly Ser Gly  Val Pro Gly
    1880                1885            1890

Ser Gly Val Pro Gly Ser Gly Val Pro Gly Ser Gly  Val Pro Gly
    1895                1900            1905
```

Ser Gly Val Pro Gly Ser Gly Val Pro Gly Ser Gly Val Pro Gly
1910                1915                1920

Ser Gly Val Pro Gly Ser Gly Val Pro Gly Ser Gly Val Pro Gly
1925                1930                1935

Ser Gly Val Pro Gly Ser Gly Val Pro Gly Ser Gly Val Pro Gly
1940                1945                1950

Ser Gly Val Pro Gly Ser Gly Val Pro Gly Ser Gly Val Pro Gly
1955                1960                1965

Ser Gly Val Pro Gly Ser Gly Val Pro Gly Ser Gly Val Pro Gly
1970                1975                1980

Ser Gly Val Pro Gly Ser Gly Val Pro Gly Ser Gly Val Pro Gly
1985                1990                1995

Ser Gly Val Pro Gly Ser Gly Val Pro Gly Ser Gly Val Pro Gly
2000                2005                2010

Ser Gly Val Pro Gly Ser Gly Val Pro Gly Ser Gly Val Pro Gly
2015                2020                2025

Ser Gly Val Pro Gly Ser Gly Val Pro Gly Ser Gly Val Pro Gly
2030                2035                2040

Ser Gly Val Pro Gly Ser Gly Val Pro Gly Ser Gly Val Pro Gly
2045                2050                2055

Ser Gly Val Pro Gly Ser Gly Val Pro Gly Ser Gly Val Pro Gly
2060                2065                2070

Ser Gly Val Pro Gly Ser Gly Val Pro Gly Ser Gly Val Pro Gly
2075                2080                2085

Ser Gly Val Pro Gly Ser Gly Val Pro Gly Ser Gly Val Pro Gly
2090                2095                2100

Ser Gly Val Pro Gly Ser Gly Val Pro Gly Ser Gly Val Pro Gly
2105                2110                2115

Ser Gly Val Pro Gly Ser Gly Val Pro Gly Ser Gly Val Pro Gly
2120                2125                2130

Ser Gly Val Pro Gly Ser Gly Val Pro Gly Ser Gly Val Pro Gly
2135                2140                2145

Ser Gly Val Pro Gly Ser Gly Val Pro Gly Ser Gly Val Pro Gly
2150                2155                2160

Ser Gly Val Pro Gly Ser Gly Val Pro Gly Ser Gly Val Pro Gly
2165                2170                2175

Ser Gly Val Pro Gly Ser Gly Val Pro Gly Ser Gly Val Pro Gly
2180                2185                2190

Ser Gly Val Pro Gly Ser Gly Val Pro Gly Ser Gly Val Pro Gly
2195                2200                2205

Ser Gly Val Pro Gly Ser Gly Val Pro Gly Ser Gly Val Pro Gly
2210                2215                2220

Ser Gly Val Pro Gly Ser Gly Val Pro Gly Ser Gly Val Pro Gly
2225                2230                2235

Ser Gly Val Pro Gly Ser Gly Val Pro Gly Ser Gly Val Pro Gly
2240                2245                2250

Ser Gly Val Pro Gly Ser Gly Val Pro Gly Ser Gly Val Pro Gly
2255                2260                2265

Ser Gly Val Pro Gly Ser Gly Val Pro Gly Ser Gly Val Pro Gly
2270                2275                2280

Ser Gly Val Pro Gly Ser Gly Val Pro Gly Ser Gly Val Pro Gly
2285                2290                2295

Ser Gly Val Pro Gly Ser Gly Val Pro Gly Ser Gly Val Pro Gly

```
                2300                2305                2310

Ser Gly Val Pro Gly Ser Gly Val Pro Gly Ser Gly Val Pro Gly
    2315                2320                2325

Ser Gly Val Pro Gly Ser Gly Val Pro Gly Ser Gly Val Pro Gly
    2330                2335                2340

Ser Gly Val Pro Gly Ser Gly Val Pro Gly Ser Gly Val Pro Gly
    2345                2350                2355

Ser Gly Val Pro Gly Ser Gly Val Pro Gly Ser Gly Val Pro Gly
    2360                2365                2370

Ser Gly Val Pro Gly Ser Gly Val Pro Gly Ser Gly Val Pro Gly
    2375                2380                2385

Ser Gly Val Pro Gly Ser Gly Val Pro Gly Ser Gly Val Pro Gly
    2390                2395                2400

Ser Gly Val Pro Gly Ser Gly Val Pro Gly Ser Gly Val Pro Gly
    2405                2410                2415

Ser Gly Val Pro Gly Ser Gly Val Pro Gly Ser Gly Val Pro Gly
    2420                2425                2430

Ser Gly Val Pro Gly Ser Gly Val Pro Gly Ser Gly Val Pro Gly
    2435                2440                2445

Ser Gly Val Pro Gly Ser Gly Val Pro Gly Ser Gly Val Pro Gly
    2450                2455                2460

Ser Gly Val Pro Gly Ser Gly Val Pro Gly Ser Gly Val Pro Gly
    2465                2470                2475

Ser Gly Val Pro Gly Ser Gly Val Pro Gly Ser Gly Val Pro Gly
    2480                2485                2490

Ser Gly Val Pro Gly Ser Gly Val Pro Gly Ile Gly Val Pro Gly
    2495                2500                2505

Ile Gly Val Pro Gly Ile Gly Val Pro Gly Ile Gly Val Pro Gly
    2510                2515                2520

Ile Gly Val Pro Gly Ile Gly Val Pro Gly Ile Gly Val Pro Gly
    2525                2530                2535

Ile Gly Val Pro Gly Ile Gly Val Pro Gly Ile Gly Val Pro Gly
    2540                2545                2550

Ile Gly Val Pro Gly Ile Gly Val Pro Gly Ile Gly Val Pro Gly
    2555                2560                2565

Ile Gly Val Pro Gly Ile Gly Val Pro Gly Ile Gly Val Pro Gly
    2570                2575                2580

Ile Gly Val Pro Gly Ile Gly Val Pro Gly Ile Gly Val Pro Gly
    2585                2590                2595

Ile Gly Val Pro Gly Ile Gly Val Pro Gly Ile Gly Val Pro Gly
    2600                2605                2610

Ile Gly Val Pro Gly Ile Gly Val Pro Gly Ile Gly Val Pro Gly
    2615                2620                2625

Ile Gly Val Pro Gly Ile Gly Val Pro Gly Ile Gly Val Pro Gly
    2630                2635                2640

Ile Gly Val Pro Gly Ile Gly Val Pro Gly Ile Gly Val Pro Gly
    2645                2650                2655

Ile Gly Val Pro Gly Ile Gly Val Pro Gly Ile Gly Val Pro Gly
    2660                2665                2670

Ile Gly Val Pro Gly Ile Gly Val Pro Gly Ile Gly Val Pro Gly
    2675                2680                2685

Ile Gly Val Pro Gly Ile Gly Val Pro Gly Ile Gly Val Pro Gly
    2690                2695                2700
```

-continued

```
Ile Gly Val Pro Gly Ile Gly Val Pro Gly Ile Gly Val Pro Gly
    2705                2710                2715
Ile Gly Val Pro Gly Ile Gly Val Pro Gly Ile Gly Val Pro Gly
    2720                2725                2730
Ile Gly Val Pro Gly Ile Gly Val Pro Gly Ile Gly Val Pro Gly
    2735                2740                2745
Ile Gly Val Pro Gly Ile Gly Val Pro Gly Ile Gly Val Pro Gly
    2750                2755                2760
Ile Gly Val Pro Gly Ile Gly Val Pro Gly Ile Gly Val Pro Gly
    2765                2770                2775
Ile Gly Val Pro Gly Ile Gly Val Pro Gly Ile Gly Val Pro Gly
    2780                2785                2790
Ile Gly Val Pro Gly Ile Gly Val Pro Gly Ile Gly Val Pro Gly
    2795                2800                2805
Ile Gly Val Pro Gly Ile Gly Val Pro Gly Ile Gly Val Pro Gly
    2810                2815                2820
Ile Gly Val Pro Gly Ile Gly Val Pro Gly Ile Gly Val Pro Gly
    2825                2830                2835
Ile Gly Val Pro Gly Ile Gly Val Pro Gly Ile Gly Val Pro Gly
    2840                2845                2850
Ile Gly Val Pro Gly Ile Gly Val Pro Gly Ile Gly Val Pro Gly
    2855                2860                2865
Ile Gly Val Pro Gly Ile Gly Val Pro Gly Ile Gly Val Pro Gly
    2870                2875                2880
Ile Gly Val Pro Gly Ile Gly Val Pro Gly Ile Gly Val Pro Gly
    2885                2890                2895
Ile Gly Val Pro Gly Ile Gly Val Pro Gly Ile Gly Val Pro Gly
    2900                2905                2910
Ile Gly Val Pro Gly Ile Gly Val Pro Gly Ile Gly Val Pro Gly
    2915                2920                2925
Ile Gly Val Pro Gly Ile Gly Val Pro Gly Ile Gly Val Pro Gly
    2930                2935                2940
Ile Gly Val Pro Gly Ile Gly Val Pro Gly Ile Gly Val Pro Gly
    2945                2950                2955
Ile Gly Val Pro Gly Ile Gly Val Pro Gly Ile Gly Val Pro Gly
    2960                2965                2970
Ile Gly Val Pro Gly Ile Gly Val Pro Gly Ile Gly Val Pro Gly
    2975                2980                2985
Ile Gly Val Pro Gly Ile Gly Val Pro Gly Ile Gly Val Pro Gly
    2990                2995                3000
Ile Gly Val Pro Gly Ile Gly Val Pro Gly Ile Gly Val Pro Gly
    3005                3010                3015
Ile Gly Val Pro Gly Ile Gly Val Pro Gly Ile Gly Val Pro Gly
    3020                3025                3030
Ile Gly Val Pro Gly Ile Gly Val Pro Gly Ile Gly Val Pro Gly
    3035                3040                3045
Ile Gly Val Pro Gly Ile Gly Val Pro Gly Ile Gly Val Pro Gly
    3050                3055                3060
Ile Gly Val Pro Gly Ile Gly Val Pro Gly Ile Gly Val Pro Gly
    3065                3070                3075
Ile Gly Val Pro Gly Ile Gly Val Pro Gly Ile Gly Val Pro Gly
    3080                3085                3090
```

Ile Gly Val Pro Gly Ile Gly Val Pro Gly Ile Gly Val Pro Gly
3095                3100                3105

Ile Gly Val Pro Gly Ile Gly Val Pro Gly Ile Gly Val Pro Gly
3110                3115                3120

Ile Gly Val Pro Gly Ile Gly Val Pro Gly Ile Gly Val Pro Gly
3125                3130                3135

Ile Gly Val Pro Gly Ile Gly Val Pro Gly Ile Gly Val Pro Gly
3140                3145                3150

Ile Gly Val Pro Gly Ile Gly Val Pro Gly Ile Gly Val Pro Gly
3155                3160                3165

Ile Gly Val Pro Gly Ile Gly Val Pro Gly Ile Gly Val Pro Gly
3170                3175                3180

Ile Gly Val Pro Gly Ile Gly Val Pro Gly Ile Gly Val Pro Gly
3185                3190                3195

Ile Gly Val Pro Gly Ile Gly Val Pro Gly Ile Gly Val Pro Gly
3200                3205                3210

Ile Gly Val Pro Gly Ile Gly Val Pro Gly Ile Gly Val Pro Gly
3215                3220                3225

Ile Gly Val Pro Gly Ile Gly Val Pro Gly Ile Gly Val Pro Gly
3230                3235                3240

Ile Gly Val Pro Gly Ile Gly Val Pro Gly Ile Gly Val Pro Gly
3245                3250                3255

Ile Gly Val Pro Gly Ile Gly Val Pro Gly Ile Gly Val Pro Gly
3260                3265                3270

Ile Gly Val Pro Gly Ile Gly Val Pro Gly Ile Gly Val Pro Gly
3275                3280                3285

Ile Gly Val Pro Gly Ile Gly Val Pro Gly Ile Gly Val Pro Gly
3290                3295                3300

Ile Gly Val Pro Gly Ile Gly Val Pro Gly Ile Gly Val Pro Gly
3305                3310                3315

Ile Gly Val Pro Gly Ile Gly Val Pro Gly Ile Gly Val Pro Gly
3320                3325                3330

Ile Gly Val Pro Gly Ile Gly Val Pro Gly Ile Gly Val Pro Gly
3335                3340                3345

Ile Gly Val Pro Gly Ile Gly Val Pro Gly Ile Gly Val Pro Gly
3350                3355                3360

Ile Gly Val Pro Gly Ile Gly Val Pro Gly Ile Gly Val Pro Gly
3365                3370                3375

Ile Gly Val Pro Gly Ile Gly Val Pro Gly Ile Gly Val Pro Gly
3380                3385                3390

Ile Gly Val Pro Gly Ile Gly Val Pro Gly Ile Gly Val Pro Gly
3395                3400                3405

Ile Gly Val Pro Gly Ile Gly Val Pro Gly Ile Gly Val Pro Gly
3410                3415                3420

Ile Gly Val Pro Gly Ile Gly Val Pro Gly Ile Gly Val Pro Gly
3425                3430                3435

Ile Gly Val Pro Gly Ile Gly Val Pro Gly Ile Gly Val Pro Gly
3440                3445                3450

Ile Gly Val Pro Gly Ile Gly Val Pro Gly Ile Gly Val Pro Gly
3455                3460                3465

Ile Gly Val Pro Gly Ile Gly Val Pro Gly Ile Gly Val Pro Gly
3470                3475                3480

Ile Gly Val Pro Gly Ile Gly Val Pro Gly Ile Gly Val Pro Gly

-continued

```
             3485                3490                3495

Ile Gly Val Pro Gly Ile Gly Val Pro Gly Ile Gly Val Pro Gly
        3500                3505                3510

Ile Gly Val Pro Gly Ile Gly Val Pro Gly Ile Gly Val Pro Gly
        3515                3520                3525

Ile Gly Val Pro Gly Ile Gly Val Pro Gly Ile Gly Val Pro Gly
        3530                3535                3540

Ile Gly Val Pro Gly Ile Gly Val Pro Gly Ile Gly Val Pro Gly
        3545                3550                3555

Ile Gly Val Pro Gly Ile Gly Val Pro Gly Ile Gly Val Pro Gly
        3560                3565                3570

Ile Gly Val Pro Gly Ile Gly Val Pro Gly Ile Gly Val Pro Gly
        3575                3580                3585

Ile Gly Val Pro Gly Ile Gly Val Pro Gly Ile Gly Val Pro Gly
        3590                3595                3600

Ile Gly Val Pro Gly Ile Gly Val Pro Gly Ile Gly Val Pro Gly
        3605                3610                3615

Ile Gly Val Pro Gly Ile Gly Val Pro Gly Ile Gly Val Pro Gly
        3620                3625                3630

Ile Gly Val Pro Gly Ile Gly Val Pro Gly Ile Gly Val Pro Gly
        3635                3640                3645

Ile Gly Val Pro Gly Ile Gly Val Pro Gly Ile Gly Val Pro Gly
        3650                3655                3660

Ile Gly Val Pro Gly Ile Gly Val Pro Gly Ile Gly Val Pro Gly
        3665                3670                3675

Ile Gly Val Pro Gly Ile Gly Val Pro Gly Ile Gly Val Pro Gly
        3680                3685                3690

Ile Gly Val Pro Gly Ile Gly Val Pro Gly Ile Gly Val Pro Gly
        3695                3700                3705

Ile Gly Val Pro Gly Ile Gly Val Pro Gly Ile Gly Val Pro Gly
        3710                3715                3720

Ile Gly Val Pro Gly Ile Gly Val Pro Gly Ile Gly Val Pro Gly
        3725                3730                3735

Ile Gly Val Pro Gly Ile Gly Val Pro Gly Ile Gly Val Pro Gly
        3740                3745                3750

Ile Gly Val Pro Gly Ile Gly Val Pro Gly Ile Gly Val Pro Gly
        3755                3760                3765

Ile Gly Val Pro Gly Ile Gly Val Pro Gly Ile Gly Val Pro Gly
        3770                3775                3780

Ile Gly Val Pro Gly Ile Gly Val Pro Gly Ile Gly Val Pro Gly
        3785                3790                3795

Ile Gly Val Pro Gly Ile Gly Val Pro Gly Ile Gly Val Pro Gly
        3800                3805                3810

Ile Gly Val Pro Gly Ile Gly Val Pro Gly Ile Gly Val Pro Gly
        3815                3820                3825

Ile Gly Val Pro Gly Ile Gly Val Pro Gly Ile Gly Val Pro Gly
        3830                3835                3840

Ile Gly Val Pro Gly Ile Gly Val Pro Gly Ile Gly Val Pro Gly
        3845                3850                3855

Ile Gly Val Pro Gly Ile Gly Val Pro Gly Ile Gly Val Pro Gly
        3860                3865                3870

Ile Gly Val Pro Gly Ile Gly Val Pro Gly Ile Gly Val Pro Gly
        3875                3880                3885
```

Ile Gly Val Pro Gly Ile Gly Val Pro Gly Ile Gly Val Pro Gly
    3890                3895                3900

Ile Gly Val Pro Gly Ile Gly Val Pro Gly Ile Gly Val Pro Gly
    3905                3910                3915

Ile Gly Val Pro Gly Ile Gly Val Pro Gly Ile Gly Val Pro Gly
    3920                3925                3930

Ile Gly Val Pro Gly Ile Gly Val Pro Gly Ile Gly Val Pro Gly
    3935                3940                3945

Ile Gly Val Pro Gly Ile Gly Val Pro Gly Ile Gly Val Pro Gly
    3950                3955                3960

Ile Gly Val Pro Gly Ile Gly Val Pro Gly Ile Gly Val Pro Gly
    3965                3970                3975

Ile Gly Val Pro Gly Ile Gly Val Pro Gly Ile Gly Val Pro Gly
    3980                3985                3990

Ile Gly Val Pro Gly Ile Gly Val Pro Gly Ile Gly Val Pro Gly
    3995                4000                4005

Ile Gly Val Pro Gly Ile Gly Val Pro Gly Ile Gly Val Pro Gly
    4010                4015                4020

Ile Gly Val Pro Gly Ile Gly Val Pro Gly Ile Gly Val Pro Gly
    4025                4030                4035

Ile Gly Val Pro Gly Ile Gly Val Pro Gly Ile Gly Val Pro Gly
    4040                4045                4050

Ile Gly Val Pro Gly Ile Gly Val Pro Gly Ile Gly Val Pro Gly
    4055                4060                4065

Ile Gly Val Pro Gly Ile Gly Val Pro Gly Ile Gly Val Pro Gly
    4070                4075                4080

Ile Gly Val Pro Gly Ile Gly Val Pro Gly Ile Gly Val Pro Gly
    4085                4090                4095

Ile Gly Val Pro Gly Ile Gly Val Pro Gly Ile Gly Val Pro Gly
    4100                4105                4110

Ile Gly Val Pro Gly Ile Gly Val Pro Gly Ile Gly Val Pro Gly
    4115                4120                4125

Ile Gly Val Pro Gly Ile Gly Val Pro Gly Ile Gly Val Pro Gly
    4130                4135                4140

Ile Gly Val Pro Gly Ile Gly Val Pro Gly Ile Gly Val Pro Gly
    4145                4150                4155

Ile Gly Val Pro Gly Ile Gly Val Pro Gly Ile Gly Val Pro Gly
    4160                4165                4170

Ile Gly Val Pro Gly Ile Gly Val Pro Gly Ile Gly Val Pro Gly
    4175                4180                4185

Ile Gly Val Pro Gly Ile Gly Val Pro Gly Ile Gly Val Pro Gly
    4190                4195                4200

Ile Gly Val Pro Gly Ile Gly Val Pro Gly Ile Gly Val Pro Gly
    4205                4210                4215

Ile Gly Val Pro Gly Ile Gly Val Pro Gly Ile Gly Val Pro Gly
    4220                4225                4230

Ile Gly Val Pro Gly Ile Gly Val Pro Gly Ile Gly Val Pro Gly
    4235                4240                4245

Ile Gly Val Pro Gly Ile Gly Val Pro Gly Ile Gly Val Pro Gly
    4250                4255                4260

Ile Gly Val Pro Gly Ile Gly Val Pro Gly Ile Gly Val Pro Gly
    4265                4270                4275

-continued

```
Ile Gly Val Pro Gly Ile Gly Val Pro Gly Ile Gly Val Pro Gly
    4280                4285                4290

Ile Gly Val Pro Gly Ile Gly Val Pro Gly Ile Gly Val Pro Gly
    4295                4300                4305

Ile Gly Val Pro Gly Ile Gly Val Pro Gly Ile Gly Val Pro Gly
    4310                4315                4320

Ile Gly Val Pro Gly Ile Gly Val Pro Gly Ile Gly Val Pro Gly
    4325                4330                4335

Ile Gly Val Pro Gly Ile Gly Val Pro Gly Ile Gly Val Pro Gly
    4340                4345                4350

Ile Gly Val Pro Gly Ile Gly Val Pro Gly Ile Gly Val Pro Gly
    4355                4360                4365

Ile Gly Val Pro Gly Ile Gly Val Pro Gly Ile Gly Val Pro Gly
    4370                4375                4380

Ile Gly Val Pro Gly Ile Gly Val Pro Gly Ile Gly Val Pro Gly
    4385                4390                4395

Ile Gly Val Pro Gly Ile Gly Val Pro Gly Ile Gly Val Pro Gly
    4400                4405                4410

Ile Gly Val Pro Gly Ile Gly Val Pro Gly Ile Gly Val Pro Gly
    4415                4420                4425

Ile Gly Val Pro Gly Ile Gly Val Pro Gly Ile Gly Val Pro Gly
    4430                4435                4440

Ile Gly Val Pro Gly Ile Gly Val Pro Gly Ile Gly Val Pro Gly
    4445                4450                4455

Ile Gly Val Pro Gly Ile Gly Val Pro Gly Ile Gly Val Pro Gly
    4460                4465                4470

Ile Gly Val Pro Gly Ile Gly Val Pro Gly Ile Gly Val Pro Gly
    4475                4480                4485

Ile Gly Val Pro Gly Ile Gly Val Pro Gly Ile Gly Val Pro Gly
    4490                4495                4500

Ile Gly Val Pro Gly Ile Gly Val Pro Gly Ile Gly Val Pro Gly
    4505                4510                4515

Ile Gly Val Pro Gly Ile Gly Val Pro Gly Ile Gly Val Pro Gly
    4520                4525                4530

Ile Gly Val Pro Gly Ile Gly Val Pro Gly Ile Gly Val Pro Gly
    4535                4540                4545

Ile Gly Val Pro Gly Ile Gly Val Pro Gly Ile Gly Val Pro Gly
    4550                4555                4560

Ile Gly Val Pro Gly Ile Gly Val Pro Gly Ile Gly Val Pro Gly
    4565                4570                4575

Ile Gly Val Pro Gly Ile Gly Val Pro Gly Ile Gly Val Pro Gly
    4580                4585                4590

Ile Gly Val Pro Gly Ile Gly Val Pro Gly Ile Gly Val Pro Gly
    4595                4600                4605

Ile Gly Val Pro Gly Ile Gly Val Pro Gly Ile Gly Val Pro Gly
    4610                4615                4620

Ile Gly Val Pro Gly Ile Gly Val Pro Gly Ile Gly Val Pro Gly
    4625                4630                4635

Ile Gly Val Pro Gly Ile Gly Val Pro Gly Ile Gly Val Pro Gly
    4640                4645                4650

Ile Gly Val Pro Gly Ile Gly Val Pro Gly Ile Gly Val Pro Gly
    4655                4660                4665

Ile Gly Val Pro Gly Ile Gly Val Pro Gly Ile Gly Val Pro Gly
```

```
                    4670                4675                4680

Ile Gly Val Pro Gly Ile Gly Val Pro Gly Ile Gly Val Pro Gly
    4685                4690                4695

Ile Gly Val Pro Gly Ile Gly Val Pro Gly Ile Gly Val Pro Gly
    4700                4705                4710

Ile Gly Val Pro Gly Ile Gly Val Pro Gly Ile Gly Val Pro Gly
    4715                4720                4725

Ile Gly Val Pro Gly Ile Gly Val Pro Gly Ile Gly Val Pro Gly
    4730                4735                4740

Ile Gly Val Pro Gly Ile Gly Val Pro Gly Ile Gly Val Pro Gly
    4745                4750                4755

Ile Gly Val Pro Gly Ile Gly Val Pro Gly Ile Gly Val Pro Gly
    4760                4765                4770

Ile Gly Val Pro Gly Ile Gly Val Pro Gly Ile Gly Val Pro Gly
    4775                4780                4785

Ile Gly Val Pro Gly Ile Gly Val Pro Gly Ile Gly Val Pro Gly
    4790                4795                4800

Ile Gly Val Pro Gly Ile Gly Val Pro Gly Ile Gly Val Pro Gly
    4805                4810                4815

Ile Gly Val Pro Gly Ile Gly Val Pro Gly Ile Gly Val Pro Gly
    4820                4825                4830

Ile Gly Val Pro Gly Ile Gly Val Pro Gly Ile Gly Val Pro Gly
    4835                4840                4845

Ile Gly Val Pro Gly Ile Gly Val Pro Gly Ile Gly Val Pro Gly
    4850                4855                4860

Ile Gly Val Pro Gly Ile Gly Val Pro Gly Ile Gly Val Pro Gly
    4865                4870                4875

Ile Gly Val Pro Gly Ile Gly Val Pro Gly Ile Gly Val Pro Gly
    4880                4885                4890

Ile Gly Val Pro Gly Ile Gly Val Pro Gly Ile Gly Val Pro Gly
    4895                4900                4905

Ile Gly Val Pro Gly Ile Gly Val Pro Gly Ile Gly Val Pro Gly
    4910                4915                4920

Ile Gly Val Pro Gly Ile Gly Val Pro Gly Ile Gly Val Pro Gly
    4925                4930                4935

Ile Gly Val Pro Gly Ile Gly Val Pro Gly Ile Gly Val Pro Gly
    4940                4945                4950

Ile Gly Val Pro Gly Ile Gly Val Pro Gly Ile Gly Val Pro Gly
    4955                4960                4965

Ile Gly Val Pro Gly Ile Gly Val Pro Gly Ile Gly Val Pro Gly
    4970                4975                4980

Ile Gly Val Pro Gly Ile Gly Val Pro Gly Ile Gly Val Pro Gly
    4985                4990                4995

Ile Gly
    5000

<210> SEQ ID NO 10
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

-continued

```
Gly Val Pro Gly Val Gly Val Pro Gly Val Gly Val Pro Gly Val Gly
  1               5                  10                 15
Val Pro Gly Val Gly Val Pro Gly Val Gly Val Pro Gly Val Gly Val
             20                  25                  30
Pro Gly Val Gly Val Pro Gly Val Gly Val Pro Gly Val Gly Val Pro
             35                  40                  45
Gly Val Gly Val Pro Gly Val Gly Val Pro Gly Val Gly Val Pro Gly
         50                  55                  60
Val Gly Val Pro Gly Val Gly Val Pro Gly Val Gly Val Pro Gly Val
 65              70                  75                  80
Gly Val Pro Gly Val Gly Val Pro Gly Val Gly Val Pro Gly Val Gly
             85                  90                  95
Val Pro Gly Val Gly Val Pro Gly Val Gly Val Pro Gly Val Gly Val
            100                 105                 110
Pro Gly Val Gly Val Pro Gly Val Gly Val Pro Gly Val Gly Val Pro
            115                 120                 125
Gly Val Gly Val Pro Gly Val Gly Val Pro Gly Val Gly Val Pro Gly
        130                 135                 140
Val Gly Val Pro Gly Val Gly Val Pro Gly Val Gly Val Pro Gly Val
145             150                 155                 160
Gly Val Pro Gly Val Gly Val Pro Gly Val Gly Val Pro Gly Val Gly
            165                 170                 175
Val Pro Gly Val Gly Val Pro Gly Val Gly Val Pro Gly Val Gly Val
            180                 185                 190
Pro Gly Val Gly Val Pro Gly Val Gly Val Pro Gly Val Gly Val Pro
            195                 200                 205
Gly Val Gly Val Pro Gly Val Gly Val Pro Gly Val Gly Val Pro Gly
        210                 215                 220
Val Gly Val Pro Gly Val Gly Val Pro Gly Val Gly Val Pro Gly Val
225             230                 235                 240
Gly Val Pro Gly Val Gly Val Pro Gly Val Gly Val Pro Gly Val Gly
            245                 250                 255
Val Pro Gly Val Gly Val Pro Gly Val Gly Val Pro Gly Val Gly Val
            260                 265                 270
Pro Gly Val Gly Val Pro Gly Val Gly Val Pro Gly Val Gly Val Pro
            275                 280                 285
Gly Val Gly Val Pro Gly Val Gly Val Pro Gly Val Gly Val Pro Gly
        290                 295                 300
Val Gly Val Pro Gly Val Gly Val Pro Gly Val Gly Val Pro Gly Val
305             310                 315                 320
Gly Val Pro Gly Val Gly Val Pro Gly Val Gly Val Pro Gly Val Gly
            325                 330                 335
Val Pro Gly Val Gly Val Pro Gly Val Gly Val Pro Gly Val Gly Val
            340                 345                 350
Pro Gly Val Gly Val Pro Gly Val Gly Val Pro Gly Val Gly Val Pro
            355                 360                 365
Gly Val Gly Val Pro Gly Val Gly Val Pro Gly Val Gly Val Pro Gly
        370                 375                 380
Val Gly Val Pro Gly Val Gly Val Pro Gly Val Gly Val Pro Gly Val
385             390                 395                 400
Gly Val Pro Gly Val Gly Val Pro Gly Val Gly Val Pro Gly Val Gly
            405                 410                 415
Val Pro Gly Val Gly Val Pro Gly Val Gly Val Pro Gly Val Gly Val
```

-continued

```
                420                 425                 430
Pro Gly Val Gly Val Pro Gly Val Gly Val Pro Gly Val Gly Val Pro
            435                 440                 445

Gly Val Gly Val Pro Gly Val Gly Val Pro Gly Val Gly Val Pro Gly
        450                 455                 460

Val Gly Val Pro Gly Val Gly Val Pro Gly Val Gly Val Pro Gly Val
465                 470                 475                 480

Gly Tyr

<210> SEQ ID NO 11
<211> LENGTH: 962
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Val Pro Gly Ala Gly Val Pro Gly Ala Gly Val Pro Gly Ala Gly
1               5                   10                  15

Val Pro Gly Ala Gly Val Pro Gly Ala Gly Val Pro Gly Ala Gly Val
            20                  25                  30

Pro Gly Ala Gly Val Pro Gly Ala Gly Val Pro Gly Ala Gly Val Pro
        35                  40                  45

Gly Ala Gly Val Pro Gly Ala Gly Val Pro Gly Ala Gly Val Pro Gly
    50                  55                  60

Ala Gly Val Pro Gly Ala Gly Val Pro Gly Ala Gly Val Pro Gly Ala
65                  70                  75                  80

Gly Val Pro Gly Ala Gly Val Pro Gly Ala Gly Val Pro Gly Ala Gly
                85                  90                  95

Val Pro Gly Ala Gly Val Pro Gly Ala Gly Val Pro Gly Ala Gly Val
            100                 105                 110

Pro Gly Ala Gly Val Pro Gly Ala Gly Val Pro Gly Ala Gly Val Pro
        115                 120                 125

Gly Ala Gly Val Pro Gly Ala Gly Val Pro Gly Ala Gly Val Pro Gly
    130                 135                 140

Ala Gly Val Pro Gly Ala Gly Val Pro Gly Ala Gly Val Pro Gly Ala
145                 150                 155                 160

Gly Val Pro Gly Ala Gly Val Pro Gly Ala Gly Val Pro Gly Ala Gly
                165                 170                 175

Val Pro Gly Ala Gly Val Pro Gly Ala Gly Val Pro Gly Ala Gly Val
            180                 185                 190

Pro Gly Ala Gly Val Pro Gly Ala Gly Val Pro Gly Ala Gly Val Pro
        195                 200                 205

Gly Ala Gly Val Pro Gly Ala Gly Val Pro Gly Ala Gly Val Pro Gly
    210                 215                 220

Ala Gly Val Pro Gly Ala Gly Val Pro Gly Ala Gly Val Pro Gly Ala
225                 230                 235                 240

Gly Val Pro Gly Ala Gly Val Pro Gly Ala Gly Val Pro Gly Ala Gly
                245                 250                 255

Val Pro Gly Ala Gly Val Pro Gly Ala Gly Val Pro Gly Ala Gly Val
            260                 265                 270

Pro Gly Ala Gly Val Pro Gly Ala Gly Val Pro Gly Ala Gly Val Pro
        275                 280                 285

Gly Ala Gly Val Pro Gly Ala Gly Val Pro Gly Ala Gly Val Pro Gly
```

```
                290                 295                 300
Ala Gly Val Pro Gly Ala Gly Val Pro Gly Ala Gly Val Pro Gly Ala
305                 310                 315                 320

Gly Val Pro Gly Ala Gly Val Pro Gly Ala Gly Val Pro Gly Ala Gly
                325                 330                 335

Val Pro Gly Ala Gly Val Pro Gly Ala Gly Val Pro Gly Ala Gly Val
                340                 345                 350

Pro Gly Ala Gly Val Pro Gly Ala Gly Val Pro Gly Ala Gly Val Pro
            355                 360                 365

Gly Ala Gly Val Pro Gly Ala Gly Val Pro Gly Ala Gly Val Pro Gly
        370                 375                 380

Ala Gly Val Pro Gly Ala Gly Val Pro Gly Ala Gly Val Pro Gly Ala
385                 390                 395                 400

Gly Val Pro Gly Ala Gly Val Pro Gly Ala Gly Val Pro Gly Ala Gly
                405                 410                 415

Val Pro Gly Ala Gly Val Pro Gly Ala Gly Val Pro Gly Ala Gly Val
                420                 425                 430

Pro Gly Ala Gly Val Pro Gly Ala Gly Val Pro Gly Ala Gly Val Pro
            435                 440                 445

Gly Ala Gly Val Pro Gly Ala Gly Val Pro Gly Ala Gly Val Pro Gly
        450                 455                 460

Ala Gly Val Pro Gly Ala Gly Val Pro Gly Ala Gly Val Pro Gly Ala
465                 470                 475                 480

Gly Val Pro Gly Ala Gly Val Pro Gly Ala Gly Val Pro Gly Ala Gly
                485                 490                 495

Val Pro Gly Ala Gly Val Pro Gly Ala Gly Val Pro Gly Ala Gly Val
                500                 505                 510

Pro Gly Ala Gly Val Pro Gly Ala Gly Val Pro Gly Ala Gly Val Pro
            515                 520                 525

Gly Ala Gly Val Pro Gly Ala Gly Val Pro Gly Ala Gly Val Pro Gly
        530                 535                 540

Ala Gly Val Pro Gly Ala Gly Val Pro Gly Ala Gly Val Pro Gly Ala
545                 550                 555                 560

Gly Val Pro Gly Ala Gly Val Pro Gly Ala Gly Val Pro Gly Ala Gly
                565                 570                 575

Val Pro Gly Ala Gly Val Pro Gly Ala Gly Val Pro Gly Ala Gly Val
                580                 585                 590

Pro Gly Ala Gly Val Pro Gly Ala Gly Val Pro Gly Ala Gly Val Pro
            595                 600                 605

Gly Ala Gly Val Pro Gly Ala Gly Val Pro Gly Ala Gly Val Pro Gly
        610                 615                 620

Ala Gly Val Pro Gly Ala Gly Val Pro Gly Ala Gly Val Pro Gly Ala
625                 630                 635                 640

Gly Val Pro Gly Ala Gly Val Pro Gly Ala Gly Val Pro Gly Ala Gly
                645                 650                 655

Val Pro Gly Ala Gly Val Pro Gly Ala Gly Val Pro Gly Ala Gly Val
                660                 665                 670

Pro Gly Ala Gly Val Pro Gly Ala Gly Val Pro Gly Ala Gly Val Pro
            675                 680                 685

Gly Ala Gly Val Pro Gly Ala Gly Val Pro Gly Ala Gly Val Pro Gly
        690                 695                 700

Ala Gly Val Pro Gly Ala Gly Val Pro Gly Ala Gly Val Pro Gly Ala
705                 710                 715                 720
```

```
Gly Val Pro Gly Ala Gly Val Pro Gly Ala Gly Val Pro Gly Ala Gly
            725                 730                 735
Val Pro Gly Ala Gly Val Pro Gly Ala Gly Val Pro Gly Ala Gly Val
        740                 745                 750
Pro Gly Ala Gly Val Pro Gly Ala Gly Val Pro Gly Ala Gly Val Pro
            755                 760                 765
Gly Ala Gly Val Pro Gly Ala Gly Val Pro Gly Ala Gly Val Pro Gly
770                 775                 780
Ala Gly Val Pro Gly Ala Gly Val Pro Gly Ala Gly Val Pro Gly Ala
785                 790                 795                 800
Gly Val Pro Gly Ala Gly Val Pro Gly Ala Gly Val Pro Gly Ala Gly
            805                 810                 815
Val Pro Gly Ala Gly Val Pro Gly Ala Gly Val Pro Gly Ala Gly Val
        820                 825                 830
Pro Gly Ala Gly Val Pro Gly Ala Gly Val Pro Gly Ala Gly Val Pro
            835                 840                 845
Gly Ala Gly Val Pro Gly Ala Gly Val Pro Gly Ala Gly Val Pro Gly
        850                 855                 860
Ala Gly Val Pro Gly Ala Gly Val Pro Gly Ala Gly Val Pro Gly Ala
865                 870                 875                 880
Gly Val Pro Gly Ala Gly Val Pro Gly Ala Gly Val Pro Gly Ala Gly
            885                 890                 895
Val Pro Gly Ala Gly Val Pro Gly Ala Gly Val Pro Gly Ala Gly Val
        900                 905                 910
Pro Gly Ala Gly Val Pro Gly Ala Gly Val Pro Gly Ala Gly Val Pro
            915                 920                 925
Gly Ala Gly Val Pro Gly Ala Gly Val Pro Gly Ala Gly Val Pro Gly
        930                 935                 940
Ala Gly Val Pro Gly Ala Gly Val Pro Gly Ala Gly Val Pro Gly Ala
945                 950                 955                 960

Gly Tyr

<210> SEQ ID NO 12
<211> LENGTH: 962
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Val Pro Gly Ala Gly Val Pro Gly Ala Gly Val Pro Gly Ala Gly
1               5                   10                  15
Val Pro Gly Ala Gly Val Pro Gly Ala Gly Val Pro Gly Ala Gly Val
            20                  25                  30
Pro Gly Ala Gly Val Pro Gly Ala Gly Val Pro Gly Ala Gly Val Pro
        35                  40                  45
Gly Ala Gly Val Pro Gly Ala Gly Val Pro Gly Ala Gly Val Pro Gly
    50                  55                  60
Ala Gly Val Pro Gly Ala Gly Val Pro Gly Ala Gly Val Pro Gly Ala
65                  70                  75                  80
Gly Val Pro Gly Ala Gly Val Pro Gly Ala Gly Val Pro Gly Ala Gly
                85                  90                  95
Val Pro Gly Ala Gly Val Pro Gly Ala Gly Val Pro Gly Ala Gly Val
            100                 105                 110
```

```
Pro Gly Ala Gly Val Pro Gly Ala Gly Val Pro Gly Ala Gly Val Pro
        115                 120                 125
Gly Ala Gly Val Pro Gly Ala Gly Val Pro Gly Ala Gly Val Pro Gly
    130                 135                 140
Ala Gly Val Pro Gly Ala Gly Val Pro Gly Ala Gly Val Pro Gly Ala
145                 150                 155                 160
Gly Val Pro Gly Ala Gly Val Pro Gly Ala Gly Val Pro Gly Ala Gly
            165                 170                 175
Val Pro Gly Ala Gly Val Pro Gly Ala Gly Val Pro Gly Ala Gly Val
        180                 185                 190
Pro Gly Ala Gly Val Pro Gly Ala Gly Val Pro Gly Ala Gly Val Pro
        195                 200                 205
Gly Ala Gly Val Pro Gly Ala Gly Val Pro Gly Ala Gly Val Pro Gly
    210                 215                 220
Ala Gly Val Pro Gly Ala Gly Val Pro Gly Ala Gly Val Pro Gly Ala
225                 230                 235                 240
Gly Val Pro Gly Ala Gly Val Pro Gly Ala Gly Val Pro Gly Ala Gly
            245                 250                 255
Val Pro Gly Ala Gly Val Pro Gly Ala Gly Val Pro Gly Ala Gly Val
        260                 265                 270
Pro Gly Ala Gly Val Pro Gly Ala Gly Val Pro Gly Ala Gly Val Pro
        275                 280                 285
Gly Ala Gly Val Pro Gly Ala Gly Val Pro Gly Ala Gly Val Pro Gly
    290                 295                 300
Ala Gly Val Pro Gly Ala Gly Val Pro Gly Ala Gly Val Pro Gly Ala
305                 310                 315                 320
Gly Val Pro Gly Ala Gly Val Pro Gly Ala Gly Val Pro Gly Ala Gly
            325                 330                 335
Val Pro Gly Ala Gly Val Pro Gly Ala Gly Val Pro Gly Ala Gly Val
        340                 345                 350
Pro Gly Ala Gly Val Pro Gly Ala Gly Val Pro Gly Ala Gly Val Pro
        355                 360                 365
Gly Ala Gly Val Pro Gly Ala Gly Val Pro Gly Ala Gly Val Pro Gly
    370                 375                 380
Ala Gly Val Pro Gly Ala Gly Val Pro Gly Ala Gly Val Pro Gly Ala
385                 390                 395                 400
Gly Val Pro Gly Ala Gly Val Pro Gly Ala Gly Val Pro Gly Ala Gly
            405                 410                 415
Val Pro Gly Ala Gly Val Pro Gly Ala Gly Val Pro Gly Ala Gly Val
        420                 425                 430
Pro Gly Ala Gly Val Pro Gly Ala Gly Val Pro Gly Ala Gly Val Pro
        435                 440                 445
Gly Ala Gly Val Pro Gly Ala Gly Val Pro Gly Ala Gly Val Pro Gly
    450                 455                 460
Ala Gly Val Pro Gly Ala Gly Val Pro Gly Ala Gly Val Pro Gly Ala
465                 470                 475                 480
Gly Val Pro Gly Ile Gly Val Pro Gly Ile Gly Val Pro Gly Ile Gly
            485                 490                 495
Val Pro Gly Ile Gly Val Pro Gly Ile Gly Val Pro Gly Ile Gly Val
        500                 505                 510
Pro Gly Ile Gly Val Pro Gly Ile Gly Val Pro Gly Ile Gly Val Pro
        515                 520                 525
```

```
Gly Ile Gly Val Pro Gly Ile Gly Val Pro Gly Ile Gly Val Pro Gly
        530                 535                 540
Ile Gly Val Pro Gly Ile Gly Val Pro Gly Ile Gly Val Pro Gly Ile
545                 550                 555                 560
Gly Val Pro Gly Ile Gly Val Pro Gly Ile Gly Val Pro Gly Ile Gly
                565                 570                 575
Val Pro Gly Ile Gly Val Pro Gly Ile Gly Val Pro Gly Ile Gly Val
            580                 585                 590
Pro Gly Ile Gly Val Pro Gly Ile Gly Val Pro Gly Ile Gly Val Pro
        595                 600                 605
Gly Ile Gly Val Pro Gly Ile Gly Val Pro Gly Ile Gly Val Pro Gly
    610                 615                 620
Ile Gly Val Pro Gly Ile Gly Val Pro Gly Ile Gly Val Pro Gly Ile
625                 630                 635                 640
Gly Val Pro Gly Ile Gly Val Pro Gly Ile Gly Val Pro Gly Ile Gly
                645                 650                 655
Val Pro Gly Ile Gly Val Pro Gly Ile Gly Val Pro Gly Ile Gly Val
            660                 665                 670
Pro Gly Ile Gly Val Pro Gly Ile Gly Val Pro Gly Ile Gly Val Pro
        675                 680                 685
Gly Ile Gly Val Pro Gly Ile Gly Val Pro Gly Ile Gly Val Pro Gly
    690                 695                 700
Ile Gly Val Pro Gly Ile Gly Val Pro Gly Ile Gly Val Pro Gly Ile
705                 710                 715                 720
Gly Val Pro Gly Ile Gly Val Pro Gly Ile Gly Val Pro Gly Ile Gly
                725                 730                 735
Val Pro Gly Ile Gly Val Pro Gly Ile Gly Val Pro Gly Ile Gly Val
            740                 745                 750
Pro Gly Ile Gly Val Pro Gly Ile Gly Val Pro Gly Ile Gly Val Pro
        755                 760                 765
Gly Ile Gly Val Pro Gly Ile Gly Val Pro Gly Ile Gly Val Pro Gly
    770                 775                 780
Ile Gly Val Pro Gly Ile Gly Val Pro Gly Ile Gly Val Pro Gly Ile
785                 790                 795                 800
Gly Val Pro Gly Ile Gly Val Pro Gly Ile Gly Val Pro Gly Ile Gly
                805                 810                 815
Val Pro Gly Ile Gly Val Pro Gly Ile Gly Val Pro Gly Ile Gly Val
            820                 825                 830
Pro Gly Ile Gly Val Pro Gly Ile Gly Val Pro Gly Ile Gly Val Pro
        835                 840                 845
Gly Ile Gly Val Pro Gly Ile Gly Val Pro Gly Ile Gly Val Pro Gly
    850                 855                 860
Ile Gly Val Pro Gly Ile Gly Val Pro Gly Ile Gly Val Pro Gly Ile
865                 870                 875                 880
Gly Val Pro Gly Ile Gly Val Pro Gly Ile Gly Val Pro Gly Ile Gly
                885                 890                 895
Val Pro Gly Ile Gly Val Pro Gly Ile Gly Val Pro Gly Ile Gly Val
            900                 905                 910
Pro Gly Ile Gly Val Pro Gly Ile Gly Val Pro Gly Ile Gly Val Pro
        915                 920                 925
Gly Ile Gly Val Pro Gly Ile Gly Val Pro Gly Ile Gly Val Pro Gly
    930                 935                 940
Ile Gly Val Pro Gly Ile Gly Val Pro Gly Ile Gly Val Pro Gly Ile
```

```
<210> SEQ ID NO 13
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Gly Gly Gly Ser Gly Gly
            115                 120                 125

Gly Gly Ser Gly Gly Gly Ser Gln Ile Val Leu Ser Gln Ser Pro
    130                 135                 140

Ala Ile Leu Ser Ala Ser Pro Gly Glu Lys Val Thr Met Thr Cys Arg
145                 150                 155                 160

Ala Ser Ser Ser Val Ser Tyr Ile His Trp Phe Gln Gln Lys Pro Gly
                165                 170                 175

Ser Ser Pro Lys Pro Trp Ile Tyr Ala Thr Ser Asn Leu Ala Ser Gly
            180                 185                 190

Val Pro Val Arg Phe Ser Gly Ser Gly Ser Gly Thr Ser Tyr Ser Leu
        195                 200                 205

Thr Ile Ser Arg Val Glu Ala Glu Asp Ala Ala Thr Tyr Tyr Cys Gln
    210                 215                 220

Gln Trp Thr Ser Asn Pro Pro Thr Phe Gly Gly Gly Thr Lys Leu Glu
225                 230                 235                 240

Ile Lys Arg Thr

```
<210> SEQ ID NO 14
<211> LENGTH: 2500
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(2500)
<223> OTHER INFORMATION: This sequence may encompass 1 to 500 "VPGXG"
      repeats
<220> FEATURE:
<221> NAME/KEY: MOD_RES
<222> LOCATION: (4)..(4)
<223> OTHER INFORMATION: Any amino acid
```

```
-continued

<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (39)..(39)
<223> OTHER INFORMATION: Any amino acid
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (64)..(64)
<223> OTHER INFORMATION: Any amino acid
<220> FEATURE:
<221> NAME/KEY: MOD_RES
<222> LOCATION: (69)..(69)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (84)..(84)
<223> OTHER INFORMATION: Any amino acid
<220> FEATURE:
<221> NAME/KEY: MOD_RES
<222> LOCATION: (89)..(89)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (99)..(99)
<223> OTHER INFORMATION: Any amino acid
<220> FEATURE:
<221> NAME/KEY: MOD_RES
<222> LOCATION: (104)..(104)
```

```
<223> OTHER INFORMATION: Any amino acid
<220> FEATURE:
<221> NAME/KEY: MOD_RES
<222> LOCATION: (109)..(109)
<223> OTHER INFORMATION: Any amino acid
<220> FEATURE:
<221> NAME/KEY: MOD_RES
<222> LOCATION: (114)..(114)
<223> OTHER INFORMATION: Any amino acid
<220> FEATURE:
<221> NAME/KEY: MOD_RES
<222> LOCATION: (119)..(119)
<223> OTHER INFORMATION: Any amino acid
<220> FEATURE:
<221> NAME/KEY: MOD_RES
<222> LOCATION: (124)..(124)
<223> OTHER INFORMATION: Any amino acid
<220> FEATURE:
<221> NAME/KEY: MOD_RES
<222> LOCATION: (129)..(129)
<223> OTHER INFORMATION: Any amino acid
<220> FEATURE:
<221> NAME/KEY: MOD_RES
<222> LOCATION: (134)..(134)
<223> OTHER INFORMATION: Any amino acid
<220> FEATURE:
<221> NAME/KEY: MOD_RES
<222> LOCATION: (139)..(139)
<223> OTHER INFORMATION: Any amino acid
<220> FEATURE:
<221> NAME/KEY: MOD_RES
<222> LOCATION: (144)..(144)
<223> OTHER INFORMATION: Any amino acid
<220> FEATURE:
<221> NAME/KEY: MOD_RES
<222> LOCATION: (149)..(149)
<223> OTHER INFORMATION: Any amino acid
<220> FEATURE:
<221> NAME/KEY: MOD_RES
<222> LOCATION: (154)..(154)
<223> OTHER INFORMATION: Any amino acid
<220> FEATURE:
<221> NAME/KEY: MOD_RES
<222> LOCATION: (159)..(159)
<223> OTHER INFORMATION: Any amino acid
<220> FEATURE:
<221> NAME/KEY: MOD_RES
<222> LOCATION: (164)..(164)
<223> OTHER INFORMATION: Any amino acid
<220> FEATURE:
<221> NAME/KEY: MOD_RES
<222> LOCATION: (169)..(169)
<223> OTHER INFORMATION: Any amino acid
<220> FEATURE:
<221> NAME/KEY: MOD_RES
<222> LOCATION: (174)..(174)
<223> OTHER INFORMATION: Any amino acid
<220> FEATURE:
<221> NAME/KEY: MOD_RES
<222> LOCATION: (179)..(179)
<223> OTHER INFORMATION: Any amino acid
<220> FEATURE:
<221> NAME/KEY: MOD_RES
<222> LOCATION: (184)..(184)
<223> OTHER INFORMATION: Any amino acid
<220> FEATURE:
<221> NAME/KEY: MOD_RES
<222> LOCATION: (189)..(189)
<223> OTHER INFORMATION: Any amino acid
<220> FEATURE:
<221> NAME/KEY: MOD_RES
<222> LOCATION: (194)..(194)
<223> OTHER INFORMATION: Any amino acid
<220> FEATURE:
<221> NAME/KEY: MOD_RES
<222> LOCATION: (199)..(199)
<223> OTHER INFORMATION: Any amino acid
<220> FEATURE:
<221> NAME/KEY: MOD_RES
```

-continued

```
<222> LOCATION: (204)..(204)
<223> OTHER INFORMATION: Any amino acid
<220> FEATURE:
<221> NAME/KEY: MOD_RES
<222> LOCATION: (209)..(209)
<223> OTHER INFORMATION: Any amino acid
<220> FEATURE:
<221> NAME/KEY: MOD_RES
<222> LOCATION: (214)..(214)
<223> OTHER INFORMATION: Any amino acid
<220> FEATURE:
<221> NAME/KEY: MOD_RES
<222> LOCATION: (219)..(219)
<223> OTHER INFORMATION: Any amino acid
<220> FEATURE:
<221> NAME/KEY: MOD_RES
<222> LOCATION: (224)..(224)
<223> OTHER INFORMATION: Any amino acid
<220> FEATURE:
<221> NAME/KEY: MOD_RES
<222> LOCATION: (229)..(229)
<223> OTHER INFORMATION: Any amino acid
<220> FEATURE:
<221> NAME/KEY: MOD_RES
<222> LOCATION: (234)..(234)
<223> OTHER INFORMATION: Any amino acid
<220> FEATURE:
<221> NAME/KEY: MOD_RES
<222> LOCATION: (239)..(239)
<223> OTHER INFORMATION: Any amino acid
<220> FEATURE:
<221> NAME/KEY: MOD_RES
<222> LOCATION: (244)..(244)
<223> OTHER INFORMATION: Any amino acid
<220> FEATURE:
<221> NAME/KEY: MOD_RES
<222> LOCATION: (249)..(249)
<223> OTHER INFORMATION: Any amino acid
<220> FEATURE:
<221> NAME/KEY: MOD_RES
<222> LOCATION: (254)..(254)
<223> OTHER INFORMATION: Any amino acid
<220> FEATURE:
<221> NAME/KEY: MOD_RES
<222> LOCATION: (259)..(259)
<223> OTHER INFORMATION: Any amino acid
<220> FEATURE:
<221> NAME/KEY: MOD_RES
<222> LOCATION: (264)..(264)
<223> OTHER INFORMATION: Any amino acid
<220> FEATURE:
<221> NAME/KEY: MOD_RES
<222> LOCATION: (269)..(269)
<223> OTHER INFORMATION: Any amino acid
<220> FEATURE:
<221> NAME/KEY: MOD_RES
<222> LOCATION: (274)..(274)
<223> OTHER INFORMATION: Any amino acid
<220> FEATURE:
<221> NAME/KEY: MOD_RES
<222> LOCATION: (279)..(279)
<223> OTHER INFORMATION: Any amino acid
<220> FEATURE:
<221> NAME/KEY: MOD_RES
<222> LOCATION: (284)..(284)
<223> OTHER INFORMATION: Any amino acid
<220> FEATURE:
<221> NAME/KEY: MOD_RES
<222> LOCATION: (289)..(289)
<223> OTHER INFORMATION: Any amino acid
<220> FEATURE:
<221> NAME/KEY: MOD_RES
<222> LOCATION: (294)..(294)
<223> OTHER INFORMATION: Any amino acid
<220> FEATURE:
<221> NAME/KEY: MOD_RES
<222> LOCATION: (299)..(299)
<223> OTHER INFORMATION: Any amino acid
<220> FEATURE:
```

```
<221> NAME/KEY: MOD_RES
<222> LOCATION: (304)..(304)
<223> OTHER INFORMATION: Any amino acid
<220> FEATURE:
<221> NAME/KEY: MOD_RES
<222> LOCATION: (309)..(309)
<223> OTHER INFORMATION: Any amino acid
<220> FEATURE:
<221> NAME/KEY: MOD_RES
<222> LOCATION: (314)..(314)
<223> OTHER INFORMATION: Any amino acid
<220> FEATURE:
<221> NAME/KEY: MOD_RES
<222> LOCATION: (319)..(319)
<223> OTHER INFORMATION: Any amino acid
<220> FEATURE:
<221> NAME/KEY: MOD_RES
<222> LOCATION: (324)..(324)
<223> OTHER INFORMATION: Any amino acid
<220> FEATURE:
<221> NAME/KEY: MOD_RES
<222> LOCATION: (329)..(329)
<223> OTHER INFORMATION: Any amino acid
<220> FEATURE:
<221> NAME/KEY: MOD_RES
<222> LOCATION: (334)..(334)
<223> OTHER INFORMATION: Any amino acid
<220> FEATURE:
<221> NAME/KEY: MOD_RES
<222> LOCATION: (339)..(339)
<223> OTHER INFORMATION: Any amino acid
<220> FEATURE:
<221> NAME/KEY: MOD_RES
<222> LOCATION: (344)..(344)
<223> OTHER INFORMATION: Any amino acid
<220> FEATURE:
<221> NAME/KEY: MOD_RES
<222> LOCATION: (349)..(349)
<223> OTHER INFORMATION: Any amino acid
<220> FEATURE:
<221> NAME/KEY: MOD_RES
<222> LOCATION: (354)..(354)
<223> OTHER INFORMATION: Any amino acid
<220> FEATURE:
<221> NAME/KEY: MOD_RES
<222> LOCATION: (359)..(359)
<223> OTHER INFORMATION: Any amino acid
<220> FEATURE:
<221> NAME/KEY: MOD_RES
<222> LOCATION: (364)..(364)
<223> OTHER INFORMATION: Any amino acid
<220> FEATURE:
<221> NAME/KEY: MOD_RES
<222> LOCATION: (369)..(369)
<223> OTHER INFORMATION: Any amino acid
<220> FEATURE:
<221> NAME/KEY: MOD_RES
<222> LOCATION: (374)..(374)
<223> OTHER INFORMATION: Any amino acid
<220> FEATURE:
<221> NAME/KEY: MOD_RES
<222> LOCATION: (379)..(379)
<223> OTHER INFORMATION: Any amino acid
<220> FEATURE:
<221> NAME/KEY: MOD_RES
<222> LOCATION: (384)..(384)
<223> OTHER INFORMATION: Any amino acid
<220> FEATURE:
<221> NAME/KEY: MOD_RES
<222> LOCATION: (389)..(389)
<223> OTHER INFORMATION: Any amino acid
<220> FEATURE:
<221> NAME/KEY: MOD_RES
<222> LOCATION: (394)..(394)
<223> OTHER INFORMATION: Any amino acid
<220> FEATURE:
<221> NAME/KEY: MOD_RES
<222> LOCATION: (399)..(399)
<223> OTHER INFORMATION: Any amino acid
```

-continued

```
<220> FEATURE:
<221> NAME/KEY: MOD_RES
<222> LOCATION: (404)..(404)
<223> OTHER INFORMATION: Any amino acid
<220> FEATURE:
<221> NAME/KEY: MOD_RES
<222> LOCATION: (409)..(409)
<223> OTHER INFORMATION: Any amino acid
<220> FEATURE:
<221> NAME/KEY: MOD_RES
<222> LOCATION: (414)..(414)
<223> OTHER INFORMATION: Any amino acid
<220> FEATURE:
<221> NAME/KEY: MOD_RES
<222> LOCATION: (419)..(419)
<223> OTHER INFORMATION: Any amino acid
<220> FEATURE:
<221> NAME/KEY: MOD_RES
<222> LOCATION: (424)..(424)
<223> OTHER INFORMATION: Any amino acid
<220> FEATURE:
<221> NAME/KEY: MOD_RES
<222> LOCATION: (429)..(429)
<223> OTHER INFORMATION: Any amino acid
<220> FEATURE:
<221> NAME/KEY: MOD_RES
<222> LOCATION: (434)..(434)
<223> OTHER INFORMATION: Any amino acid
<220> FEATURE:
<221> NAME/KEY: MOD_RES
<222> LOCATION: (439)..(439)
<223> OTHER INFORMATION: Any amino acid
<220> FEATURE:
<221> NAME/KEY: MOD_RES
<222> LOCATION: (444)..(444)
<223> OTHER INFORMATION: Any amino acid
<220> FEATURE:
<221> NAME/KEY: MOD_RES
<222> LOCATION: (449)..(449)
<223> OTHER INFORMATION: Any amino acid
<220> FEATURE:
<221> NAME/KEY: MOD_RES
<222> LOCATION: (454)..(454)
<223> OTHER INFORMATION: Any amino acid
<220> FEATURE:
<221> NAME/KEY: MOD_RES
<222> LOCATION: (459)..(459)
<223> OTHER INFORMATION: Any amino acid
<220> FEATURE:
<221> NAME/KEY: MOD_RES
<222> LOCATION: (464)..(464)
<223> OTHER INFORMATION: Any amino acid
<220> FEATURE:
<221> NAME/KEY: MOD_RES
<222> LOCATION: (469)..(469)
<223> OTHER INFORMATION: Any amino acid
<220> FEATURE:
<221> NAME/KEY: MOD_RES
<222> LOCATION: (474)..(474)
<223> OTHER INFORMATION: Any amino acid
<220> FEATURE:
<221> NAME/KEY: MOD_RES
<222> LOCATION: (479)..(479)
<223> OTHER INFORMATION: Any amino acid
<220> FEATURE:
<221> NAME/KEY: MOD_RES
<222> LOCATION: (484)..(484)
<223> OTHER INFORMATION: Any amino acid
<220> FEATURE:
<221> NAME/KEY: MOD_RES
<222> LOCATION: (489)..(489)
<223> OTHER INFORMATION: Any amino acid
<220> FEATURE:
<221> NAME/KEY: MOD_RES
<222> LOCATION: (494)..(494)
<223> OTHER INFORMATION: Any amino acid
<220> FEATURE:
<221> NAME/KEY: MOD_RES
<222> LOCATION: (499)..(499)
```

```
<223> OTHER INFORMATION: Any amino acid
<220> FEATURE:
<221> NAME/KEY: MOD_RES
<222> LOCATION: (504)..(504)
<223> OTHER INFORMATION: Any amino acid
<220> FEATURE:
<221> NAME/KEY: MOD_RES
<222> LOCATION: (509)..(509)
<223> OTHER INFORMATION: Any amino acid
<220> FEATURE:
<221> NAME/KEY: MOD_RES
<222> LOCATION: (514)..(514)
<223> OTHER INFORMATION: Any amino acid
<220> FEATURE:
<221> NAME/KEY: MOD_RES
<222> LOCATION: (519)..(519)
<223> OTHER INFORMATION: Any amino acid
<220> FEATURE:
<221> NAME/KEY: MOD_RES
<222> LOCATION: (524)..(524)
<223> OTHER INFORMATION: Any amino acid
<220> FEATURE:
<221> NAME/KEY: MOD_RES
<222> LOCATION: (529)..(529)
<223> OTHER INFORMATION: Any amino acid
<220> FEATURE:
<221> NAME/KEY: MOD_RES
<222> LOCATION: (534)..(534)
<223> OTHER INFORMATION: Any amino acid
<220> FEATURE:
<221> NAME/KEY: MOD_RES
<222> LOCATION: (539)..(539)
<223> OTHER INFORMATION: Any amino acid
<220> FEATURE:
<221> NAME/KEY: MOD_RES
<222> LOCATION: (544)..(544)
<223> OTHER INFORMATION: Any amino acid
<220> FEATURE:
<221> NAME/KEY: MOD_RES
<222> LOCATION: (549)..(549)
<223> OTHER INFORMATION: Any amino acid
<220> FEATURE:
<221> NAME/KEY: MOD_RES
<222> LOCATION: (554)..(554)
<223> OTHER INFORMATION: Any amino acid
<220> FEATURE:
<221> NAME/KEY: MOD_RES
<222> LOCATION: (559)..(559)
<223> OTHER INFORMATION: Any amino acid
<220> FEATURE:
<221> NAME/KEY: MOD_RES
<222> LOCATION: (564)..(564)
<223> OTHER INFORMATION: Any amino acid
<220> FEATURE:
<221> NAME/KEY: MOD_RES
<222> LOCATION: (569)..(569)
<223> OTHER INFORMATION: Any amino acid
<220> FEATURE:
<221> NAME/KEY: MOD_RES
<222> LOCATION: (574)..(574)
<223> OTHER INFORMATION: Any amino acid
<220> FEATURE:
<221> NAME/KEY: MOD_RES
<222> LOCATION: (579)..(579)
<223> OTHER INFORMATION: Any amino acid
<220> FEATURE:
<221> NAME/KEY: MOD_RES
<222> LOCATION: (584)..(584)
<223> OTHER INFORMATION: Any amino acid
<220> FEATURE:
<221> NAME/KEY: MOD_RES
<222> LOCATION: (589)..(589)
<223> OTHER INFORMATION: Any amino acid
<220> FEATURE:
<221> NAME/KEY: MOD_RES
<222> LOCATION: (594)..(594)
<223> OTHER INFORMATION: Any amino acid
<220> FEATURE:
<221> NAME/KEY: MOD_RES
```

```
<222> LOCATION: (599)..(599)
<223> OTHER INFORMATION: Any amino acid
<220> FEATURE:
<221> NAME/KEY: MOD_RES
<222> LOCATION: (604)..(604)
<223> OTHER INFORMATION: Any amino acid
<220> FEATURE:
<221> NAME/KEY: MOD_RES
<222> LOCATION: (609)..(609)
<223> OTHER INFORMATION: Any amino acid
<220> FEATURE:
<221> NAME/KEY: MOD_RES
<222> LOCATION: (614)..(614)
<223> OTHER INFORMATION: Any amino acid
<220> FEATURE:
<221> NAME/KEY: MOD_RES
<222> LOCATION: (619)..(619)
<223> OTHER INFORMATION: Any amino acid
<220> FEATURE:
<221> NAME/KEY: MOD_RES
<222> LOCATION: (624)..(624)
<223> OTHER INFORMATION: Any amino acid
<220> FEATURE:
<221> NAME/KEY: MOD_RES
<222> LOCATION: (629)..(629)
<223> OTHER INFORMATION: Any amino acid
<220> FEATURE:
<221> NAME/KEY: MOD_RES
<222> LOCATION: (634)..(634)
<223> OTHER INFORMATION: Any amino acid
<220> FEATURE:
<221> NAME/KEY: MOD_RES
<222> LOCATION: (639)..(639)
<223> OTHER INFORMATION: Any amino acid
<220> FEATURE:
<221> NAME/KEY: MOD_RES
<222> LOCATION: (644)..(644)
<223> OTHER INFORMATION: Any amino acid
<220> FEATURE:
<221> NAME/KEY: MOD_RES
<222> LOCATION: (649)..(649)
<223> OTHER INFORMATION: Any amino acid
<220> FEATURE:
<221> NAME/KEY: MOD_RES
<222> LOCATION: (654)..(654)
<223> OTHER INFORMATION: Any amino acid
<220> FEATURE:
<221> NAME/KEY: MOD_RES
<222> LOCATION: (659)..(659)
<223> OTHER INFORMATION: Any amino acid
<220> FEATURE:
<221> NAME/KEY: MOD_RES
<222> LOCATION: (664)..(664)
<223> OTHER INFORMATION: Any amino acid
<220> FEATURE:
<221> NAME/KEY: MOD_RES
<222> LOCATION: (669)..(669)
<223> OTHER INFORMATION: Any amino acid
<220> FEATURE:
<221> NAME/KEY: MOD_RES
<222> LOCATION: (674)..(674)
<223> OTHER INFORMATION: Any amino acid
<220> FEATURE:
<221> NAME/KEY: MOD_RES
<222> LOCATION: (679)..(679)
<223> OTHER INFORMATION: Any amino acid
<220> FEATURE:
<221> NAME/KEY: MOD_RES
<222> LOCATION: (684)..(684)
<223> OTHER INFORMATION: Any amino acid
<220> FEATURE:
<221> NAME/KEY: MOD_RES
<222> LOCATION: (689)..(689)
<223> OTHER INFORMATION: Any amino acid
<220> FEATURE:
<221> NAME/KEY: MOD_RES
<222> LOCATION: (694)..(694)
<223> OTHER INFORMATION: Any amino acid
<220> FEATURE:
```

-continued

```
<221> NAME/KEY: MOD_RES
<222> LOCATION: (699)..(699)
<223> OTHER INFORMATION: Any amino acid
<220> FEATURE:
<221> NAME/KEY: MOD_RES
<222> LOCATION: (704)..(704)
<223> OTHER INFORMATION: Any amino acid
<220> FEATURE:
<221> NAME/KEY: MOD_RES
<222> LOCATION: (709)..(709)
<223> OTHER INFORMATION: Any amino acid
<220> FEATURE:
<221> NAME/KEY: MOD_RES
<222> LOCATION: (714)..(714)
<223> OTHER INFORMATION: Any amino acid
<220> FEATURE:
<221> NAME/KEY: MOD_RES
<222> LOCATION: (719)..(719)
<223> OTHER INFORMATION: Any amino acid
<220> FEATURE:
<221> NAME/KEY: MOD_RES
<222> LOCATION: (724)..(724)
<223> OTHER INFORMATION: Any amino acid
<220> FEATURE:
<221> NAME/KEY: MOD_RES
<222> LOCATION: (729)..(729)
<223> OTHER INFORMATION: Any amino acid
<220> FEATURE:
<221> NAME/KEY: MOD_RES
<222> LOCATION: (734)..(734)
<223> OTHER INFORMATION: Any amino acid
<220> FEATURE:
<221> NAME/KEY: MOD_RES
<222> LOCATION: (739)..(739)
<223> OTHER INFORMATION: Any amino acid
<220> FEATURE:
<221> NAME/KEY: MOD_RES
<222> LOCATION: (744)..(744)
<223> OTHER INFORMATION: Any amino acid
<220> FEATURE:
<221> NAME/KEY: MOD_RES
<222> LOCATION: (749)..(749)
<223> OTHER INFORMATION: Any amino acid
<220> FEATURE:
<221> NAME/KEY: MOD_RES
<222> LOCATION: (754)..(754)
<223> OTHER INFORMATION: Any amino acid
<220> FEATURE:
<221> NAME/KEY: MOD_RES
<222> LOCATION: (759)..(759)
<223> OTHER INFORMATION: Any amino acid
<220> FEATURE:
<221> NAME/KEY: MOD_RES
<222> LOCATION: (764)..(764)
<223> OTHER INFORMATION: Any amino acid
<220> FEATURE:
<221> NAME/KEY: MOD_RES
<222> LOCATION: (769)..(769)
<223> OTHER INFORMATION: Any amino acid
<220> FEATURE:
<221> NAME/KEY: MOD_RES
<222> LOCATION: (774)..(774)
<223> OTHER INFORMATION: Any amino acid
<220> FEATURE:
<221> NAME/KEY: MOD_RES
<222> LOCATION: (779)..(779)
<223> OTHER INFORMATION: Any amino acid
<220> FEATURE:
<221> NAME/KEY: MOD_RES
<222> LOCATION: (784)..(784)
<223> OTHER INFORMATION: Any amino acid
<220> FEATURE:
<221> NAME/KEY: MOD_RES
<222> LOCATION: (789)..(789)
<223> OTHER INFORMATION: Any amino acid
<220> FEATURE:
<221> NAME/KEY: MOD_RES
<222> LOCATION: (794)..(794)
<223> OTHER INFORMATION: Any amino acid
```

-continued

```
<220> FEATURE:
<221> NAME/KEY: MOD_RES
<222> LOCATION: (799)..(799)
<223> OTHER INFORMATION: Any amino acid
<220> FEATURE:
<221> NAME/KEY: MOD_RES
<222> LOCATION: (804)..(804)
<223> OTHER INFORMATION: Any amino acid
<220> FEATURE:
<221> NAME/KEY: MOD_RES
<222> LOCATION: (809)..(809)
<223> OTHER INFORMATION: Any amino acid
<220> FEATURE:
<221> NAME/KEY: MOD_RES
<222> LOCATION: (814)..(814)
<223> OTHER INFORMATION: Any amino acid
<220> FEATURE:
<221> NAME/KEY: MOD_RES
<222> LOCATION: (819)..(819)
<223> OTHER INFORMATION: Any amino acid
<220> FEATURE:
<221> NAME/KEY: MOD_RES
<222> LOCATION: (824)..(824)
<223> OTHER INFORMATION: Any amino acid
<220> FEATURE:
<221> NAME/KEY: MOD_RES
<222> LOCATION: (829)..(829)
<223> OTHER INFORMATION: Any amino acid
<220> FEATURE:
<221> NAME/KEY: MOD_RES
<222> LOCATION: (834)..(834)
<223> OTHER INFORMATION: Any amino acid
<220> FEATURE:
<221> NAME/KEY: MOD_RES
<222> LOCATION: (839)..(839)
<223> OTHER INFORMATION: Any amino acid
<220> FEATURE:
<221> NAME/KEY: MOD_RES
<222> LOCATION: (844)..(844)
<223> OTHER INFORMATION: Any amino acid
<220> FEATURE:
<221> NAME/KEY: MOD_RES
<222> LOCATION: (849)..(849)
<223> OTHER INFORMATION: Any amino acid
<220> FEATURE:
<221> NAME/KEY: MOD_RES
<222> LOCATION: (854)..(854)
<223> OTHER INFORMATION: Any amino acid
<220> FEATURE:
<221> NAME/KEY: MOD_RES
<222> LOCATION: (859)..(859)
<223> OTHER INFORMATION: Any amino acid
<220> FEATURE:
<221> NAME/KEY: MOD_RES
<222> LOCATION: (864)..(864)
<223> OTHER INFORMATION: Any amino acid
<220> FEATURE:
<221> NAME/KEY: MOD_RES
<222> LOCATION: (869)..(869)
<223> OTHER INFORMATION: Any amino acid
<220> FEATURE:
<221> NAME/KEY: MOD_RES
<222> LOCATION: (874)..(874)
<223> OTHER INFORMATION: Any amino acid
<220> FEATURE:
<221> NAME/KEY: MOD_RES
<222> LOCATION: (879)..(879)
<223> OTHER INFORMATION: Any amino acid
<220> FEATURE:
<221> NAME/KEY: MOD_RES
<222> LOCATION: (884)..(884)
<223> OTHER INFORMATION: Any amino acid
<220> FEATURE:
<221> NAME/KEY: MOD_RES
<222> LOCATION: (889)..(889)
<223> OTHER INFORMATION: Any amino acid
<220> FEATURE:
<221> NAME/KEY: MOD_RES
<222> LOCATION: (894)..(894)
```

-continued

```
<223> OTHER INFORMATION: Any amino acid
<220> FEATURE:
<221> NAME/KEY: MOD_RES
<222> LOCATION: (899)..(899)
<223> OTHER INFORMATION: Any amino acid
<220> FEATURE:
<221> NAME/KEY: MOD_RES
<222> LOCATION: (904)..(904)
<223> OTHER INFORMATION: Any amino acid
<220> FEATURE:
<221> NAME/KEY: MOD_RES
<222> LOCATION: (909)..(909)
<223> OTHER INFORMATION: Any amino acid
<220> FEATURE:
<221> NAME/KEY: MOD_RES
<222> LOCATION: (914)..(914)
<223> OTHER INFORMATION: Any amino acid
<220> FEATURE:
<221> NAME/KEY: MOD_RES
<222> LOCATION: (919)..(919)
<223> OTHER INFORMATION: Any amino acid
<220> FEATURE:
<221> NAME/KEY: MOD_RES
<222> LOCATION: (924)..(924)
<223> OTHER INFORMATION: Any amino acid
<220> FEATURE:
<221> NAME/KEY: MOD_RES
<222> LOCATION: (929)..(929)
<223> OTHER INFORMATION: Any amino acid
<220> FEATURE:
<221> NAME/KEY: MOD_RES
<222> LOCATION: (934)..(934)
<223> OTHER INFORMATION: Any amino acid
<220> FEATURE:
<221> NAME/KEY: MOD_RES
<222> LOCATION: (939)..(939)
<223> OTHER INFORMATION: Any amino acid
<220> FEATURE:
<221> NAME/KEY: MOD_RES
<222> LOCATION: (944)..(944)
<223> OTHER INFORMATION: Any amino acid
<220> FEATURE:
<221> NAME/KEY: MOD_RES
<222> LOCATION: (949)..(949)
<223> OTHER INFORMATION: Any amino acid
<220> FEATURE:
<221> NAME/KEY: MOD_RES
<222> LOCATION: (954)..(954)
<223> OTHER INFORMATION: Any amino acid
<220> FEATURE:
<221> NAME/KEY: MOD_RES
<222> LOCATION: (959)..(959)
<223> OTHER INFORMATION: Any amino acid
<220> FEATURE:
<221> NAME/KEY: MOD_RES
<222> LOCATION: (964)..(964)
<223> OTHER INFORMATION: Any amino acid
<220> FEATURE:
<221> NAME/KEY: MOD_RES
<222> LOCATION: (969)..(969)
<223> OTHER INFORMATION: Any amino acid
<220> FEATURE:
<221> NAME/KEY: MOD_RES
<222> LOCATION: (974)..(974)
<223> OTHER INFORMATION: Any amino acid
<220> FEATURE:
<221> NAME/KEY: MOD_RES
<222> LOCATION: (979)..(979)
<223> OTHER INFORMATION: Any amino acid
<220> FEATURE:
<221> NAME/KEY: MOD_RES
<222> LOCATION: (984)..(984)
<223> OTHER INFORMATION: Any amino acid
<220> FEATURE:
<221> NAME/KEY: MOD_RES
<222> LOCATION: (989)..(989)
<223> OTHER INFORMATION: Any amino acid
<220> FEATURE:
<221> NAME/KEY: MOD_RES
```

```
<222> LOCATION: (994)..(994)
<223> OTHER INFORMATION: Any amino acid
<220> FEATURE:
<221> NAME/KEY: MOD_RES
<222> LOCATION: (999)..(999)
<223> OTHER INFORMATION: Any amino acid
<220> FEATURE:
<221> NAME/KEY: MOD_RES
<222> LOCATION: (1004)..(1004)
<223> OTHER INFORMATION: Any amino acid
<220> FEATURE:
<221> NAME/KEY: MOD_RES
<222> LOCATION: (1009)..(1009)
<223> OTHER INFORMATION: Any amino acid
<220> FEATURE:
<221> NAME/KEY: MOD_RES
<222> LOCATION: (1014)..(1014)
<223> OTHER INFORMATION: Any amino acid
<220> FEATURE:
<221> NAME/KEY: MOD_RES
<222> LOCATION: (1019)..(1019)
<223> OTHER INFORMATION: Any amino acid
<220> FEATURE:
<221> NAME/KEY: MOD_RES
<222> LOCATION: (1024)..(1024)
<223> OTHER INFORMATION: Any amino acid
<220> FEATURE:
<221> NAME/KEY: MOD_RES
<222> LOCATION: (1029)..(1029)
<223> OTHER INFORMATION: Any amino acid
<220> FEATURE:
<221> NAME/KEY: MOD_RES
<222> LOCATION: (1034)..(1034)
<223> OTHER INFORMATION: Any amino acid
<220> FEATURE:
<221> NAME/KEY: MOD_RES
<222> LOCATION: (1039)..(1039)
<223> OTHER INFORMATION: Any amino acid
<220> FEATURE:
<221> NAME/KEY: MOD_RES
<222> LOCATION: (1044)..(1044)
<223> OTHER INFORMATION: Any amino acid
<220> FEATURE:
<221> NAME/KEY: MOD_RES
<222> LOCATION: (1049)..(1049)
<223> OTHER INFORMATION: Any amino acid
<220> FEATURE:
<221> NAME/KEY: MOD_RES
<222> LOCATION: (1054)..(1054)
<223> OTHER INFORMATION: Any amino acid
<220> FEATURE:
<221> NAME/KEY: MOD_RES
<222> LOCATION: (1059)..(1059)
<223> OTHER INFORMATION: Any amino acid
<220> FEATURE:
<221> NAME/KEY: MOD_RES
<222> LOCATION: (1064)..(1064)
<223> OTHER INFORMATION: Any amino acid
<220> FEATURE:
<221> NAME/KEY: MOD_RES
<222> LOCATION: (1069)..(1069)
<223> OTHER INFORMATION: Any amino acid
<220> FEATURE:
<221> NAME/KEY: MOD_RES
<222> LOCATION: (1074)..(1074)
<223> OTHER INFORMATION: Any amino acid
<220> FEATURE:
<221> NAME/KEY: MOD_RES
<222> LOCATION: (1079)..(1079)
<223> OTHER INFORMATION: Any amino acid
<220> FEATURE:
<221> NAME/KEY: MOD_RES
<222> LOCATION: (1084)..(1084)
<223> OTHER INFORMATION: Any amino acid
<220> FEATURE:
<221> NAME/KEY: MOD_RES
<222> LOCATION: (1089)..(1089)
<223> OTHER INFORMATION: Any amino acid
<220> FEATURE:
```

```
<221> NAME/KEY: MOD_RES
<222> LOCATION: (1094)..(1094)
<223> OTHER INFORMATION: Any amino acid
<220> FEATURE:
<221> NAME/KEY: MOD_RES
<222> LOCATION: (1099)..(1099)
<223> OTHER INFORMATION: Any amino acid
<220> FEATURE:
<221> NAME/KEY: MOD_RES
<222> LOCATION: (1104)..(1104)
<223> OTHER INFORMATION: Any amino acid
<220> FEATURE:
<221> NAME/KEY: MOD_RES
<222> LOCATION: (1109)..(1109)
<223> OTHER INFORMATION: Any amino acid
<220> FEATURE:
<221> NAME/KEY: MOD_RES
<222> LOCATION: (1114)..(1114)
<223> OTHER INFORMATION: Any amino acid
<220> FEATURE:
<221> NAME/KEY: MOD_RES
<222> LOCATION: (1119)..(1119)
<223> OTHER INFORMATION: Any amino acid
<220> FEATURE:
<221> NAME/KEY: MOD_RES
<222> LOCATION: (1124)..(1124)
<223> OTHER INFORMATION: Any amino acid
<220> FEATURE:
<221> NAME/KEY: MOD_RES
<222> LOCATION: (1129)..(1129)
<223> OTHER INFORMATION: Any amino acid
<220> FEATURE:
<221> NAME/KEY: MOD_RES
<222> LOCATION: (1134)..(1134)
<223> OTHER INFORMATION: Any amino acid
<220> FEATURE:
<221> NAME/KEY: MOD_RES
<222> LOCATION: (1139)..(1139)
<223> OTHER INFORMATION: Any amino acid
<220> FEATURE:
<221> NAME/KEY: MOD_RES
<222> LOCATION: (1144)..(1144)
<223> OTHER INFORMATION: Any amino acid
<220> FEATURE:
<221> NAME/KEY: MOD_RES
<222> LOCATION: (1149)..(1149)
<223> OTHER INFORMATION: Any amino acid
<220> FEATURE:
<221> NAME/KEY: MOD_RES
<222> LOCATION: (1154)..(1154)
<223> OTHER INFORMATION: Any amino acid
<220> FEATURE:
<221> NAME/KEY: MOD_RES
<222> LOCATION: (1159)..(1159)
<223> OTHER INFORMATION: Any amino acid
<220> FEATURE:
<221> NAME/KEY: MOD_RES
<222> LOCATION: (1164)..(1164)
<223> OTHER INFORMATION: Any amino acid
<220> FEATURE:
<221> NAME/KEY: MOD_RES
<222> LOCATION: (1169)..(1169)
<223> OTHER INFORMATION: Any amino acid
<220> FEATURE:
<221> NAME/KEY: MOD_RES
<222> LOCATION: (1174)..(1174)
<223> OTHER INFORMATION: Any amino acid
<220> FEATURE:
<221> NAME/KEY: MOD_RES
<222> LOCATION: (1179)..(1179)
<223> OTHER INFORMATION: Any amino acid
<220> FEATURE:
<221> NAME/KEY: MOD_RES
<222> LOCATION: (1184)..(1184)
<223> OTHER INFORMATION: Any amino acid
<220> FEATURE:
<221> NAME/KEY: MOD_RES
<222> LOCATION: (1189)..(1189)
<223> OTHER INFORMATION: Any amino acid
```

-continued

```
<220> FEATURE:
<221> NAME/KEY: MOD_RES
<222> LOCATION: (1194)..(1194)
<223> OTHER INFORMATION: Any amino acid
<220> FEATURE:
<221> NAME/KEY: MOD_RES
<222> LOCATION: (1199)..(1199)
<223> OTHER INFORMATION: Any amino acid
<220> FEATURE:
<221> NAME/KEY: MOD_RES
<222> LOCATION: (1204)..(1204)
<223> OTHER INFORMATION: Any amino acid
<220> FEATURE:
<221> NAME/KEY: MOD_RES
<222> LOCATION: (1209)..(1209)
<223> OTHER INFORMATION: Any amino acid
<220> FEATURE:
<221> NAME/KEY: MOD_RES
<222> LOCATION: (1214)..(1214)
<223> OTHER INFORMATION: Any amino acid
<220> FEATURE:
<221> NAME/KEY: MOD_RES
<222> LOCATION: (1219)..(1219)
<223> OTHER INFORMATION: Any amino acid
<220> FEATURE:
<221> NAME/KEY: MOD_RES
<222> LOCATION: (1224)..(1224)
<223> OTHER INFORMATION: Any amino acid
<220> FEATURE:
<221> NAME/KEY: MOD_RES
<222> LOCATION: (1229)..(1229)
<223> OTHER INFORMATION: Any amino acid
<220> FEATURE:
<221> NAME/KEY: MOD_RES
<222> LOCATION: (1234)..(1234)
<223> OTHER INFORMATION: Any amino acid
<220> FEATURE:
<221> NAME/KEY: MOD_RES
<222> LOCATION: (1239)..(1239)
<223> OTHER INFORMATION: Any amino acid
<220> FEATURE:
<221> NAME/KEY: MOD_RES
<222> LOCATION: (1244)..(1244)
<223> OTHER INFORMATION: Any amino acid
<220> FEATURE:
<221> NAME/KEY: MOD_RES
<222> LOCATION: (1249)..(1249)
<223> OTHER INFORMATION: Any amino acid
<220> FEATURE:
<221> NAME/KEY: MOD_RES
<222> LOCATION: (1254)..(1254)
<223> OTHER INFORMATION: Any amino acid
<220> FEATURE:
<221> NAME/KEY: MOD_RES
<222> LOCATION: (1259)..(1259)
<223> OTHER INFORMATION: Any amino acid
<220> FEATURE:
<221> NAME/KEY: MOD_RES
<222> LOCATION: (1264)..(1264)
<223> OTHER INFORMATION: Any amino acid
<220> FEATURE:
<221> NAME/KEY: MOD_RES
<222> LOCATION: (1269)..(1269)
<223> OTHER INFORMATION: Any amino acid
<220> FEATURE:
<221> NAME/KEY: MOD_RES
<222> LOCATION: (1274)..(1274)
<223> OTHER INFORMATION: Any amino acid
<220> FEATURE:
<221> NAME/KEY: MOD_RES
<222> LOCATION: (1279)..(1279)
<223> OTHER INFORMATION: Any amino acid
<220> FEATURE:
<221> NAME/KEY: MOD_RES
<222> LOCATION: (1284)..(1284)
<223> OTHER INFORMATION: Any amino acid
<220> FEATURE:
<221> NAME/KEY: MOD_RES
<222> LOCATION: (1289)..(1289)
```

```
<223> OTHER INFORMATION: Any amino acid
<220> FEATURE:
<221> NAME/KEY: MOD_RES
<222> LOCATION: (1294)..(1294)
<223> OTHER INFORMATION: Any amino acid
<220> FEATURE:
<221> NAME/KEY: MOD_RES
<222> LOCATION: (1299)..(1299)
<223> OTHER INFORMATION: Any amino acid
<220> FEATURE:
<221> NAME/KEY: MOD_RES
<222> LOCATION: (1304)..(1304)
<223> OTHER INFORMATION: Any amino acid
<220> FEATURE:
<221> NAME/KEY: MOD_RES
<222> LOCATION: (1309)..(1309)
<223> OTHER INFORMATION: Any amino acid
<220> FEATURE:
<221> NAME/KEY: MOD_RES
<222> LOCATION: (1314)..(1314)
<223> OTHER INFORMATION: Any amino acid
<220> FEATURE:
<221> NAME/KEY: MOD_RES
<222> LOCATION: (1319)..(1319)
<223> OTHER INFORMATION: Any amino acid
<220> FEATURE:
<221> NAME/KEY: MOD_RES
<222> LOCATION: (1324)..(1324)
<223> OTHER INFORMATION: Any amino acid
<220> FEATURE:
<221> NAME/KEY: MOD_RES
<222> LOCATION: (1329)..(1329)
<223> OTHER INFORMATION: Any amino acid
<220> FEATURE:
<221> NAME/KEY: MOD_RES
<222> LOCATION: (1334)..(1334)
<223> OTHER INFORMATION: Any amino acid
<220> FEATURE:
<221> NAME/KEY: MOD_RES
<222> LOCATION: (1339)..(1339)
<223> OTHER INFORMATION: Any amino acid
<220> FEATURE:
<221> NAME/KEY: MOD_RES
<222> LOCATION: (1344)..(1344)
<223> OTHER INFORMATION: Any amino acid
<220> FEATURE:
<221> NAME/KEY: MOD_RES
<222> LOCATION: (1349)..(1349)
<223> OTHER INFORMATION: Any amino acid
<220> FEATURE:
<221> NAME/KEY: MOD_RES
<222> LOCATION: (1354)..(1354)
<223> OTHER INFORMATION: Any amino acid
<220> FEATURE:
<221> NAME/KEY: MOD_RES
<222> LOCATION: (1359)..(1359)
<223> OTHER INFORMATION: Any amino acid
<220> FEATURE:
<221> NAME/KEY: MOD_RES
<222> LOCATION: (1364)..(1364)
<223> OTHER INFORMATION: Any amino acid
<220> FEATURE:
<221> NAME/KEY: MOD_RES
<222> LOCATION: (1369)..(1369)
<223> OTHER INFORMATION: Any amino acid
<220> FEATURE:
<221> NAME/KEY: MOD_RES
<222> LOCATION: (1374)..(1374)
<223> OTHER INFORMATION: Any amino acid
<220> FEATURE:
<221> NAME/KEY: MOD_RES
<222> LOCATION: (1379)..(1379)
<223> OTHER INFORMATION: Any amino acid
<220> FEATURE:
<221> NAME/KEY: MOD_RES
<222> LOCATION: (1384)..(1384)
<223> OTHER INFORMATION: Any amino acid
<220> FEATURE:
<221> NAME/KEY: MOD_RES
```

```
-continued

<222> LOCATION: (1389)..(1389)
<223> OTHER INFORMATION: Any amino acid
<220> FEATURE:
<221> NAME/KEY: MOD_RES
<222> LOCATION: (1394)..(1394)
<223> OTHER INFORMATION: Any amino acid
<220> FEATURE:
<221> NAME/KEY: MOD_RES
<222> LOCATION: (1399)..(1399)
<223> OTHER INFORMATION: Any amino acid
<220> FEATURE:
<221> NAME/KEY: MOD_RES
<222> LOCATION: (1404)..(1404)
<223> OTHER INFORMATION: Any amino acid
<220> FEATURE:
<221> NAME/KEY: MOD_RES
<222> LOCATION: (1409)..(1409)
<223> OTHER INFORMATION: Any amino acid
<220> FEATURE:
<221> NAME/KEY: MOD_RES
<222> LOCATION: (1414)..(1414)
<223> OTHER INFORMATION: Any amino acid
<220> FEATURE:
<221> NAME/KEY: MOD_RES
<222> LOCATION: (1419)..(1419)
<223> OTHER INFORMATION: Any amino acid
<220> FEATURE:
<221> NAME/KEY: MOD_RES
<222> LOCATION: (1424)..(1424)
<223> OTHER INFORMATION: Any amino acid
<220> FEATURE:
<221> NAME/KEY: MOD_RES
<222> LOCATION: (1429)..(1429)
<223> OTHER INFORMATION: Any amino acid
<220> FEATURE:
<221> NAME/KEY: MOD_RES
<222> LOCATION: (1434)..(1434)
<223> OTHER INFORMATION: Any amino acid
<220> FEATURE:
<221> NAME/KEY: MOD_RES
<222> LOCATION: (1439)..(1439)
<223> OTHER INFORMATION: Any amino acid
<220> FEATURE:
<221> NAME/KEY: MOD_RES
<222> LOCATION: (1444)..(1444)
<223> OTHER INFORMATION: Any amino acid
<220> FEATURE:
<221> NAME/KEY: MOD_RES
<222> LOCATION: (1449)..(1449)
<223> OTHER INFORMATION: Any amino acid
<220> FEATURE:
<221> NAME/KEY: MOD_RES
<222> LOCATION: (1454)..(1454)
<223> OTHER INFORMATION: Any amino acid
<220> FEATURE:
<221> NAME/KEY: MOD_RES
<222> LOCATION: (1459)..(1459)
<223> OTHER INFORMATION: Any amino acid
<220> FEATURE:
<221> NAME/KEY: MOD_RES
<222> LOCATION: (1464)..(1464)
<223> OTHER INFORMATION: Any amino acid
<220> FEATURE:
<221> NAME/KEY: MOD_RES
<222> LOCATION: (1469)..(1469)
<223> OTHER INFORMATION: Any amino acid
<220> FEATURE:
<221> NAME/KEY: MOD_RES
<222> LOCATION: (1474)..(1474)
<223> OTHER INFORMATION: Any amino acid
<220> FEATURE:
<221> NAME/KEY: MOD_RES
<222> LOCATION: (1479)..(1479)
<223> OTHER INFORMATION: Any amino acid
<220> FEATURE:
<221> NAME/KEY: MOD_RES
<222> LOCATION: (1484)..(1484)
<223> OTHER INFORMATION: Any amino acid
<220> FEATURE:
```

```
<221> NAME/KEY: MOD_RES
<222> LOCATION: (1489)..(1489)
<223> OTHER INFORMATION: Any amino acid
<220> FEATURE:
<221> NAME/KEY: MOD_RES
<222> LOCATION: (1494)..(1494)
<223> OTHER INFORMATION: Any amino acid
<220> FEATURE:
<221> NAME/KEY: MOD_RES
<222> LOCATION: (1499)..(1499)
<223> OTHER INFORMATION: Any amino acid
<220> FEATURE:
<221> NAME/KEY: MOD_RES
<222> LOCATION: (1504)..(1504)
<223> OTHER INFORMATION: Any amino acid
<220> FEATURE:
<221> NAME/KEY: MOD_RES
<222> LOCATION: (1509)..(1509)
<223> OTHER INFORMATION: Any amino acid
<220> FEATURE:
<221> NAME/KEY: MOD_RES
<222> LOCATION: (1514)..(1514)
<223> OTHER INFORMATION: Any amino acid
<220> FEATURE:
<221> NAME/KEY: MOD_RES
<222> LOCATION: (1519)..(1519)
<223> OTHER INFORMATION: Any amino acid
<220> FEATURE:
<221> NAME/KEY: MOD_RES
<222> LOCATION: (1524)..(1524)
<223> OTHER INFORMATION: Any amino acid
<220> FEATURE:
<221> NAME/KEY: MOD_RES
<222> LOCATION: (1529)..(1529)
<223> OTHER INFORMATION: Any amino acid
<220> FEATURE:
<221> NAME/KEY: MOD_RES
<222> LOCATION: (1534)..(1534)
<223> OTHER INFORMATION: Any amino acid
<220> FEATURE:
<221> NAME/KEY: MOD_RES
<222> LOCATION: (1539)..(1539)
<223> OTHER INFORMATION: Any amino acid
<220> FEATURE:
<221> NAME/KEY: MOD_RES
<222> LOCATION: (1544)..(1544)
<223> OTHER INFORMATION: Any amino acid
<220> FEATURE:
<221> NAME/KEY: MOD_RES
<222> LOCATION: (1549)..(1549)
<223> OTHER INFORMATION: Any amino acid
<220> FEATURE:
<221> NAME/KEY: MOD_RES
<222> LOCATION: (1554)..(1554)
<223> OTHER INFORMATION: Any amino acid
<220> FEATURE:
<221> NAME/KEY: MOD_RES
<222> LOCATION: (1559)..(1559)
<223> OTHER INFORMATION: Any amino acid
<220> FEATURE:
<221> NAME/KEY: MOD_RES
<222> LOCATION: (1564)..(1564)
<223> OTHER INFORMATION: Any amino acid
<220> FEATURE:
<221> NAME/KEY: MOD_RES
<222> LOCATION: (1569)..(1569)
<223> OTHER INFORMATION: Any amino acid
<220> FEATURE:
<221> NAME/KEY: MOD_RES
<222> LOCATION: (1574)..(1574)
<223> OTHER INFORMATION: Any amino acid
<220> FEATURE:
<221> NAME/KEY: MOD_RES
<222> LOCATION: (1579)..(1579)
<223> OTHER INFORMATION: Any amino acid
<220> FEATURE:
<221> NAME/KEY: MOD_RES
<222> LOCATION: (1584)..(1584)
<223> OTHER INFORMATION: Any amino acid
```

-continued

```
<220> FEATURE:
<221> NAME/KEY: MOD_RES
<222> LOCATION: (1589)..(1589)
<223> OTHER INFORMATION: Any amino acid
<220> FEATURE:
<221> NAME/KEY: MOD_RES
<222> LOCATION: (1594)..(1594)
<223> OTHER INFORMATION: Any amino acid
<220> FEATURE:
<221> NAME/KEY: MOD_RES
<222> LOCATION: (1599)..(1599)
<223> OTHER INFORMATION: Any amino acid
<220> FEATURE:
<221> NAME/KEY: MOD_RES
<222> LOCATION: (1604)..(1604)
<223> OTHER INFORMATION: Any amino acid
<220> FEATURE:
<221> NAME/KEY: MOD_RES
<222> LOCATION: (1609)..(1609)
<223> OTHER INFORMATION: Any amino acid
<220> FEATURE:
<221> NAME/KEY: MOD_RES
<222> LOCATION: (1614)..(1614)
<223> OTHER INFORMATION: Any amino acid
<220> FEATURE:
<221> NAME/KEY: MOD_RES
<222> LOCATION: (1619)..(1619)
<223> OTHER INFORMATION: Any amino acid
<220> FEATURE:
<221> NAME/KEY: MOD_RES
<222> LOCATION: (1624)..(1624)
<223> OTHER INFORMATION: Any amino acid
<220> FEATURE:
<221> NAME/KEY: MOD_RES
<222> LOCATION: (1629)..(1629)
<223> OTHER INFORMATION: Any amino acid
<220> FEATURE:
<221> NAME/KEY: MOD_RES
<222> LOCATION: (1634)..(1634)
<223> OTHER INFORMATION: Any amino acid
<220> FEATURE:
<221> NAME/KEY: MOD_RES
<222> LOCATION: (1639)..(1639)
<223> OTHER INFORMATION: Any amino acid
<220> FEATURE:
<221> NAME/KEY: MOD_RES
<222> LOCATION: (1644)..(1644)
<223> OTHER INFORMATION: Any amino acid
<220> FEATURE:
<221> NAME/KEY: MOD_RES
<222> LOCATION: (1649)..(1649)
<223> OTHER INFORMATION: Any amino acid
<220> FEATURE:
<221> NAME/KEY: MOD_RES
<222> LOCATION: (1654)..(1654)
<223> OTHER INFORMATION: Any amino acid
<220> FEATURE:
<221> NAME/KEY: MOD_RES
<222> LOCATION: (1659)..(1659)
<223> OTHER INFORMATION: Any amino acid
<220> FEATURE:
<221> NAME/KEY: MOD_RES
<222> LOCATION: (1664)..(1664)
<223> OTHER INFORMATION: Any amino acid
<220> FEATURE:
<221> NAME/KEY: MOD_RES
<222> LOCATION: (1669)..(1669)
<223> OTHER INFORMATION: Any amino acid
<220> FEATURE:
<221> NAME/KEY: MOD_RES
<222> LOCATION: (1674)..(1674)
<223> OTHER INFORMATION: Any amino acid
<220> FEATURE:
<221> NAME/KEY: MOD_RES
<222> LOCATION: (1679)..(1679)
<223> OTHER INFORMATION: Any amino acid
<220> FEATURE:
<221> NAME/KEY: MOD_RES
<222> LOCATION: (1684)..(1684)
```

```
<223> OTHER INFORMATION: Any amino acid
<220> FEATURE:
<221> NAME/KEY: MOD_RES
<222> LOCATION: (1689)..(1689)
<223> OTHER INFORMATION: Any amino acid
<220> FEATURE:
<221> NAME/KEY: MOD_RES
<222> LOCATION: (1694)..(1694)
<223> OTHER INFORMATION: Any amino acid
<220> FEATURE:
<221> NAME/KEY: MOD_RES
<222> LOCATION: (1699)..(1699)
<223> OTHER INFORMATION: Any amino acid
<220> FEATURE:
<221> NAME/KEY: MOD_RES
<222> LOCATION: (1704)..(1704)
<223> OTHER INFORMATION: Any amino acid
<220> FEATURE:
<221> NAME/KEY: MOD_RES
<222> LOCATION: (1709)..(1709)
<223> OTHER INFORMATION: Any amino acid
<220> FEATURE:
<221> NAME/KEY: MOD_RES
<222> LOCATION: (1714)..(1714)
<223> OTHER INFORMATION: Any amino acid
<220> FEATURE:
<221> NAME/KEY: MOD_RES
<222> LOCATION: (1719)..(1719)
<223> OTHER INFORMATION: Any amino acid
<220> FEATURE:
<221> NAME/KEY: MOD_RES
<222> LOCATION: (1724)..(1724)
<223> OTHER INFORMATION: Any amino acid
<220> FEATURE:
<221> NAME/KEY: MOD_RES
<222> LOCATION: (1729)..(1729)
<223> OTHER INFORMATION: Any amino acid
<220> FEATURE:
<221> NAME/KEY: MOD_RES
<222> LOCATION: (1734)..(1734)
<223> OTHER INFORMATION: Any amino acid
<220> FEATURE:
<221> NAME/KEY: MOD_RES
<222> LOCATION: (1739)..(1739)
<223> OTHER INFORMATION: Any amino acid
<220> FEATURE:
<221> NAME/KEY: MOD_RES
<222> LOCATION: (1744)..(1744)
<223> OTHER INFORMATION: Any amino acid
<220> FEATURE:
<221> NAME/KEY: MOD_RES
<222> LOCATION: (1749)..(1749)
<223> OTHER INFORMATION: Any amino acid
<220> FEATURE:
<221> NAME/KEY: MOD_RES
<222> LOCATION: (1754)..(1754)
<223> OTHER INFORMATION: Any amino acid
<220> FEATURE:
<221> NAME/KEY: MOD_RES
<222> LOCATION: (1759)..(1759)
<223> OTHER INFORMATION: Any amino acid
<220> FEATURE:
<221> NAME/KEY: MOD_RES
<222> LOCATION: (1764)..(1764)
<223> OTHER INFORMATION: Any amino acid
<220> FEATURE:
<221> NAME/KEY: MOD_RES
<222> LOCATION: (1769)..(1769)
<223> OTHER INFORMATION: Any amino acid
<220> FEATURE:
<221> NAME/KEY: MOD_RES
<222> LOCATION: (1774)..(1774)
<223> OTHER INFORMATION: Any amino acid
<220> FEATURE:
<221> NAME/KEY: MOD_RES
<222> LOCATION: (1779)..(1779)
<223> OTHER INFORMATION: Any amino acid
<220> FEATURE:
<221> NAME/KEY: MOD_RES
```

-continued

```
<222> LOCATION: (1784)..(1784)
<223> OTHER INFORMATION: Any amino acid
<220> FEATURE:
<221> NAME/KEY: MOD_RES
<222> LOCATION: (1789)..(1789)
<223> OTHER INFORMATION: Any amino acid
<220> FEATURE:
<221> NAME/KEY: MOD_RES
<222> LOCATION: (1794)..(1794)
<223> OTHER INFORMATION: Any amino acid
<220> FEATURE:
<221> NAME/KEY: MOD_RES
<222> LOCATION: (1799)..(1799)
<223> OTHER INFORMATION: Any amino acid
<220> FEATURE:
<221> NAME/KEY: MOD_RES
<222> LOCATION: (1804)..(1804)
<223> OTHER INFORMATION: Any amino acid
<220> FEATURE:
<221> NAME/KEY: MOD_RES
<222> LOCATION: (1809)..(1809)
<223> OTHER INFORMATION: Any amino acid
<220> FEATURE:
<221> NAME/KEY: MOD_RES
<222> LOCATION: (1814)..(1814)
<223> OTHER INFORMATION: Any amino acid
<220> FEATURE:
<221> NAME/KEY: MOD_RES
<222> LOCATION: (1819)..(1819)
<223> OTHER INFORMATION: Any amino acid
<220> FEATURE:
<221> NAME/KEY: MOD_RES
<222> LOCATION: (1824)..(1824)
<223> OTHER INFORMATION: Any amino acid
<220> FEATURE:
<221> NAME/KEY: MOD_RES
<222> LOCATION: (1829)..(1829)
<223> OTHER INFORMATION: Any amino acid
<220> FEATURE:
<221> NAME/KEY: MOD_RES
<222> LOCATION: (1834)..(1834)
<223> OTHER INFORMATION: Any amino acid
<220> FEATURE:
<221> NAME/KEY: MOD_RES
<222> LOCATION: (1839)..(1839)
<223> OTHER INFORMATION: Any amino acid
<220> FEATURE:
<221> NAME/KEY: MOD_RES
<222> LOCATION: (1844)..(1844)
<223> OTHER INFORMATION: Any amino acid
<220> FEATURE:
<221> NAME/KEY: MOD_RES
<222> LOCATION: (1849)..(1849)
<223> OTHER INFORMATION: Any amino acid
<220> FEATURE:
<221> NAME/KEY: MOD_RES
<222> LOCATION: (1854)..(1854)
<223> OTHER INFORMATION: Any amino acid
<220> FEATURE:
<221> NAME/KEY: MOD_RES
<222> LOCATION: (1859)..(1859)
<223> OTHER INFORMATION: Any amino acid
<220> FEATURE:
<221> NAME/KEY: MOD_RES
<222> LOCATION: (1864)..(1864)
<223> OTHER INFORMATION: Any amino acid
<220> FEATURE:
<221> NAME/KEY: MOD_RES
<222> LOCATION: (1869)..(1869)
<223> OTHER INFORMATION: Any amino acid
<220> FEATURE:
<221> NAME/KEY: MOD_RES
<222> LOCATION: (1874)..(1874)
<223> OTHER INFORMATION: Any amino acid
<220> FEATURE:
<221> NAME/KEY: MOD_RES
<222> LOCATION: (1879)..(1879)
<223> OTHER INFORMATION: Any amino acid
<220> FEATURE:
```

-continued

```
<221> NAME/KEY: MOD_RES
<222> LOCATION: (1884)..(1884)
<223> OTHER INFORMATION: Any amino acid
<220> FEATURE:
<221> NAME/KEY: MOD_RES
<222> LOCATION: (1889)..(1889)
<223> OTHER INFORMATION: Any amino acid
<220> FEATURE:
<221> NAME/KEY: MOD_RES
<222> LOCATION: (1894)..(1894)
<223> OTHER INFORMATION: Any amino acid
<220> FEATURE:
<221> NAME/KEY: MOD_RES
<222> LOCATION: (1899)..(1899)
<223> OTHER INFORMATION: Any amino acid
<220> FEATURE:
<221> NAME/KEY: MOD_RES
<222> LOCATION: (1904)..(1904)
<223> OTHER INFORMATION: Any amino acid
<220> FEATURE:
<221> NAME/KEY: MOD_RES
<222> LOCATION: (1909)..(1909)
<223> OTHER INFORMATION: Any amino acid
<220> FEATURE:
<221> NAME/KEY: MOD_RES
<222> LOCATION: (1914)..(1914)
<223> OTHER INFORMATION: Any amino acid
<220> FEATURE:
<221> NAME/KEY: MOD_RES
<222> LOCATION: (1919)..(1919)
<223> OTHER INFORMATION: Any amino acid
<220> FEATURE:
<221> NAME/KEY: MOD_RES
<222> LOCATION: (1924)..(1924)
<223> OTHER INFORMATION: Any amino acid
<220> FEATURE:
<221> NAME/KEY: MOD_RES
<222> LOCATION: (1929)..(1929)
<223> OTHER INFORMATION: Any amino acid
<220> FEATURE:
<221> NAME/KEY: MOD_RES
<222> LOCATION: (1934)..(1934)
<223> OTHER INFORMATION: Any amino acid
<220> FEATURE:
<221> NAME/KEY: MOD_RES
<222> LOCATION: (1939)..(1939)
<223> OTHER INFORMATION: Any amino acid
<220> FEATURE:
<221> NAME/KEY: MOD_RES
<222> LOCATION: (1944)..(1944)
<223> OTHER INFORMATION: Any amino acid
<220> FEATURE:
<221> NAME/KEY: MOD_RES
<222> LOCATION: (1949)..(1949)
<223> OTHER INFORMATION: Any amino acid
<220> FEATURE:
<221> NAME/KEY: MOD_RES
<222> LOCATION: (1954)..(1954)
<223> OTHER INFORMATION: Any amino acid
<220> FEATURE:
<221> NAME/KEY: MOD_RES
<222> LOCATION: (1959)..(1959)
<223> OTHER INFORMATION: Any amino acid
<220> FEATURE:
<221> NAME/KEY: MOD_RES
<222> LOCATION: (1964)..(1964)
<223> OTHER INFORMATION: Any amino acid
<220> FEATURE:
<221> NAME/KEY: MOD_RES
<222> LOCATION: (1969)..(1969)
<223> OTHER INFORMATION: Any amino acid
<220> FEATURE:
<221> NAME/KEY: MOD_RES
<222> LOCATION: (1974)..(1974)
<223> OTHER INFORMATION: Any amino acid
<220> FEATURE:
<221> NAME/KEY: MOD_RES
<222> LOCATION: (1979)..(1979)
<223> OTHER INFORMATION: Any amino acid
```

```
<220> FEATURE:
<221> NAME/KEY: MOD_RES
<222> LOCATION: (1984)..(1984)
<223> OTHER INFORMATION: Any amino acid
<220> FEATURE:
<221> NAME/KEY: MOD_RES
<222> LOCATION: (1989)..(1989)
<223> OTHER INFORMATION: Any amino acid
<220> FEATURE:
<221> NAME/KEY: MOD_RES
<222> LOCATION: (1994)..(1994)
<223> OTHER INFORMATION: Any amino acid
<220> FEATURE:
<221> NAME/KEY: MOD_RES
<222> LOCATION: (1999)..(1999)
<223> OTHER INFORMATION: Any amino acid
<220> FEATURE:
<221> NAME/KEY: MOD_RES
<222> LOCATION: (2004)..(2004)
<223> OTHER INFORMATION: Any amino acid
<220> FEATURE:
<221> NAME/KEY: MOD_RES
<222> LOCATION: (2009)..(2009)
<223> OTHER INFORMATION: Any amino acid
<220> FEATURE:
<221> NAME/KEY: MOD_RES
<222> LOCATION: (2014)..(2014)
<223> OTHER INFORMATION: Any amino acid
<220> FEATURE:
<221> NAME/KEY: MOD_RES
<222> LOCATION: (2019)..(2019)
<223> OTHER INFORMATION: Any amino acid
<220> FEATURE:
<221> NAME/KEY: MOD_RES
<222> LOCATION: (2024)..(2024)
<223> OTHER INFORMATION: Any amino acid
<220> FEATURE:
<221> NAME/KEY: MOD_RES
<222> LOCATION: (2029)..(2029)
<223> OTHER INFORMATION: Any amino acid
<220> FEATURE:
<221> NAME/KEY: MOD_RES
<222> LOCATION: (2034)..(2034)
<223> OTHER INFORMATION: Any amino acid
<220> FEATURE:
<221> NAME/KEY: MOD_RES
<222> LOCATION: (2039)..(2039)
<223> OTHER INFORMATION: Any amino acid
<220> FEATURE:
<221> NAME/KEY: MOD_RES
<222> LOCATION: (2044)..(2044)
<223> OTHER INFORMATION: Any amino acid
<220> FEATURE:
<221> NAME/KEY: MOD_RES
<222> LOCATION: (2049)..(2049)
<223> OTHER INFORMATION: Any amino acid
<220> FEATURE:
<221> NAME/KEY: MOD_RES
<222> LOCATION: (2054)..(2054)
<223> OTHER INFORMATION: Any amino acid
<220> FEATURE:
<221> NAME/KEY: MOD_RES
<222> LOCATION: (2059)..(2059)
<223> OTHER INFORMATION: Any amino acid
<220> FEATURE:
<221> NAME/KEY: MOD_RES
<222> LOCATION: (2064)..(2064)
<223> OTHER INFORMATION: Any amino acid
<220> FEATURE:
<221> NAME/KEY: MOD_RES
<222> LOCATION: (2069)..(2069)
<223> OTHER INFORMATION: Any amino acid
<220> FEATURE:
<221> NAME/KEY: MOD_RES
<222> LOCATION: (2074)..(2074)
<223> OTHER INFORMATION: Any amino acid
<220> FEATURE:
<221> NAME/KEY: MOD_RES
<222> LOCATION: (2079)..(2079)
```

-continued

```
<223> OTHER INFORMATION: Any amino acid
<220> FEATURE:
<221> NAME/KEY: MOD_RES
<222> LOCATION: (2084)..(2084)
<223> OTHER INFORMATION: Any amino acid
<220> FEATURE:
<221> NAME/KEY: MOD_RES
<222> LOCATION: (2089)..(2089)
<223> OTHER INFORMATION: Any amino acid
<220> FEATURE:
<221> NAME/KEY: MOD_RES
<222> LOCATION: (2094)..(2094)
<223> OTHER INFORMATION: Any amino acid
<220> FEATURE:
<221> NAME/KEY: MOD_RES
<222> LOCATION: (2099)..(2099)
<223> OTHER INFORMATION: Any amino acid
<220> FEATURE:
<221> NAME/KEY: MOD_RES
<222> LOCATION: (2104)..(2104)
<223> OTHER INFORMATION: Any amino acid
<220> FEATURE:
<221> NAME/KEY: MOD_RES
<222> LOCATION: (2109)..(2109)
<223> OTHER INFORMATION: Any amino acid
<220> FEATURE:
<221> NAME/KEY: MOD_RES
<222> LOCATION: (2114)..(2114)
<223> OTHER INFORMATION: Any amino acid
<220> FEATURE:
<221> NAME/KEY: MOD_RES
<222> LOCATION: (2119)..(2119)
<223> OTHER INFORMATION: Any amino acid
<220> FEATURE:
<221> NAME/KEY: MOD_RES
<222> LOCATION: (2124)..(2124)
<223> OTHER INFORMATION: Any amino acid
<220> FEATURE:
<221> NAME/KEY: MOD_RES
<222> LOCATION: (2129)..(2129)
<223> OTHER INFORMATION: Any amino acid
<220> FEATURE:
<221> NAME/KEY: MOD_RES
<222> LOCATION: (2134)..(2134)
<223> OTHER INFORMATION: Any amino acid
<220> FEATURE:
<221> NAME/KEY: MOD_RES
<222> LOCATION: (2139)..(2139)
<223> OTHER INFORMATION: Any amino acid
<220> FEATURE:
<221> NAME/KEY: MOD_RES
<222> LOCATION: (2144)..(2144)
<223> OTHER INFORMATION: Any amino acid
<220> FEATURE:
<221> NAME/KEY: MOD_RES
<222> LOCATION: (2149)..(2149)
<223> OTHER INFORMATION: Any amino acid
<220> FEATURE:
<221> NAME/KEY: MOD_RES
<222> LOCATION: (2154)..(2154)
<223> OTHER INFORMATION: Any amino acid
<220> FEATURE:
<221> NAME/KEY: MOD_RES
<222> LOCATION: (2159)..(2159)
<223> OTHER INFORMATION: Any amino acid
<220> FEATURE:
<221> NAME/KEY: MOD_RES
<222> LOCATION: (2164)..(2164)
<223> OTHER INFORMATION: Any amino acid
<220> FEATURE:
<221> NAME/KEY: MOD_RES
<222> LOCATION: (2169)..(2169)
<223> OTHER INFORMATION: Any amino acid
<220> FEATURE:
<221> NAME/KEY: MOD_RES
<222> LOCATION: (2174)..(2174)
<223> OTHER INFORMATION: Any amino acid
<220> FEATURE:
<221> NAME/KEY: MOD_RES
```

-continued

```
<222> LOCATION: (2179)..(2179)
<223> OTHER INFORMATION: Any amino acid
<220> FEATURE:
<221> NAME/KEY: MOD_RES
<222> LOCATION: (2184)..(2184)
<223> OTHER INFORMATION: Any amino acid
<220> FEATURE:
<221> NAME/KEY: MOD_RES
<222> LOCATION: (2189)..(2189)
<223> OTHER INFORMATION: Any amino acid
<220> FEATURE:
<221> NAME/KEY: MOD_RES
<222> LOCATION: (2194)..(2194)
<223> OTHER INFORMATION: Any amino acid
<220> FEATURE:
<221> NAME/KEY: MOD_RES
<222> LOCATION: (2199)..(2199)
<223> OTHER INFORMATION: Any amino acid
<220> FEATURE:
<221> NAME/KEY: MOD_RES
<222> LOCATION: (2204)..(2204)
<223> OTHER INFORMATION: Any amino acid
<220> FEATURE:
<221> NAME/KEY: MOD_RES
<222> LOCATION: (2209)..(2209)
<223> OTHER INFORMATION: Any amino acid
<220> FEATURE:
<221> NAME/KEY: MOD_RES
<222> LOCATION: (2214)..(2214)
<223> OTHER INFORMATION: Any amino acid
<220> FEATURE:
<221> NAME/KEY: MOD_RES
<222> LOCATION: (2219)..(2219)
<223> OTHER INFORMATION: Any amino acid
<220> FEATURE:
<221> NAME/KEY: MOD_RES
<222> LOCATION: (2224)..(2224)
<223> OTHER INFORMATION: Any amino acid
<220> FEATURE:
<221> NAME/KEY: MOD_RES
<222> LOCATION: (2229)..(2229)
<223> OTHER INFORMATION: Any amino acid
<220> FEATURE:
<221> NAME/KEY: MOD_RES
<222> LOCATION: (2234)..(2234)
<223> OTHER INFORMATION: Any amino acid
<220> FEATURE:
<221> NAME/KEY: MOD_RES
<222> LOCATION: (2239)..(2239)
<223> OTHER INFORMATION: Any amino acid
<220> FEATURE:
<221> NAME/KEY: MOD_RES
<222> LOCATION: (2244)..(2244)
<223> OTHER INFORMATION: Any amino acid
<220> FEATURE:
<221> NAME/KEY: MOD_RES
<222> LOCATION: (2249)..(2249)
<223> OTHER INFORMATION: Any amino acid
<220> FEATURE:
<221> NAME/KEY: MOD_RES
<222> LOCATION: (2254)..(2254)
<223> OTHER INFORMATION: Any amino acid
<220> FEATURE:
<221> NAME/KEY: MOD_RES
<222> LOCATION: (2259)..(2259)
<223> OTHER INFORMATION: Any amino acid
<220> FEATURE:
<221> NAME/KEY: MOD_RES
<222> LOCATION: (2264)..(2264)
<223> OTHER INFORMATION: Any amino acid
<220> FEATURE:
<221> NAME/KEY: MOD_RES
<222> LOCATION: (2269)..(2269)
<223> OTHER INFORMATION: Any amino acid
<220> FEATURE:
<221> NAME/KEY: MOD_RES
<222> LOCATION: (2274)..(2274)
<223> OTHER INFORMATION: Any amino acid
<220> FEATURE:
```

```
<221> NAME/KEY: MOD_RES
<222> LOCATION: (2279)..(2279)
<223> OTHER INFORMATION: Any amino acid
<220> FEATURE:
<221> NAME/KEY: MOD_RES
<222> LOCATION: (2284)..(2284)
<223> OTHER INFORMATION: Any amino acid
<220> FEATURE:
<221> NAME/KEY: MOD_RES
<222> LOCATION: (2289)..(2289)
<223> OTHER INFORMATION: Any amino acid
<220> FEATURE:
<221> NAME/KEY: MOD_RES
<222> LOCATION: (2294)..(2294)
<223> OTHER INFORMATION: Any amino acid
<220> FEATURE:
<221> NAME/KEY: MOD_RES
<222> LOCATION: (2299)..(2299)
<223> OTHER INFORMATION: Any amino acid
<220> FEATURE:
<221> NAME/KEY: MOD_RES
<222> LOCATION: (2304)..(2304)
<223> OTHER INFORMATION: Any amino acid
<220> FEATURE:
<221> NAME/KEY: MOD_RES
<222> LOCATION: (2309)..(2309)
<223> OTHER INFORMATION: Any amino acid
<220> FEATURE:
<221> NAME/KEY: MOD_RES
<222> LOCATION: (2314)..(2314)
<223> OTHER INFORMATION: Any amino acid
<220> FEATURE:
<221> NAME/KEY: MOD_RES
<222> LOCATION: (2319)..(2319)
<223> OTHER INFORMATION: Any amino acid
<220> FEATURE:
<221> NAME/KEY: MOD_RES
<222> LOCATION: (2324)..(2324)
<223> OTHER INFORMATION: Any amino acid
<220> FEATURE:
<221> NAME/KEY: MOD_RES
<222> LOCATION: (2329)..(2329)
<223> OTHER INFORMATION: Any amino acid
<220> FEATURE:
<221> NAME/KEY: MOD_RES
<222> LOCATION: (2334)..(2334)
<223> OTHER INFORMATION: Any amino acid
<220> FEATURE:
<221> NAME/KEY: MOD_RES
<222> LOCATION: (2339)..(2339)
<223> OTHER INFORMATION: Any amino acid
<220> FEATURE:
<221> NAME/KEY: MOD_RES
<222> LOCATION: (2344)..(2344)
<223> OTHER INFORMATION: Any amino acid
<220> FEATURE:
<221> NAME/KEY: MOD_RES
<222> LOCATION: (2349)..(2349)
<223> OTHER INFORMATION: Any amino acid
<220> FEATURE:
<221> NAME/KEY: MOD_RES
<222> LOCATION: (2354)..(2354)
<223> OTHER INFORMATION: Any amino acid
<220> FEATURE:
<221> NAME/KEY: MOD_RES
<222> LOCATION: (2359)..(2359)
<223> OTHER INFORMATION: Any amino acid
<220> FEATURE:
<221> NAME/KEY: MOD_RES
<222> LOCATION: (2364)..(2364)
<223> OTHER INFORMATION: Any amino acid
<220> FEATURE:
<221> NAME/KEY: MOD_RES
<222> LOCATION: (2369)..(2369)
<223> OTHER INFORMATION: Any amino acid
<220> FEATURE:
<221> NAME/KEY: MOD_RES
<222> LOCATION: (2374)..(2374)
<223> OTHER INFORMATION: Any amino acid
```

```
<220> FEATURE:
<221> NAME/KEY: MOD_RES
<222> LOCATION: (2379)..(2379)
<223> OTHER INFORMATION: Any amino acid
<220> FEATURE:
<221> NAME/KEY: MOD_RES
<222> LOCATION: (2384)..(2384)
<223> OTHER INFORMATION: Any amino acid
<220> FEATURE:
<221> NAME/KEY: MOD_RES
<222> LOCATION: (2389)..(2389)
<223> OTHER INFORMATION: Any amino acid
<220> FEATURE:
<221> NAME/KEY: MOD_RES
<222> LOCATION: (2394)..(2394)
<223> OTHER INFORMATION: Any amino acid
<220> FEATURE:
<221> NAME/KEY: MOD_RES
<222> LOCATION: (2399)..(2399)
<223> OTHER INFORMATION: Any amino acid
<220> FEATURE:
<221> NAME/KEY: MOD_RES
<222> LOCATION: (2404)..(2404)
<223> OTHER INFORMATION: Any amino acid
<220> FEATURE:
<221> NAME/KEY: MOD_RES
<222> LOCATION: (2409)..(2409)
<223> OTHER INFORMATION: Any amino acid
<220> FEATURE:
<221> NAME/KEY: MOD_RES
<222> LOCATION: (2414)..(2414)
<223> OTHER INFORMATION: Any amino acid
<220> FEATURE:
<221> NAME/KEY: MOD_RES
<222> LOCATION: (2419)..(2419)
<223> OTHER INFORMATION: Any amino acid
<220> FEATURE:
<221> NAME/KEY: MOD_RES
<222> LOCATION: (2424)..(2424)
<223> OTHER INFORMATION: Any amino acid
<220> FEATURE:
<221> NAME/KEY: MOD_RES
<222> LOCATION: (2429)..(2429)
<223> OTHER INFORMATION: Any amino acid
<220> FEATURE:
<221> NAME/KEY: MOD_RES
<222> LOCATION: (2434)..(2434)
<223> OTHER INFORMATION: Any amino acid
<220> FEATURE:
<221> NAME/KEY: MOD_RES
<222> LOCATION: (2439)..(2439)
<223> OTHER INFORMATION: Any amino acid
<220> FEATURE:
<221> NAME/KEY: MOD_RES
<222> LOCATION: (2444)..(2444)
<223> OTHER INFORMATION: Any amino acid
<220> FEATURE:
<221> NAME/KEY: MOD_RES
<222> LOCATION: (2449)..(2449)
<223> OTHER INFORMATION: Any amino acid
<220> FEATURE:
<221> NAME/KEY: MOD_RES
<222> LOCATION: (2454)..(2454)
<223> OTHER INFORMATION: Any amino acid
<220> FEATURE:
<221> NAME/KEY: MOD_RES
<222> LOCATION: (2459)..(2459)
<223> OTHER INFORMATION: Any amino acid
<220> FEATURE:
<221> NAME/KEY: MOD_RES
<222> LOCATION: (2464)..(2464)
<223> OTHER INFORMATION: Any amino acid
<220> FEATURE:
<221> NAME/KEY: MOD_RES
<222> LOCATION: (2469)..(2469)
<223> OTHER INFORMATION: Any amino acid
<220> FEATURE:
<221> NAME/KEY: MOD_RES
<222> LOCATION: (2474)..(2474)
```

```
<223> OTHER INFORMATION: Any amino acid
<220> FEATURE:
<221> NAME/KEY: MOD_RES
<222> LOCATION: (2479)..(2479)
<223> OTHER INFORMATION: Any amino acid
<220> FEATURE:
<221> NAME/KEY: MOD_RES
<222> LOCATION: (2484)..(2484)
<223> OTHER INFORMATION: Any amino acid
<220> FEATURE:
<221> NAME/KEY: MOD_RES
<222> LOCATION: (2489)..(2489)
<223> OTHER INFORMATION: Any amino acid
<220> FEATURE:
<221> NAME/KEY: MOD_RES
<222> LOCATION: (2494)..(2494)
<223> OTHER INFORMATION: Any amino acid
<220> FEATURE:
<221> NAME/KEY: MOD_RES
<222> LOCATION: (2499)..(2499)
<223> OTHER INFORMATION: Any amino acid
<220> FEATURE:
<223> OTHER INFORMATION: See specification as filed for detailed
      description of substitutions and preferred embodiments

<400> SEQUENCE: 14

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
```

-continued

```
            275                 280                 285
Xaa Gly Val Pro Gly Xaa Gly Val Pro Gly Xaa Gly Val Pro Gly Xaa
    290                 295                 300
Gly Val Pro Gly Xaa Gly Val Pro Gly Xaa Gly Val Pro Gly Xaa Gly
305                 310                 315                 320
Val Pro Gly Xaa Gly Val Pro Gly Xaa Gly Val Pro Gly Xaa Gly Val
                325                 330                 335
Pro Gly Xaa Gly Val Pro Gly Xaa Gly Val Pro Gly Xaa Gly Val Pro
            340                 345                 350
Gly Xaa Gly Val Pro Gly Xaa Gly Val Pro Gly Xaa Gly Val Pro Gly
        355                 360                 365
Xaa Gly Val Pro Gly Xaa Gly Val Pro Gly Xaa Gly Val Pro Gly Xaa
    370                 375                 380
Gly Val Pro Gly Xaa Gly Val Pro Gly Xaa Gly Val Pro Gly Xaa Gly
385                 390                 395                 400
Val Pro Gly Xaa Gly Val Pro Gly Xaa Gly Val Pro Gly Xaa Gly Val
                405                 410                 415
Pro Gly Xaa Gly Val Pro Gly Xaa Gly Val Pro Gly Xaa Gly Val Pro
            420                 425                 430
Gly Xaa Gly Val Pro Gly Xaa Gly Val Pro Gly Xaa Gly Val Pro Gly
        435                 440                 445
Xaa Gly Val Pro Gly Xaa Gly Val Pro Gly Xaa Gly Val Pro Gly Xaa
    450                 455                 460
Gly Val Pro Gly Xaa Gly Val Pro Gly Xaa Gly Val Pro Gly Xaa Gly
465                 470                 475                 480
Val Pro Gly Xaa Gly Val Pro Gly Xaa Gly Val Pro Gly Xaa Gly Val
                485                 490                 495
Pro Gly Xaa Gly Val Pro Gly Xaa Gly Val Pro Gly Xaa Gly Val Pro
            500                 505                 510
Gly Xaa Gly Val Pro Gly Xaa Gly Val Pro Gly Xaa Gly Val Pro Gly
        515                 520                 525
Xaa Gly Val Pro Gly Xaa Gly Val Pro Gly Xaa Gly Val Pro Gly Xaa
    530                 535                 540
Gly Val Pro Gly Xaa Gly Val Pro Gly Xaa Gly Val Pro Gly Xaa Gly
545                 550                 555                 560
Val Pro Gly Xaa Gly Val Pro Gly Xaa Gly Val Pro Gly Xaa Gly Val
                565                 570                 575
Pro Gly Xaa Gly Val Pro Gly Xaa Gly Val Pro Gly Xaa Gly Val Pro
            580                 585                 590
Gly Xaa Gly Val Pro Gly Xaa Gly Val Pro Gly Xaa Gly Val Pro Gly
        595                 600                 605
Xaa Gly Val Pro Gly Xaa Gly Val Pro Gly Xaa Gly Val Pro Gly Xaa
    610                 615                 620
Gly Val Pro Gly Xaa Gly Val Pro Gly Xaa Gly Val Pro Gly Xaa Gly
625                 630                 635                 640
Val Pro Gly Xaa Gly Val Pro Gly Xaa Gly Val Pro Gly Xaa Gly Val
                645                 650                 655
Pro Gly Xaa Gly Val Pro Gly Xaa Gly Val Pro Gly Xaa Gly Val Pro
            660                 665                 670
Gly Xaa Gly Val Pro Gly Xaa Gly Val Pro Gly Xaa Gly Val Pro Gly
        675                 680                 685
Xaa Gly Val Pro Gly Xaa Gly Val Pro Gly Xaa Gly Val Pro Gly Xaa
    690                 695                 700
```

-continued

```
Gly Val Pro Gly Xaa Gly Val Pro Gly Xaa Gly Val Pro Gly Xaa Gly
705                 710                 715                 720
Val Pro Gly Xaa Gly Val Pro Gly Xaa Gly Val Pro Gly Xaa Gly Val
                725                 730                 735
Pro Gly Xaa Gly Val Pro Gly Xaa Gly Val Pro Gly Xaa Gly Val Pro
            740                 745                 750
Gly Xaa Gly Val Pro Gly Xaa Gly Val Pro Gly Xaa Gly Val Pro Gly
        755                 760                 765
Xaa Gly Val Pro Gly Xaa Gly Val Pro Gly Xaa Gly Val Pro Gly Xaa
    770                 775                 780
Gly Val Pro Gly Xaa Gly Val Pro Gly Xaa Gly Val Pro Gly Xaa Gly
785                 790                 795                 800
Val Pro Gly Xaa Gly Val Pro Gly Xaa Gly Val Pro Gly Xaa Gly Val
                805                 810                 815
Pro Gly Xaa Gly Val Pro Gly Xaa Gly Val Pro Gly Xaa Gly Val Pro
            820                 825                 830
Gly Xaa Gly Val Pro Gly Xaa Gly Val Pro Gly Xaa Gly Val Pro Gly
        835                 840                 845
Xaa Gly Val Pro Gly Xaa Gly Val Pro Gly Xaa Gly Val Pro Gly Xaa
    850                 855                 860
Gly Val Pro Gly Xaa Gly Val Pro Gly Xaa Gly Val Pro Gly Xaa Gly
865                 870                 875                 880
Val Pro Gly Xaa Gly Val Pro Gly Xaa Gly Val Pro Gly Xaa Gly Val
                885                 890                 895
Pro Gly Xaa Gly Val Pro Gly Xaa Gly Val Pro Gly Xaa Gly Val Pro
            900                 905                 910
Gly Xaa Gly Val Pro Gly Xaa Gly Val Pro Gly Xaa Gly Val Pro Gly
        915                 920                 925
Xaa Gly Val Pro Gly Xaa Gly Val Pro Gly Xaa Gly Val Pro Gly Xaa
    930                 935                 940
Gly Val Pro Gly Xaa Gly Val Pro Gly Xaa Gly Val Pro Gly Xaa Gly
945                 950                 955                 960
Val Pro Gly Xaa Gly Val Pro Gly Xaa Gly Val Pro Gly Xaa Gly Val
                965                 970                 975
Pro Gly Xaa Gly Val Pro Gly Xaa Gly Val Pro Gly Xaa Gly Val Pro
            980                 985                 990
Gly Xaa Gly Val Pro Gly Xaa Gly  Val Pro Gly Xaa Gly  Val Pro Gly
        995                 1000                 1005
Xaa Gly  Val Pro Gly Xaa Gly  Val Pro Gly Xaa Gly  Val Pro Gly
    1010                 1015                 1020
Xaa Gly  Val Pro Gly Xaa Gly  Val Pro Gly Xaa Gly  Val Pro Gly
    1025                 1030                 1035
Xaa Gly  Val Pro Gly Xaa Gly  Val Pro Gly Xaa Gly  Val Pro Gly
    1040                 1045                 1050
Xaa Gly  Val Pro Gly Xaa Gly  Val Pro Gly Xaa Gly  Val Pro Gly
    1055                 1060                 1065
Xaa Gly  Val Pro Gly Xaa Gly  Val Pro Gly Xaa Gly  Val Pro Gly
    1070                 1075                 1080
Xaa Gly  Val Pro Gly Xaa Gly  Val Pro Gly Xaa Gly  Val Pro Gly
    1085                 1090                 1095
Xaa Gly  Val Pro Gly Xaa Gly  Val Pro Gly Xaa Gly  Val Pro Gly
    1100                 1105                 1110
```

```
Xaa Gly Val Pro Gly Xaa Gly Val Pro Gly Xaa Gly Val Pro Gly
1115                1120                1125

Xaa Gly Val Pro Gly Xaa Gly Val Pro Gly Xaa Gly Val Pro Gly
1130                1135                1140

Xaa Gly Val Pro Gly Xaa Gly Val Pro Gly Xaa Gly Val Pro Gly
1145                1150                1155

Xaa Gly Val Pro Gly Xaa Gly Val Pro Gly Xaa Gly Val Pro Gly
1160                1165                1170

Xaa Gly Val Pro Gly Xaa Gly Val Pro Gly Xaa Gly Val Pro Gly
1175                1180                1185

Xaa Gly Val Pro Gly Xaa Gly Val Pro Gly Xaa Gly Val Pro Gly
1190                1195                1200

Xaa Gly Val Pro Gly Xaa Gly Val Pro Gly Xaa Gly Val Pro Gly
1205                1210                1215

Xaa Gly Val Pro Gly Xaa Gly Val Pro Gly Xaa Gly Val Pro Gly
1220                1225                1230

Xaa Gly Val Pro Gly Xaa Gly Val Pro Gly Xaa Gly Val Pro Gly
1235                1240                1245

Xaa Gly Val Pro Gly Xaa Gly Val Pro Gly Xaa Gly Val Pro Gly
1250                1255                1260

Xaa Gly Val Pro Gly Xaa Gly Val Pro Gly Xaa Gly Val Pro Gly
1265                1270                1275

Xaa Gly Val Pro Gly Xaa Gly Val Pro Gly Xaa Gly Val Pro Gly
1280                1285                1290

Xaa Gly Val Pro Gly Xaa Gly Val Pro Gly Xaa Gly Val Pro Gly
1295                1300                1305

Xaa Gly Val Pro Gly Xaa Gly Val Pro Gly Xaa Gly Val Pro Gly
1310                1315                1320

Xaa Gly Val Pro Gly Xaa Gly Val Pro Gly Xaa Gly Val Pro Gly
1325                1330                1335

Xaa Gly Val Pro Gly Xaa Gly Val Pro Gly Xaa Gly Val Pro Gly
1340                1345                1350

Xaa Gly Val Pro Gly Xaa Gly Val Pro Gly Xaa Gly Val Pro Gly
1355                1360                1365

Xaa Gly Val Pro Gly Xaa Gly Val Pro Gly Xaa Gly Val Pro Gly
1370                1375                1380

Xaa Gly Val Pro Gly Xaa Gly Val Pro Gly Xaa Gly Val Pro Gly
1385                1390                1395

Xaa Gly Val Pro Gly Xaa Gly Val Pro Gly Xaa Gly Val Pro Gly
1400                1405                1410

Xaa Gly Val Pro Gly Xaa Gly Val Pro Gly Xaa Gly Val Pro Gly
1415                1420                1425

Xaa Gly Val Pro Gly Xaa Gly Val Pro Gly Xaa Gly Val Pro Gly
1430                1435                1440

Xaa Gly Val Pro Gly Xaa Gly Val Pro Gly Xaa Gly Val Pro Gly
1445                1450                1455

Xaa Gly Val Pro Gly Xaa Gly Val Pro Gly Xaa Gly Val Pro Gly
1460                1465                1470

Xaa Gly Val Pro Gly Xaa Gly Val Pro Gly Xaa Gly Val Pro Gly
1475                1480                1485

Xaa Gly Val Pro Gly Xaa Gly Val Pro Gly Xaa Gly Val Pro Gly
1490                1495                1500

Xaa Gly Val Pro Gly Xaa Gly Val Pro Gly Xaa Gly Val Pro Gly
```

```
            1505                1510                1515

Xaa Gly Val Pro Gly Xaa Gly Val Pro Gly Xaa Gly Val Pro Gly
    1520                1525                1530

Xaa Gly Val Pro Gly Xaa Gly Val Pro Gly Xaa Gly Val Pro Gly
    1535                1540                1545

Xaa Gly Val Pro Gly Xaa Gly Val Pro Gly Xaa Gly Val Pro Gly
    1550                1555                1560

Xaa Gly Val Pro Gly Xaa Gly Val Pro Gly Xaa Gly Val Pro Gly
    1565                1570                1575

Xaa Gly Val Pro Gly Xaa Gly Val Pro Gly Xaa Gly Val Pro Gly
    1580                1585                1590

Xaa Gly Val Pro Gly Xaa Gly Val Pro Gly Xaa Gly Val Pro Gly
    1595                1600                1605

Xaa Gly Val Pro Gly Xaa Gly Val Pro Gly Xaa Gly Val Pro Gly
    1610                1615                1620

Xaa Gly Val Pro Gly Xaa Gly Val Pro Gly Xaa Gly Val Pro Gly
    1625                1630                1635

Xaa Gly Val Pro Gly Xaa Gly Val Pro Gly Xaa Gly Val Pro Gly
    1640                1645                1650

Xaa Gly Val Pro Gly Xaa Gly Val Pro Gly Xaa Gly Val Pro Gly
    1655                1660                1665

Xaa Gly Val Pro Gly Xaa Gly Val Pro Gly Xaa Gly Val Pro Gly
    1670                1675                1680

Xaa Gly Val Pro Gly Xaa Gly Val Pro Gly Xaa Gly Val Pro Gly
    1685                1690                1695

Xaa Gly Val Pro Gly Xaa Gly Val Pro Gly Xaa Gly Val Pro Gly
    1700                1705                1710

Xaa Gly Val Pro Gly Xaa Gly Val Pro Gly Xaa Gly Val Pro Gly
    1715                1720                1725

Xaa Gly Val Pro Gly Xaa Gly Val Pro Gly Xaa Gly Val Pro Gly
    1730                1735                1740

Xaa Gly Val Pro Gly Xaa Gly Val Pro Gly Xaa Gly Val Pro Gly
    1745                1750                1755

Xaa Gly Val Pro Gly Xaa Gly Val Pro Gly Xaa Gly Val Pro Gly
    1760                1765                1770

Xaa Gly Val Pro Gly Xaa Gly Val Pro Gly Xaa Gly Val Pro Gly
    1775                1780                1785

Xaa Gly Val Pro Gly Xaa Gly Val Pro Gly Xaa Gly Val Pro Gly
    1790                1795                1800

Xaa Gly Val Pro Gly Xaa Gly Val Pro Gly Xaa Gly Val Pro Gly
    1805                1810                1815

Xaa Gly Val Pro Gly Xaa Gly Val Pro Gly Xaa Gly Val Pro Gly
    1820                1825                1830

Xaa Gly Val Pro Gly Xaa Gly Val Pro Gly Xaa Gly Val Pro Gly
    1835                1840                1845

Xaa Gly Val Pro Gly Xaa Gly Val Pro Gly Xaa Gly Val Pro Gly
    1850                1855                1860

Xaa Gly Val Pro Gly Xaa Gly Val Pro Gly Xaa Gly Val Pro Gly
    1865                1870                1875

Xaa Gly Val Pro Gly Xaa Gly Val Pro Gly Xaa Gly Val Pro Gly
    1880                1885                1890

Xaa Gly Val Pro Gly Xaa Gly Val Pro Gly Xaa Gly Val Pro Gly
    1895                1900                1905
```

Xaa Gly Val Pro Gly Xaa Gly Val Pro Gly Xaa Gly Val Pro Gly
    1910                1915                1920

Xaa Gly Val Pro Gly Xaa Gly Val Pro Gly Xaa Gly Val Pro Gly
    1925                1930                1935

Xaa Gly Val Pro Gly Xaa Gly Val Pro Gly Xaa Gly Val Pro Gly
    1940                1945                1950

Xaa Gly Val Pro Gly Xaa Gly Val Pro Gly Xaa Gly Val Pro Gly
    1955                1960                1965

Xaa Gly Val Pro Gly Xaa Gly Val Pro Gly Xaa Gly Val Pro Gly
    1970                1975                1980

Xaa Gly Val Pro Gly Xaa Gly Val Pro Gly Xaa Gly Val Pro Gly
    1985                1990                1995

Xaa Gly Val Pro Gly Xaa Gly Val Pro Gly Xaa Gly Val Pro Gly
    2000                2005                2010

Xaa Gly Val Pro Gly Xaa Gly Val Pro Gly Xaa Gly Val Pro Gly
    2015                2020                2025

Xaa Gly Val Pro Gly Xaa Gly Val Pro Gly Xaa Gly Val Pro Gly
    2030                2035                2040

Xaa Gly Val Pro Gly Xaa Gly Val Pro Gly Xaa Gly Val Pro Gly
    2045                2050                2055

Xaa Gly Val Pro Gly Xaa Gly Val Pro Gly Xaa Gly Val Pro Gly
    2060                2065                2070

Xaa Gly Val Pro Gly Xaa Gly Val Pro Gly Xaa Gly Val Pro Gly
    2075                2080                2085

Xaa Gly Val Pro Gly Xaa Gly Val Pro Gly Xaa Gly Val Pro Gly
    2090                2095                2100

Xaa Gly Val Pro Gly Xaa Gly Val Pro Gly Xaa Gly Val Pro Gly
    2105                2110                2115

Xaa Gly Val Pro Gly Xaa Gly Val Pro Gly Xaa Gly Val Pro Gly
    2120                2125                2130

Xaa Gly Val Pro Gly Xaa Gly Val Pro Gly Xaa Gly Val Pro Gly
    2135                2140                2145

Xaa Gly Val Pro Gly Xaa Gly Val Pro Gly Xaa Gly Val Pro Gly
    2150                2155                2160

Xaa Gly Val Pro Gly Xaa Gly Val Pro Gly Xaa Gly Val Pro Gly
    2165                2170                2175

Xaa Gly Val Pro Gly Xaa Gly Val Pro Gly Xaa Gly Val Pro Gly
    2180                2185                2190

Xaa Gly Val Pro Gly Xaa Gly Val Pro Gly Xaa Gly Val Pro Gly
    2195                2200                2205

Xaa Gly Val Pro Gly Xaa Gly Val Pro Gly Xaa Gly Val Pro Gly
    2210                2215                2220

Xaa Gly Val Pro Gly Xaa Gly Val Pro Gly Xaa Gly Val Pro Gly
    2225                2230                2235

Xaa Gly Val Pro Gly Xaa Gly Val Pro Gly Xaa Gly Val Pro Gly
    2240                2245                2250

Xaa Gly Val Pro Gly Xaa Gly Val Pro Gly Xaa Gly Val Pro Gly
    2255                2260                2265

Xaa Gly Val Pro Gly Xaa Gly Val Pro Gly Xaa Gly Val Pro Gly
    2270                2275                2280

Xaa Gly Val Pro Gly Xaa Gly Val Pro Gly Xaa Gly Val Pro Gly
    2285                2290                2295

```
Xaa Gly Val Pro Gly Xaa Gly Val Pro Gly Xaa Gly Val Pro Gly
    2300                2305                2310

Xaa Gly Val Pro Gly Xaa Gly Val Pro Gly Xaa Gly Val Pro Gly
    2315                2320                2325

Xaa Gly Val Pro Gly Xaa Gly Val Pro Gly Xaa Gly Val Pro Gly
    2330                2335                2340

Xaa Gly Val Pro Gly Xaa Gly Val Pro Gly Xaa Gly Val Pro Gly
    2345                2350                2355

Xaa Gly Val Pro Gly Xaa Gly Val Pro Gly Xaa Gly Val Pro Gly
    2360                2365                2370

Xaa Gly Val Pro Gly Xaa Gly Val Pro Gly Xaa Gly Val Pro Gly
    2375                2380                2385

Xaa Gly Val Pro Gly Xaa Gly Val Pro Gly Xaa Gly Val Pro Gly
    2390                2395                2400

Xaa Gly Val Pro Gly Xaa Gly Val Pro Gly Xaa Gly Val Pro Gly
    2405                2410                2415

Xaa Gly Val Pro Gly Xaa Gly Val Pro Gly Xaa Gly Val Pro Gly
    2420                2425                2430

Xaa Gly Val Pro Gly Xaa Gly Val Pro Gly Xaa Gly Val Pro Gly
    2435                2440                2445

Xaa Gly Val Pro Gly Xaa Gly Val Pro Gly Xaa Gly Val Pro Gly
    2450                2455                2460

Xaa Gly Val Pro Gly Xaa Gly Val Pro Gly Xaa Gly Val Pro Gly
    2465                2470                2475

Xaa Gly Val Pro Gly Xaa Gly Val Pro Gly Xaa Gly Val Pro Gly
    2480                2485                2490

Xaa Gly Val Pro Gly Xaa Gly
    2495                2500

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

His His His His His His
1               5
```

CD20 SCFV-ELPS METHODS AND THERAPEUTICS

CROSS-REFERENCE TO RELATED APPLICATIONS

This application is a continuation of U.S. application Ser. No. 14/420,308, filed on Feb. 6, 2015, now abandoned, which is a national stage application under 35 U.S.C. § 371 of International Application No. PCT/US2013/054218, filed Aug. 8, 2013, which in turn claims the benefit under 35 U.S.C. § 119(e) of U.S. Provisional Application Ser. No. 61/682,029, filed Aug. 10, 2012, the contents of each of which is incorporated by reference into the present disclosure in its entirety.

SEQUENCE LISTING

The instant application contains a Sequence Listing which has been submitted in ASCII format via EFS-Web and is hereby incorporated by reference in its entirety. Said ASCII copy, created on Sep. 13, 2019, is named 075405-1862_SL.txt and is 223,467 bytes in size.

BACKGROUND

Non-Hodgkin Lymphoma (NHL) accounts for 4% of all reported cancers. The most prescribed course of treatment is a regimen of cyclophosphamide, doxorubicin, vincristine and prednisone (CHOP). The CHOP regimen, developed in the 70's, is effective in 90% of the patients but is responsible for severe side effects.

NHL is characterized by increased production of malignant B-cells, which can be targeted specifically through cell-surface CD20. Antibodies against CD20 have been developed for NHL and have successfully made their way to the clinic. The most prominent example is Rituximab™, a chimeric antibody that targets malignant as well as normal B-cells. Crosslinking of Rituximab™ using a secondary antibody against the Fc region promotes cell apoptosis, which led to the observation that CD20-mediated apoptosis can be potentiated through strategies that induce multivalency. Multivalent antibodies against CD20 are potent inhibitors of the MAP Kinase pathway and upregulate Raf-1 kinase inhibitor protein (RKIP), which promotes apoptosis. In combination with chemotherapy, immunotherapeutics overcome resistance in greater than 50% of NHL patients. Particles targeting CD20 may also be effective in drug resistant NHL.

Autoimmune disorders and cancers including NHL are currently being treated by surgery, radiotherapy, chemotherapy, and more recently immunotherapy. Substantial efforts have been expended to explore these modalities, but more innovative ideas are needed to gain ground against tumor resistance. In addition, many cancer therapeutics have an associated risk of cytotoxicity to healthy tissue. Therefore, there is a need in the art for therapeutics with reduced toxicity.

SUMMARY

Disclosed herein are recombinant polypeptides, methods and compositions for the specific targeting scFv-ELPs to cells. One aspect relates to a recombinant polypeptide comprising, or alternatively consisting essentially of, or yet further consisting of an elastin-like peptide (ELP) and a scFv, or a biological equivalent of the scFv. A scFv refers to a single-chain variable fragment of an antibody or ligand.

Another aspect relates to isolated polynucleotides encoding the recombinant scFv-ELP polypeptides as described herein. Further aspects relate to vectors and/or host cells comprising the polynucleotides encoding the recombinant scFv-ELP. In yet further aspects relate to compositions comprising, or alternatively consisting essentially of, or yet further consisting of at least two polypeptides, described herein, organized in a cylindrical particle or a spherical particle, further consisting of a core comprised of the scFv of the recombinant polypeptide. In still further aspects, compositions comprising, or alternatively consisting essentially of, or yet further consisting of a carrier and the polypeptide described herein, a polynucleotide described herein, or vectors and/or host cells comprising, or alternatively consisting essentially of, or yet further consisting of a polynucleotide described herein.

Further aspects relate to methods for preparing a therapeutic polypeptide, comprising, or alternatively consisting essentially of, or yet further consisting of: expressing the polypeptide of this disclosure in a suitable expression system. Still further aspects relate to methods for denaturing and refolding the polypeptide of this disclosure. Also provided are methods of denaturing and refolding of the polypeptide at least twice, or at least thrice, or at least four times.

Another method aspect relates to a method for inducing apoptosis of a CD20+ cell comprising, or alternatively consisting essentially of, or yet further consisting of contacting the cell with an effective amount of the polypeptide of a recombinant scFv-ELP polypeptide described herein where the scFv component of the ELP is the single chain variable region from the anti-CD20 antibody. Also provided are methods for CD20-related disorder such as treating CD20 expressing cancer or autoimmune disease, comprising, or alternatively consisting essentially of, or yet further consisting of administering to a patient in need of such treatment a recombinant scFv-ELP polypeptide described herein where the scFv component of the ELP is the single chain variable region from the anti-CD20 antibody or administering the polynucleotide encoding such polypeptides.

A further aspect relates to a method for targeting a scFv-ELP to a cell comprising, or alternatively consisting essentially of, or yet further consisting of contacting the cell with an effective amount of the polypeptide described herein, wherein the scFv component of the scFv-ELP binds to a cellular component of the cell. The method is useful therapeutically and to screen for new molecules or agents that may affect the apoptotic pathway. For example, a test drug or agent is contacted with the cell, the polypeptide under conditions favorable to binding of the polypeptide to the cell receptor. The ability of the agent to inhibit the binding of the polypeptide to the cell receptor would be an indication that the test drug or agent is a candidate therapeutic for regulation of the cell through that receptor, e.g., apoptosis through binding of the CD20 cell surface receptor.

BRIEF DESCRIPTION OF THE FIGURES

FIG. 1A: Phase diagram of ELP A192; FIG. 1B: Phase diagram of scFv A192; and FIG. 1C: Linear regression shows a concentration dependent change in transition temperature.

FIG. 3 depicts the structure of the scFv-ELP. The scFv fragment was genetically fused to the N-terminus of ELP. The ELP was fused to the variable light chain of the scFv. The plasmid containing the fusion was transformed into *E. coli* and expressed.

FIG. 4A: scFv A192 can be purified using inverse temperature cycling (ITC). R-Reducing conditions, NP-Non-reducing conditions FIG. 4B: scFv A192 assembles particles with hydrodynamic radius of ~32 nm whereas A192 is ~6 nm.

FIGS. 5A-5B depict the genetically expressed scFv assemble monodisperse spherical particles. FIG. 5A: Uranyl Acetate contrast enhanced transmission electron microscopy (TEM) images of scFv A192 reveals nanoparticles, which are 51.7±12.4 nm wide. FIG. 5B: Cryo TEM images of scFv A192 show monodisperse particles of 48.1±11.8 nm in diameter. Scale bar represents 50 nm.

FIGS. 7A-H demonstrates scFv CD20 recognition using confocal microscopy. Panels A to D show Rhodamine (RHD) labeled scFV A192 forms distinct punctate bodies on Raji cell surface. Panels E to H show no scFv A192 binding on CEM cells.

FIGS. 8A to 8C show RDH labeled scFv A192 forms distinct punctate bodies on CD20'+'ve Raji cell surface. FIGS. 8D-F show no scFv A192 binding on CD20'−'ve CEM cells.

FIGS. 9A-9H show that unlabeled CD20 antibody abolishes scFv CD20 binding. Antibody treated CD20+ Raji cells, FIG. 9A-D, show no scFv A192 binding. Untreated Raji cells, FIG. 9E-H show scFv A192 binding.

FIG. 13 depicts the scheme used to make the scFv-ELP DNA constructs described in Example 1.

FIGS. 14A-14B show that Antibody Core Protein Polymer Nanoworms (ACPPNs) enhance apoptotic signaling. FIG. 14A: Expression of a fusion between a single chain antibody (scFv) and an environmentally-responsive protein polymer (i.e. ELPs) yields stable nanoworms. The nanoworms target cell-surface CD20 receptor, inducing apoptosis in B-cells and hence will be ideal for lymphoma therapies. FIG. 14B: An anti-CD20 scFv consisting of both a heavy and light chain was fused to the amino terminus of an elastin-like polypeptide (ELP). The ELP protein polymer, A192, was selected to promote solubility at physiological conditions and phase separation upon binding the cell surface.

FIGS. 15A-15B depict renaturation of scFv fusion forms ACPPNs. FIG. 15A: cryoTEM images of 'raw' scFv fusion form spherical assemblies with a diameter of 48.1±11.8 nm. FIG. 15B: cryoTEM images of 'refolded' particles show a major population of 'nanoworms' with lengths of 56.2±15.9 nm with a minor spherical particles with a diameter of 27.4±7.5 nm. Scale bar represents 100 nm.

FIGS. 16A-16C show that ACPPNs competitively target CD20+ cells. FIG. 16A: Panels i-iii and vii-ix show CD20 recognition by RHD labeled RTXN on both Raji and SU-DHL-7 cells. RHD labeled RTXN forms a ring pattern around the target cell. Crosslinking surface bound RTXN by a 2° goat Anti human Fc (Panels iv-vi and x-xii) shows the ring pattern shift to a more punctate appearance. FIG. 16B: Panels i-iii show recognition of surface CD20 by RHD labeled ACPPNs. ACPPNs binding also forms a punctate appearance similar to crosslinked RTXN. FIG. 16C: ACPPNs binding was significantly higher than unmodified A192 and RTXN block (P=0.031*, 0.038**). Normalized intensity of RHD was calculated using image J (n=4 slides). Scale bar represents 5 μm.

FIGS. 17A-17F show ACPPNs reduce viability of CD20+ human lymphoma cell lines by inducing apoptosis. FIG. 17A: Trypan blue exclusion showed a significant increase in trypan blue positive cells with increasing concentrations of ACPPNs. FIG. 17B: CD20+ cells, Raji, and SU-DHL-7, show a concentration dependent reduction in cell viability. The calculated IC50s for Raji and SU-DHL-7 are 32 and 41 μM respectively CD20−, CEM, are less effected by ACPPNs treatment. The IC50 for CEM cells is 294 μM which is ten times higher than ACPPNs. FIG. 17C: Raji and SU-DHL-7 cells both show a significant increase in ANXV/PI staining after ACPPNs treatment when compared to plain RTXN (P=0.003*, P=0.0005**). RTXN crosslinked by 2° GAH and apoptosis control, chLym-1, both induce apoptosis. FIG. 17D: TUNEL staining confirms ACPPNs induction of apoptosis. ACPPNs outperform plain RTXN in both cell lines (P=0.006*, P=0.006**). ACPPNs induces apoptosis to the same extent as 2° GAH crosslinked RTXN. FIGS. FIGS. E-F: ACPPN treatment substantially increased caspase activity in both Raji and SU-DHL-7 cells.

FIGS. 18A-18J show that ACPPNs treatment shows relatively high tumor accumulation and reduces tumor burden in Raji xenografts. FIGS. 18A-H: ACPPNs microdistribution (2.5 mgs/dose, n=3) using laser confocal microscopy shows accumulation of RHD labeled ACPPNs in liver (A, E), spleen (B, F), tumor (C, G), and kidney (D, H). There was minimal accumulation of these particles in the lungs and heart. Interestingly particle accumulation can be seen in the spleen marginal zone (MZ) and the bowman capsule (BC). Scale bar represents 20 μm. FIG. 18I: As of day 25, ACPPNs significantly reduced mean tumor burden when compared to PBS and RTXN treated groups (n=5/group, P=0.0011). FIG. 18J: ACPPNs treatment significantly enhances survival when compared to PBS and RTXN control groups (P=0.013). The highlighted tick marks indicate days of dose administration.

DETAILED DESCRIPTION

Definitions

Figure 1A:
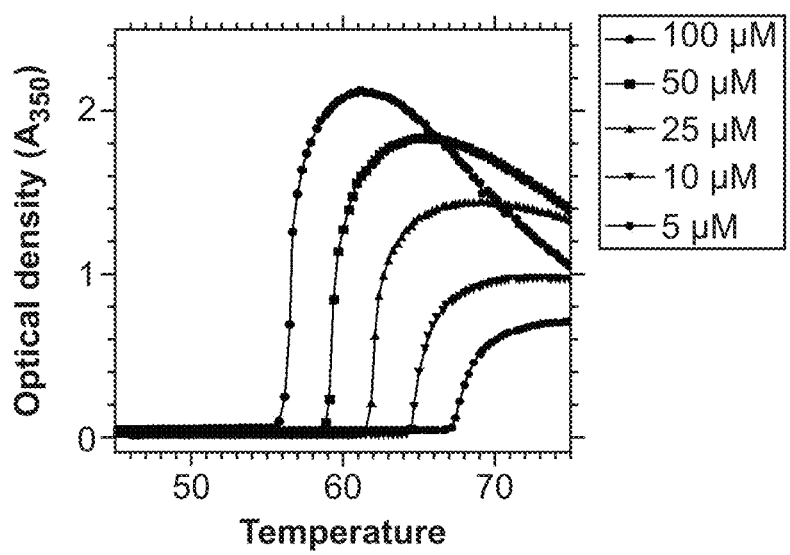
FIGS. 1A-1C show phase diagrams of ELP and scFv ELP fusions.

The practice of the present invention will employ, unless otherwise indicated, conventional techniques of tissue culture, immunology, molecular biology, microbiology, cell biology and recombinant DNA, which are within the skill of the art. See, e.g., Sambrook et al., (1989) Molecular Cloning: A Laboratory Manual, 2nd edition; Ausubel et al., eds. (1987) Current Protocols In Molecular Biology; MacPherson, B. D. Hames and G. R. Taylor eds., (1995) PCR 2: A Practical Approach; Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term "pharmaceutically acceptable carrier" (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

A "pharmaceutical composition" is intended to include the combination of an active agent with a carrier, inert or active, making the composition suitable for diagnostic or therapeutic use in vitro, in vivo or ex vivo.

As used herein, the term "patient" or "subject" intends an animal, a mammal or yet further a human patient. For the purpose of illustration only, a mammal includes but is not limited to a human, a feline, a canine, a simian, a murine, a bovine, an equine, a porcine or an ovine.

The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

The term "therapeutic" refers to an agent or component capable of inducing a biological effect in vivo and/or in vitro. The biological effect may be useful for treating and/or preventing a condition, disorder, or disease in a subject or patient. A therapeutic may include, without limitation, a small molecule, a nucleic acid, or a polypeptide.

As used herein, the term "CD20" or "B-lymphocyte antigen CD20" refers to a protein expressed on the surface of B-cells. In humans, CD20 is encoded by the MS4A1 gene. "Anti-CD20" or "Anti-CD20 antibody" refers to an antibody that specifically recognizes the CD20 antigen. Some current therapeutics are anti-CD20 antibodies. These include, for example, Rituximab, Ofatumumab, AME-133v (by Applied Molecular Evolution), Ocrelizumab for multiple sclerosis, TRU-015 (by Trubion), and IMMU-106 (veltuzumab).

As used herein, the term "biological equivalent thereof" is used synonymously with "equivalent" unless otherwise specifically intended. When referring to a reference protein, polypeptide or nucleic acid, the term intends those having minimal homology while still maintaining desired structure or functionality. Unless specifically recited herein, it is contemplated that any polynucleotide, polypeptide or protein mentioned herein also includes equivalents thereof. For example, an equivalent intends at least about 60%, or 65%, or 70%, or 75%, or 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Alternatively, a biological equivalent is a peptide encoded by a nucleic acid that hybridizes under stringent conditions to a nucleic acid or complement that encodes the peptide. Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell. An equivalent polynucleotide is one that hybridizes under stringent conditions to the reference polynucleotide or the complement of the reference polynucleotide, an in one aspect, having similar biological activity as the reference polynucleotide.

A polynucleotide or polynucleotide region (or a polypeptide or polypeptide region) having a certain percentage (for example, about 60%, 65%, 70%, 75%, 80%, 85%, 90%, 95% or 97%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

An "equivalent" of a polynucleotide or polypeptide refers to a polynucleotide or a polypeptide having a substantial homology or identity to the reference polynucleotide or polypeptide or one that hybridizes under conditions of high stringency to the reference polynucleotide or its complement. An equivalent polypeptide is encoded by a polynucleotide that hybridizes to a polynucleotide or its complement that expresses the reference polypeptide. In one aspect, a "substantial homology" is greater than about 60%, 65%, 70%, 75%, 80%, 85%, 90%, 95% or 98% homology.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

"Regulatory polynucleotide sequences" intends any one or more of promoters, operons, enhancers, as known to those skilled in the art to facilitate and enhance expression of polynucleotides.

An "expression vehicle" is a vehicle or a vector, non-limiting examples of which include viral vectors or plasmids, that assist with or facilitate expression of a gene or polynucleotide that has been inserted into the vehicle or vector.

A "delivery vehicle" is a vehicle or a vector that assists with the delivery of an exogenous polynucleotide into a target cell. The delivery vehicle may assist with expression or it may not, such as traditional calcium phosphate transfection compositions.

The term "scFv" refers to a single-chain variable fragment. scFv is a fusion protein of the variable regions of the heavy (VH) and light chains (VL) of immunoglobulins, connected with a linker peptide. The linker peptide can be from about 5 to 40 amino acids or from about 10 to 30 amino acids or about 5, 10, 15, 20, 25, 30, 35, or 40 amino acids in length. Single-chain variable fragments lack the constant Fc region found in complete antibody molecules, and, thus, the common binding sites (e.g., Protein G) used to purify antibodies. These fragments can often be purified or immobilized using Protein L, since Protein L interacts with the variable region of kappa light chains. More commonly, scientists incorporate a six histidine tag (SEQ ID NO: 15) on the c-terminus of the scFv molecule and purify them using immobilized metal affinity chromatography (IMAC). For unknown reasons, some scFv can also be captured by Protein A.

"An effective amount" refers to the amount of an active agent or a pharmaceutical composition sufficient to induce a desired biological and/or therapeutic result. That result can be alleviation of the signs, symptoms, or causes of a disease, or any other desired alteration of a biological system. The effective amount will vary depending upon the health condition or disease stage of the subject being treated, timing of administration, the manner of administration and the like, all of which can be determined readily by one of ordinary skill in the art.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

As used herein, the term CD20+ or CD20-related disorder intends a disease or condition marked by the expression of the CD20 receptor on the diseased or cell or tissue. In one aspect the disease is cancer such as lymphoma (non-Hodgkin's lymphoma) or CD20 expressing leukemias. In another aspect, the disease is an autoimmune disease such as Sjogren's syndrome, rheumatoid arthritis, coeliac disease, Crohn's disease and systemic lupus erythematosus. Tarella et al. (2013) Autoimmunity Reviews 12:802-813. In another aspect, a CD20-related disorder is any that has been treated by conventional CD20 antibody therapies such as rituximab.

As used herein, the term "nanoparticle" and "nanoworm" are intended to encompass the ELP-antibody fusion constructs unless otherwise noted. Applicants have discovered that denaturing and renaturing the nanoparticles will yield nanoworms having distinct dimensions from the more spherical nanoparticles.

As used herein, to "treat" further includes systemic amelioration of the symptoms associated with the pathology and/or a delay in onset of symptoms. Clinical and subclinical evidence of "treatment" will vary with the pathology, the subject and the treatment.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. It also includes in some aspects, antibody variants, polyclonal antibodies, human antibodies, humanized antibodies, chimeric antibodies, antibody derivatives, a bispecific molecule, a multispecific molecule, a heterospecific molecule, heteroantibodies and human monoclonal antibodies.

Examples of binding fragments encompassed within the term "antigen binding portion" of an antibody include a Fab fragment, a monovalent fragment consisting of the $V_L$, $V_H$, $C_L$ and CH, domains; a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intrapentoneal, intravenous and by inhalation. An agent of the present invention can be administered for therapy by any suitable route of administration. It will also be appreciated that the preferred route will vary with the condition and age of the recipient, and the disease being treated.

The agents and compositions of the present invention can be used in the manufacture of medicaments and for the treatment of humans and other animals by administration in accordance with conventional procedures, such as an active ingredient in pharmaceutical compositions.

As used herein, the term "detectable label" intends a directly or indirectly detectable compound or composition that is conjugated directly or indirectly to the composition to be detected. In one aspect, the detectable label is a non-naturally occurring detectable label in that it is not normally associated with the compound or composition as found in nature. In another aspect, a combination of a compound or composition and detectable label excludes combination that occur in nature. Non-limiting examples of such tags include, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. For example, a radioisotope is not attached to a nucleic acid in nature. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

MODES FOR CARRYING OUT THE DISCLOSURE

This disclosure relates to genetically engineered polypeptide nanoparticles targeted to CD20+ cells. To develop new treatments for CD20+ cancers (such as non-Hodgkin lymphoma, for example), new drug carriers are required that are biocompatible and easily modified with bioactive peptides. An emerging solution to this challenge utilizes genetically engineered polypeptides to drive the assembly of nanostructures. Elastin-like-polypeptide engages in a unique phase transition behavior, which can mediate self-assembly of nanoparticles. Described herein is a class of ELP fusion proteins with scFv fragments which are intended for inducing apoptosis in the target cell. The scFv-ELP fusion proteins are able to self-assemble to nanoparticles, which can also be utilized for gene therapy and drug delivery to the target cancerous cells.

Elastin-Like Polypeptides (ELPs)

Elastin-like-polypeptides (ELPs) are a genetically engineered polypeptide with unique phase behavior (see for e.g. S. R. MacEwan, et al., Biopolymers 94(1) (2010) 60-77) which promotes recombinant expression, protein purification and self-assembly of nanostructures (see for e.g. A. Chilkoti, et al., Advanced Drug Delivery Reviews 54 (2002) 1093-1111). ELPs are artificial polypeptides composed of repeated pentapeptide sequences, (Val-Pro-Gly-Xaa-Gly)n (SEQ ID NO: 6) derived from human tropoelastin, where Xaa is the "guest residue" Which is any amino acid. In one embodiment, Xaa is any amino acid except proline and n is an integer of at least one. This peptide motif displays rapid and reversible de-mixing from aqueous solutions above a transition temperature, $T_t$. Below $T_t$, ELPs adopt a highly water soluble random coil conformation; however, above $T_t$, they separate from solution, coalescing into a second aqueous phase. The $T_t$ of ELPs can be tuned by choosing the guest residue and ELP chain length as well as fusion peptides at the design level (see for e.g. MacEwan S R, et al., Biopolymers 94(1): 60-77). The ELP phase is both biocompatible and highly specific for ELPs or ELP fusion proteins, even in complex biological mixtures. Genetically engineered ELPs are monodisperse, biodegradable, non-toxic. Throughout this description, ELPs are identified by the single letter amino acid code of the guest residue followed by the number of repeat units, n. For example, S48I48 represents a diblock copolymer ELP with 48 serine (S) pentamers at the amino terminus and 48 isoleucine (I) pentamers at the carboxy terminus.

Described herein are ELP fusion proteins, which can be self-assembled into nanoparticles or nanoworms. The diameter of the substantially spherical nanoparticle can be from about 1 to about 1000 nm or from about 1 to about 500 nm, or from about 1 to about 100 nm, or from about 1 to about 50 nm, or from about 1 to 5 nm, or from about 3 to 20 nm, or from about 20 to about 50 nm, or from about 30 to about 50 nm, or from about 35 to about 45 nm. In one embodiment, the diameter is about 30 nm. The length of the nanoworm can be from about 10 to 1000 nm, or from about 10 to 500 nm, or from about 1 to about 100 nm or from about 5 to about 75 nm, or from about 5 to about 75 nm, or from about 10 to about 50 nm, or from about 15 to about 65 nm, or from about 10 to about 65 nm, or from about 15 to about 60 nm. The width of the nanoworm can be from about 50 to 1 nm, or from about 40 to 1 nm, or from about 35 to about 1 nm or from about 30 to about 1 nm, or from about 25 to about 1 nm, or from about 20 to about 1 nm. The fusion proteins are composed of elastin-like-polypeptides and high affinity polypeptides. These fusion proteins can be expressed from a variety of expression systems known to those skilled in the art and easily purified by the phase transition behavior of ELPs. These ELP fusion proteins are able to conjugate small molecules, such as, for example, chemotherapeutic agents, anti-inflammation agents, antibiotics and polypeptides such as antibodies and antibody fragments and other water soluble drugs. In addition, the ELP nanoparticles are useful for carrying DNA, RNA, protein and peptide-based therapeutics.

ELPs have potential advantages over chemically synthesized polymers as drug delivery agents. First, because they are biosynthesized from a genetically encoded template, ELPs can be made with precise molecular weight. Chemical synthesis of long linear polymers does not typically produce an exact length, but instead a range of lengths. Consequently, fractions containing both small and large polymers yield mixed pharmacokinetics and biodistribution. Second, ELP biosynthesis produces very complex amino acid sequences with nearly perfect reproducibility. This enables very precise selection of the location of drug attachment. Thus drug can be selectively placed on the corona, buried in the core, or dispersed equally throughout the polymer. Third, ELP can self-assemble into multivalent nanoparticles that can have excellent site-specific accumulation and drug carrying properties. Fourth, because ELP are designed from native amino acid sequences found extensively in the human body they are biodegradable, biocompatible, and tolerated by the immune system. Fifth, ELPs undergo an inverse phase transition temperature, $T_t$, above which they phase separate into large aggregates. By localized heating, additional ELP can be drawn into the target site, which may be beneficial for increasing drug concentrations.

A therapeutic such as a drug, for example, may be attached to the ELP through cysteine, lysine, glutamic acid or aspartic acid residues present in the polymer. In some embodiments, the cysteine, lysine, glutamic acid or aspartic acid residues are generally present throughout the length of the polymer. In some embodiments, the cysteine, lysine, glutamic acid or aspartic acid residues are clustered at the end of the polymer. In some embodiments of the presently described subject matter, therapeutics are attached to the cysteine residues of the ELP using thiol reactive linkers. In some embodiments of the presently described subject matter, therapeutics are attached to the lysine residues of the high molecular weight polymer sequence using NHS (N-hydroxysuccinimide) chemistry to modify the primary amine group present on these residues. In some embodiments of the presently described subject matter, therapeutics are attached to the glutamic acid or aspartic acid residues of the ELP using EDC (1-Ethyl-3-[3-dimethylaminopropyl]carbodiimide Hydrochloride) chemistry to modify the carboxylic acid group present on the ELP residues.

The therapeutic associated with the ELP may be hydrophobic or hydrophilic. Which the drug is hydrophobic, attachment to the terminus of the ELP may facilitate formation of the multivalent nanoparticle. The number of drug particles attached to the ELP can be from about 1 to about 30, or from about 1 to about 10, or about 1, 2, 3, 4, 5, 6, 7, 8, 9, or 10. In some embodiments, the attachment points for a therapeutic are equally distributed along the backbone of the ELP, and the resulting drug-ELP is prevented from forming nanoparticle structures under physiological salt and temperature conditions.

In addition to therapeutics, the ELPs may also be associated with a detectable label that allows for the visual detection of in vivo uptake of the ELPs. Suitable labels include, for example, fluorescein, rhodamine, tetramethylrhodamine, eosin, erythrosin, coumarin, methyl-coumarins, pyrene, Malacite green, Alexa-Fluor®, stilbene, Lucifer Yellow, Cascade Blue™, and Texas Red. Other suitable optical dyes are described in Haugland, Richard P. (1996) Molecular Probes Handbook.

In certain embodiments, the ELP components comprise, or alternatively consist essentially of, or yet further consist of: polymeric or oligomeric repeats of the pentapeptide [VPGXG]$_n$ (SEQ ID NO: 6), where the guest residue X is any amino acid, that in one aspect, excludes proline and n is the number of repeats. X may be a naturally occurring or non-naturally occurring amino acid. In some embodiments, X is selected from alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine. In some embodiments, X is a natural amino acid other than proline or cysteine. In a further embodiment, the ELP comprises, or alternatively consists essentially of, or yet further consists of: the primary sequence of [VPGAG]$_n$ (SEQ ID NO: 7), [VPGAG]$_n$[VPGIG]$_n$ (SEQ ID NO: 8), or [VPGSG]$_n$[VPGIG]$_n$ (SEQ ID NO: 9). "n" or the number of repeats can be from the group of about 1 to 500, about 30-500, about 20-200, about 20-100, about 30-200, about 40-200, about 45-200, about 30-100, about 40-100, about 45-100, about 20, about 35, about 40, about 45, about 50, about 55, about 60, about 65, about 70, about 75, about 80, about 85, about 90, about 100, about 105, about 110, about 120, about 130, about 140, about 150, about 160, about 170, about 180, about 190, or about 200. In certain embodiments, n is about 96, about 48, or about 192.

The guest residue X may be a non-classical (non-genetically encoded) amino acid. Examples of non-classical amino acids include: D-isomers of the common amino acids, 2, 4-diaminobutyric acid, α-amino isobutyric acid, A-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general.

Selection of X is independent in each ELP structural unit (e.g., for each structural unit defined herein having a guest residue X). For example, X may be independently selected for each structural unit as an amino acid having a positively charged side chain, an amino acid having a negatively charged side chain, or an amino acid having a neutral side chain, including in some embodiments, a hydrophobic side chain.

In each embodiment, the structural units, or in some cases polymeric or oligomeric repeats, of the ELP sequences may be separated by one or more amino acid residues that do not eliminate the overall effect of the molecule, that is, in imparting certain improvements to the therapeutic component as described. In certain embodiments, such one or more amino acids also do not eliminate or substantially affect the phase transition properties of the ELP component (relative to the deletion of such one or more amino acids).

The ELP component in some embodiments is selected or designed to provide a $T_t$ ranging from about 10 to about 80° C., such as from about 35 to about 60° C., or from about 38 to about 45° C. In some embodiments, the $T_t$ is greater than about 40° C. or greater than about 42° C., or greater than about 45° C., or greater than about 50° C. The transition temperature, in some embodiments, is above the body temperature of the subject or patient (e.g., >37° C.) thereby remaining soluble in vivo, or in other embodiments, the $T_t$ is below the body temperature (e.g., <37° C.) to provide alternative advantages, such as in vivo formation of a drug depot for sustained release of the therapeutic agent. For example, the transition temperature may be about 38, about 39, about 40, about 41, about 42, about 43, about 44, about 45, about 50, about 55, about 60, about 65, or about 70° C. In further embodiments, the transition temperature is at or below physiological level such that the ELPs are assembled into nanoparticles when administered to a patient. In some embodiments, the transition temperature of the ELP-scFv is less than or equal to 37° C. In further embodiments, the transition temperature is about 36, about 35, about 34, about 33, about 32, about 31, about 30, about 29, about 28, about 27, about 26, about 25, about 20, about 15, or about 10° C.

The $T_t$ of the ELP component can be modified by varying ELP chain length. For polypeptides having a molecular weight >100,000, the hydrophobicity scale developed by Urry et al. (PCT/US96/05186, which is hereby incorporated by reference in its entirety) is preferred for predicting the approximate $T_t$ of a specific ELP sequence. However, in some embodiments, ELP component length can be kept relatively small, while maintaining a target $T_t$, by incorporating a larger fraction of hydrophobic guest residues (e.g., amino acid residues having hydrophobic side chains) in the ELP sequence. For polypeptides having a molecular weight <100,000, the $T_t$ may be predicted or determined by the following quadratic function: $T_t = M_0 + M_1 X + M_2 X^2$ where X is the MW of the fusion protein, and $M_0 = 116.21$; $M_1 = -1.7499$; $M_2 = 0.010349$.

While the $T_t$ of the ELP component, and therefore of the ELP component coupled to a therapeutic component, is affected by the identity and hydrophobicity of the guest residue, X, additional properties of the molecule may also be affected. Such properties include, but are not limited to solubility, bioavailability, persistence, and half-life of the molecule.

scFv Polypeptides

Described herein are polypeptides comprising, or alternatively consisting essentially of, or yet further consisting of: an elastin-like peptide (ELP) and a scFv, or a biological equivalent of the scFv. These polypeptides may be referred to herein as "ELP fusions" "scFv fusions" "scFv assemblies" "antibody core protein polymer nanoworms" or "ACPPNs" and which are essentially synonymous. The scFv is a polypeptide that recognizes, has affinity, and/or binds to a specific antigen. In one embodiment, the scFv comprises, or alternatively consists essentially of or yet further consists of the single chain variable region from the anti-CD20 antibody. Examples of the single chain variable region from the scFv include the polypeptides of SEQ ID NOS: 1 and 2. In certain embodiments, the scFv comprises, or alternatively consists essentially of or yet further consists of the sequence of SEQ ID NO: 1 or SEQ ID NO: 2 or a biological equivalent thereof. In further embodiments, the scFv-ELP polypeptide corresponds to a sequence selected from the group consisting of SEQ ID NOS: 3, 4, and 5 or a biological equivalent thereof.

The scFv can have a peptide linker between the heavy and light chains. The linker is variable in length and, in certain embodiments, comprise amino acid residues such as glycine or serine. It is also within the scope of this disclosure to have scFvs with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Consequently, diabody drugs could be dosed much lower than other therapeutic antibodies and are capable of highly specific targeting of tumors in vivo. Still shorter linkers (one or two amino acids) lead to the formation of trimers, so-called triabodies or tribodies. Tetrabodies have also been produced. They exhibit an even higher affinity to their targets than diabodies. All of these formats can be composed from variable fragments with specificity for two different antigens, in which case they are types of bispecific antibodies.

Expression of Recombinant Proteins

ELPs, ELP fusions and other recombinant proteins described herein can be prepared by expressing polynucleotides encoding the polypeptide sequences of this invention in an appropriate host cell, i.e., a prokaryotic or eukaryotic host cell. This can be accomplished by methods of recombinant DNA technology known to those skilled in the art. It is known to those skilled in the art that modifications can be made to any peptide to provide it with altered properties. Polypeptides of the invention can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that beta-turn spiral secondary structure or random secondary structure is preferred.

The ELPs can be expressed and purified from a suitable host cell system. Suitable host cells include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escherichia coli, Salmonella enterica* and *Streptococcus gordonii*. In one embodiment, the host cell is *E. coli*. The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia,* or *Pichia*. See e.g., U.S. Pat. Nos. 4,812,405; 4,818,700; 4,929,555; 5,736,383; 5,955,349; 5,888,768 and 6,258,559.

Protein Purification

The phase transition behavior of the ELPs allows for easy purification. The ELPs may also be purified from host cells using methods known to those skilled in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide or polypeptide are filtration, ion-exchange chromatography, exclusion chromatography, polyacrylamide gel electrophoresis, affinity chromatography, or isoelectric focusing. A particularly efficient method of purifying peptides is fast protein liquid chromatography or even HPLC. In the case of ELP compositions, protein purification may also be aided by the thermal transition properties of the ELP domain as described in U.S. Pat. No. 6,852,834.

Additional techniques include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Nanoworms and their Preparation

Upon purification, scFv-ELP assembles predominantly spherical nanostructures that have moderate activity; however, their potency can be significantly enhanced through denaturation and refolding. When optimized, refolding of the scFv domain results in the formation of high-aspect ratio cylindrical micelles (also known as nanoworms). These high aspect ratio particles morphologies exhibit enhanced apoptotic signaling and potency. Refolding can be achieved either in the absence or presence of reducing regents (including, but not limited to, dithiothreitol, beta mercaptoethanol, or tris carboxyethyl phosphine). Denaturation is accomplished by incubation with chaotropic salts (including, but not limited to, Guanadinium hydrochloride or Urea) at concentrations between 2 and 8 M. To refold the scFv-ELP, chaotropic salts can be removed slowly using dialysis against successive changes of buffers with decreasing concentrations of the chaotropic salt. When the scFv-ELP is again suspended in buffer alone, the refolding process is complete. In addition to the chaotropic salts, dialysis buffers may include, but are not limited to, tris hydrochloride or phosphate buffered saline. The molecular weight cutoff for dialysis can be selected between 3 and 20 kD. Dialysis can occur at temperatures between 4 and 37 Celsius over a period of 1-2 days with successive changes in buffer. After the completion of dialysis, the scFv-ELP retentate may be clarified using ultracentrifugation at 4,000-13,000 RPM. If desired, the scFv-ELP nanoworms may be concentrated by inducing the ELP-mediated phase separation through the addition of 1-4 M sodium chloride at temperatures between 25 and 42 degrees Celsius. If desired, the nanoworms can be sterile filtered through a 0.2 um filter.

Pharmaceutical Compositions

Pharmaceutical compositions are further provided. The compositions comprise a carrier and ELPs as described herein. The carriers can be one or more of a solid support or a pharmaceutically acceptable carrier. In one aspect, the compositions are formulated with one or more pharmaceutically acceptable excipients, diluents, carriers and/or adjuvants. In addition, embodiments of the compositions include ELPs, formulated with one or more pharmaceutically acceptable auxiliary substances.

The invention provides pharmaceutical formulations in which the one or more of an isolated polypeptide of the invention, an isolated polynucleotide of the invention, a vector of the invention, an isolated host cell of the invention, or an antibody of the invention can be formulated into preparations for injection in accordance with the invention by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is an antimicrobial agent such as other vaccine components such as surface antigens, e.g. a Type IV Pilin protein (see Jurcisek and Bakaletz (2007) J. of Bacteriology 189(10):3868-3875) and antibacterial agents.

Embodiments of the pharmaceutical formulations of the invention include those in which the ELP is formulated in an injectable composition. Injectable pharmaceutical formulations of the invention are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations of the invention.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Routes of administration applicable to the methods and compositions described herein include intranasal, intramuscular, subcutaneous, intradermal, topical application, intravenous, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes.

Treatment of Disease

The scFv polypeptides described herein are useful for the specific targeting of scFv-ELPs to cells. One aspect relates to a method for targeting a scFv-ELP to a cell comprising, or alternatively consisting essentially of, or yet further consisting of: contacting the cell with an effective amount of the scFv-ELP polypeptide, wherein the scFv component of the scFv-ELP binds to a cellular component of the cell. The contacting can be to a cell in vitro or in vivo. In one embodiment, the scFv component binds to a cell surface receptor of the cell. In further embodiment, the scFv component binds to an intercellular receptor or a cellular component found on the surface or inside of the cell. These polypeptides may be used to target cell populations with a specific component by using a scFv that recognizes the specific component. The targeting can facilitate drug delivery by conjugating a drug to the scFv-ELP or facilitate cellular signaling by agonizing or antagonizing a cellular receptor. The cellular signaling may induce a specific cellular response. In the case of CD20, multivalent biding of the anti-CD20 to the cell-surface receptor induces apoptosis of the cell. Accordingly, one aspect relates to a method for inducing apoptosis of a CD20+ cell comprising contacting the cell with an effective amount of the scFv-ELP polypeptide wherein the scFv component comprises, or alternatively consists essentially of or yet further consists of the single chain variable region from the anti-CD20 antibody. In a related embodiment, the cell is a malignant B-cell. In another aspect, the compositions are useful to treat a CD20-related disease or disorder, e.g., a CD20-expressing cancer, by administering to a patient in need of such treatment the polypeptide of any one of the compositions of this invention. In one aspect, the CD2-expressing cancer is non-Hodgkin lymphoma.

In some embodiments of the disclosure, the entire anti-CD20 antibody is linked to the ELP. Linking the entire antibody to the ELP may provide additional benefits to therapeutic applications utilizing the anti-CD20 antibody alone. For example, the ELP-conjugated CD20 antibody may provide a more efficient mechanism for crosslinking the antibody. Since activation of apoptosis in CD20+ cells requires multivalent binding of the CD20 cell surface antigen, the ELP-conjugated anti-CD20 antibody may provide more efficient activation of apoptosis. In one aspect, a portion of the anti-CD20 antibody is used.

A further aspect relates to a method for treating a CD20 expressing cancer, comprising administering to a patient in need of such treatment the scFv-ELP polypeptide wherein the scFv component comprises, or alternatively consists essentially of or yet further consists of the single chain variable region from the anti-CD20 antibody or a polynucleotide encoding such polypeptide. One example of a CD20 expressing cancer is non-Hodgkin lymphoma. Also provided are kits for treating a CD20 expressing cancer in a subject, comprising the scFv-ELP polypeptide wherein the scFv component comprises the single chain variable region from the anti-CD20 antibody or a polynucleotide encoding such polypeptide, and optionally, instructions for use.

Combination Treatments

Administration of the therapeutic agent or substance of the present invention to a patient will follow general protocols for the administration of that particular secondary therapy, taking into account the toxicity, if any, of the treatment. It is expected that the treatment cycles would be repeated as necessary. It also is contemplated that various standard therapies, as well as surgical intervention, may be applied in combination with the described therapy.

Kits

Also provided is a kit for treating a CD20 expressing cancer in a subject or for conducting a screen, as outlined below, containing an ELP-CD20 polypeptide and/or polynucleotide, and optionally, instructions for use.

Screens

The present invention also provides methods to identify leads and methods for inducing apoptosis or treating CD20+ cancers and/or disorders. In one aspect, the screen identifies lead compounds or biologics agents that mimic the ELP fusion polypeptide identified above and which are useful to treat these disorders or to treat or ameliorate the symptoms associated with the disorders. Test substances for screening can come from any source. They can be libraries of natural products, combinatorial chemical libraries, biological products made by recombinant libraries, etc. The source of the test substances is not critical to the invention. The present invention provides means for screening compounds and compositions which may previously have been overlooked in other screening schemes.

To practice the screen or assay in vitro, suitable cell cultures or tissue cultures are first provided. The cell can be a cultured cell or a genetically modified cell which differentially expresses the receptor and/or receptor complex. Alternatively, the cells can be from a tissue culture. The cells are cultured under conditions (temperature, growth or culture medium and gas ($CO_2$)) and for an appropriate amount of time to attain exponential proliferation without density dependent constraints. It also is desirable to maintain an additional separate cell culture; one which does not receive the agent being tested as a control.

As is apparent to one of skill in the art, suitable cells may be cultured in microtiter plates and several agents may be assayed at the same time by noting genotypic changes, phenotypic changes and/or cell death.

When the agent is a composition other than a DNA or RNA nucleic acid molecule, the suitable conditions may be by directly added to the cell culture or added to culture medium for addition. As is apparent to those skilled in the art, an "effective" amount must be added which can be empirically determined.

The screen involves contacting the agent with a test cell expressing the complex and then assaying the cell its ability to provide a biological response similar to the ELP fusions described herein. In yet another aspect, the test cell or tissue sample is isolated from the subject to be treated and one or more potential agents are screened to determine the optimal therapeutic and/or course of treatment for that individual patient. A control wherein the ELP fusion of this invention is applied can be performed and the test agent can be compared to the control.

For the purposes of this invention, an "agent" is intended to include, but not be limited to a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies. They can be administered concurrently or sequentially.

Use of the screen in an animal such as a rat or mouse, the method provides a convenient animal model system which can be used prior to clinical testing of the therapeutic agent or alternatively, for lead optimization. In this system, a candidate agent is a potential drug, and may therefore be suitable for further development, if the agent binds the receptor or receptor complex each as compared to untreated, animal expressing the receptor and/or complex. It also can be useful to have a separate negative control group of cells or animals which are healthy and not treated, which provides a further basis for comparison.

EXAMPLES

Example 1

Characterization of scFv-ELP Fusion Proteins

Cancers including NHL are currently being treated by surgery, radiotherapy, chemotherapy, and more recently immunotherapy. Substantial efforts have been expended to explore these modalities, but more innovative ideas are needed to gain ground against tumor resistance. To develop a new modality based on cancer nanomedicine, Applicants have invented novel methods that combine cell expression biology, bioresponsive peptides, and self-assembly. The nanoparticles are derived from protein polymers that are biologically inspired from a five amino acid motif identified in tropoelastin, a human extracellular matrix protein. These Elastin-Like Polypeptides (ELPs) are ideal for NHL cancer nanomedicines because: (i) the development of a simple, recombinant approach to generate targeted nanomedicines, can become a platform for developing antibody nanomedicines targeted at other receptors; (ii) due to their low MW and lack of an Fc domain, scFv fragments are rapidly cleared by the kidney and have short circulation times. Because this approach will generate significantly higher molecular weight scFv fusion proteins and nanoparticles, these reagents will have more favorable pharmacokinetics in vivo; (iii) for Rituximab, the Fc domain is responsible for complement and antibody dependent cytotoxicity, both of which are relatively non-specific in comparison to the CD20-mediated direct induction of apoptosis. The scFv-ELP nanomedicines, therefore present a unique opportunity to shift the mechanism of cell-killing to direct induction of apoptosis; (iv) the potential for local deposition of heat to target the hyperactivation of scFv-ELPs predominantly to tumors; and (v) ELP nanoparticles designed to phase separate under the skin, are a new approach to form slow-release depots that can extend the interval between dosing.

The fusions in Table 1 have been cloned and expressed. The scFv ELPs were purified using inverse temperature cycling. The scFv fusion have similar phase behavior to ELP. Applicants have observed that scFv-ELPs promote nanoparticle assembly independent of temperature. The scFv-A192 nanoparticles have transition temperatures above physiological temperature; therefore they are expected to remain soluble in the body unless the tissue is deliberately heated (FIG. 1).

using agarose gel extraction. The purified sequence is then inserted into a pET25b(+) plasmid which is digested similarly. The insert and the plasmid are ligated with DNA ligase (NEB). The pET25b(+) plasmid with the scFv insert is again double digested with BseR1 and XbaI and ligated to a pET25b(+) plasmid containing the desired ELP sequence. The ligated plasmid is sequence confirmed and transformed into Origami B cells (Novagen) and plated on agar plate with ampicillin. All colonies obtained are screened for expression of required protein and DMSO stocks made. The cloning scheme is depicted in FIG. 13.

TABLE 1

| Label | Peptide sequence | *ELP MW (kD) | Target behavior in body | **Assembly Temp. (° C.) | ***Hydrodynamic Radius at 37° C., $R_h$ = (nm) |
|---|---|---|---|---|---|
| V96 | G(VPGVG)$_{96}$Y (SEQ ID NO: 10) | 39.5 | depot, control | 30 | n.d. |
| 192 | G(VPGAG)$_{192}$Y (SEQ ID NO: 11) | 73.5 | soluble, control | 55 | 6 |
| scAB-V96 | anti-CD20 scAB-G(VPGVG)$_{96}$Y (G(VPGVG)$_{96}$Y disclosed as SEQ ID NO: 10) | 65.3 | Depot | n.d. | n.d. |
| scAB-A192 | anti-CD20 scAB G(VPGAG)$_{192}$Y (G(VPGAG)$_{192}$Y disclosed as SEQ ID NO: 11) | 99.3 | soluble, thermally triggered | 41 | 32 |

*Molecular weight estimated for expressed ELP gene product.
**Assembly temperature determined using optical density at 350 nm on a temperature gradient of 1° C. min$^{-1}$. n.d. not yet determined.
***Radii determined using dynamic light scattering at 25 µM ELP in phosphate buffered saline.

Figure 1B:
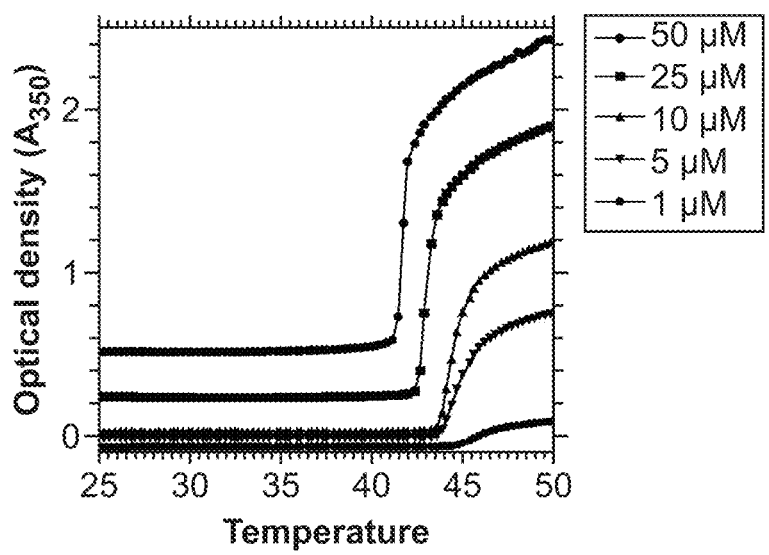
Figure 1C:
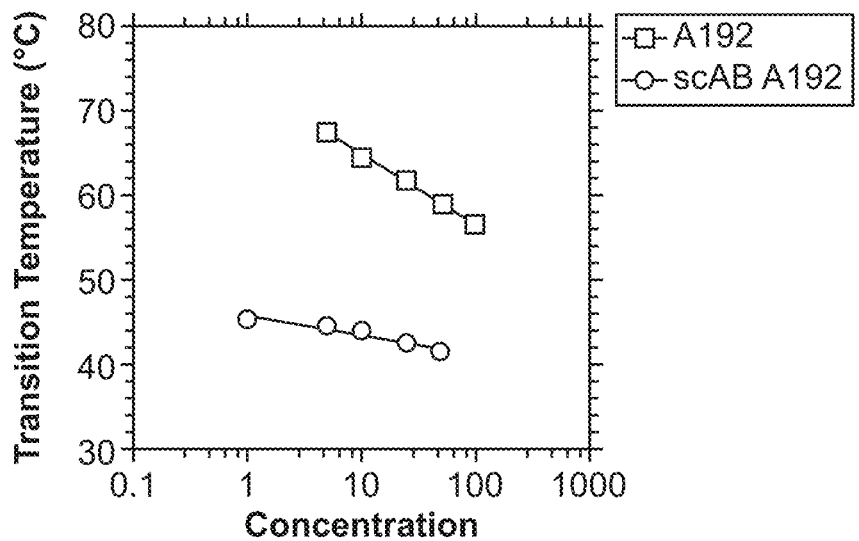

FIG. 1 shows phase diagrams of ELP and scFv ELP fusions including ELP A192 (FIG. 1A) and scFv A192 (FIG. 1B). The linear regression depicted in FIG. 1C shows a concentration dependent change in transition temperature.

Protein Polymer Therapeutics for Non-Hodgkins Lymphoma Therapy

Non-Hodgkin's lymphomas are usually characterized by the uncontrolled replication of malignant B-cells. B-cell surface receptor, CD20, is an established surface marker which has been targeted using antibody therapeutics (for example, Rituximab). Antibody-mediated crosslinking of CD20 induces colocalization to lipid rafts and apoptotic signaling. Utilizing the CD20 crosslinking phenomenon, Applicants have genetically fused a single chain antibody variable fragment (scFv) of the CD20 IgG to environmentally responsive biopolymers called Elastin like polypeptides (ELPs). The resulting fusion proteins are: i) thermally sensitive; ii) target CD20; and iii) induce malignant B-cell apoptosis; and unexpectedly assemble uniform, spherical nanoparticles.

Cloning of scFv-ELP Fusions

Figure 2:
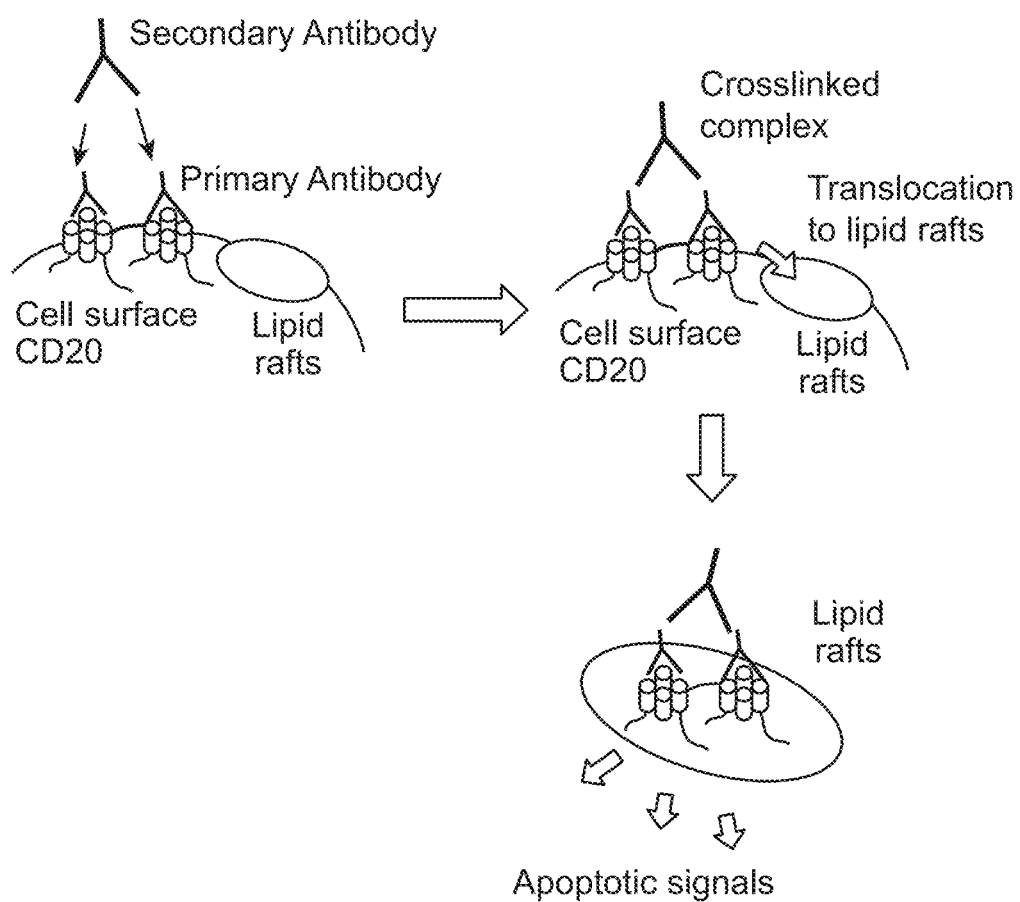
FIG. 2 shows the crosslinking of surface bound CD20 by a secondary antibody promotes translocation of the crosslinked complex to lipid rafts causing downstream signaling of apoptotic pathways.
Figure 4A:
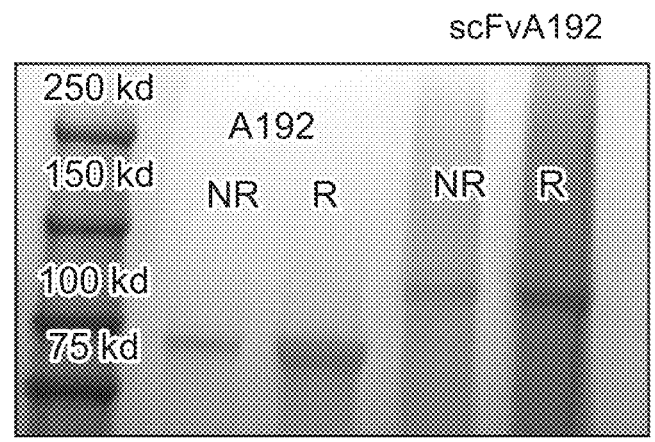
FIGS. 4A-4B demonstrate the properties of the genetically expressed scFv ELP fusions.
Figure 4B:
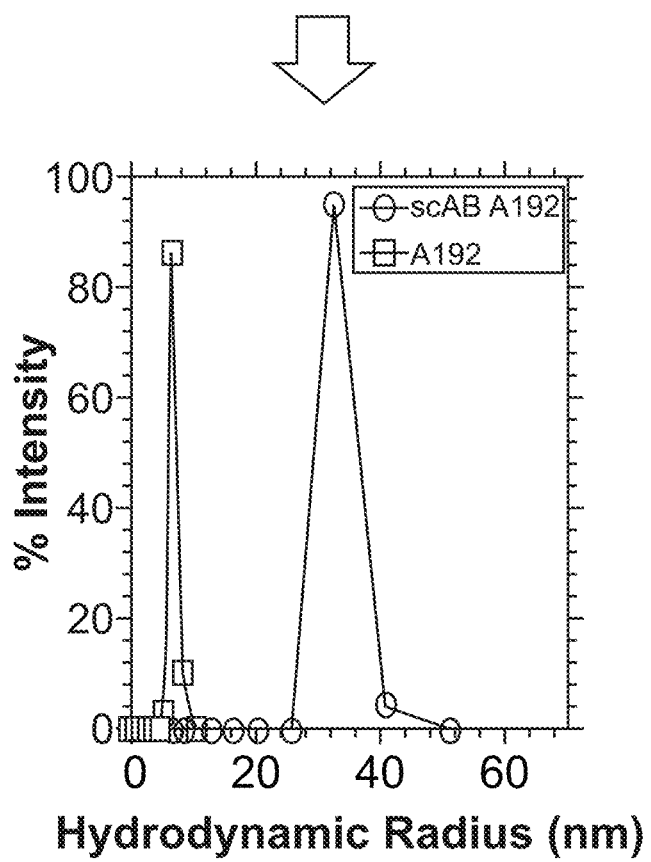
Figure 6:
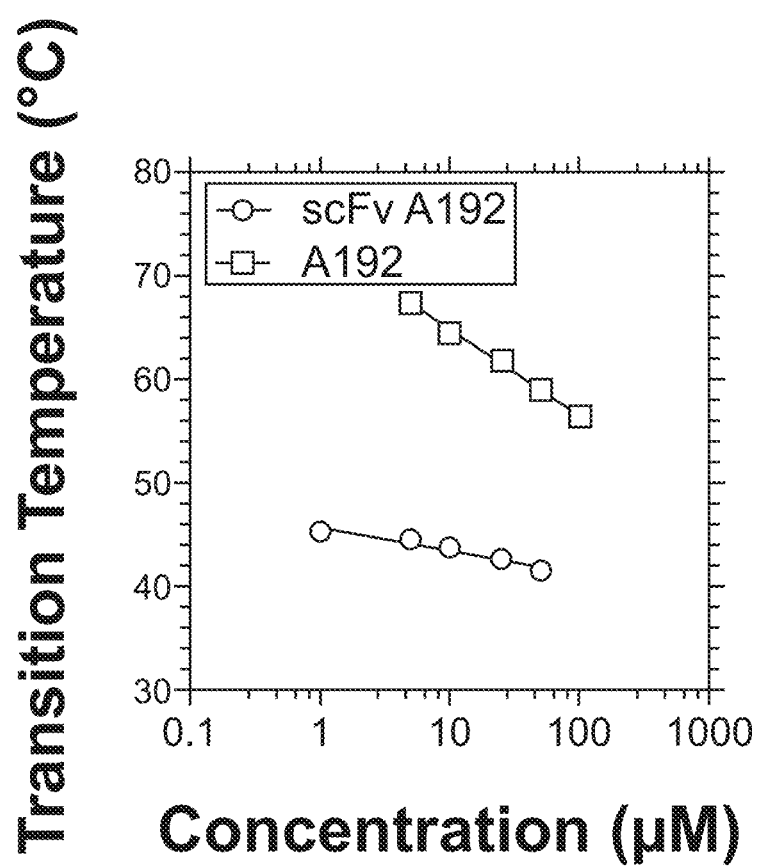
FIG. 6 shows that scFv fusion reduces ELP transition temperature. Fusion of scFv to the ELP drops the transition temperature ~20° C. The drop in transition temperature correlates with nanoparticle assembly.

The scFv sequence was ordered from IDT in a pIDTsmart vector. pIDTsmart vector is double digested with Nde1 (NEB) and BamH1 (NEB) and the scFv sequence purified Crosslinking of surface bound CD20 by a secondary antibody promotes translocation of the cross-linked complex to lipid rafts causing downstream signaling of apoptotic pathways (FIG. 2). The scFv fragment of anti-CD20 was genetically fused to the N-terminus of ELP (FIG. 3). The ELP was fused to the variable light chain of the scFv. The plasmid containing the fusion was transformed into E. coli and expressed. The scFv A192 can be purified using inverse temperature cycling (ITC) (FIG. 4A) and assembles particles with hydrodynamic radius of ~32 nm whereas A192 is ~6 nm (FIG. 4B). Uranyl Acetate contrast enhanced transmission electron microscopy (TEM) images of scFv A192 reveals nanoparticles, which are 51.7±12.4 nm wide (FIG. 5A) and Cryo TEM images of scFv A192 show monodisperse particles of 48.1±11.8 nm in diameter (FIG. 5B). Fusion of scFv to the ELP drops the transition temperature ~20° C. The drop in transition temperature correlates with nanoparticle assembly (FIG. 6).

Binding and Activity

Figures 8A, 8B, 8C, 8D, 8E, 8F:
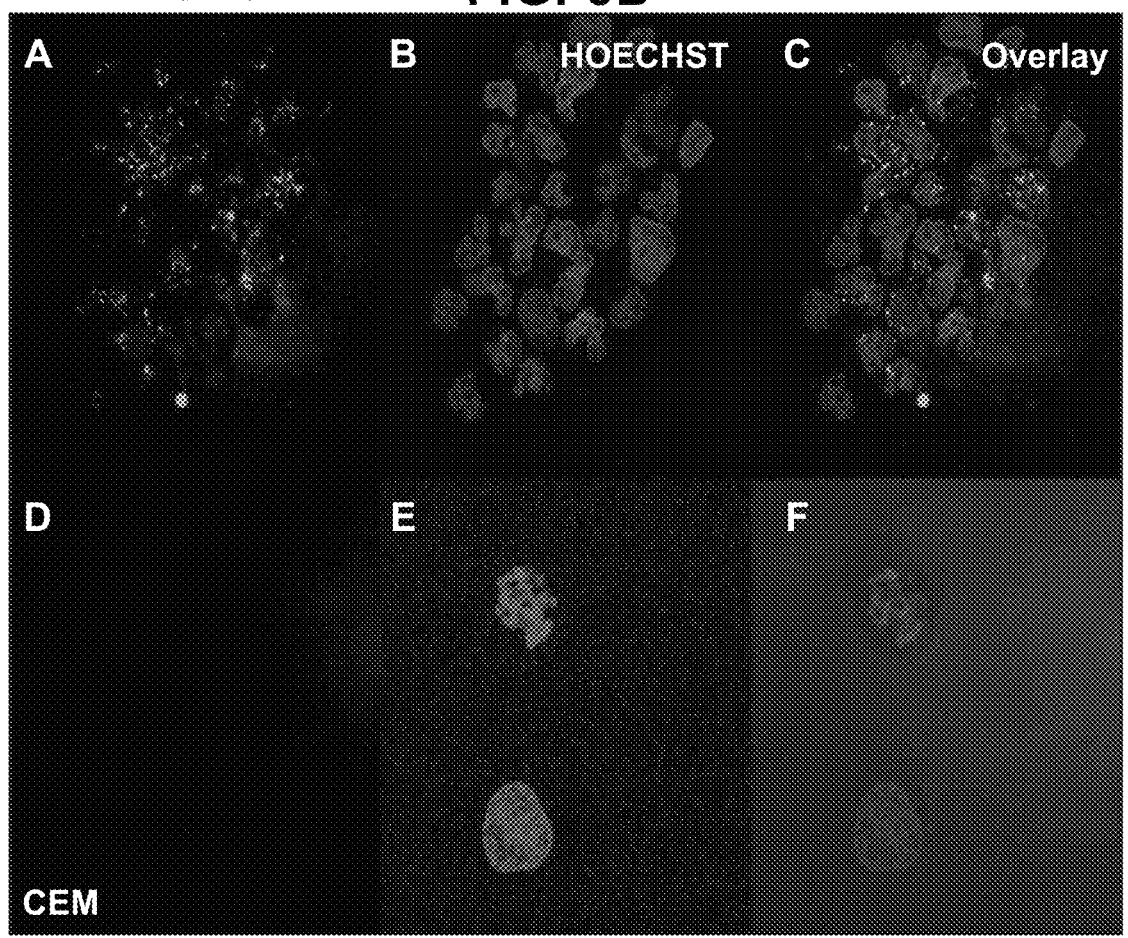
FIGS. 8A-F show the recognition of CD20 surface antigen by the scFv-ELPs.

The scFv ELP fusion recognizes surface CD20. Rhodamine (RHD) labeled scFv A192 fusions bind CD20+ Raji cells (FIG. 7A-D). scFv A192 forms distinct punctate bodies on the cell surface (FIG. 7C). CD20− CEM cells are not stained by scFv A192 (FIG. 7E-H). scFv A192 induces cell aggregation in CD20+ Raji cells. FIG. 8 also demonstrates the scFV ELP fusion recognition of cell surface CD20 receptors.

The CD20 antibody abolishes scFv binding (FIG. 9). Raji and CEM cells were treated with unlabeled CD20 antibody and washed. The washed cells were treated with RHD labeled scFv ELP to check CD20 binding. Pretreatment with CD20 antibody abolished scFv binding on Raji cells (FIG. 9A-D). The untreated cells show scFv binding (FIG. 9E-H) suggesting competitive CD20 binding.

Figure 10:
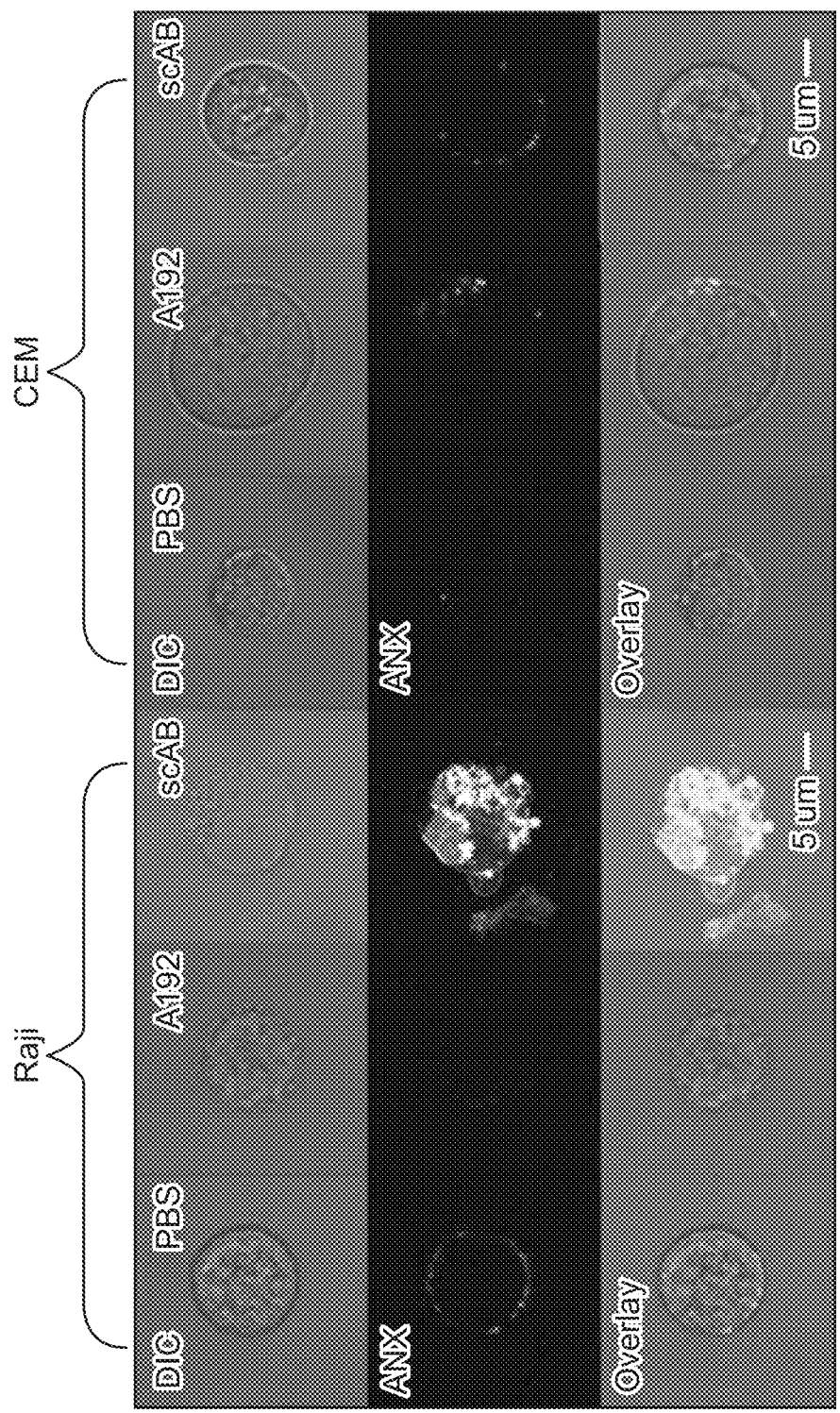
FIG. 10 (right and left panels) show scFv ELP induce Raji cell apoptosis. Annexin V staining show induction of apoptosis in CD20+ Raji cells (Left) and not in CD20− CEM cells (Right).
Figure 11:
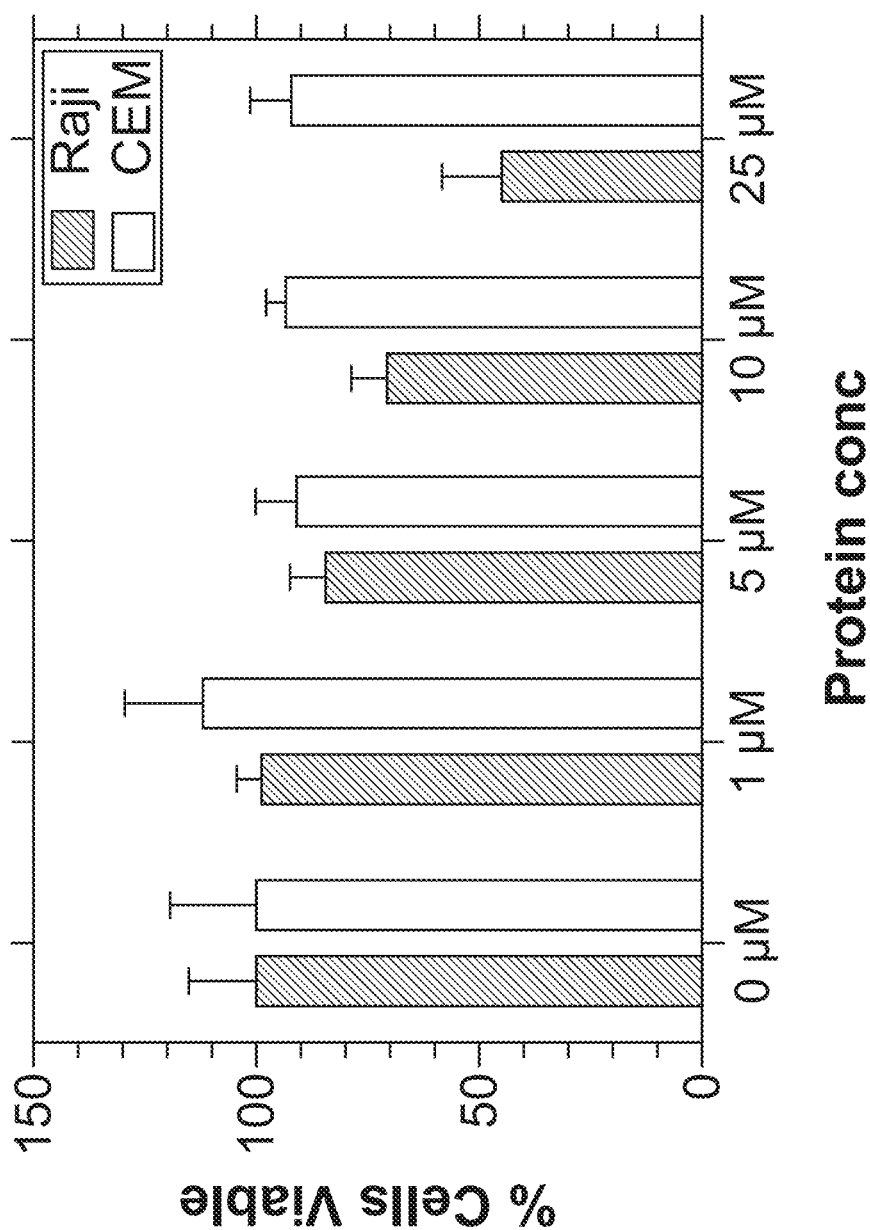
FIG. 11 depicts a MTS assay that shows selective killing of CD20+ Raji cells. The high IC50 of scFV ELP can be attributed to self-assembly of scFv ELP into nanoparticles initiated by the scFv tag.
Figure 12:
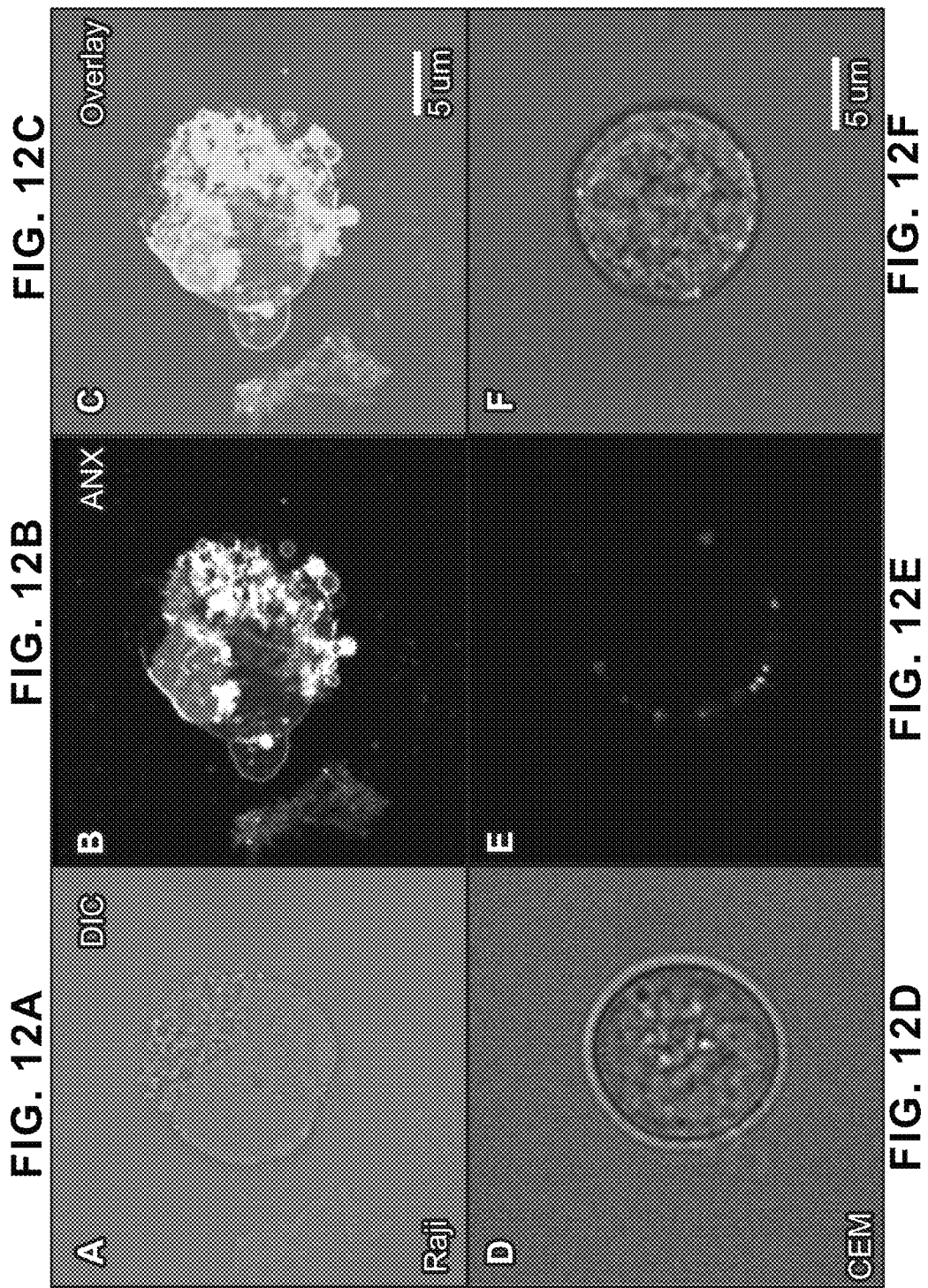
FIGS. 12A-F show that scFv ELP induce Raji cell apoptosis. Annexin V (ANX) staining show induction of apoptosis in Cd20 '+'ve Raji cells (top) and not in Cd20 '−'ve CEM cells (bottom).

The scFv ELP fusion induce apoptosis in Raji cells. scFv ELP treated cells were stained with Annexin V to detect early stage apoptosis. scFv ELPs induced apoptosis in CD20+ Raji cells (FIG. 10, left panel) and not in CD20− CEM cells (FIG. 10, right panel).

scFv ELP fusion selectively kill Raji cells. MTS assay performed on Raji and CEM cells show selective killing on Raji cells (FIG. 11). The selectivity illustrates CD20 targeting. It is worth noting the high IC50 value of the fusion. This can be attributed to self-assembly of scFv particles initiated by the scFv tag. The assembly reduces the number of available active scFv tag causing the increase in IC50.

scFv ELP also induce Raji cell apoptosis. As shown in FIG. 12, Annexin V (ANX) staining show induction of apoptosis in CD20 '+'ve Raji cells (FIGS. 12A-C) and not in CD20 '−'ve CEM cells (FIGS. 12D-F).

ELPs are versatile polymers which can be modified by simple genetic modification. The ELP serves as a purification tag similar to Poly-histidine, which can be used to display single chain antibody fragments. The scFv region promotes assembly of multivalent particles that crosslink surface CD20 and induces apoptosis.

Multivalent CD20 crosslinking does promote apoptosis in human B-cell lymphomas. Utilizing the versatile ELP polymers Applicants were able to successfully express and purify scFv-ELP fusions which specifically target CD20+ cells. The flexibility of ELPs can be exploited to create an array of multifunctional particles with varied pharmacokinetic properties and potential enhanced biological activity. This crosslinking approach can drastically enhance the clinical activity of available B-cell lymphoma immunotherapy. Further modification of the scFv sequence can lead to development of fusions with better targeting and higher tumor killing efficiencies.

Example No. 2

In an extension of Experiment No. 1, the following experiments were conducted.

Materials and Methods

The DNA sequence for anti CD20 scFv (Table 2) was designed and purchased from Integrated DNA Technologies (Coralville, Iowa). Cloning vector (Pet25b(+)), Top 10, and Origami B (DE3) were purchased from Novagen (Darmstadt, Germany). Terrific broth (TB) dry powder was purchased from Mo-bio Laboratories (Carlsbad, Calif.). All restriction enzymes were purchased from New England Biolabs (Ipswich, Mass.). SYBR® safe DNA stain, low and high melting point agarose, AnnexinV/PI apoptosis kit and TUNEL staining kit were purchased from Invitrogen (Grand Island, N.Y.). DNA mini prep and DNA purification kits were purchased from Qiagen (Germantown, Md.). Bacteriological grade agar and sodium chloride was purchased from Sigma Aldrich (St. Louis, Mo.). Non-radioactive cell viability MTS assay kit was purchased from Promega (Madison, Wis.). Precast 4-20% SDS PAGE gels were purchased from Lonza (Basel, Switzerland). Raji, CEM, SU-DHL-7, RTXN, and chimeric Lym1(chLym-1) antibodies were provided to us by Dr. Alan Epstein (USC, Los Angeles, Calif.). Polyclonal goat anti human Fc antibody (2° GAH) was purchased from Thermo Scientific (Rockford, Ill.). Cell culture media, Roswell Park Memorial Institute medium (RPMI 1640), was purchased from Corning (Tewksbury, Mass.). All cells were cultured in RPMI 1640 supplemented with 10% FBS at 37° C. humidified in 5% $CO_2$.

TABLE 2

Biophysical characteristics of cloned scFv ELP fusions

| ELP Nomenclature | Amino Acid Sequence* | $T_t$(° C.)[†] | ELP behavior[#] | Observed ELP MW (Da)[§] |
|---|---|---|---|---|
| A192 | $G(VPGAG)_{192}Y$ (SEQ ID NO: 11) | 55.1 | Soluble | 73,472.8 |
| A96I96 | $G(VPGAG)_{96}$ $(VPGIG)_{96}Y$ (SEQ ID NO: 12) | 56.5 | Micelle | 77,512.5 |
| scFv A192 | scFv-$G(VPGAG)_{192}Y$ (disclosed as SEQ ID NO: 11) | 42.0 | Protein core nanoparticles | 99,292.3 |
| scFv A96I96 | scFv-$G(VPGAG)_{96}$ $(VPGIG)_{96}Y$ (disclosed as SEQ ID NO: 12) | n.a. | n.a. | n.a. |

*Gene sequences confirmed by DNA sequencing from N and C terminal.
[†]Transition temperature (Tt) (25 µM, pH 7.4 determined by optical density measurements at 350 nm.
[#]ELP behavior in PBS.
[§]Molecular weight estimated using SDS-PAGE (n.a: not available).
[‡]scFv sequence:
'QVQLQQPGAELVKPGASVKMSCKASGYTFTSYNMHWVKQTPGRGLEWIGAIYPGNGDTSYNQKFKGKATLTADKSSSTAYMQLS SLTSEDSAVYYCARSTYYGGDWYFNVWGAGTTVTVSAGGGGSGGGGSGGGGSQIVLSQSPAILSASPGEKVTMTCRASSSVSYIH WFQQKPGSSPKPWIYATSNLASGVPVRFSGSGSGTSYSLTISRVEAEDAATYYCQQWTSNPPTFGGGTKLEIKRT' (SEQ ID NO: 13)

Expression and Purification of scFv ELP Fusions

The anti CD20 scFv was fused to ELPs using restriction enzyme digestion followed by sticky end ligation. The expressed protein was purified from bacterial lysates using inverse temperature cycling. Briefly, the anti-CD20 scFv sequence (756 bp) was purchased in an ampicillin resistant proprietary pIDTsmart™ vector. The scFv sequence was inserted into a pet25b(+) expression vector containing the ELP sequences (Table 2) using restriction enzyme digestion. Sequence confirmed plasmid was transformed into Origami B (DE3) *Escherichia coli* (*E. coli*) using heat shock at 42° C. for 5 mins. The heat shocked bacteria was plated onto an ampicillin (100 µg/l) agar plates and incubated at 37° C. for 15-18 hrs and transformed colonies selected. The selected colonies were grown in 5 ml TB culture media with 100 µg/l ampicillin for 15-18 hrs at 37° C. The cultures were pelleted at 4,000 rpm for 15 mins and lysed to check for protein expression using SDS-PAGE. A colony with high protein expression was selected and grown out in a 50 ml starter culture with 100 µg/l ampicillin at 37° C. The bacterial culture was then pelleted and inoculated into 1 liter TB media with 100 µg/l ampicillin. The cultures were grown for 24 hrs and bacteria suspended in filtered PBS (4 L of culture in 25 ml of PBS) for downstream cell lysis. The bacteria were lysed using ultrasonication to release expressed cytosolic fusion protein and bacterial DNA was complexed out using polyethylenimine (50% w/v PEI) at 12,000 rpm for 15 mins. The supernatant containing the fusion protein was filtered through a 0.2 µm filter before protein purification using inverse temperature cycling (ITC).

Refolding Enhances Efficacy

The DNA free supernatant was equilibrated to room temperature and ELP phase transition induced by 3M NaCl (i.e. for 50 ml of supernatant 8 gms of NaCl). The ELP coacervate was spun down at 25° C. for 20 mins at 4000 rpm (HOT SPIN). The supernatant was discarded and the pellet solubilized in cold PBS. The solubilized pellet contains the ELP fusion with insoluble bacterial proteins which were centrifuged out at 4° C. at 12,000 rpm for 15 mins (COLD SPIN). The hot and cold cycle was repeated twice and 6M Guanidine HCl added to perform scFv refolding. Added guanidine is slowly removed by dialysis to promote scFv renaturation using a 20 kD cut off dialysis cassette against cold PBS at 4° C. Dialysis is carried out with a 100:1 sink condition with 4 changes of buffer. A cold spin is performed on the dialyzed protein and a final temperature cycling step performed to ensure complete removal of guanidine. The final protein stock is filtered through a sterile 0.2 µm filter and protein concentration determined using the molar extinction coefficient at 280 nm by:

$$\text{Concentration}(M) = \frac{A_{280} - A_{350}}{MEC(\varepsilon) \times l}$$

Where,
$A_{280}$: Absorbance at 280 nm
$A_{350}$: Absorbance at 350 nm
MEC ($\varepsilon$): Molar extinction coefficient (67,900 $M^{-1}C^{-1}$)
l: Path length (cm)

Determination of Purity and Transition Temperature (Tt) of scFv Assemblies

Purity of the constructs was determined using SDS-PAGE. Briefly, 10-15 µg of protein was added to SDS page loading buffer and boiled at 95° C. for 5 mins. The sample was then run on 4-20% precast SDS-PAGE gel. After the samples are run the gel is stained using 50 ml of 0.3 M copper (II) chloride solution. The gel was imaged on a Biorad VersaDoc gel imager using white light. The purity of samples was calculated using Image J. Briefly, pictures were imported into ImageJ and converted to 8-bit files. Individual lanes are selected and an intensity plot of each lane made. The peak areas were calculated and the purity was determined using:

$$\% \text{ Purity} = \frac{A_{peak}}{A_{tot}} \times 100$$

Where,
$A_{peak}$: Area of peak
$A_{tot}$: Total area

The Tt is used to understand the effect of scFv fusion on the ELP. The Tt of the fusions was determined using optical density measurements at 350 nm. Briefly, increasing concentrations of constructs were added to 300 µl Beckman Coulter Tm microcells (Brea, Calif.) and the temperature was ramped at a rate of 1° C./min. The optical density was plotted as a function of temperature, and the maximum first derivative of this curve was defined as the Tt. The Tt for all samples was determined in PBS.

Light Scattering Analysis of scFv ELP Fusions

Light scattering was used to determine stability and assembly properties of the scFv ELP fusions. To prevent detection of artifacts, all buffers used were sterile filtered using 0.45 µm filter. Dynamic light scattering (DLS) was used to determine the hydrodynamic radius ($R_h$), temperature stability and the polydispersity of the protein in solution. Briefly, increasing concentrations of scFv ELP were pipetted into a 384-well clear bottom plate and read on a Wyatt DynaPro plate reader (Santa Barbara, Calif.) using a 830 nm laser and a 1° C./min temperature ramp from 20° C.-45° C.

Multi angle light scattering (MALS) was used to determine the $R_g$, molecular weight, and coordination number of the scFv fusions. The fusions were analyzed using tandem size exclusion chromatography and multi angle light scattering (SEC-MALS). Briefly, 250 µg of constructs were injected onto a Shodex® size exclusion column using sterile filtered PBS at 0.5 ml/min. The column eluents were analyzed on a Wyatt Helios system (Santa Barbara, Calif.) and the data fit to a Debye plot to determine the $R_g$ and the molecular weight. The coordination number for the assemblies was determined by dividing the absolute molecular weight ($M_{abs}$) by the calculated monomeric scFv ELP molecular weight. The $R_g/R_h$ ratio was used to determine the morphology of the scFv ELP fusion.

Electron Microscopy of scFv ELP Fusion

Cryogenic TEM (cryoTEM) and contrast stain TEM (conTEM) were performed to determine morphology in the presence and absence of aqueous buffer. Briefly, cryoTEM specimens were prepared using an FEI Vitrobot (Hillsboro, Oreg.). ELP solutions were kept in an ice bath (4° C.) before processing and then raised to 37° C. immediately prior to blotting. Six L of sample was pipetted onto a TEM grid coated with a lacey carbon film (LC325-Cu, Electron Microscopy Sciences). The specimen was then blotted under 95% humidity, immediately transferred into liquid ethane, and stored in liquid nitrogen environment. Micrographs were acquired using FEI Tecnai 12 TWIN TEM equipped with 16 bit 2K×2K FEI eagle bottom mount camera (Hillsboro, Oreg.). All cryoTEM images were acquired at an accelerating voltage of 100 kV. Images were analyzed using ImageJ (NIH, USA).

Secondary Structure Determination Using Circular Dichroism (CD)

CD was performed to determine the secondary structure of the scFv constructs. The constructs were run on a Jasco J-815 CD spectrometer (Easton, Md.) using a quartz cuvette (path length~1 mm). The ellipticity was monitored from 185-250 nm and the spectra of buffer subtracted post run. All the constructs were prepared in filtered diH$_2$O. Deconvolution was performed under the assumption that the observed molar ellipticity [θ] is a weighted linear sum of the ellipticity for known secondary structures. The data was fit using nonlinear regression on Microsoft Excel using $$\theta = \Sigma \theta_{std} C_{std}$$

Where,
θ: Observed ellipticity
$\theta_{std}$: Ellipticity of standard
$C_{std}$: Fraction of standard Antibody Core Protein Polymer 'Nanoworms' (ACPPNs) Design and Purification In order to exploit the CD20 induced tumorcidal effect, recombinant scFv was fused (FIG. 14A, Table 2) with elastin like polypeptide (ELP). ELPs are hydrophilic biopolymers with pentameric repeats of [VPGXG]$_n$, (SEQ ID NO: 6) where X can be any amino acid and n is an integer of at least 1. ELPs undergo a characteristic reversible phase transition above a certain critical temperature (LCST) (Urry, D. et al. (1997) J Phys Chem B 101:11007-11028. The recombinant scFv fusion was designed with the RTXN scFv fragment fused to the N-terminus of a large molecular weight (MW) ELP (FIG. 14B). The large MW ELPs were chosen for several reasons. ELP tags enable quick and efficient purification via inverse temperature cycling (ITC) and serve as biodegradable carriers for scFvs, improving their circulation time. Genetic engineering and biological synthesis allows for accurate control over length and sequence, and by designing the construct as a direct fusion of the scFv and ELP, chemical conjugation is avoided. Additionally, the bacterial expression of these fusions allows for a commercially viable product.

Utilizing the ELP tag, the scFv fusions were purified from bacterial lysate using ITC. The purity determined through Coomassie stained SDS-PAGE was 91.4±1.3%. The yield of the fusion was estimated to be 20-30 mg/L of bacterial culture. The purified fusion retained its phase transitioning property but transitioned at a lower temperature due to the conjugation of the scFv fragment. The high absorbance at 350 nm suggests formation of large scFv A192 assemblies even at room temperature. The scFv A192 fusion transitions at ~41° C. when compared to the plain A192 ELP at ~55° C. DLS confirmed formation of assemblies with a $R_h$ of 85.7±16.5 nm. The $R_h$ for unmodified A192 is 6.7±0.2 nm, suggesting that the fusion assembled particles. The assembly of particles could be due to the scFv fusion and it is likely that the scFv is forming the core of these particles.

scFv Renaturation Stabilizes Secondary Structure and Forms ACPPNs

To address this unexpected particle assembly, 6M guanidine was added to disrupt these structures. The secondary structure and particle parameters of scFv-A192 were compared before (raw) and after renaturation (refolded). Using circular dichroism, the secondary structure of raw scFv-A192 particles showed no characteristic spectra, but deconvolution revealed a mixture of secondary structures. The change in refolded secondary structure for ACPPNs was confirmed by a substantial reduction in β-turn content. This suggests a decrease in ELP-mediated aggregation. The ACPPNs are stable to temperatures below 41° C. and do not phase separate under normothermic conditions (~37° C.), which makes them suitable for therapeutic evaluation.

Microscopy of raw protein, utilizing cryoTEM, confirmed monodisperse spherical particles in solution with a diameter of 48.1±11.8 nm. In contrast, the refolded nanoparticles showed a major population of high aspect ratio nanoparticles with lengths of 56.2±15.9 nm and widths of 17.9±3.5 nm. A minor population of spherical particles with a diameter of 27.4±7.5 nm was also observed. The spherical particles may also be nanoworms with their long axes parallel to the electron beam. Based on their size, composition, and morphology, these refolded nanoparticles are defined as Antibody Core Protein Polymer Nanoworms (ACPPNs).

The particle assemblies were compared independently using multi angle light scattering (MALS). MALS analysis performed on raw scFv-A192 confirmed assembly of particles with an absolute molecular weight ($M_{abs}$) of 25,490 kD. The $M_{abs}$ confirmed particle assembly with each particle made up of ~250 scFv-A192 monomers with an $R_g$ of 47.7±0.1 nm. In fact, the refolded particles showed a significant reduction in $M_{abs}$ giving rise to a mixture of 8,372 kD and 8,073 kD particles. The reduction in $M_{abs}$ translates to about 80 scFv A192 monomers making up these particles. The two populations have similar $M_{abs}$ but with varying radii of gyration of 45.2±0.1 and 33.7±0.1 nm respectively. Interestingly, the two particle populations appear as a single population with an $R_h$ of 65.3±15.5 nm using DLS. The $R_g/R_h$ ratios were used to determine the morphology changes due to refolding. The raw scFv-A192 $R_g/R_h$ of 0.56 shifted as high as 0.7 after refolding. The low $R_g/R_h$ value for the scFv-A192 (<0.7 for polymeric micelles) is consistent with the assembly of spherical particles with a densely packed core. In contrast, the refolded scFv-A192 consists of two populations with apparently different shapes and packing densities. Data obtained through MALS experiments is consistent with Applicants' cryoTEM observations, but an accurate measurement of $R_h$ for the subpopulations was not possible due to challenges with separating the two particles.

In Vitro CD20 Recognition Using Laser Confocal Microscopy

CD20 recognition was tested in CD20+ and CD20− cells. For CD20+ cells, Burkitt's (Raji) and diffuse large B-cell lymphoma (SU-DHL-7) cell lines were evaluated against ACPPNs. A CD20− T-acute lymphoblastic leukemia (T-ALL), CEM, was used as a CD20− control. scFv CD20 recognition was performed using rhodamine (RHD) labeled proteins under laser assisted confocal microscopy. Briefly, 50 μg of RHD labeled scFv ELP and RTXN were added to 1 ml of 2×10$^5$ cells suspended in 1% BSA DPBS. The cells were incubated with the protein for 15 mins at room temperature with occasional agitation. After incubation, cells were transferred to 3 ml test tubes and centrifuged at 750 rpm for 5 mins to remove unbound proteins. The cell pellets were washed twice with DPBS and suspended in 100 μl 1% BSA DPBS. The cells were mounted onto glass slides and observed under a Zeiss LSM510 confocal microscope with a 543 nm green excitation laser. For RTXN competition studies, the cells were incubated with 1 mg of unlabeled antibody for 15 mins and washed. Prior to incubation with RHD labeled scFv constructs for a further 15 mins. GAH crosslinked RTXN was imaged in a similar fashion to RHD RTXN treated cells but 10 μg of 2° GAH was added to the washed cells and incubated for a further 15 mins to induce crosslinking. After the incubation, the cells were washed and imaged. Images were analyzed using Image J (NIH, USA).

Cell Viability Assays

A formazan based colorimetric assay was used to determine cell viability. Viability assays were performed on CD20+ and CD20− cell lines used in CD20 binding assays. All assays were performed in 5% FBS RPMI 1640 supplemented with Pen-Strep. Briefly, $2 \times 10^4$ cells/well were pipetted in to 96-well plates and serial dilutions of scFv ELP and RTXN were added in triplicates. RPMI 1640 with appropriate protein dilution was used as blank control. The cells were incubated with the protein for 24 hrs, after which 30 μl of MTS/PMS was added to determine the number of viable cells. The cells were further incubated for 2 hrs and read at 490 nm using a Biorad benchmark Plus® plate reader (Hercules, Calif.). The % cell viability was calculated and plotted versus protein concentration and viability determined by:

$$\% \text{ Cell viability} = \frac{(A_{treated} - A_{cont}) \times 100}{(A_{untreated} - A_0)}$$

Where, $A_{treated}$: Treated cell absorbance at 490 nm $A_{cont}$: Control absorbance at 490 nm with appropriate protein concentration $A_{untreated}$: Untreated cell absorbance at 490 nm $A_0$: Control absorbance at 490 nm with no cells Detection of Apoptosis Through Flow Cytometry Induction of apoptosis was determined using early and late stage apoptotic markers. Annexin V (ANXV)/PI staining was used to detect early induction of apoptosis. An antibody against HLA-Dr10 tumor cells, chLym-1, was used as a positive control for direct induction of apoptosis. The chLym-1 antibody binds HLA-Dr10 expressing tumor cells inducing cell lysis. Briefly, $2 \times 10^5$ cells in 10% FBS RPMI 1640 supplemented with Pen-Strep were added to each well in a 12 well plate. The cells were incubated with equivalent scFv concentrations of scFv ELP, RTXN, RTXN+2° GAH and chLym-1 at 37° C. with humidified 5% $CO_2$ for 18 hrs. For ANXV+ and PI+ compensation controls, cells were treated with 50 μg of paclitaxel. For 2° GAH mediated crosslinking the cells were incubated with RTXN for 30 mins and resuspended in fresh cell culture media. After washing, 100 μgs of 2° GAH was added the cells and incubated for 18 hrs. After incubation the cells were pelleted, washed twice with PBS, and suspended in 100 μl ANXV staining buffer. The cells were stained with ANXV and PI as per the manufacturer's instructions i.e. 5 μl of Alexa Fluor® 488-ANXV stock and 1 μl of 5-fold diluted PI stock were added to the cell and incubated for 15 mins. The volume of cells was made up to 500 μl with ANXV binding buffer and analyzed on an Attune™ acoustic focusing flow cytometer (Life technologies, Grand Island, N.Y.). The data were collected as .fcs files and analyzed on Flowjo.

Late stage apoptosis was detected using terminal deoxynucleotidyl transferase dUTP nick end labeling (TUNEL). The labeling was performed as per the manufacturer's protocol. Briefly, $2 \times 10^6$ cells in 10% FBS RPMI 1640 supplemented with Pen-Strep were added to each well in a 12 well plate. The cells were treated with equivalent scFv concentrations of scFv ELP, RTXN, and RTXN+2° GAH and incubated at 37° C. with humidified 5% $CO_2$ for 18 hrs. The RTXN crosslinking by 2° GAH (100 μg) was performed similar to ANXV/PI staining procedure. After incubation the samples were fixed in 1% formaldehyde for 15 mins and dehydrated using 70% ethanol for 5 hrs on ice. The fixed cells were washed, transferred to a BrdUTP labeling buffer and labeled with BrdU overnight at room temperature. After completion of reaction Alexa488 labeled anti-BrdUTP antibody was added and incubated for 2 hrs. PI was added 30 mins before sample analysis and data collected as .fcs files. Analysis of .fcs files was performed on Flowjo.

Activation of the caspase cascade (Caspase 3, 8, & 9) was detected using an FITC labeled cell penetrating irreversible caspase inhibitor, Z-VAD-FMK (carbobenzoxy-valyl-alanyl-aspartyl-fluoromethylketone)[29]. VAD-FMK binds different caspases with varying affinities[29]. Briefly, $2 \times 10^5$ cells/well in 10% FBS RPMI 1640 supplemented with Penn-Strep were added to 12 well plate and ACPPNs (Fv dose-1.5 mgs/ml) added to appropriate wells. The cells were incubated at 37° C. with humidified 5% $CO_2$ for 18 hrs. After incubation 2 μl of 20 mM FITC-VAD-FMK added for 1 ml of culture. The cells were incubated for a further 1 hr at 37° C. with humidified 5% $CO_2$. The labeled cells were washed with PBS and fixed in 4% formaldehyde and analyzed using flow cytometry. Recorded data was saved as .fcs files and analyzed on Flowjo.

In Vivo Tumor Regression and Biodistribution Studies

Human Burkitts' lymphoma xenografts (Raji) were used to determine in vivo efficacy of scFv constructs. All procedures performed were in accordance to the university approved IACUC protocol. Briefly, Athymic nude mice were irradiated using an X-ray irradiator (400 rads) to lower their NK cell population and allowed to recover for 24 hrs. After recovery, a 200 μl inoculum of $5 \times 10^6$ Raji cells and $10^5$ human fetal fibroblasts, used to support early tumor growth, were implanted subcutaneously on the right flank of the mouse. The mice were divided into 3 treatment groups (n=5): PBS, RTXN (1.7 mgs/dose) and ACPPNs (scFv A192, 2.5 mgs/dose). RTXN and ACPPNs were dosed at an equivalent scFv dose of 600 μg. Animal dosing was started once all tumors reached 150 $mm^3$ and the total number of doses limited to 8 per mouse. The first two doses were administered on consecutive days and the following six doses given every other day. The weight of the mice and the tumor volumes were monitored and animals were sacrificed after reaching the tumor volume end point (1000 $mm^3$) or due to occurrence of any adverse reactions to treatment. Organs from sacrificed animals were harvested and fixed in zinc formalin for 18 hrs and dehydrated in 70% alcohol for 24 hrs before paraffin embedding. After dehydration the dry weights of the liver, spleen, and tumor recorded. After paraffin embedding, fine 5 μm slices of the organs were stained with Hematoxylin and eosin (H & E) and studied for histological changes. The tumor volume for this study was calculated using the following formula:

$$\text{Tumor volume} = \frac{\pi}{6}(w^2 \times l)$$

Where, $\pi = 3.14$.

w=Measured width of tumor.

l=Measured length of tumor.

In vivo biodistribution studies were performed using RHD labeled scFv A192 in Raji xenografted mice (n=3). A therapeutic dose of scFv A192 (2.5 mgs) was administered to the animals and the animals sacrificed after 8 hrs. The organs of the animals were harvested and fixed in zinc formalin for 18 hrs and dehydrated in 70% alcohol for a further 24 hrs prior to paraffin embedding. Paraffin was removed and the sections permeabilized with 10% SDS. The nuclei were stained by incubation in a 1:1000 dilution of DAPI for 1 hr. After incubation, the sections were washed with 1% BSA PBS and slides prepared with antifade reagent. The slides were dried overnight and imaged under a Zeiss LSM510 laser confocal microscope. A 543 nm and 790 nm excitation lasers were used to image RHD and DAPI, respectively. All images were processed on ImageJ.

ACPPNs Target Recognition and In Vitro Efficacy

RHD labeled RTXN and ACPPNs successfully recognized two CD20+ B-cell lymphomas (FIG. 16B (i-iii, vii-xi)). RTXN efficiently bound CD20 with equal distribution of CD20 on the cell surface (FIG. 16A (i-iii, vii-xi)). On addition of 2° GAH the surface bound RTXN showed a speckled or punctate pattern on the cell surface due to translocation of crosslinked RTXN into lipid rafts (FIG. 16A (iv-vi, x-xii)). ACPPNs also bound CD20 forming a punctate pattern similar in appearance to crosslinked RTXN. The binding of ACPPNs can be blocked by pretreating both CD20+ cells with unlabeled RTXN suggesting competitive binding of cell surface CD20. (FIG. 16B (vii-xi, vii-xi)). Conversely, RTXN and ACPPNs showed minimal binding to CD20– CEM cells. Unmodified A192 also showed minimal binding of Raji and SU-DHL-7 cells.

Preliminary experiments with trypan blue exclusion show a significant increase in trypan positive cells when CD20+ B-cells, Raji, and SU-DHL-7, were treated with increasing concentration of ACPPNs (FIG. 17A). A formazan (MTS/PMS) based colorimetric assay confirmed a concentration dependent reduction in cell viability of CD20+ cells with an IC50 of 32 µM and 41 µM in Raji and SU-DHL-7 cells, respectively (FIG. 17B). In contrast, RTXN treatment showed minimal changes in cell viability of Raji cells. RTXN treatment reduced cell viability by 20-25% in Raji cells irrespective of concentration used and therefore an IC50 could not be calculated. Interestingly RTXN showed potent concentration dependent reduction in viability of SU-DHL-7 cells with an IC50 of 4. µM. CD20– cells, CEM, did not respond to RTXN treatment but showed a slight decrease in viability at higher ACPPN concentrations. The IC50 of ACPPNs for CEM cells was 29 µM.

Induction of early and late stage apoptosis was detected by ANXV/PI staining and TUNEL, respectively. ACPPN treatment (scFv dose-1.5 mg/ml) significantly enhanced induction of early apoptosis in both CD20+ cell lines as detected using ANXV/PI staining. RTXN dosed at the same scFv concentration showed variable induction of apoptosis in CD20+ cell lines with Raji cells responding better than SU-DHL-7 cells (FIG. 17C). On crosslinking RTXN with 2° GAH, both cell lines showed an increase in early apoptosis. Since ACPPNs induce apoptosis on binding, a positive control antibody, Chimeric lym1 (chLym-1), with similar mechanism of action was used. The chLym-1 control is an anti HLA-Dr10 antibody which is an effective inducer of apoptosis on direct cell binding (Zhang, N. et al. (2007) Cancer Biother Radiopharm 22: 342-356 and Tobin, E. et al. Leuk Lymphoma 48: 944-956) (FIG. 17C). Treatment with an equi-scFv dose of chLym-1 performed better than plain ACPPNs in Raji cells but was less effective in SU-DHL-7 cells. The variable response could be due to a lower expression of surface HLA-dr10 on SU-DHL-7 cells (FIG. 17C) (Rimsza, L. M. et al. (2004) Blood 103: 4251-4258. Unlike chLym-1, ACPPNs were equally potent in both cell lines. It is interesting to note that results for RTXN treated SU-DHL-7 cells from the formazan based viability assay are contrary to findings from ANXV/PI staining. CEM cells treated with ACPPNs showed minimal induction of apoptosis and hence were not evaluated further (FIG. 17C).

TUNEL staining was used to determine the induction of late apoptosis because ANXV/PI staining is known to detect early apoptosis. All proteins were compared with an equivalent Fv dose of 2.5 mg/ml. ACPPN treatment significantly enhances apoptosis compared to plain RTXN (Unpaired 2 tail t-test, $\alpha=0.05$, P=0.006*, P=0.006**) in both CD20+ cell lines (FIG. 17D). The efficacy of RTXN can be enhanced to the same extent as ACPPNs by crosslinking with 2° GAH (FIG. 17D). Subsequently, the activation of apoptotic caspase cascade was confirmed using FITC-VAD-FMK (FIG. 17 E-F). A substantial increase in the FITC signal was observed after ACPPN treatment in both Raji and SU-DHL-7 cells. The activation of the caspase cascade by ACPPNs is similar to hypercrosslinked RTXN. Zhang, N. et al. (2005) Clinical Cancer Research, Vol. 11:5971-5980. Hence the ACPPNs are effective inducers of apoptosis in both B-cell lymphoma cell lines and outperform RTXN in vitro.

ACPPNs Biodistribution and Tumor Regression

RHD labeled ACPPNs injected in Raji xenografted athymic nude mice (n=3) showed accumulation in various organs (FIG. 18A-H). RHD signal was seen in the liver (FIG. 18 A, E), spleen (FIG. 18B, F), tumor (FIG. 18C, G) and kidney (FIG. 18D, H), and, minimal accumulation was observed in the heart and lungs. Tumor regression studies were performed in mice with Raji xenografts implanted in the right flank of athymic nude mice (n=5/group). The mice were dosed every other day until 8 doses were administered, and tumor volume was monitored until the tumor volume endpoint (1000 mm$^3$) was reached. ACPPNs treatment significantly retarded tumor growth compared to plain RTXN and PBS groups (FIG. 18I). Repeated measures 1-way ANOVA performed on the mean tumor volumes showed a significant difference between ACPPNs, RTXN, and PBS treated group (P=0.0011). Tukey post hoc analysis show a statistically significant difference between ACPPNs, RTXN (P=0.0015), and PBS (P=0.018) treatment. Tumor volumes of RTXN and PBS showed no statistically significant difference (P=0.148). ACPPNs treatment significantly improved survival when compared to RTXN and PBS treatment groups (P=0.013, FIG. 18J). The median survival times for ACPPN, RTXN, and PBS were 33, 19 and 25 days, respectively. The administered doses were adequately tolerated but produced a weight loss (~20%) observed in ACPPNs group after the first dose. The weight was recovered by day 13 with no causalities to treatment.

The dry weight of the organs in the three groups did not change appreciably except for the spleen. A slight increase in dry spleen weight was observed in RTXN and ACPPNs groups when compared to the PBS treatment group (Table 3). Similarly, major organs collected showed no observable histological changes in the three groups except for the tumor. The tumors in the RTXN and ACPPNs treatment groups showed similar histology with prominent necrotic regions compared to that seen in the PBS groups.

TABLE 3

Dry organ weights from tumor regression study

| Group | Liver (pg) | Spleen (pg) | Tumor (pg) |
|---|---|---|---|
| PBS | 1033.7 ± 209.2 | 91.8 ± 14.7 | 551.3 ± 195.4 |
| RTXN | 1039.3 ± 167.4 | 145.0 ± 49.9 | 474.0 ± 81.4 |
| ACPPNWs | 964.7 ± 75.9 | 118.2 ± 41.8 | 451.0 ± 104.1 |

Experimental Discussion

Utilizing simple genetic engineering, Applicants constructed scFv based therapeutics which were successfully purified from bacterial lysates using the ELPs as the purification tag. To the best of Applicants' knowledge, this is the first demonstration of ELPs being used as a purification tag for bacterially expressed recombinant scFv. The formation of large spherical particles by 'raw' protein could be due to (1) high salt concentration used to induce ELP phase transition, which could contribute to scFv denaturation leading to assembly or (2) recombinant scFv multimerization forming dimeric, trimeric, and even hexameric molecules (32,33) which could trigger particle assembly with a multimeric scFv core. The particle formation was reduced by guanidine renaturation but the process led to the formation of recombinant ACPPNs which efficiently targeted CD20 expressed on the surface of B-cells lymphomas. The formation of 'worms' was confirmed using cryoTEM which showed particles of 56.2±15.9 nm in length. The worms still assemble with a scFv core but with a lower $M_{abs}$ and relatively constant $R_g$. Due a lower mass distributed in the same volume after refolding Applicants hypothesize that the scFv core may be more accessible, allowing for CD20 recognition. The small population with a lower diameter could have a less accessible core and may not contribute to the molecules efficacy.

In vitro activity was first confirmed by a measuring cell viability which showed selective killing of CD20+ cells albeit at a relatively high IC50 (32 µM and 41 µM). Compared to the poor reduction of viability by plain RTXN, however, the IC50 seems acceptable. The reduction in cell viability was confirmed to be due to the induction of apoptosis using two separate techniques targeting different stages of apoptosis. ACPPNs treatment greatly induced apoptosis (~60%) in both cell lines and outperformed equi-scFv dose RTXN treatment. Also, 2° GAH crosslinked RTXN showed the same efficacy of induction as single agent ACPPNs treatment. An unexpected observation was that RTXN showed potent reduction in SU-DHL-7 viability using formazan based assays but minimal cell staining apoptosis in both apoptosis assays. This contradiction could have arisen due to the 100 fold less cell concentrations used for the experiment.

The in vitro activity of ACPPNs was successfully translated in vivo using a Raji cell xenograft. ACPPNs treatment showed a significant delay in tumor growth when compared a plain RTXN dosed at the same equivalent scFv dose. A high dose for ACPPNs was chosen based on its activity in vitro. Tumor accumulation of ACPPNs was confirmed by injecting Raji cell xenografted nude mice with RHD labeled reagent. The particles showed high liver, tumor and spleen accumulation (FIG. 19A-H). The high liver and spleen uptake is most likely attributed to the host reticuloendothelial system (Brigger, I., et al. (2002) Adv Drug Deliv Rev 54:631-651 and Buzea, C., et al. (2007) Biointerphases 2:MR17-71. Kupffer cells in the liver are responsible for nanoparticle clearance (Dobrovolskaia, M. A., et al. (2009) Nat Nanotechnol 4:411-414) and hence could be taking up ACPPNs from the circulation. In the spleen, the major RHD signal was present in the marginal zone (MZ) lining the white pulp region (FIG. 19B, F). The marginal zone is mainly populated by phagocytic macrophages and lymphocytes (Martin, F. et al. (2002) Nat Rev Immunol 2: 323-335 and Kraal, G. (1992) Int Rev Cytol 132:31-74) which play a significant role in filtering and clearing nanoparticles from the body (Aichele, P. et al. (2003) J of Immunol 171:1148-1155 and Demoy, M. et al. (1999) Pharm Res 16:37-41). Hence the liver and spleen signal could be due to phagocytosis and clearance by effector cells. This finding is consistent with the uptake of nanoparticles with similar size (Moghimi, S. M., et al. (2012) Annu Rev Pharmacol 52:481-503). Interestingly, kidney sections also show accumulation of ACPPN particles in the glomerulus confirming the high molecular weight (glomerulus filtration cut off=60,000 kD) of ACPPNs (Meibohm, B., et al. (2012) J Clin Pharmacol 52: 54S-62S)

In conclusion these novel first generation ACPPNs (1) outperform RTXN as a single agent, (2) are biodegradable due to their peptidic nature, (3) are genetically engineered to offer precise control over the sequence, (4) are cheaper to produce than high molecular weight antibodies, and (5) represent a simple platform to apply to various other scFv targets.

Example 3: Treatment of Subjects with Non-Hodgkin Lymphoma

Studies are conducted to determine the effects of an amount of recombinant polypeptide comprising scFv ELP fusions in subjects with Non-Hodgkin Lymphoma (NHL). For example, a multicenter, randomized, double-blind, placebo-controlled study is undertaken to evaluate treatment with a weight-based or fixed dose of scFv ELP fusions in subjects with NHL. More specifically, a clinical study is performed to examine the efficacy and safety of a recombinant polypeptide comprising scFv ELP fusions. The scFv ELP is effective to treat and/or prevent NHL.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A recombinant polypeptide comprising an elastin-like peptide (ELP) fused to an antigen binding domain of an anti-CD20 antibody or the scFv of the anti-CD20 antibody, wherein the elastin-like peptide (ELP) comprises G(VPGAG)$_{192}$Y (SEQ ID NO: 11) or G(VPGAG)$_{96}$(VPGIG)$_{96}$Y (SEQ ID NO: 12).

2. The recombinant polypeptide of claim 1, wherein the antigen binding domain or the scFv is fused to the N-terminus of ELP.

3. The polypeptide of claim 2, wherein the polypeptide comprising the amino acid sequence selected from the group consisting of: SEQ ID NOS: 3 and 4.

4. The polypeptide of claim 1 further comprising a detectable label.

5. The polypeptide of claim 1, wherein the scFv comprises the sequence of SEQ ID NO: 1 or SEQ ID NO: 2.

6. The polypeptide of claim 1 linked to a therapeutic agent.

7. The polypeptide of claim 6, wherein the therapeutic agent is an anti-cancer drug.

8. A composition comprising at least two polypeptides of claim 1.

9. A composition comprising at least two polypeptides of an elastin-like peptide (ELP) consisting essentially of primary sequence of G(VPGAG)$_{192}$Y (SEQ ID NO: 11) or G(VPGAG)$_{96}$(VPGIG)$_{96}$Y (SEQ ID NO: 12) fused to an scFv of an anti-CD20 antibody of SEQ ID NO: 13 wherein the at least two polypeptides are organized into a cylindrical particle.

10. The composition of claim 9, wherein the cylindrical particle has a core.

11. The composition of claim 10, wherein the core of the cylindrical particle comprises the anti-CD20 scFv fused to an N-terminus of an ELP.

12. The composition of claim 9, wherein the at least two polypeptides are organized into a spherical particle or a nanoworm.

13. The composition of claim 12, wherein the particle has a core.

14. The composition of claim 13, wherein the core of the particle comprises an anti-CD20 scFv that is fused to an N-terminus of the ELP.

15. A composition comprising a carrier and the at least two polypeptides of claim 9.

16. A method for inducing apoptosis of a CD20+ cell comprising contacting the cell with an effective amount of the polypeptide of claim 1.

17. A method for treating a CD20-related disease or disorder, comprising administering to a patient in need of such treatment the polypeptide of claim 1.

18. A kit for treating a CD20-related disease or disorder or inducing apoptosis of a CD20+ cell, comprising the polypeptide of claim 1.

19. A method for targeting a scFv-ELP to a cell expressing CD20 comprising contacting the cell with an effective amount of the polypeptide of claim 1, wherein the scFv component of the scFv-ELP binds to the CD20 receptor on the cell.

20. The composition of claim 9, wherein the ELP polypeptide consists essentially of the sequence $G(VPGAG)_{192}Y$ (SEQ ID NO: 11).

21. The composition of claim 9, wherein the at least two polypeptides of an elastin-like peptide (ELP) fused to the scFv of an anti-CD20 antibody comprises the sequence of SEQ ID NO: 3.

22. A kit for treating a CD20-related disease or disorder or inducing apoptosis of a CD20+ cell comprising the polypeptide of claim 9.

* * * * *